United States Patent
Burks et al.

(10) Patent No.: US 9,561,211 B2
(45) Date of Patent: *Feb. 7, 2017

(54) BENZOTHIOPHENE DERIVATIVES AND COMPOSITIONS THEREOF AS SELECTIVE ESTROGEN RECEPTOR DEGRADERS

(71) Applicants: Heather Elizabeth Burks, Cambridge, MA (US); Michael A. Dechantsreiter, Cambridge, MA (US); Guo He, Cambridge, MA (US); Jill Nunez, Cambridge, MA (US); Stefan Peukert, Cambridge, MA (US); Clayton Springer, Cambridge, MA (US); Yingchuan Sun, Cambridge, MA (US); Noel Marie-France Thomsen, Cambridge, MA (US); George Scott Tria, Cambridge, MA (US); Bing Yu, Cambridge, MA (US)

(72) Inventors: Heather Elizabeth Burks, Cambridge, MA (US); Michael A. Dechantsreiter, Cambridge, MA (US); Guo He, Cambridge, MA (US); Jill Nunez, Cambridge, MA (US); Stefan Peukert, Cambridge, MA (US); Clayton Springer, Cambridge, MA (US); Yingchuan Sun, Cambridge, MA (US); Noel Marie-France Thomsen, Cambridge, MA (US); George Scott Tria, Cambridge, MA (US); Bing Yu, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/066,425

(22) Filed: Mar. 10, 2016

(65) Prior Publication Data
US 2016/0184265 A1 Jun. 30, 2016

Related U.S. Application Data

(63) Continuation of application No. 14/768,341, filed as application No. PCT/US2014/015938 on Feb. 12, 2014, now Pat. No. 9,321,746.
(Continued)

(51) Int. Cl.
*A61K 31/00* (2006.01)
*A61K 31/381* (2006.01)
(Continued)

(52) U.S. Cl.
CPC .......... *A61K 31/381* (2013.01); *A61K 31/397* (2013.01); *A61K 31/404* (2013.01); *A61K 31/4025* (2013.01); *A61K 31/41* (2013.01); *A61K 31/4196* (2013.01); *A61K 31/422* (2013.01); *A61K 31/428* (2013.01); *A61K 31/4245* (2013.01); *A61K 31/4436* (2013.01); *A61K 31/506* (2013.01); *A61K 31/5377* (2013.01); *A61K 45/06* (2013.01); *C07D 333/64* (2013.01); *C07D 333/66* (2013.01); *C07D 409/04* (2013.01); *C07D 409/10* (2013.01); *C07D 409/12* (2013.01);
(Continued)

(58) Field of Classification Search
None
See application file for complete search history.

(56) References Cited

U.S. PATENT DOCUMENTS 5,510,357 A 4/1996 Palkowitz
5,731,342 A 3/1998 Cullinan et al.
(Continued)

FOREIGN PATENT DOCUMENTS

EP 0716855 A2 6/1996
EP 0731101 A1 9/1996
(Continued)

OTHER PUBLICATIONS

Kieser et al. Characterization of the pharmacophore properties of novel selective estrogen receptor downregulators (SERDs). J Med Chem. Apr. 22, 2010;53(8):3320-9.
(Continued)

*Primary Examiner* — Craig Ricci
(74) *Attorney, Agent, or Firm* — Scott W. Reid

(57) ABSTRACT

The present invention relates to compounds of formula I:

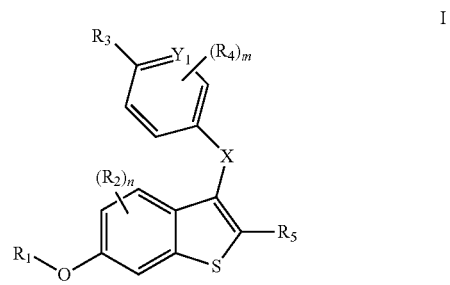

in which n, m, X, $Y_1$, $R_1$, $R_2$, $R_3$, $R_4$ and $R_5$ are defined in the Summary of the Invention; capable of being both potent antagonists and degraders of estrogen receptors. The invention further provides a process for the preparation of compounds of the invention, pharmaceutical preparations comprising such compounds and methods of using such compounds and compositions in the management of diseases or disorders associated with aberrant estrogen receptor activity.

3 Claims, No Drawings

Related U.S. Application Data

(60) Provisional application No. 61/766,439, filed on Feb. 19, 2013.

(51) Int. Cl.

| | | |
|---|---|---|
| *C07D 333/64* | (2006.01) | |
| *A61K 31/4196* | (2006.01) | |
| *A61K 31/422* | (2006.01) | |
| *A61K 31/4245* | (2006.01) | |
| *A61K 31/4436* | (2006.01) | |
| *A61K 31/506* | (2006.01) | |
| *A61K 45/06* | (2006.01) | |
| *C07D 333/66* | (2006.01) | |
| *C07D 409/12* | (2006.01) | |
| *C07D 413/04* | (2006.01) | |
| *C07D 413/12* | (2006.01) | |
| *C07D 409/04* | (2006.01) | |
| *C07D 409/10* | (2006.01) | |
| *C07D 417/12* | (2006.01) | |
| *A61K 31/397* | (2006.01) | |
| *A61K 31/4025* | (2006.01) | |
| *A61K 31/404* | (2006.01) | |
| *A61K 31/41* | (2006.01) | |
| *A61K 31/428* | (2006.01) | |
| *A61K 31/5377* | (2006.01) | |

(52) U.S. Cl.
CPC ........... *C07D 413/04* (2013.01); *C07D 413/12* (2013.01); *C07D 417/12* (2013.01)

(56) References Cited

U.S. PATENT DOCUMENTS

| 6,166,069 A | 12/2000 | Malamas et al. |
|---|---|---|
| 8,877,801 B2 | 11/2014 | Burks et al. |

| 2004/0044059 A1 | 3/2004 | Pinney et al. |
|---|---|---|
| 2004/0132776 A1 | 7/2004 | Agus |
| 2009/0069380 A1 | 3/2009 | Czarnik |

FOREIGN PATENT DOCUMENTS

| WO | 95/10513 A1 | 4/1995 |
|---|---|---|
| WO | 98/39323 A1 | 9/1998 |
| WO | 98/45286 A1 | 10/1998 |
| WO | 98/45287 A1 | 10/1998 |
| WO | 98/45288 A1 | 10/1998 |
| WO | 99/58519 A1 | 11/1999 |
| WO | 01/66098 A2 | 9/2001 |
| WO | 2004/009086 A1 | 1/2004 |
| WO | 2005/000834 A1 | 1/2005 |
| WO | 2005/073190 A1 | 8/2005 |
| WO | 2005/073205 A1 | 8/2005 |
| WO | 2006/094235 A1 | 9/2006 |
| WO | 2008/115686 A1 | 9/2008 |
| WO | 2012/084711 A1 | 6/2012 |

OTHER PUBLICATIONS

Overk et al., Structure-activity relationships for a family of benzothiophene selective estrogen receptor modulators including raloxifene and arzoxifene. ChemMedChem. Oct. 2007;2(10):1520-6.

Scott et al., "Tetrahydroisoquinoline Phenols: Selective Estrogen Receptor Downregulator Antagonists with Oral Bioavailability in Rat," ACS Med Chem Lett. Accepted Dec. 19, 2015 (pp. A-F) (6 pages).

Xiong et al., "Selective Human Estrogen Receptor Partial Agonists (ShERPAs) for Tamoxifen-Resistant Breast Cancer," J Med Chem. (pp. A-S) (19 pages).

Kieser, KJ. et al.Characterization of the Pharmacophore Properties of Novel Selective Estrogen ReceptorDownRegulators (SERDs). J. Med. Chem., 53(8): 3320-3329. (2010).

BENZOTHIOPHENE DERIVATIVES AND COMPOSITIONS THEREOF AS SELECTIVE ESTROGEN RECEPTOR DEGRADERS

This application is Continuation of U.S. application Ser. No. 14/768,341 filed on 17 Aug. 2015, which is a U.S. National Phase filing of International Application No. PCT/US2014/015938 filed 12 Feb. 2014, which claims priority to U.S. Application No. 61/766,439 filed 19 Feb. 2013, the contents of which are incorporated herein by reference in its entirety.

BACKGROUND

1. Field of the Invention

The present invention relates to compounds and compositions that are potent antagonists of estrogen receptor signaling and selective estrogen receptor degraders (SERDs). The invention further provides a process for the preparation of compounds of the invention, pharmaceutical preparations comprising such compounds and methods of using such compounds and compositions in the management of diseases or disorders associated with aberrant estrogen receptor activity.

2. Background of the Invention

Estrogens play a critical role in the development of female and male reproductive tissues and contribute to the development and progression of estrogen receptor diseases or disorders such as breast, ovarian, colon, prostate, endometrial and uterine cancers. Estrogen receptor (ERα)-positive diseases such as breast cancer are usually treated with a selective estrogen receptor modulator (SERM) or an aromatase inhibitor (AI). While these therapies have proven effective at reducing the incidence of progression of breast cancer, some patients exhibit treatment resistance and progress to advanced metastatic breast cancer.

Treatment resistance results, in part, from the evolution of tumors to a state of hypersensitivity to low estrogen levels (AI treatment) or development of dependence upon the antiestrogen for activation of transcription (SERM treatment). SERDs degrade the receptor, effectively eliminating ERα expression and in so doing circumvent the underlying mechanisms of resistance that develop to antiendocrine monotherapy. Further, clinical and preclinical data show that a significant number of the resistance pathways can be circumvented by the use of an antiestrogen that exhibits SERD activity.

The compounds of the present invention, as SERDs, can be used as therapies for the treatment of estrogen receptor diseases or disorders, for example, ovulatory dysfunction, uterine cancer, endometrium cancer, ovarian cancer, endometriosis, osteoporosis, prostate cancer, benign prostatic hypertrophy, estrogen receptor (ERα)-positive breast cancer, in particular ERα-positive breast cancer exhibiting de novo resistance to existing anti-estrogens and aromatase inhibitors.

SUMMARY OF THE INVENTION

In one aspect, the present invention provides compounds of Formula I:

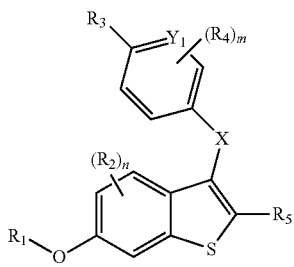

in which:

n is selected from 0, 1 and 2;

m is selected from 0, 1 and 2;

X is selected from O and $NR_6$; wherein $R_6$ is $C_{1-4}$alkyl;

$Y_1$ is selected from N and $CR_7$; wherein $R_7$ is selected from hydrogen and $C_{1-4}$alkyl;

$R_1$ is hydrogen;

$R_2$ is selected from hydrogen and halo;

$R_3$ is selected from —$CH_2CH_2R_{8b}$ and —$CR_{8a}$=$CR_{8a}R_{8b}$; wherein each $R_{8a}$ is independently selected from hydrogen, fluoro and $C_{1-4}$alkyl; and $R_{8b}$ is selected from —$C(O)OR_{9a}$, —$C(O)NR_{9a}R_{9b}$, —$C(O)NHOR_{9a}$, —$C(O)X_2R_{9a}$ and a 5-6 member heteroaryl selected from:

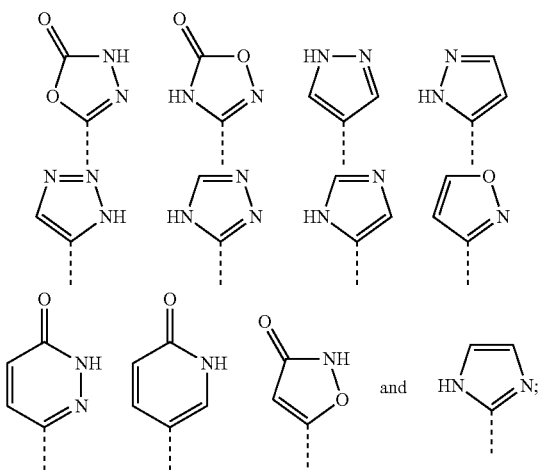

wherein the dotted line indicates the point of attachment with —$CH_2CH_2$ or —$CR_{8a}$=$CR_{8a}$ of $R_3$; wherein $X_2$ is $C_{1-4}$alkylene; $R_{9a}$ and $R_{9b}$ are independently selected from hydrogen, $C_{1-4}$alkyl, hydroxy-substituted-$C_{1-4}$alkyl, halo-substituted-$C_{1-4}$alkyl and —$X_4R_{10}$; wherein $X_4$ is selected from a bond and $C_{1-3}$alkylene; and $R_{10}$ is a 4-6 member saturated ring containing 1 to 3 atoms independently selected from O, N and S; wherein said heteroaryl of $R_{8b}$ is unsubstituted or substituted with 1 to 3 groups independently selected from $C_{1-4}$alkyl and $C_{3-8}$cycloalkyl;

$R_4$ is selected from hydrogen, $C_{1-4}$alkyl, halo and $C_{1-3}$alkoxy;

$R_5$ is selected from $C_{6-10}$aryl and a 5-6 member heteroaryl selected from:

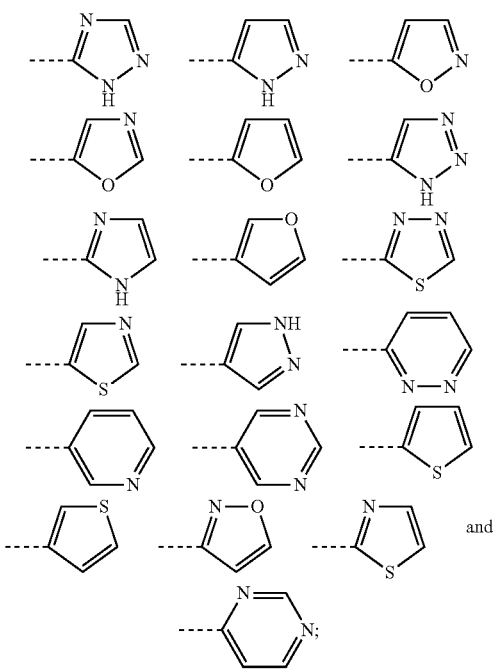

wherein the dotted line indicates the point of attachment with the benzothiophene core; wherein said $C_{6-10}$aryl or heteroaryl of $R_5$ is substituted with 1 to 3 groups selected from —$X_3$—$R_{5a}$ and $R_{5a}$; wherein $X_3$ is methylene; $R_{5a}$ is selected from hydroxy, amino, $C_{1-4}$alkyl, halo, nitro, cyano, halo-substituted-$C_{1-4}$alkyl, cyano-substituted-$C_{1-4}$alkyl, hydroxy-substituted-$C_{1-4}$alkyl, halo-substituted-$C_{1-4}$alkoxy, $C_{1-4}$alkoxy, —$SF_5$, —$NR_{11a}R_{11b}$, —$C(O)R_{11a}$, $C_{3-8}$cycloalkyl and a 4-7 member saturated, unsaturated or partially saturated ring containing one to 4 heteroatoms or groups selected from O, NH, C(O) and $S(O)_{0-2}$; wherein $R_{11a}$ and $R_{11b}$ are independently selected from hydrogen and $C_{1-4}$alkyl; or $R_{11a}$ and $R_{11b}$ together with the nitrogen to which they are both attached form a 4 to 7 member saturated ring containing one other heteroatom or group selected from O, NH, and $S(O)_{0-2}$; wherein said 4-7 member ring of $R_{5a}$ can be unsubstituted or substituted with $C_{1-4}$alkyl;

In a second aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In a third aspect, the present invention provides a method of treating a disease in an animal in which a combined selective estrogen receptor antagonist and estrogen receptor degrader can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which estrogen receptor activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DEFINITIONS

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —$S(O)_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(=Z-) or trans (=E-) form. The compounds may thus be present as mixtures of isomers or preferably as pure isomers, preferably as pure diastereomers or pure enantiomers.

Compounds of formula I have X defined as being selected from O and $NR_6$; wherein $R_6$ is $C_{1-4}$alkyl. It is known that other groups such as a bond or carbonyl at the X position is detrimental to the antagonist activity ($IC_{50}$ MCF7 μM) and degradation potential (ER percentage remaining) of the compounds. Compare the following:

| Structure | [structure 1] | [structure 2] | [structure 3] |
|---|---|---|---|
| $IC_{50}$ MCF7 μM | 0.748 | >10 | >10 |
| ER Percentage remaining | 41 | 76 | 60 |

Compounds of formula I have $R_3$ defined as being selected from —$CH_2CH_2R_{8b}$ and —$CR_{8a}$=$CR_{8a}R_{8b}$. It is known that, for example where each $R_{8a}$ and $R_{8b}$ is hydrogen, a shorter or longer bond order between the phenyl and —C(O)OH is detrimental to the antagonist activity ($IC_{50}$ MCF7 μM) and degradation potential (ER percentage remaining) of the compounds. Compare the following:

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom

| Structure | [structure 1] | [structure 2] | [structure 3] |
|---|---|---|---|
| SERD $IC_{50}$ MCF7 μM | 0.748 | 10 | 10 |
| ER Percentage remaining | 41 | 57 | 55 |

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^{3}H$ or $^{14}C$ is incorporated, are useful in drug and/or substrate tissue distribution studies. In particular examples, ³H and ¹⁴C isotopes may be used for their ease of preparation and detectability. In other examples, substitution with isotopes such as ²H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. For example, compounds of the invention can exist in a deuterated form as shown below:

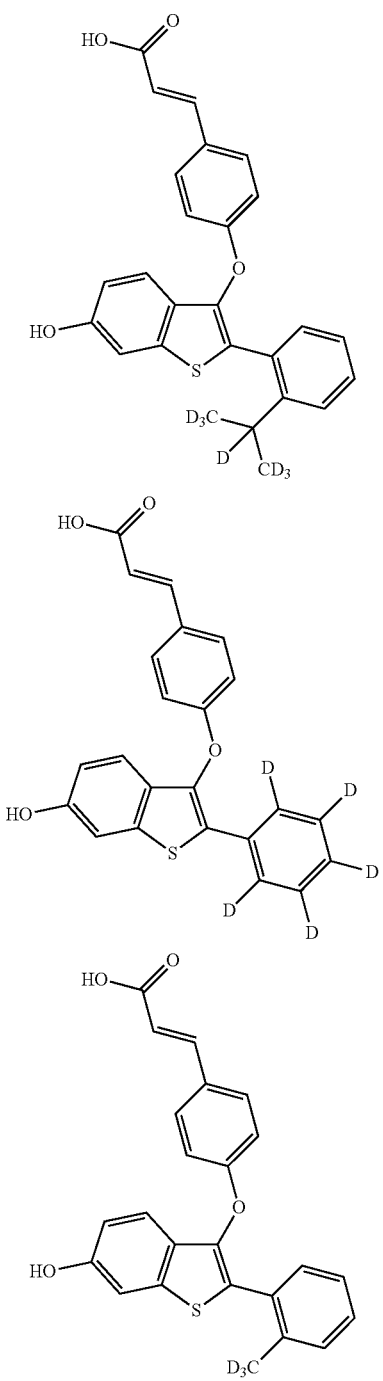

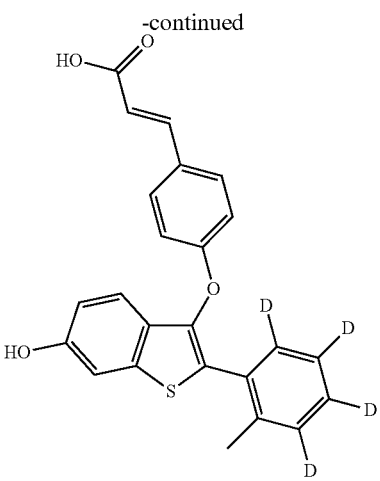

DESCRIPTION OF PREFERRED EMBODIMENTS

The present invention relates to selective estrogen receptor degraders. In one embodiment, with respect to compounds of Formula I, are compounds of Formula Ia:

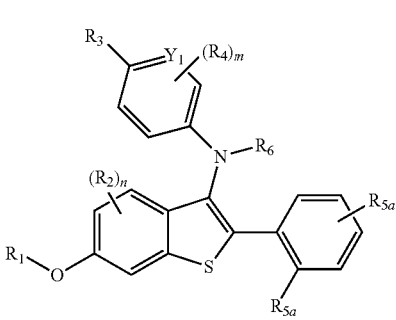

in which: n is selected from 0, 1 and 2; m is selected from 0, 1 and 2; $Y_1$ is selected from N and $CR_7$; wherein $R_7$ is selected from hydrogen and $C_{1-4}$alkyl; $R_1$ is hydrogen; $R_2$ is selected from hydrogen and halo; $R_3$ is selected from —$CH_2CH_2R_{8b}$ and —$CR_{8a}$=$CR_{8a}R_{8b}$; wherein each $R_{8a}$ is independently selected from hydrogen and $C_{1-4}$alkyl; and $R_{8b}$ is selected from —C(O)$OR_{9a}$, —C(O)$NR_{9a}R_{9b}$, —C(O)$NHOR_{9a}$, —C(O)$X_2R_{9a}$, tetrazolyl, 1,3,4-oxadiazolyl, 4H-1,2,4-triazolyl, 5-oxo-4,5-dihydro-1,3,4-oxadiazol-2-yl, 2-oxo-pyrimidinyl and imidazolyl; wherein $X_2$ is $C_{1-4}$alkylene; $R_{9a}$ and $R_{9b}$ are independently selected from hydrogen, $C_{1-4}$alkyl, hydroxy-substituted-$C_{1-4}$alkyl, halo-substituted-$C_{1-4}$alkyl and —$X_4R_{10}$; wherein $X_4$ is selected from a bond and $C_{1-3}$alkylene; and $R_{10}$ is a 4-6 member saturated ring containing 1 to 3 atoms independently selected from O, N and S; wherein said tetrazolyl, 1,3,4-oxadiazolyl, 4H-1,2,4-triazolyl, 2-oxo-pyrimidinyl or imidazolyl of $R_{8b}$ is unsubstituted or substituted with 1 to 3 groups independently selected from $C_{1-4}$alkyl and $C_{3-8}$cycloalkyl; $R_4$ is selected from hydrogen and $C_{1-4}$alkyl; and each $R_{5a}$ is independently selected from hydroxy, $C_{1-4}$alkyl, halo, nitro, cyano, halo-substituted-$C_{1-4}$alkyl, halo-substituted-$C_{1-4}$alkoxy, hydroxy-substituted-$C_{1-4}$alkyl, $C_{1-4}$alkoxy, $C_{3-8}$cycloalkyl, —$NR_{11a}R_{11b}$, —C(O)$R_{11a}$ and a 4-7 member saturated, unsaturated or partially saturated ring containing one to 4 heteroatoms or groups selected from O, NH, C(O) and S(O)$_{0-2}$; wherein X$_2$ is selected from a bond and methylene; wherein R$_{11a}$ and R$_{11b}$ are independently selected from hydrogen and C$_{1-4}$alkyl; wherein said 4-7 member ring of R$_{5a}$ can be unsubstituted or substituted with C$_{1-4}$alkyl; X$_3$ is selected from a bond and methylene; or a pharmaceutically acceptable salt thereof.

In a further embodiment, R$_3$ is selected from —CH$_2$CH$_2$R$_{8b}$ and —CR$_{8a}$=CR$_{8a}$R$_{8b}$; wherein each R$_{8a}$ is independently selected from hydrogen and C$_{1-4}$alkyl; and R$_{8b}$ is selected from —C(O)OR$_{9a}$, —C(O)NR$_{9a}$R$_{9b}$, —C(O)NHOR$_{9a}$ and —C(O)X$_2$R$_{9a}$; wherein X$_2$ is C$_{1-4}$alkylene; R$_{9a}$ and R$_{9b}$ are independently selected from hydrogen, C$_{1-4}$alkyl, hydroxy-substituted-C$_{1-4}$alkyl, halo-substituted-C$_{1-4}$alkyl and morpholino-ethyl.

In a further embodiment, R$_3$ is selected from —CH$_2$CH$_2$R$_{8b}$ and —CR$_{8a}$=CR$_{8a}$R$_{8b}$; wherein each R$_{8a}$ is independently selected from hydrogen and C$_{1-4}$alkyl; and R$_{8b}$ is independently selected from —C(O)OH, —C(O)CH$_3$, —C(O)OCH$_3$ and morpholino-ethyl.

In a further embodiment, R$_{5a}$ is selected from hydroxy, fluoro, trifluoro-methyl and 1,1-difluoro-ethyl.

In a further embodiment are compounds, or a pharmaceutically acceptable salt thereof, selected from:

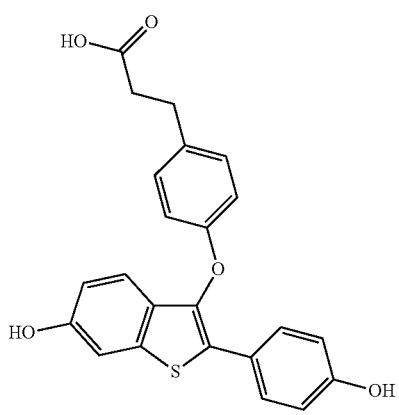

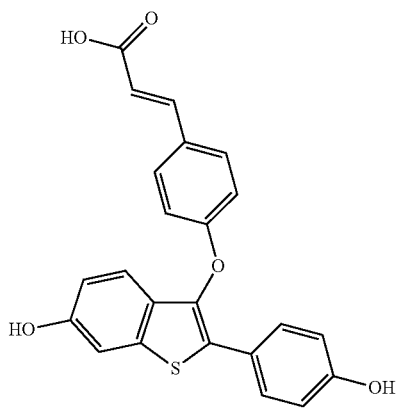

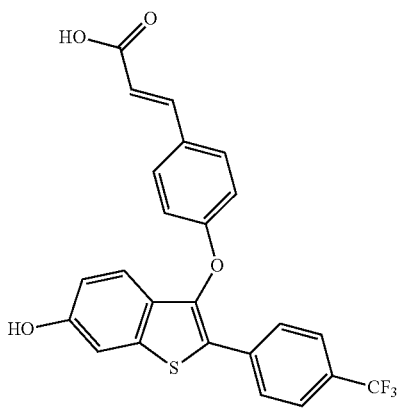 [SMILES: O=C(O)/C=C/c1ccc(Oc2c(-c3ccc(C(F)(F)F)cc3)sc3cc(O)ccc23)cc1]

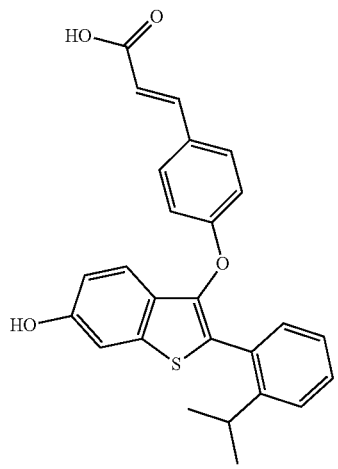 [SMILES: CC(C)c1ccccc1-c1sc2cc(O)ccc2c1Oc1ccc(/C=C/C(=O)O)cc1]

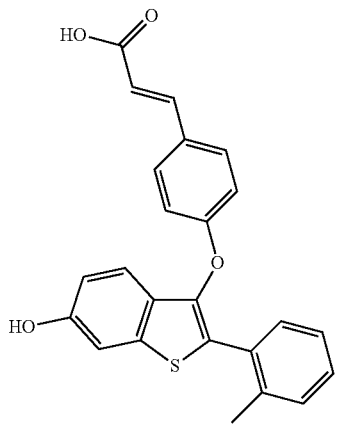

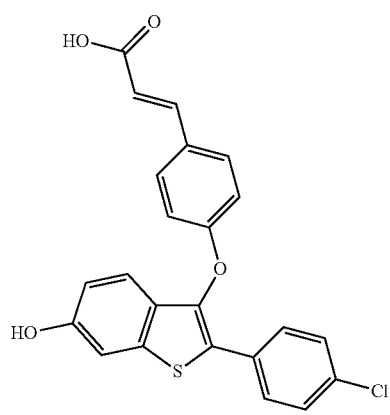 [SMILES: O=C(O)/C=C/c1ccc(Oc2c(-c3ccc(Cl)cc3)sc3cc(O)ccc23)cc1]
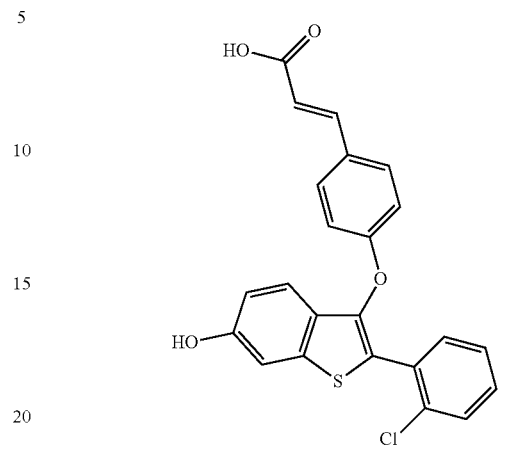
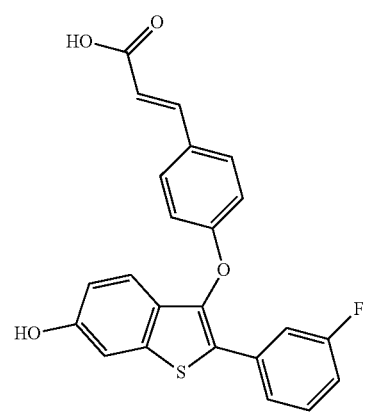 [SMILES: O=C(O)/C=C/c1ccc(Oc2c(-c3cccc(F)c3)sc3cc(O)ccc23)cc1]
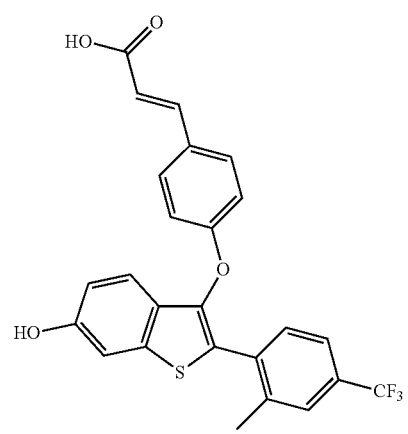 [SMILES: Cc1cc(C(F)(F)F)ccc1-c1sc2cc(O)ccc2c1Oc1ccc(/C=C/C(=O)O)cc1]
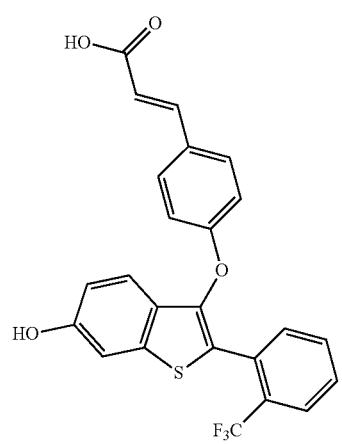
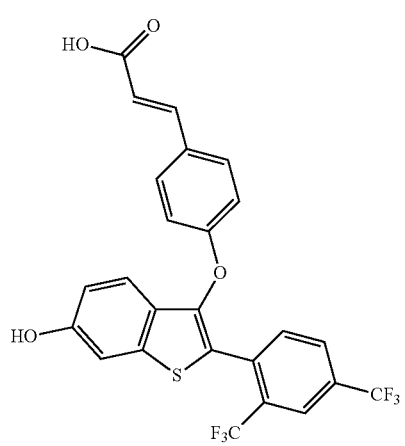 [SMILES: O=C(O)/C=C/c1ccc(Oc2c(-c3ccc(C(F)(F)F)cc3C(F)(F)F)sc3cc(O)ccc23)cc1]

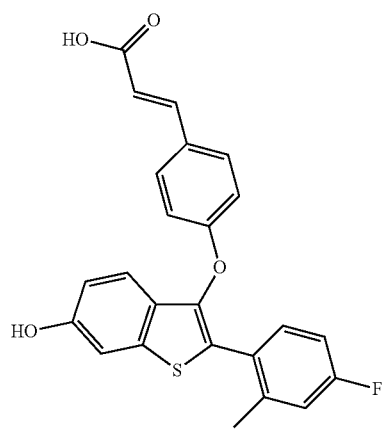
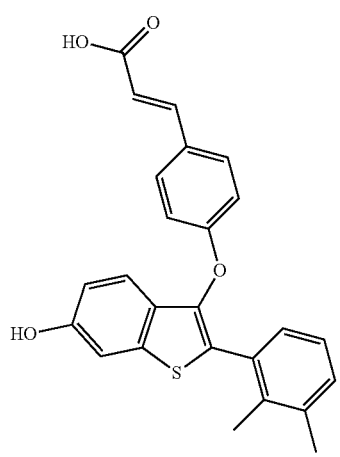 [SMILES: Cc1cccc(-c2sc3cc(O)ccc3c2Oc2ccc(/C=C/C(=O)O)cc2)c1C]
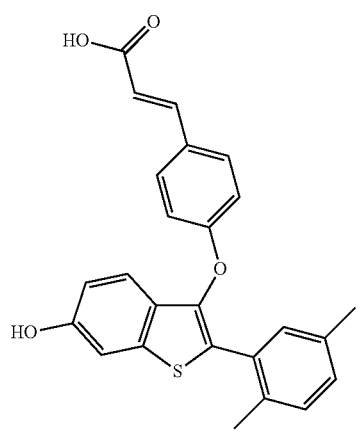 [SMILES: Cc1ccc(C)c(-c2sc3cc(O)ccc3c2Oc2ccc(/C=C/C(=O)O)cc2)c1]
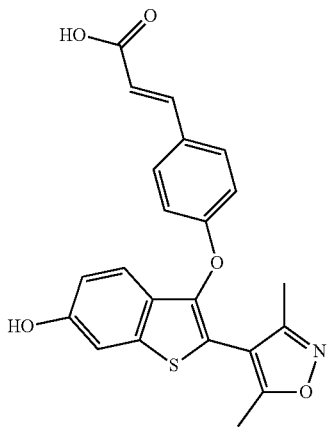 [SMILES: Cc1noc(C)c1-c1sc2cc(O)ccc2c1Oc1ccc(/C=C/C(=O)O)cc1]
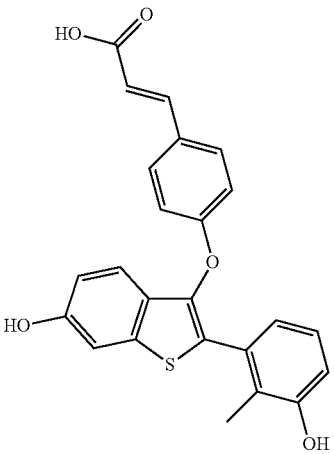 [SMILES: Cc1c(O)cccc1-c1sc2cc(O)ccc2c1Oc1ccc(/C=C/C(=O)O)cc1]
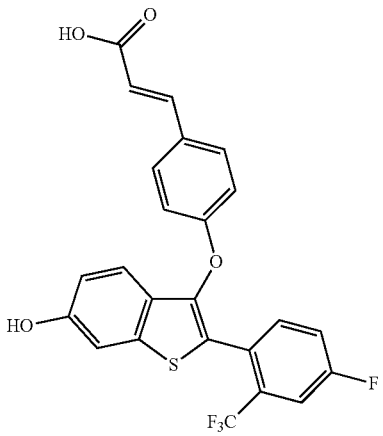 [SMILES: O=C(O)/C=C/c1ccc(Oc2c(-c3ccc(F)cc3C(F)(F)F)sc3cc(O)ccc23)cc1]

-continued
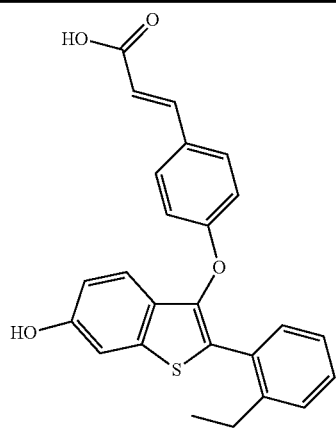
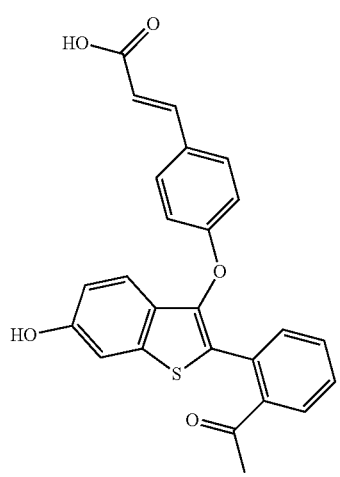 [SMILES: CC(=O)c1ccccc1-c1sc2cc(O)ccc2c1Oc1ccc(/C=C/C(=O)O)cc1]
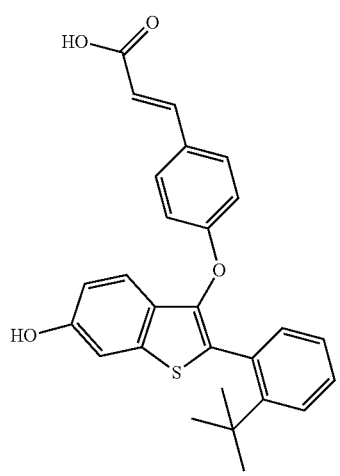 [SMILES: CC(C)(C)c1ccccc1-c1sc2cc(O)ccc2c1Oc1ccc(/C=C/C(=O)O)cc1]
-continued
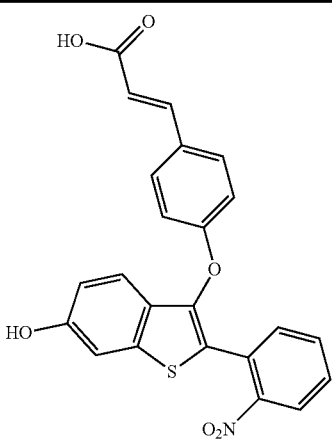
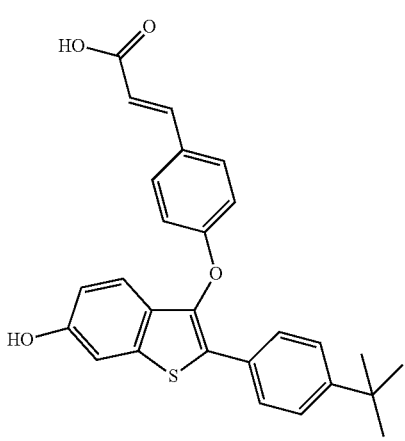 [SMILES: CC(C)(C)c1ccc(-c2sc3cc(O)ccc3c2Oc2ccc(/C=C/C(=O)O)cc2)cc1]
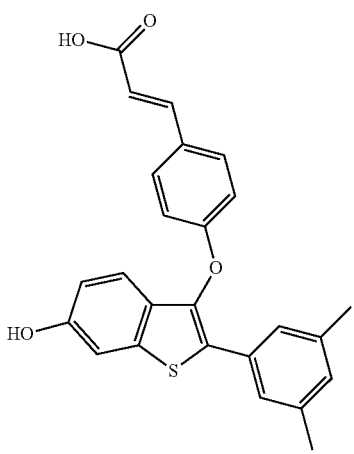 [SMILES: Cc1cc(C)cc(-c2sc3cc(O)ccc3c2Oc2ccc(/C=C/C(=O)O)cc2)c1]

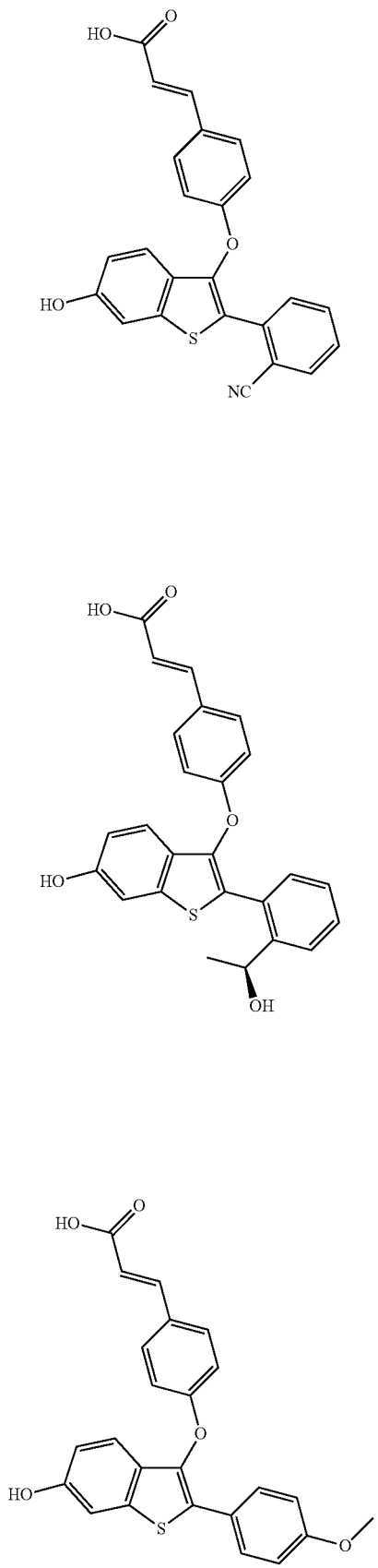
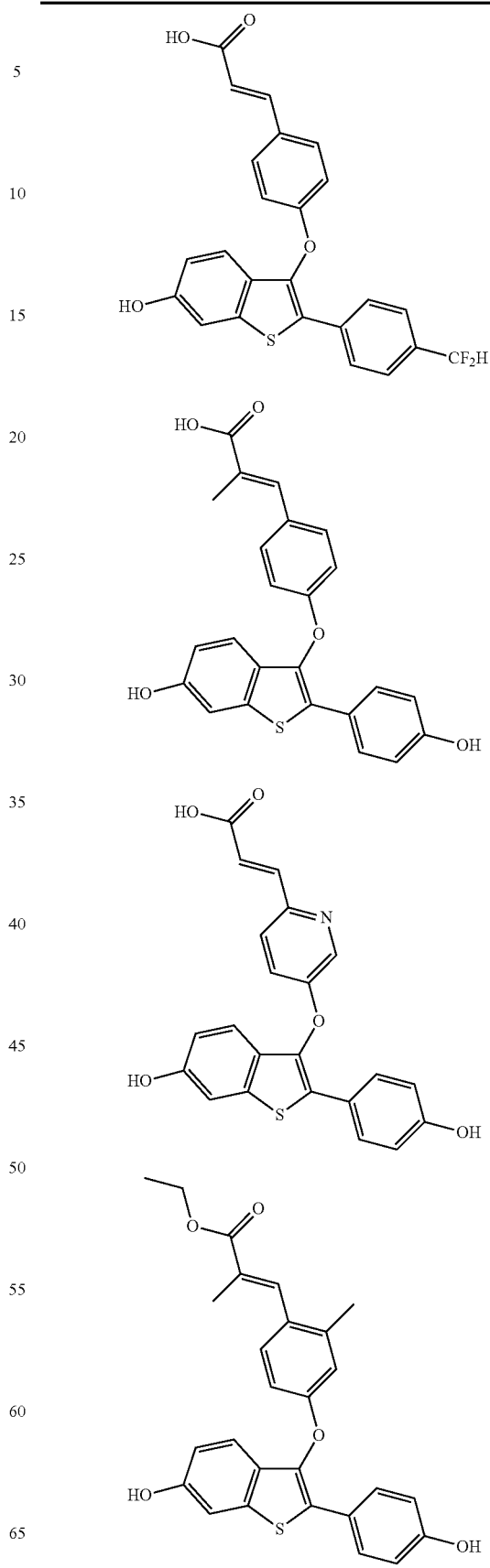

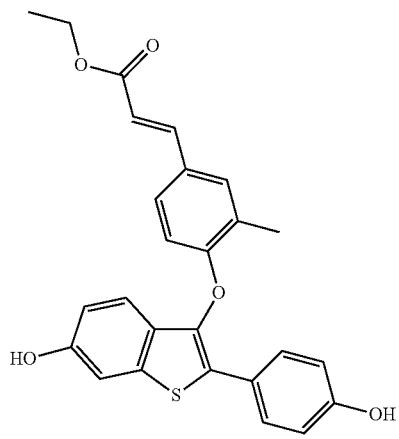 [SMILES: CCOC(=O)/C=C/c1ccc(Oc2c(-c3ccc(O)cc3)sc3cc(O)ccc23)c(C)c1]
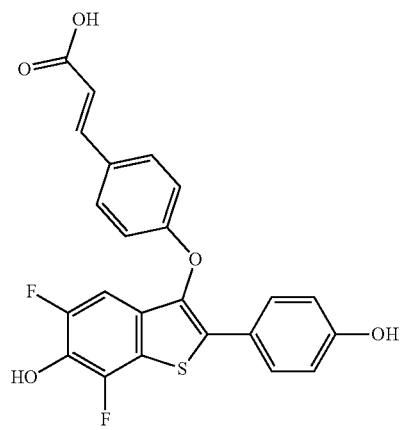
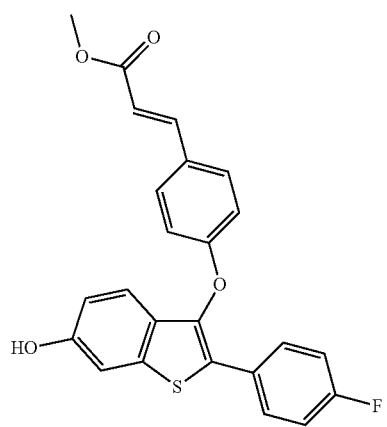 [SMILES: COC(=O)/C=C/c1ccc(Oc2c(-c3ccc(F)cc3)sc3cc(O)ccc23)cc1]
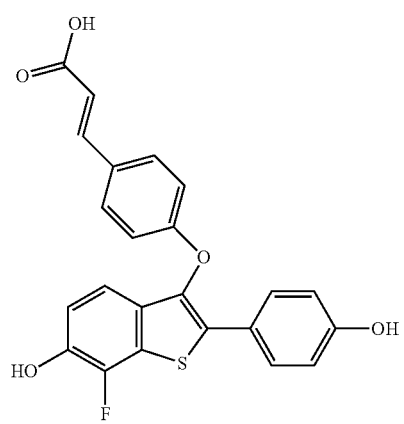
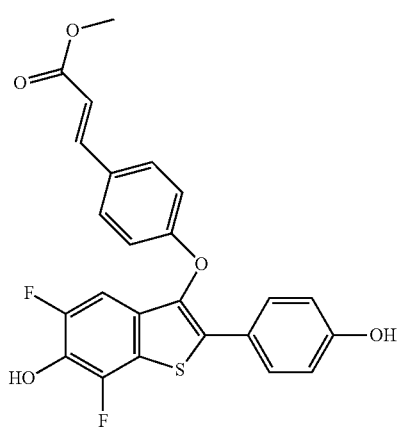 [SMILES: COC(=O)/C=C/c1ccc(Oc2c(-c3ccc(O)cc3)sc3c(F)c(O)c(F)cc23)cc1]
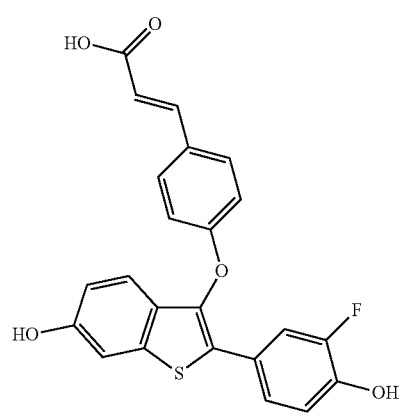

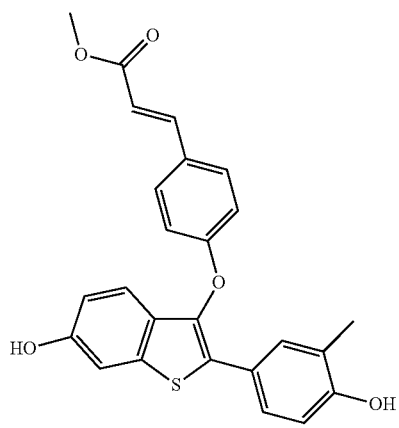
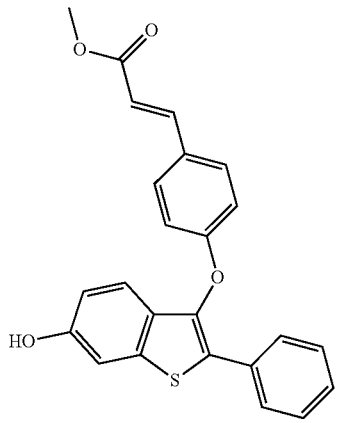
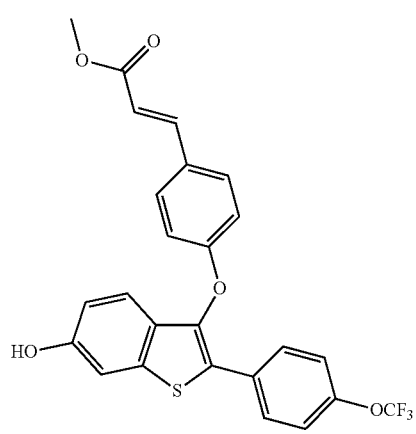 [SMILES: COC(=O)/C=C/c1ccc(Oc2c(-c3ccc(OC(F)(F)F)cc3)sc3cc(O)ccc23)cc1]
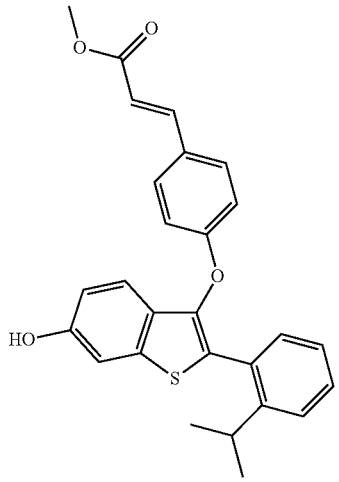
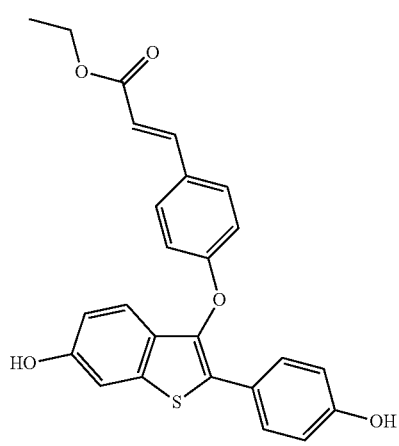 [SMILES: CCOC(=O)/C=C/c1ccc(Oc2c(-c3ccc(O)cc3)sc3cc(O)ccc23)cc1]
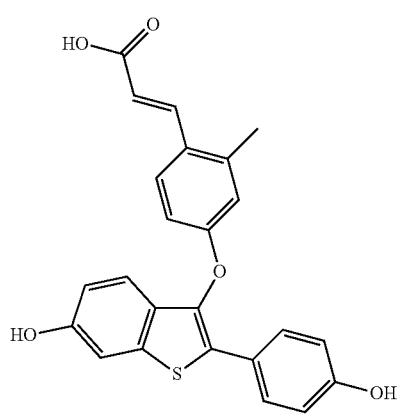

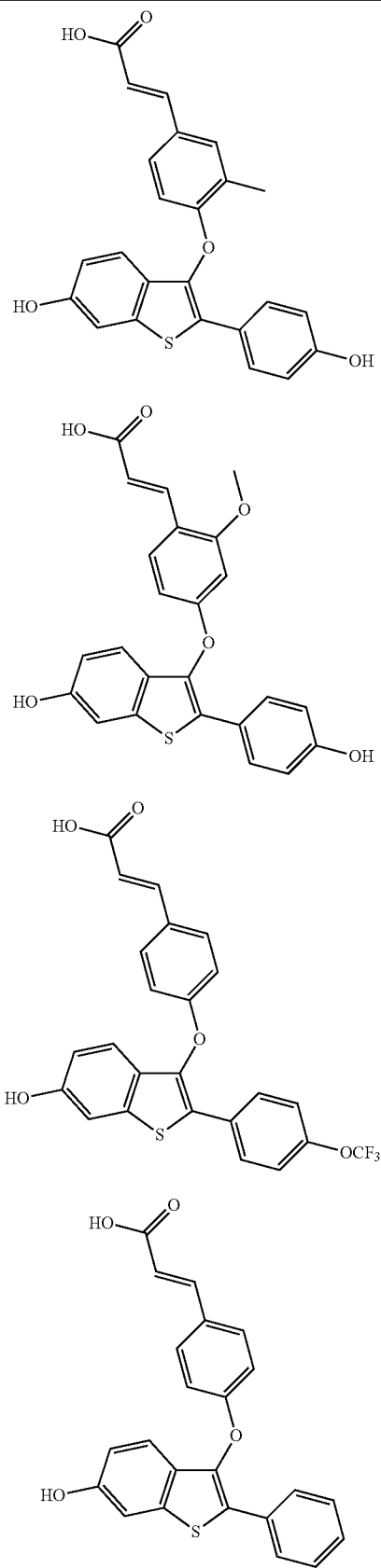
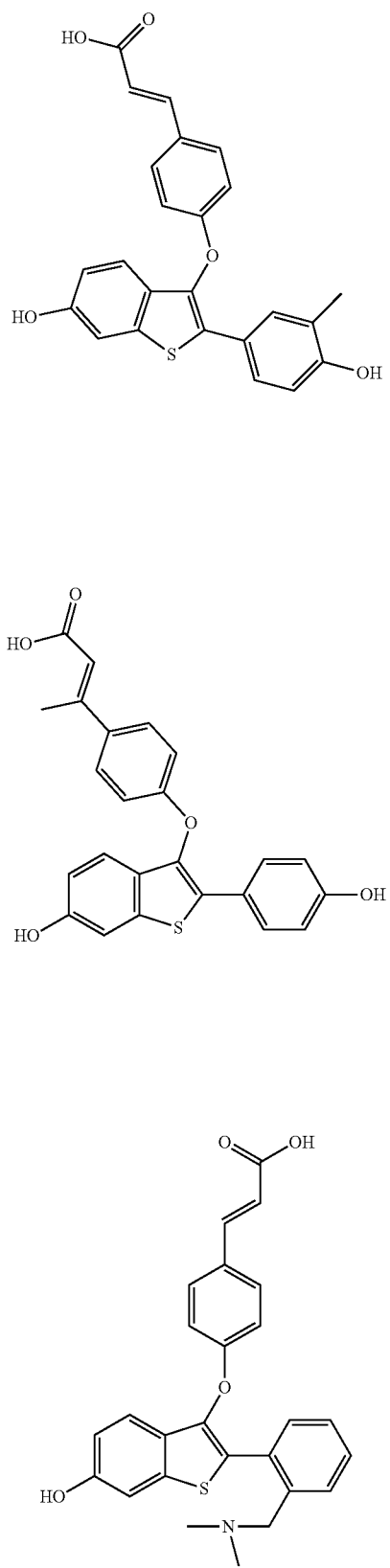

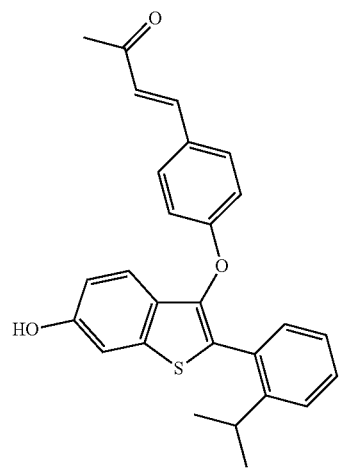 [SMILES: CC(=O)/C=C/c1ccc(Oc2c(-c3ccccc3C(C)C)sc3cc(O)ccc23)cc1]
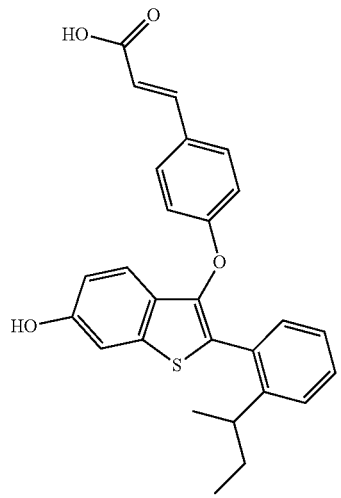
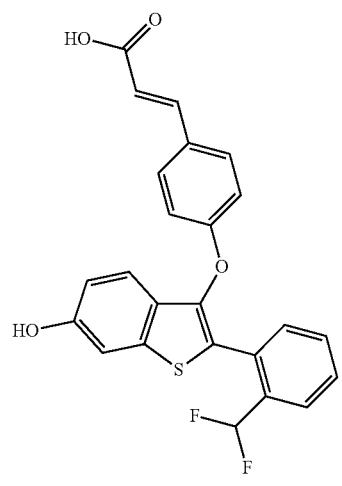 [SMILES: O=C(O)/C=C/c1ccc(Oc2c(-c3ccccc3C(F)F)sc3cc(O)ccc23)cc1]
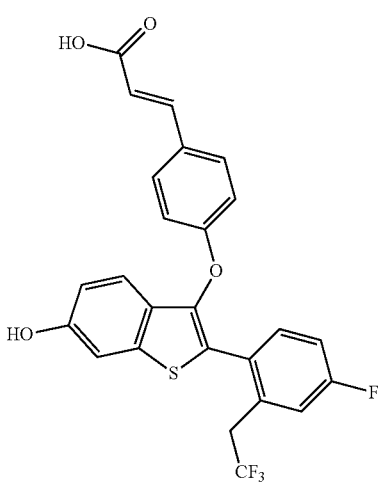 [SMILES: O=C(O)/C=C/c1ccc(Oc2c(-c3ccc(F)cc3CC(F)(F)F)sc3cc(O)ccc23)cc1]

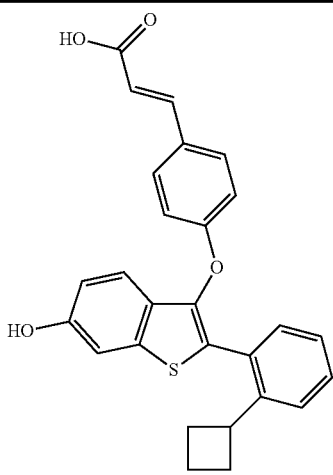
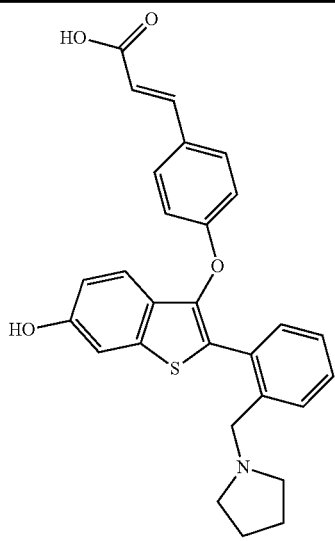
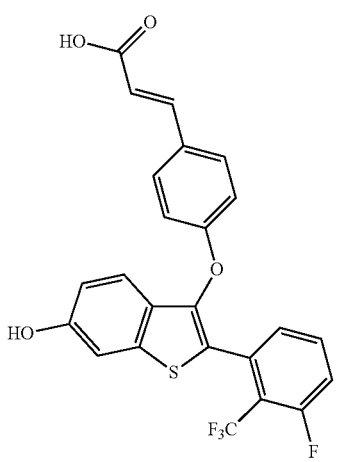 [SMILES: O=C(O)/C=C/c1ccc(Oc2c(-c3cccc(F)c3C(F)(F)F)sc3cc(O)ccc23)cc1]
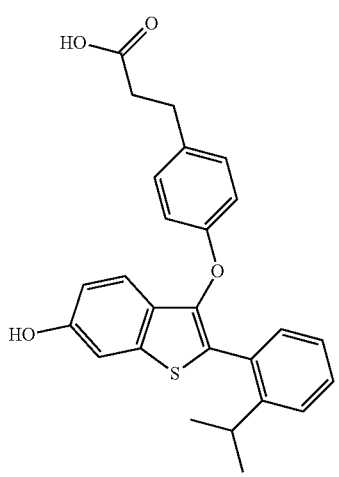
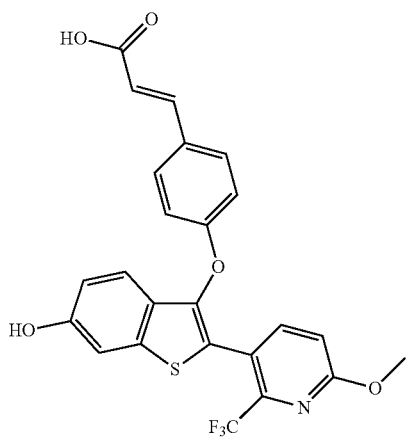 [SMILES: COc1ccc(-c2sc3cc(O)ccc3c2Oc2ccc(/C=C/C(=O)O)cc2)c(C(F)(F)F)n1]
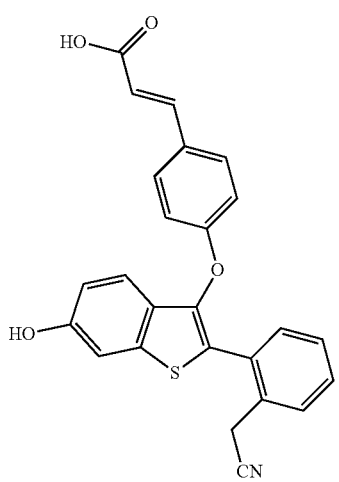 [SMILES: N#CCc1ccccc1-c1sc2cc(O)ccc2c1Oc1ccc(/C=C/C(=O)O)cc1]

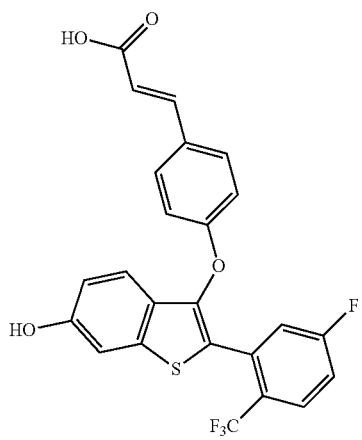 [SMILES: O=C(O)/C=C/c1ccc(Oc2c(-c3cc(F)ccc3C(F)(F)F)sc3cc(O)ccc23)cc1]
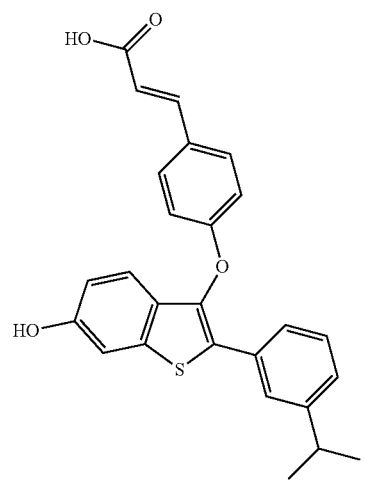
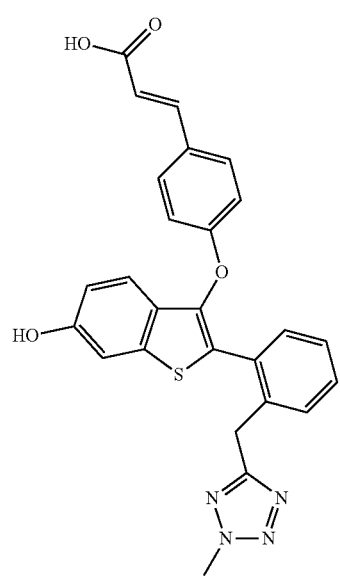 [SMILES: Cn1nnc(Cc2ccccc2-c2sc3cc(O)ccc3c2Oc2ccc(/C=C/C(=O)O)cc2)n1]
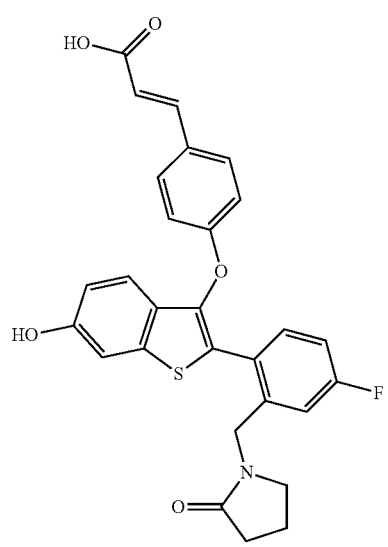
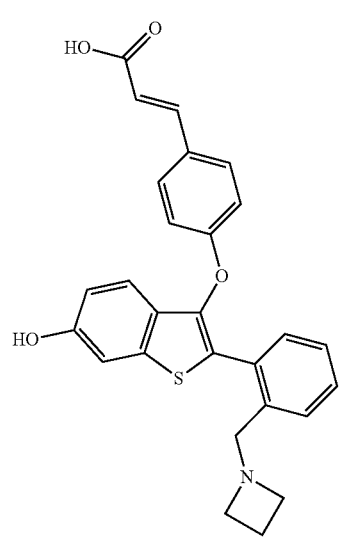 [SMILES: O=C(O)/C=C/c1ccc(Oc2c(-c3ccccc3CN3CCC3)sc3cc(O)ccc23)cc1]
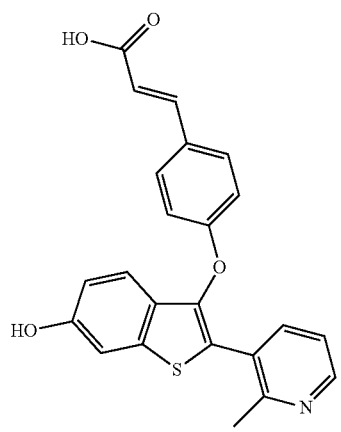 [SMILES: Cc1ncccc1-c1sc2cc(O)ccc2c1Oc1ccc(/C=C/C(=O)O)cc1]

| 31 -continued | 32 -continued |
|---|---|
| 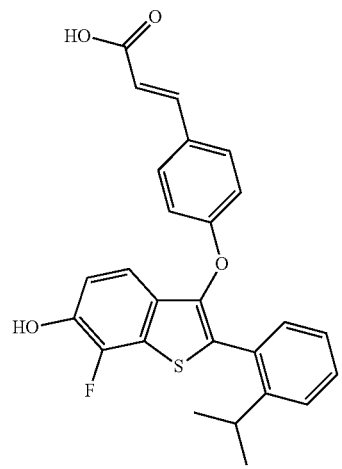 [SMILES: CC(C)c1ccccc1-c1sc2c(F)c(O)ccc2c1Oc1ccc(/C=C/C(=O)O)cc1] | 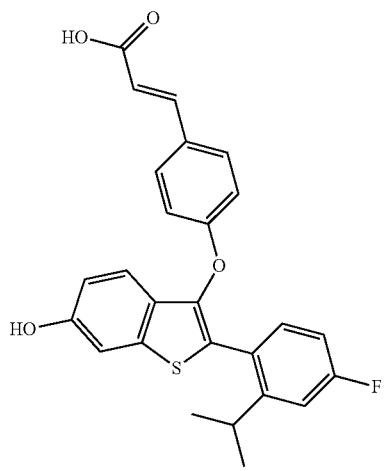 |
| 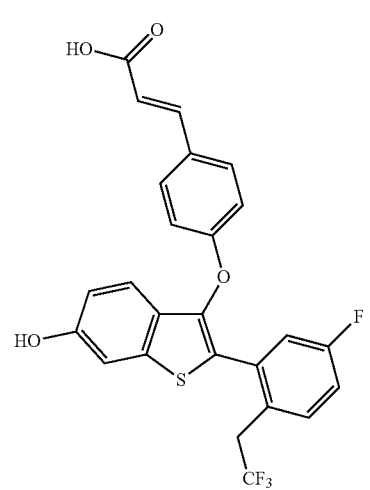 [SMILES: O=C(O)/C=C/c1ccc(Oc2c(-c3cc(F)ccc3CC(F)(F)F)sc3cc(O)ccc23)cc1] | 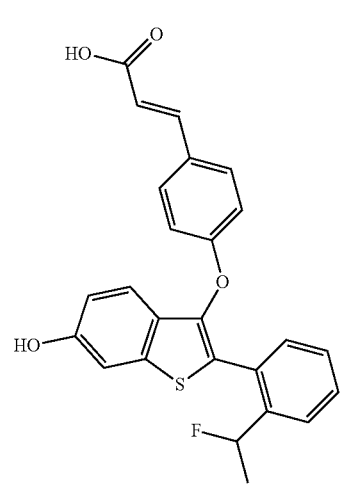 |
| 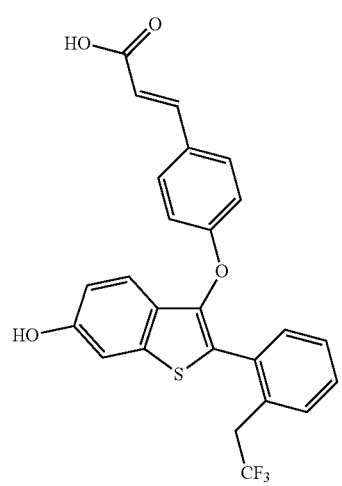 [SMILES: O=C(O)/C=C/c1ccc(Oc2c(-c3ccccc3CC(F)(F)F)sc3cc(O)ccc23)cc1] | 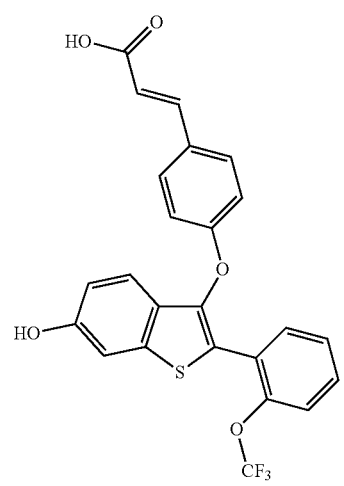 |

| 33 -continued | 34 -continued |
|---|---|
| 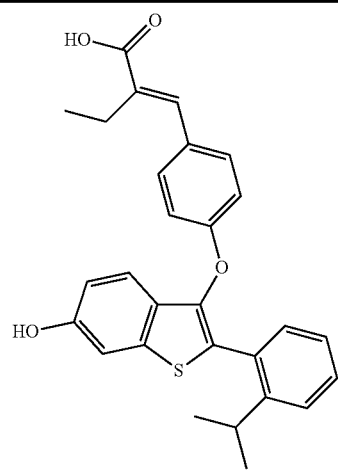 | 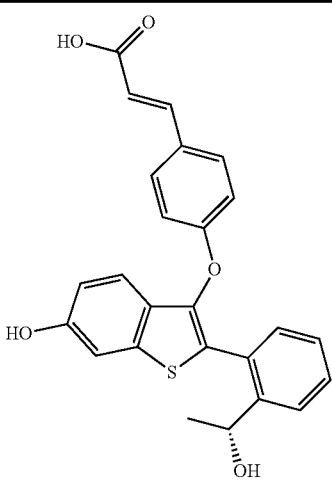 |
| 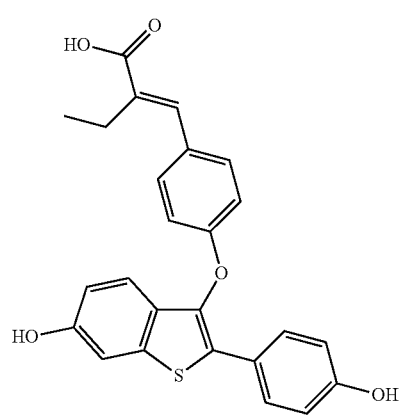 [SMILES: CC/C(=C\c1ccc(Oc2c(-c3ccc(O)cc3)sc3cc(O)ccc23)cc1)C(=O)O] | 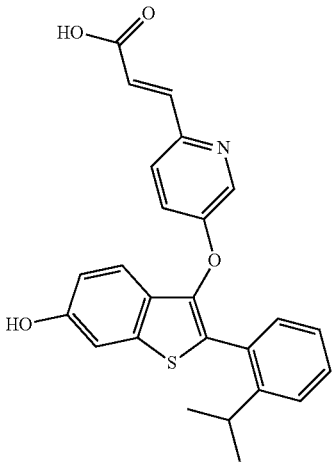 |
| 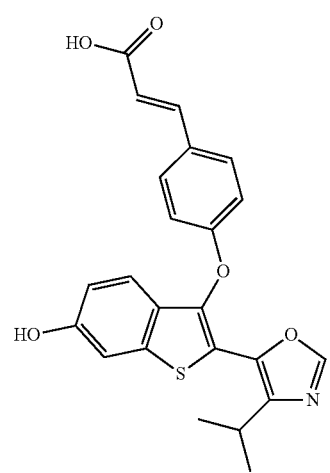 [SMILES: CC(C)c1ncoc1-c1sc2cc(O)ccc2c1Oc1ccc(/C=C/C(=O)O)cc1] | 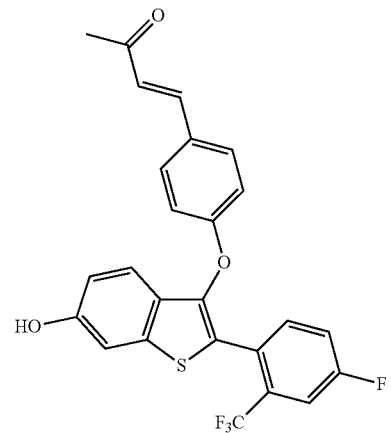 [SMILES: CC(=O)/C=C/c1ccc(Oc2c(-c3ccc(F)cc3C(F)(F)F)sc3cc(O)ccc23)cc1] |

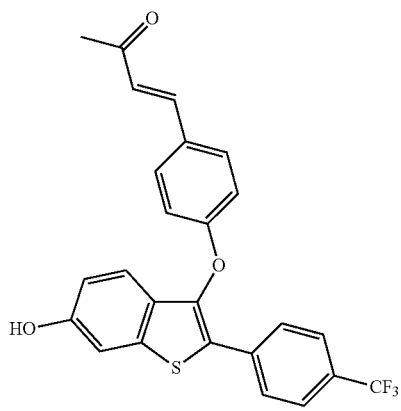 [SMILES: CC(=O)/C=C/c1ccc(Oc2c(-c3ccc(C(F)(F)F)cc3)sc3cc(O)ccc23)cc1]
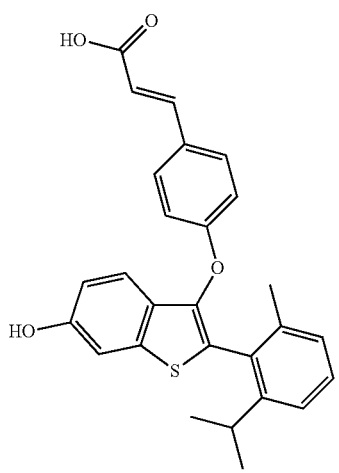
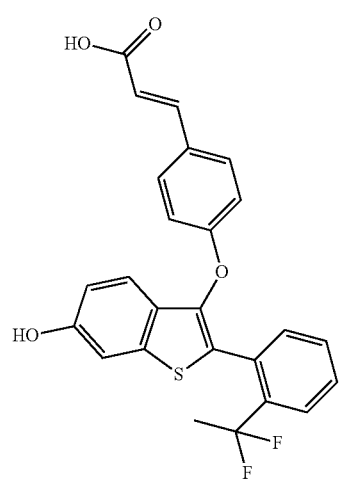 [SMILES: CC(F)(F)c1ccccc1-c1sc2cc(O)ccc2c1Oc1ccc(/C=C/C(=O)O)cc1]
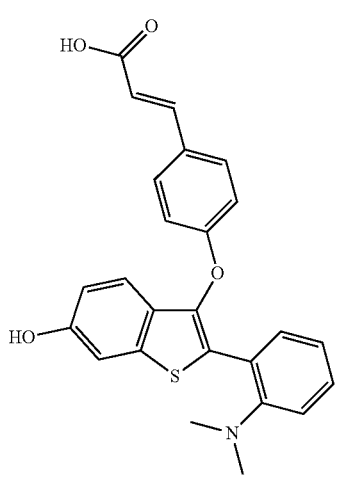
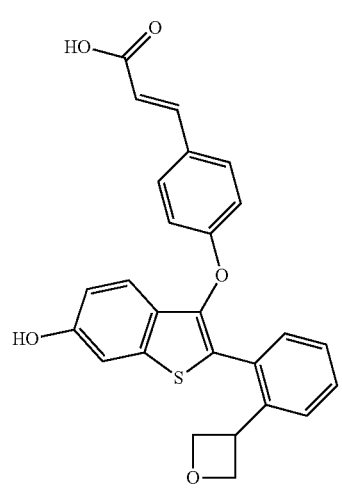 [SMILES: O=C(O)/C=C/c1ccc(Oc2c(-c3ccccc3C3COC3)sc3cc(O)ccc23)cc1]
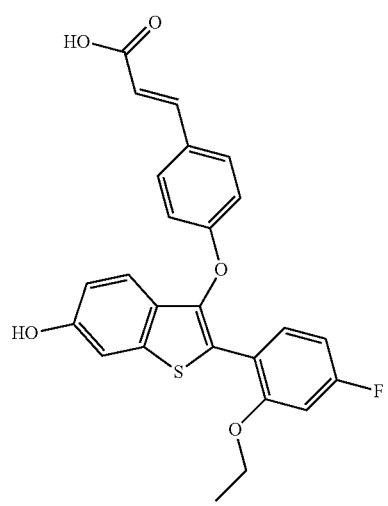 [SMILES: CCOc1cc(F)ccc1-c1sc2cc(O)ccc2c1Oc1ccc(/C=C/C(=O)O)cc1]

| 37 -continued | 38 -continued |
|---|---|
| 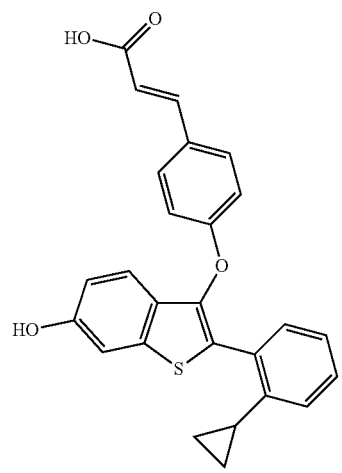 [SMILES: O=C(O)/C=C/c1ccc(Oc2c(-c3ccccc3C3CC3)sc3cc(O)ccc23)cc1] | 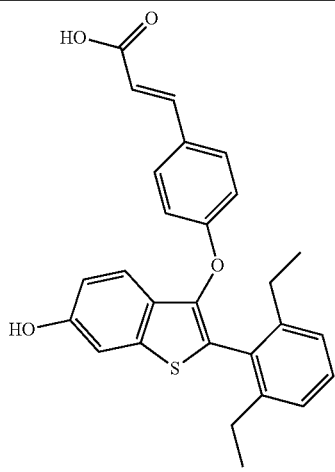 |
| 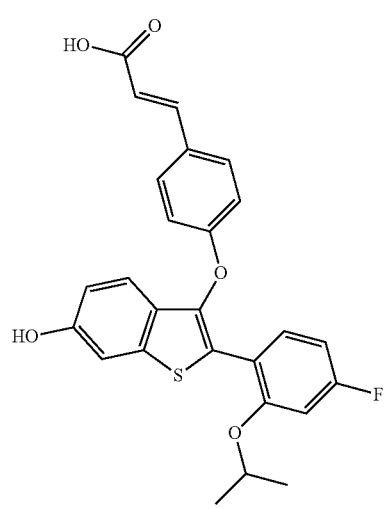 | 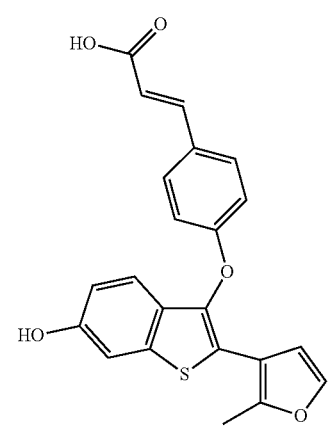 |
| 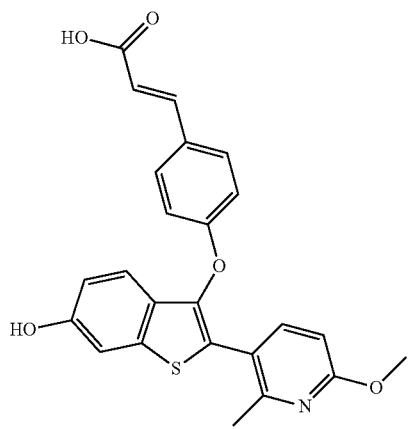 [SMILES: COc1ccc(-c2sc3cc(O)ccc3c2Oc2ccc(/C=C/C(=O)O)cc2)c(C)n1] | 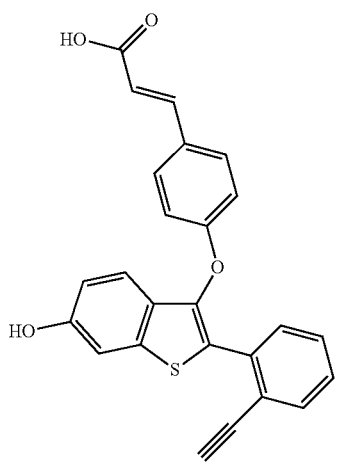 [SMILES: C#Cc1ccccc1-c1sc2cc(O)ccc2c1Oc1ccc(/C=C/C(=O)O)cc1] |

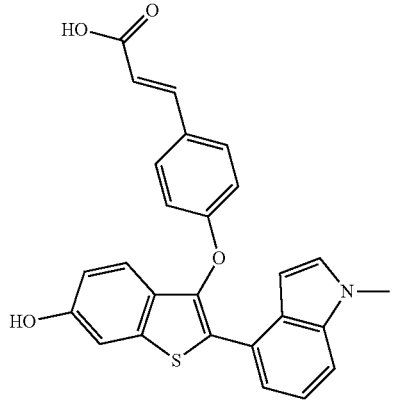 [SMILES: Cn1ccc2c(-c3sc4cc(O)ccc4c3Oc3ccc(/C=C/C(=O)O)cc3)cccc21]
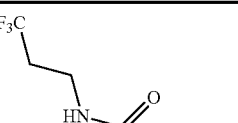
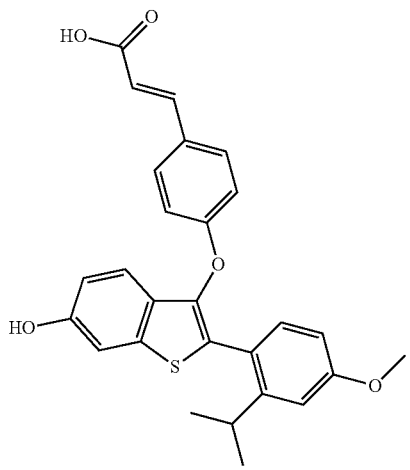 [SMILES: COc1ccc(-c2sc3cc(O)ccc3c2Oc2ccc(/C=C/C(=O)O)cc2)c(C(C)C)c1]
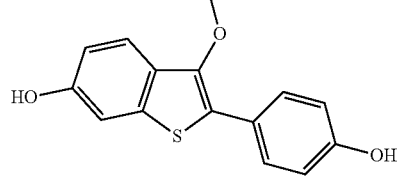
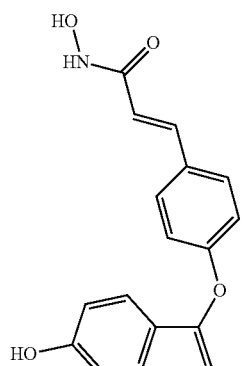
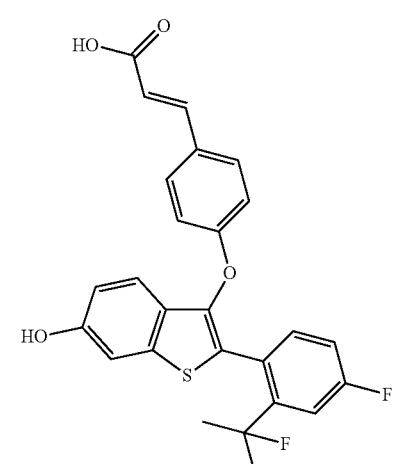
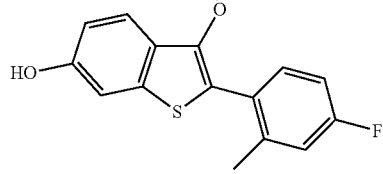
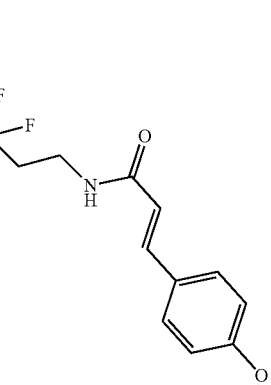
In a further embodiment is a compound, or the pharmaceutically acceptable salt thereof, selected from:

| 41 | 42 |
|---|---|
| -continued | -continued |
| 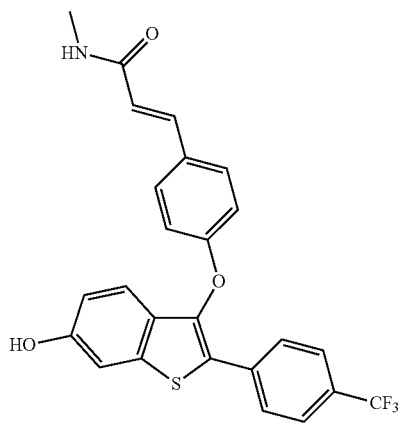 [SMILES: CNC(=O)/C=C/c1ccc(Oc2c(-c3ccc(C(F)(F)F)cc3)sc3cc(O)ccc23)cc1] | 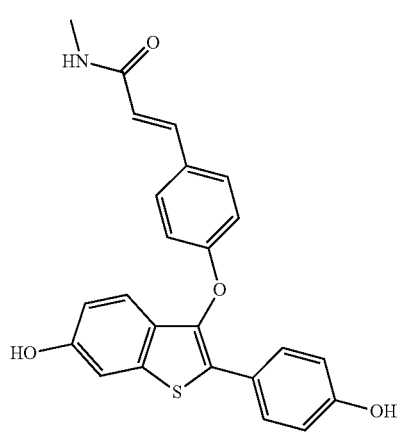 |
| 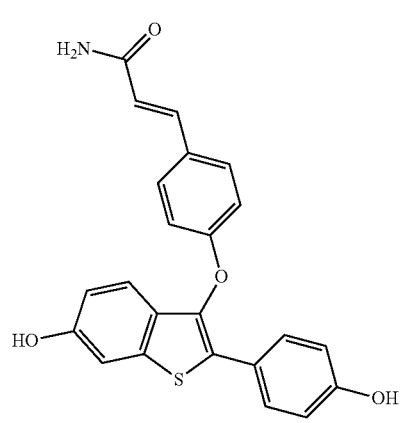 [SMILES: NC(=O)/C=C/c1ccc(Oc2c(-c3ccc(O)cc3)sc3cc(O)ccc23)cc1] | 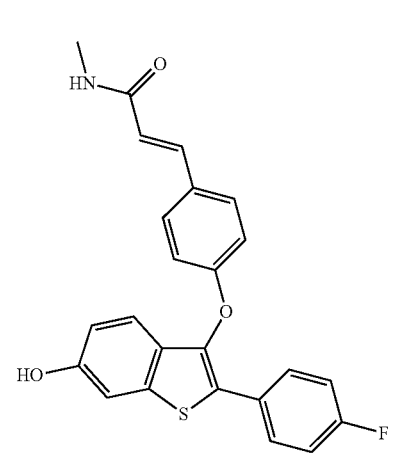 |
| 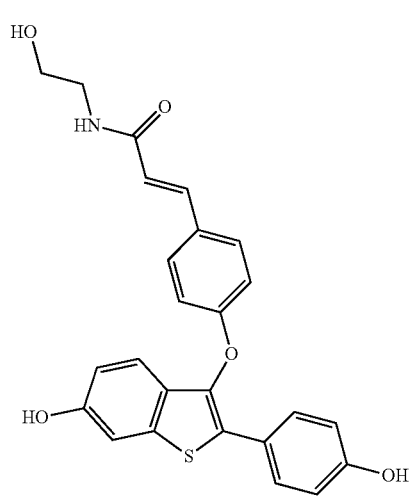 [SMILES: O=C(/C=C/c1ccc(Oc2c(-c3ccc(O)cc3)sc3cc(O)ccc23)cc1)NCCO] | 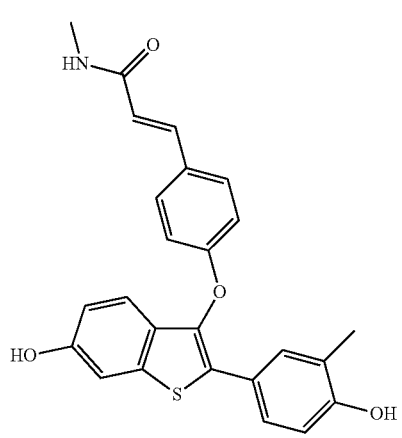 |

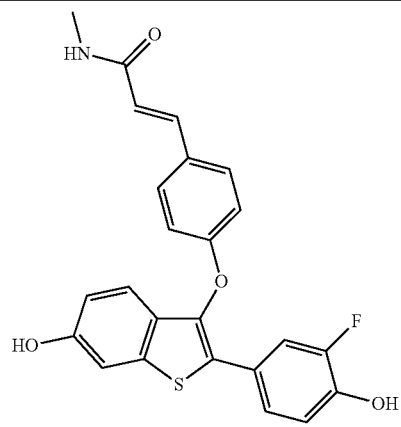
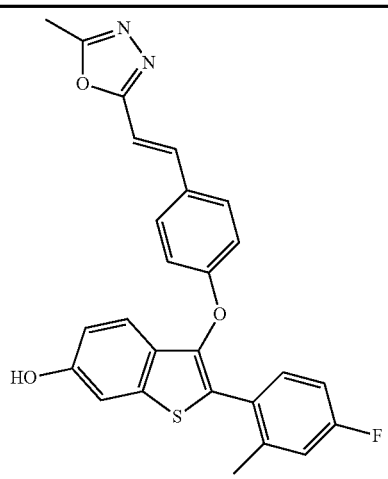
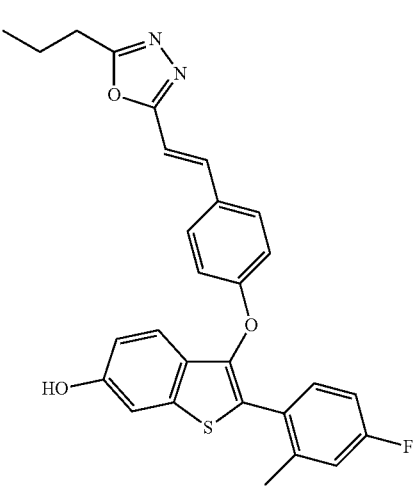 [SMILES: CCCc1nnc(/C=C/c2ccc(Oc3c(-c4ccc(F)cc4C)sc4cc(O)ccc34)cc2)o1]
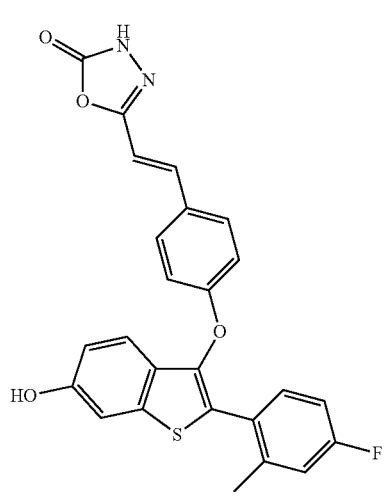 [SMILES: Cc1cc(F)ccc1-c1sc2cc(O)ccc2c1Oc1ccc(/C=C/c2n[nH]c(=O)o2)cc1]

In another embodiment, $R_3$ is selected from —$CH_2CH_2R_{8b}$ and —$CR_{8a}$=$CR_{8a}R_{8b}$; wherein each $R_{8a}$ is independently selected from hydrogen and $C_{1-4}$alkyl; and $R_{8b}$ is selected from tetrazolyl, 1,3,4-oxadiazolyl, 4H-1,2,4-triazolyl, 5-oxo-4,5-dihydro-1,3,4-oxadiazol-2-yl, 2-oxo-pyrimidinyl and imidazolyl; wherein said tetrazolyl, 1,3,4-oxadiazolyl, 4H-1,2,4-triazolyl, 2-oxo-pyrimidinyl or imidazolyl of $R_{8b}$, is unsubstituted or substituted with 1 to 3 groups independently selected from $C_{1-4}$alkyl and $C_{3-8}$cycloalkyl; wherein said phenyl, pyrrolidinyl or indolizinyl of $R_3$ is unsubstituted or substituted with a group selected from —$C(O)OR_{13}$; wherein $R_{13}$ is selected from hydrogen and $C_{1-4}$alkyl;

In a further embodiment, is a compound, or the pharmaceutically acceptable salt thereof, selected from:

45
-continued
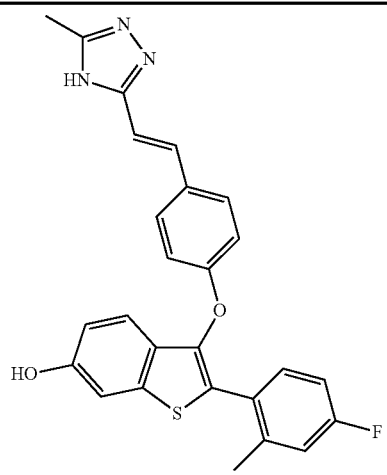
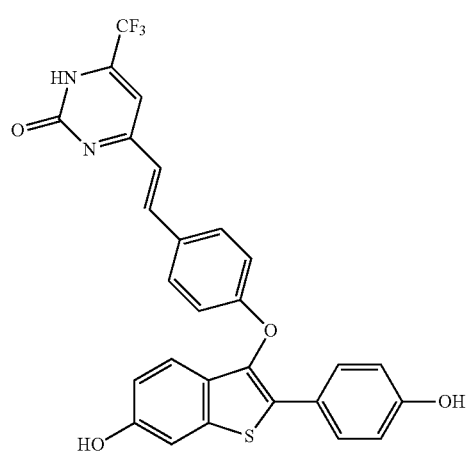 [SMILES: O=c1nc(/C=C/c2ccc(Oc3c(-c4ccc(O)cc4)sc4cc(O)ccc34)cc2)cc(C(F)(F)F)[nH]1]
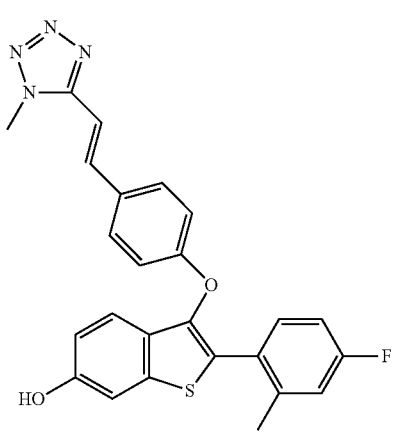 [SMILES: Cc1cc(F)ccc1-c1sc2cc(O)ccc2c1Oc1ccc(/C=C/c2nnnn2C)cc1]
46
-continued
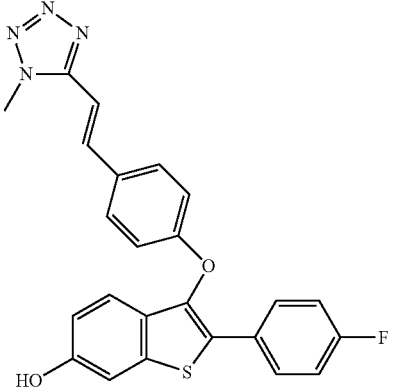 [SMILES: Cn1nnnc1/C=C/c1ccc(Oc2c(-c3ccc(F)cc3)sc3cc(O)ccc23)cc1]
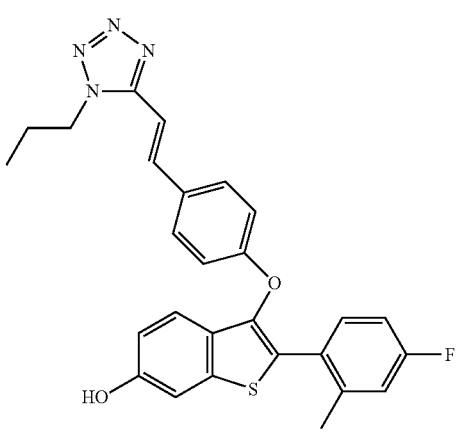 [SMILES: CCCn1nnnc1/C=C/c1ccc(Oc2c(-c3ccc(F)cc3C)sc3cc(O)ccc23)cc1]
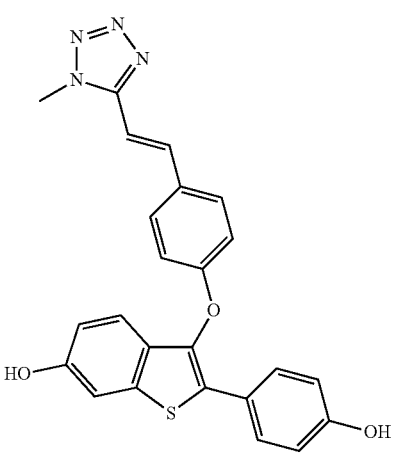 [SMILES: Cn1nnnc1/C=C/c1ccc(Oc2c(-c3ccc(O)cc3)sc3cc(O)ccc23)cc1]

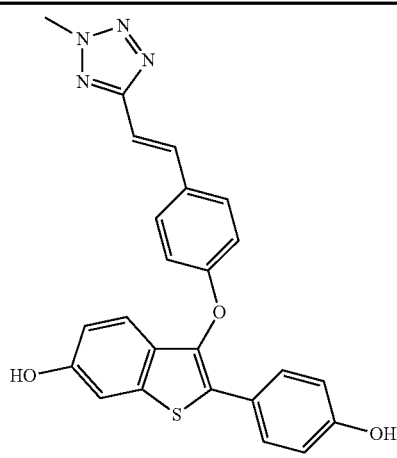
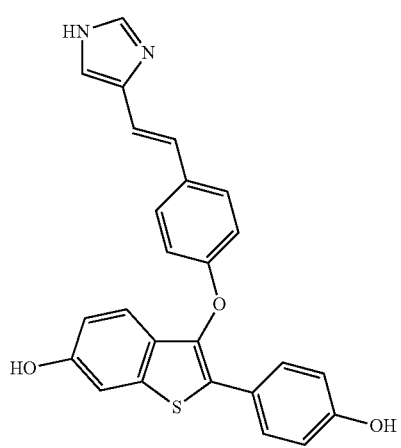 [SMILES: Oc1ccc(-c2sc3cc(O)ccc3c2Oc2ccc(/C=C/c3c[nH]cn3)cc2)cc1]
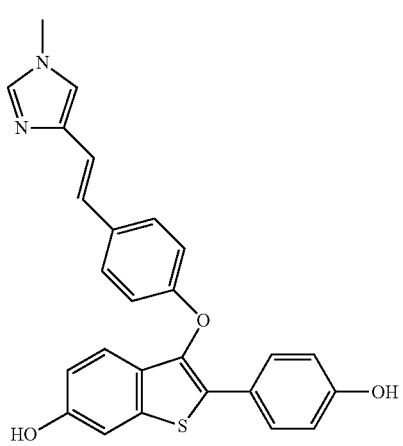 [SMILES: Cn1cnc(/C=C/c2ccc(Oc3c(-c4ccc(O)cc4)sc4cc(O)ccc34)cc2)c1]
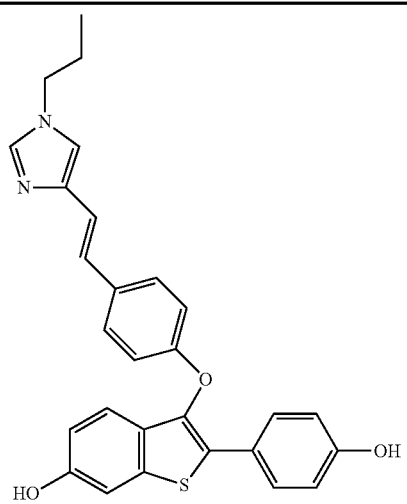
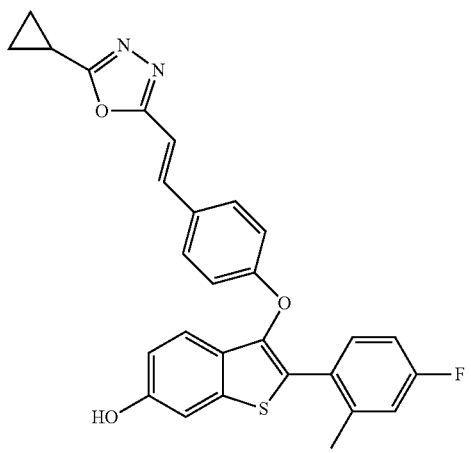 [SMILES: Cc1cc(F)ccc1-c1sc2cc(O)ccc2c1Oc1ccc(/C=C/c2nnc(C3CC3)o2)cc1]

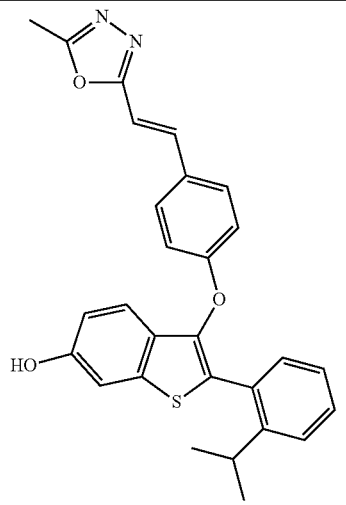
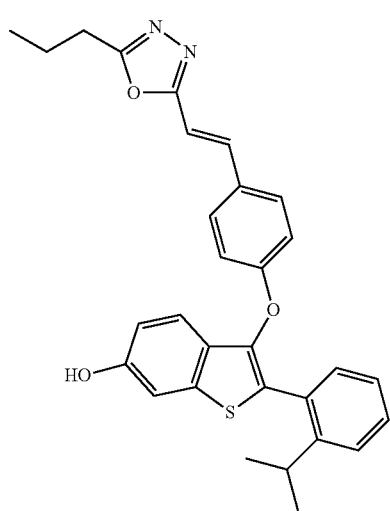 [SMILES: CCCc1nnc(/C=C/c2ccc(Oc3c(-c4ccccc4C(C)C)sc4cc(O)ccc34)cc2)o1]
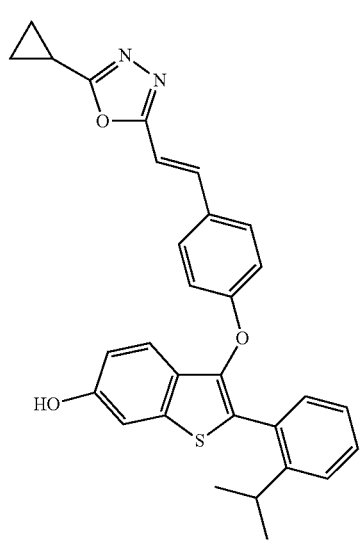 [SMILES: CC(C)c1ccccc1-c1sc2cc(O)ccc2c1Oc1ccc(/C=C/c2nnc(C3CC3)o2)cc1]
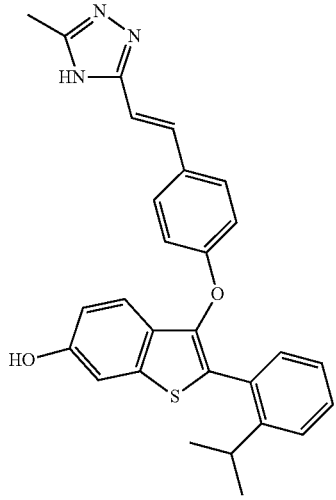
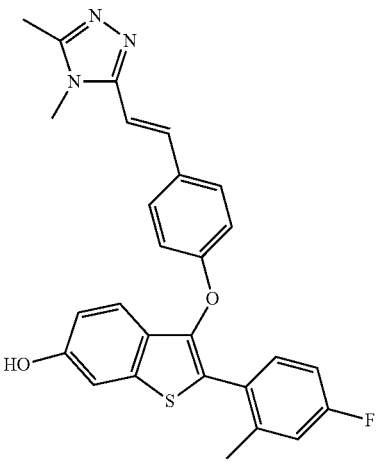 [SMILES: Cc1cc(F)ccc1-c1sc2cc(O)ccc2c1Oc1ccc(/C=C/c2nnc(C)n2C)cc1]
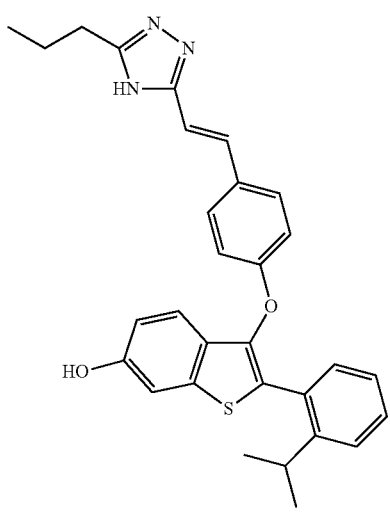 [SMILES: CCCc1nnc(/C=C/c2ccc(Oc3c(-c4ccccc4C(C)C)sc4cc(O)ccc34)cc2)[nH]1]

In another embodiment are compounds of formula Ib:

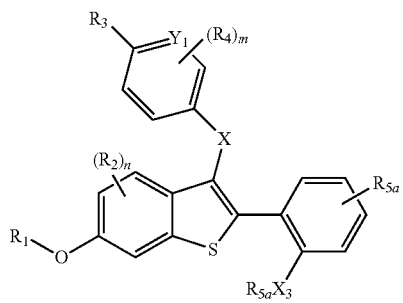

Ia in which: n is selected from 0, 1 and 2; m is selected from 0, 1 and 2; $Y_1$ is selected from N and $CR_7$; wherein $R_7$ is selected from hydrogen and $C_{1-4}$alkyl; $R_1$ is hydrogen; $R_2$ is selected from hydrogen and halo; $R_3$ is selected from —$CH_2CH_2R_{8b}$ and —$CR_{8a}$=$CR_{8a}R_{8b}$; wherein each $R_{8a}$ is independently selected from hydrogen and $C_{1-4}$alkyl; and $R_{8b}$ is selected from —$C(O)OR_{9a}$, —$C(O)NR_{9a}R_{9b}$, —$C(O)NHOR_{9a}$, —$C(O)X_2R_{9a}$, tetrazolyl, 1,3,4-oxadiazolyl, 4H-1,2,4-triazolyl, 5-oxo-4,5-dihydro-1,3,4-oxadiazol-2-yl, 2-oxo-pyrimidinyl and imidazolyl; wherein $X_2$ is $C_{1-4}$alkylene; $R_{9a}$ and $R_{9b}$ are independently selected from hydrogen, $C_{1-4}$alkyl, hydroxy-substituted-$C_{1-4}$alkyl and halo-substituted-$C_{1-4}$alkyl; wherein said tetrazolyl, 1,3,4-oxadiazolyl, 4H-1,2,4-triazolyl, 2-oxo-pyrimidinyl or imidazolyl of $R_{8b}$ is unsubstituted or substituted with a group selected from $C_{1-4}$alkyl and $C_{3-8}$cycloalkyl; $R_4$ is selected from hydrogen and $C_{1-4}$alkyl; each $R_{5a}$ is independently selected from hydroxy, $C_{1-4}$alkyl, halo, nitro, cyano, halo-substituted-$C_{1-4}$alkyl, halo-substituted-$C_{1-4}$alkoxy, hydroxy-substituted-$C_{1-4}$ alkyl, $C_{1-4}$alkoxy and —$C(O)R_{11a}$; wherein $R_{11a}$ is selected from hydrogen and $C_{1-4}$alkyl; and $R_6$ is $C_{1-4}$alkyl; or a pharmaceutically acceptable salt thereof.

In a further embodiment, $R_3$ is selected from —$CH_2CH_2R_{8b}$ and —$CR_{8a}$=$CR_{8a}R_{8b}$; wherein each $R_{8a}$ is independently selected from hydrogen and $C_{1-4}$alkyl; and $R_{8b}$ is selected from —$C(O)OR_{9a}$, —$C(O)NR_{9a}R_{9b}$, —$C(O)NHOR_{9a}$ and —$C(O)X_2R_{9a}$; wherein $X_2$ is $C_{1-4}$alkylene; $R_{9a}$ and $R_{9b}$ are independently selected from hydrogen, $C_{1-4}$alkyl, hydroxy-substituted-$C_{1-4}$alkyl and halo-substituted-$C_{1-4}$alkyl.

In a further embodiment is a compound, or a pharmaceutically acceptable salt thereof, selected from:

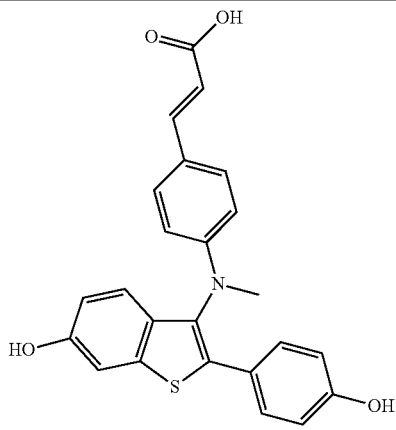

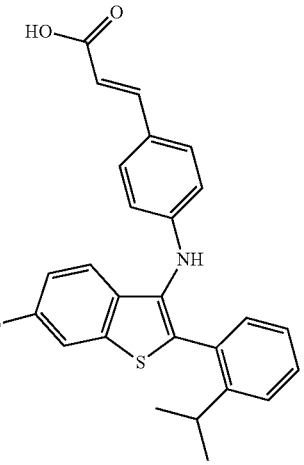

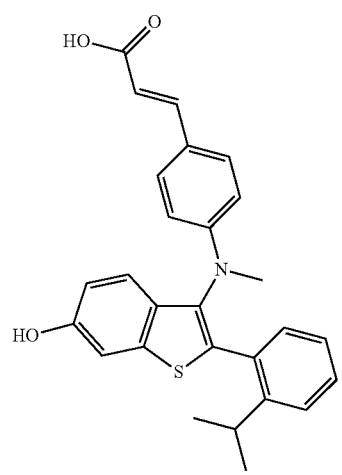 [SMILES: CC(C)c1ccccc1-c1sc2cc(O)ccc2c1N(C)c1ccc(/C=C/C(=O)O)cc1]

In another embodiment is a compound, or a pharmaceutically acceptable salt thereof, selected from:

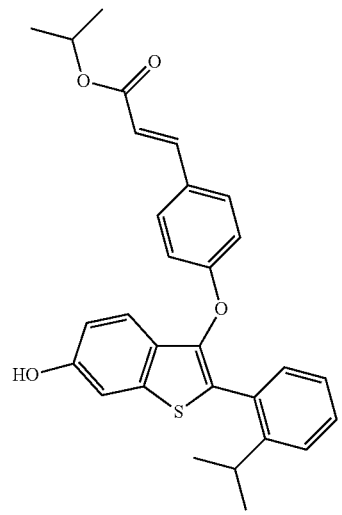 [SMILES: CC(C)OC(=O)/C=C/c1ccc(Oc2c(-c3ccccc3C(C)C)sc3cc(O)ccc23)cc1]

| 53 -continued | 54 -continued |
|---|---|
| 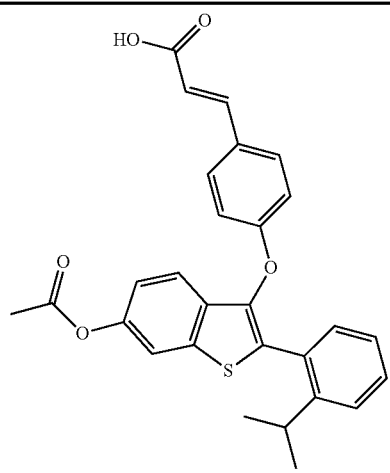 | 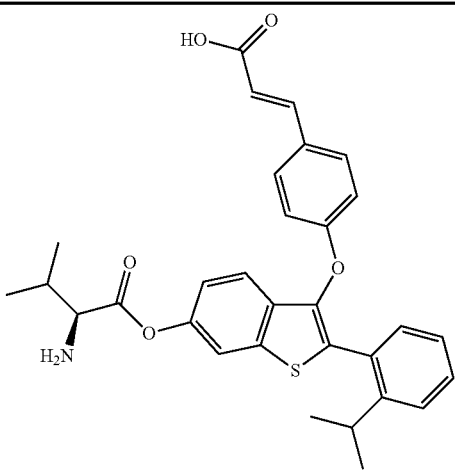 |
| 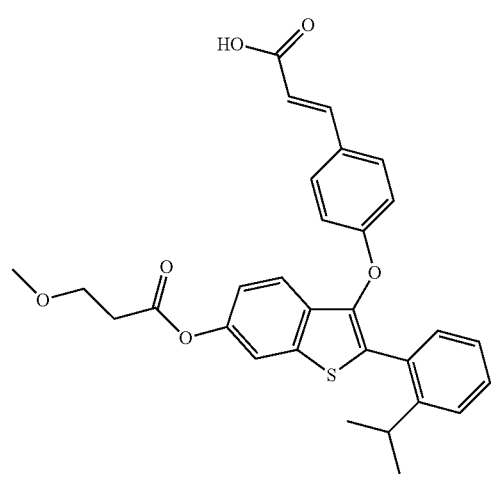 [SMILES: COCCC(=O)Oc1ccc2c(Oc3ccc(/C=C/C(=O)O)cc3)c(-c3ccccc3C(C)C)sc2c1] | 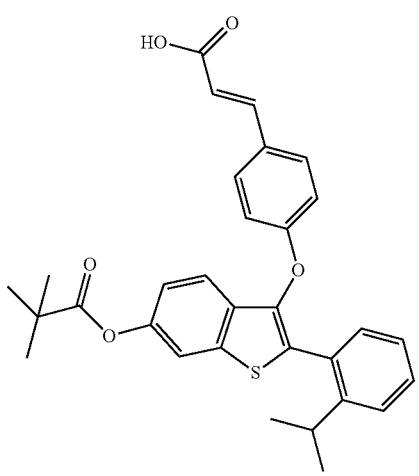 |
| 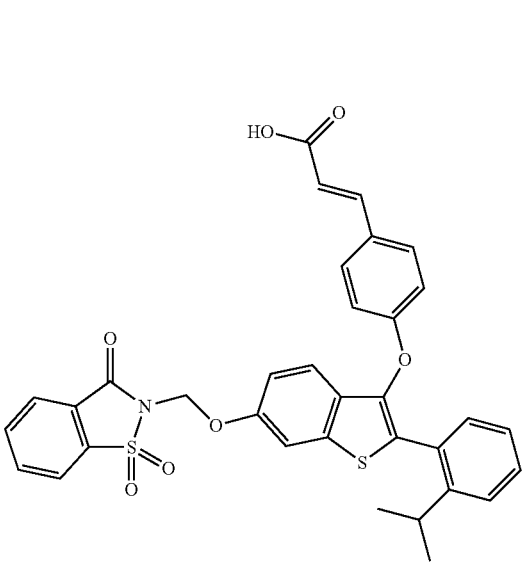 [SMILES: CC(C)c1ccccc1-c1sc2cc(OCN3C(=O)c4ccccc4S3(=O)=O)ccc2c1Oc1ccc(/C=C/C(=O)O)cc1] | 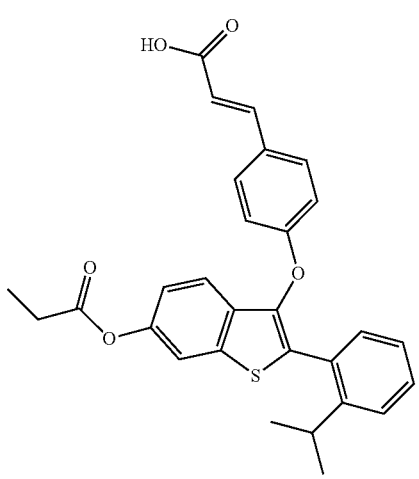 [SMILES: CCC(=O)Oc1ccc2c(Oc3ccc(/C=C/C(=O)O)cc3)c(-c3ccccc3C(C)C)sc2c1] |

-continued

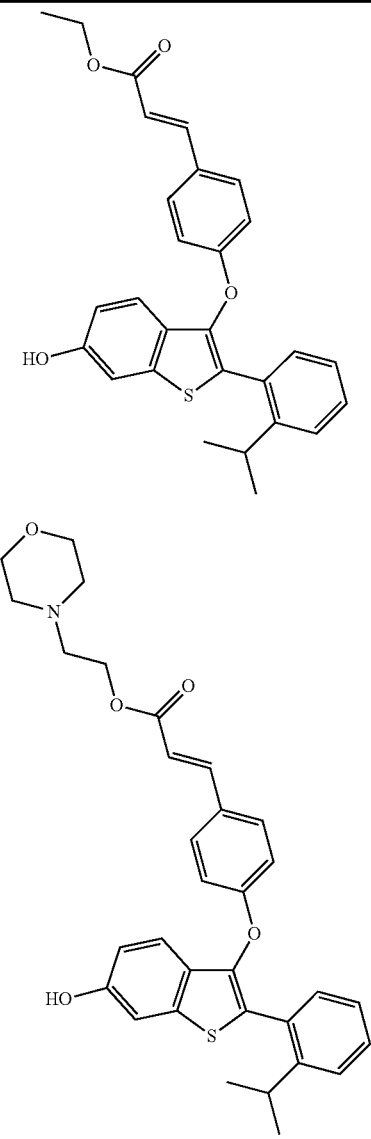

Pharmacology and Utility

The present invention relates to compounds of Formula I that diminish the effects of estrogen receptors and lower the concentrations of estrogen receptors, and therefore, are useful as agents for the treatment or prevention of diseases or conditions in which the actions of estrogens or estrogen receptors are involved in the etiology or pathology of the disease or condition or contribute to at least one symptom of the disease or condition and wherein such actions of estrogens or estrogen receptors are undesirable. Compounds of the invention are both potent estrogen receptor antagonists and selective estrogen receptor degraders (SERDS).

The estrogen receptor (ER) is a ligand-activated transcription factor that belongs to the nuclear hormone receptor superfamily. In both females and males, estrogens play an important role in the regulation of a number of physiological processes. In humans, two different ER subtypes are known: ERα, and ERβ. Each subtype has a distinct tissue distribution and with different biological roles. For example, ERα, has high presence in endometrium, breast cancer cells, ovarian stroma cells and in the hypothalamus. The expression of the ERβ protein has been documented in kidney, brain, bone, heart, lungs, intestinal mucosa, prostate, bladder, ovary, testis, and endothelial cells.

Pharmaceuticals such as tamoxifen, raloxifene and lasofoxifene are well known estrogen receptor modulators. Tamoxifen, for example, behaves like an estrogen in bone and endometrium, whereas it behaves like an anti-estrogen in breast tissue. Breast cancer is the predominant neoplastic disease in women. ERα, is a major driver of breast cancer progression. Multiple existing treatment approaches aim to reduce estrogen levels or block its binding to ERα, thereby minimizing tumor progression or even inducing tumor regression in ERα-positive breast cancer. Tamoxifen is a first-generation treatment for ERα-positive breast cancer. However, efficacy in breast cancer treatment is seriously compromised by intrinsic or newly developed resistance to anti-hormonal therapy such as treatment with tamoxifen or aromatase inhibitors. Such resistance can exist or develop as a result of ERα, phoshorylation or regulation of key components in hormone receptor and/or growth factor signal transduction pathways. Tamoxifen resistance is driven by the residual agonist activity of tamoxifen. Second generation treatments such as toremifene, droloxifene, idoxifene, arzoxifene, and raloxifene have failed to improve upon the efficacy of tamoxifen in the treatment of ERα-positive breast cancer and/or demonstrated cross-resistance with each other.

Fulvestrant is a pure ERα antagonist without the partial agonist activity which is typical for the estrogen receptor modulators. It is the only marketed selective estrogen receptor degrader (SERD) and it is efficacious in second-line treatment of breast cancer. Fulvestrant both antagonizes estrogen receptors and effectively degrades or down-regulates ERα protein levels in cells. This SERD activity inhibits ERα-driven proliferation and tumor growth. Fulvestrant, when administered once a month at 250 mg is equally effective to tamoxifen in treatment of ERα-positive advanced breast cancer. In second-line treatment of ERα-positive tamoxifen-resistant breast cancer, fulvestrant, when administered once a month at 250 mg, is equally effective to aromatase inhibitors, despite relatively poor bioavailability and/or target exposure which limits its clinical efficacy. A number of other SERDs exist, for example: "ICI 164,384", a structural analog of fulvestrant; "GW5638", a structural analog of tamoxifen; and "GW7604", a structural analogue of 4-hydroxy-tamoxifen.

Hence, there is a need for new, potent ERα antagonists, which would preferably have ER degrading or down-regulating activity in, for example, breast cancer cells without stimulating proliferation in ERα-positive, hormone treatment-resistant breast cancer cells. Such compounds would be orally administrable and be useful in the treatment of, amongst other things, ERα-positive, hormone treatment-resistant breast cancer.

Estrogen receptor-related diseases or conditions include, but are not limited to, aberrant estrogen receptor activity associated with: cancer, for example, bone cancer, breast cancer, colorectal cancer, endometrial cancer, prostate cancer, ovarian and uterine cancer; leiomyoma, for example, uterine leiomyoma; central nervous system defects, for example, alcoholism and migraine; cardiovascular system defects, for example, aortic aneurysm, susceptibility to myocardial infarction, aortic valve sclerosis, cardiovascular disease, coronary artery disease and hypertension; hematological system defects, for example, deep vein thrombosis; immune and inflammation diseases, for example, Graves' Disease, arthritis, multiple sclerosis and cirrhosis; susceptibility to infection, for example, hepatitis B and chronic liver disease; metabolic defects, for example, bone density, cholestasis, hypospadias, obesity, osteoarthritis, osteopenia and osteoporosis; neurological defects, for example, Alzheimer's disease, Parkinson's disease, migraine and vertigo; psychiatric defects, for example, anorexia nervosa, attention deficit hyperactivity disorder, dementia, major depressive disorder and psychosis; and reproductive defects, for example, age of menarche, endometriosis and infertility. In the context of treating cancers, the compound of Formula I offer improved therapeutic activity characterized by complete or longer-lasting tumor regression, a lower incidence or rate of development of resistance to treatment, and/or a reduction in tumor invasiveness.

The present invention relates to compounds that are both potent estrogen receptor antagonists and selective estrogen receptor degraders. The invention further provides a process for the preparation of compounds of the invention and pharmaceutical preparations comprising such compounds. Another aspect of the present invention relates to a method of treating disorders mediated by estrogen receptors comprising the step of administering to a patient in need thereof a therapeutically effective amount of a compound of formula I as defined in the Summary of the Invention In an embodiment, compounds of the invention are used to treat cancer in a mammal.

In a further embodiment, the cancer is selected from breast, ovarian, endometrial, prostate, uterine, cervical and lung cancers.

In a further embodiment, the cancer is breast cancer.

In another embodiment, the cancer is a hormone dependent cancer.

In another embodiment, the cancer is an estrogen receptor dependent cancer.

In a further embodiment, the cancer is an estrogen-sensitive cancer.

In another embodiment, the cancer is resistant to anti-hormonal treatment.

In a further embodiment, the cancer is an estrogen-sensitive cancer or an estrogen receptor dependent cancer that is resistant to anti-hormonal treatment.

In a further embodiment, the anti-hormonal treatment includes treatment with at least one agent selected from tamoxifen, fulvestrant, a steroidal aromatase inhibitor, and a non-steroidal aromatase inhibitor.

In another embodiment, compounds of the invention are used to treat hormone receptor positive metastatic breast cancer in a postmenopausal woman with disease progression following anti-estrogen therapy.

In another embodiment, compounds of the invention are used to treat a hormonal dependent benign or malignant disease of the breast or reproductive tract in a mammal.

In a further embodiment, the benign or malignant disease is breast cancer.

In another embodiment, compounds of the invention are used to treat cancer in a mammal, wherein the mammal is chemotherapy-naive.

In another embodiment, compounds of the invention are used to treat cancer in a mammal, wherein the mammal is being treated for cancer with at least one anti-cancer agent.

In a further embodiment, the cancer is a hormone refractory cancer.

In another embodiment, compounds of the invention are used in the treatment of endometriosis in a mammal.

In another embodiment, compounds of the invention are used in the treatment of leiomyoma in a mammal.

In a further embodiment, the leiomyoma is selected from uterine leiomyoma, esophageal leiomyoma, cutaneous leiomyoma and small bowel leiomyoma.

In another embodiment, compounds of the invention are used in the treatment of fibroids, for example, uterine fibroids, in a mammal.

Compounds of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a *vinca* alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating a disorder mediated by estrogen receptors, comprising the step of: administering to a patient in need thereof a therapeutically effective amount of a chemotherapeutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

Given the central role of ER-α in breast cancer development and progression, compounds disclosed herein are useful in the treatment of breast cancer, either alone or in combination with other agents used to treat breast cancer, including but not limited to aromatase inhibitors, anthracylines, platins, nitrogen mustard alkylating agents and taxanes. Agents used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine and ixabepilone.

Further, compounds of the invention are useful in the treatment of breast cancer, either alone or in combination with other agents that modulate other critical pathways in breast cancer, including but not limited to those that target IGF1R, EGFR, erB-B2 and the PI3K/AKT/mTOR axis, Rb axis including CDK4/6 and D-cyclins, HSP90, PARP and/or histone deacetylases.

A compound of the invention can, therefore, also be used in combination with the following:

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methyl-pyrrolo[2,1-f][1,2,4]triazin-6-yloxy)propan-2-yl)-2-amino-propanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline);

CD20 antibodies: Rituximab (sold under the trademarks Riuxan® and MabThera® by Genentech/Roche), tositumomab (sold under the trademarks Bexxar® by GlaxoSmithKline), of atumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

Bcr/Abl kinase inhibitors: nilotinib hydrochloride (sold under the tradename Tasigna® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxy-purin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc);

Pro-apoptotic receptor agonists (PARAS): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4.9}$]hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®;

Biologic response modifiers: *bacillus* calmette-guerin (sold under the tradenames TheraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-N$^2$-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α, 3ξ, 4α, 5β, 7α, 10β, 13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl)phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[α]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®);

A compound of formula (I) can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, shown here where $R_{8a}$ is hydrogen, can be prepared by proceeding as in the following General Reaction Scheme I:

General Reaction Scheme I:

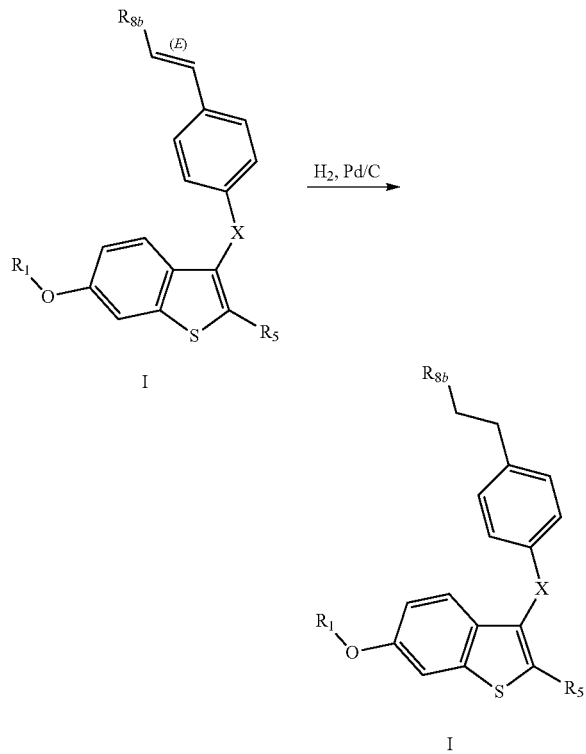

in which $R_1$, $R_5$ and $R_{8b}$ are as defined for Formula I in the Summary of the Invention. A compound of Formula I can be prepared by reacting a compound of formula I (where $R_3$ has a double bond as shown above) with a a suitable reducing agent (such as $H_2$, and the like) and a suitable catalyst (such as Palladium on carbon (Pd/C), or the like), under a suitable pressure (such as about 1 atm to about 5 atm). The reaction takes place at about 0° C.-50° C. and can take from about 1 to about 24 hours to complete.

Compounds of Formula I, shown here where $R_{8a}$ is hydrogen and $R_3$ has a double bond, can be prepared by proceeding as in the following General Reaction Scheme II:

General Reaction Scheme II:

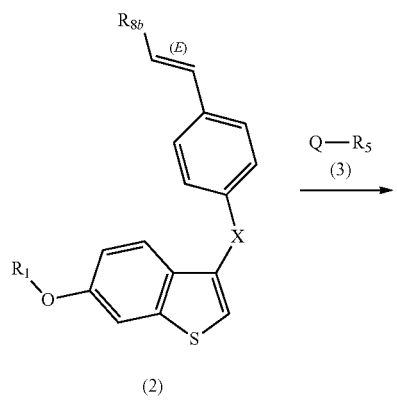

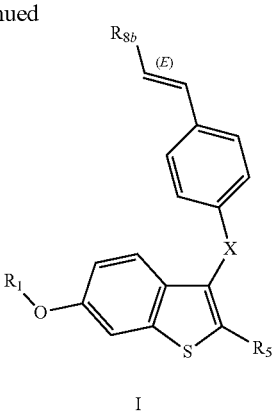

in which $R_1$, $R_5$ and $R_{8b}$ are as defined for Formula I in the Summary of the Invention and Q is a leaving group such as a halogen or triflate. A compound of Formula I can be prepared by reacting a compound of formula 2 with a compound of formula 3 in the presence of a suitable catalyst (such as Palladium, or the like), a suitable base (such as potassium carbonate, and the like), and a suitable acid (such as pivalic acid, or the like). The reaction takes place at about 120° C.-200° C. and can take from about 1 to about 18 hours to complete.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985; Férriz, J. M. et al., Current Pharmaceutical Design, 2010, 16, 2033-2052). Examples of prodrug derivatives of compounds of the invention can be:

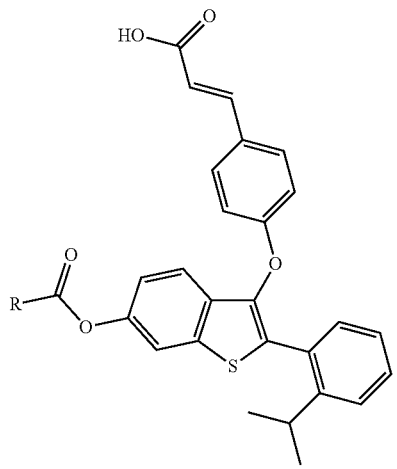

R = Me, Et, tBu

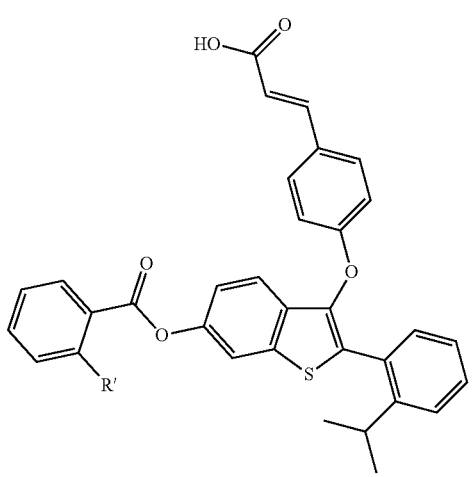

R' = NH$_2$, O(C=O)CH$_3$, Me

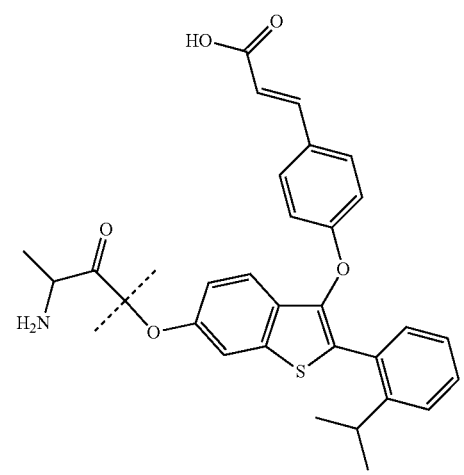

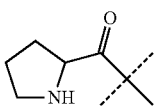

-continued

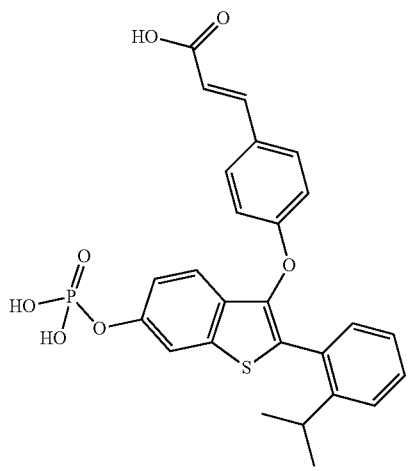

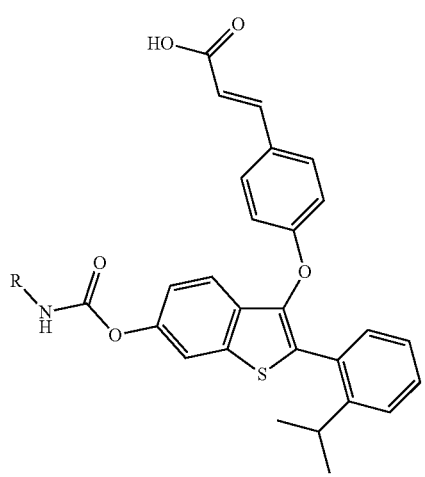

R = Me, Et, tBu

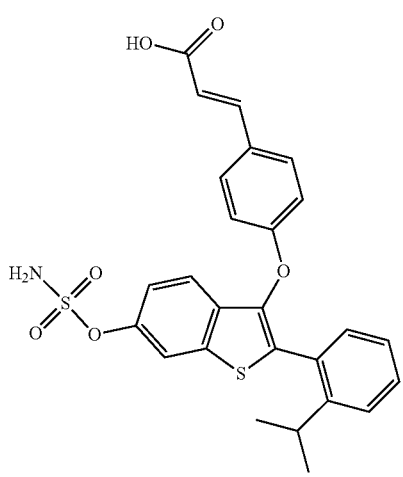

-continued

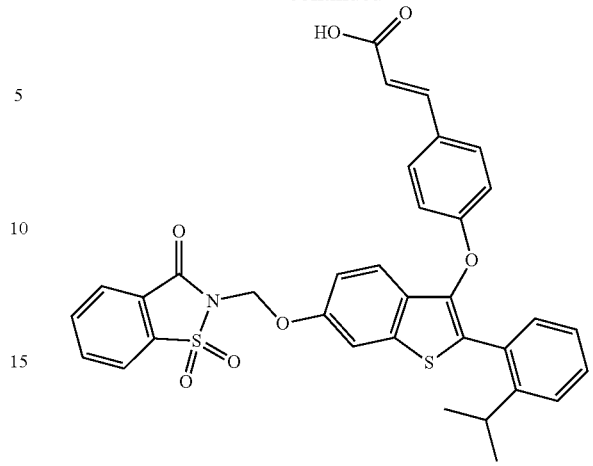

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of general reaction schemes I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof.

Some abbreviations used in the examples are as follows: aq. (aqueous); br (broad); ° C. (degrees Celsius); δ NMR chemical shift in ppm downfield from tetramethyl-silane; d (doublet); DCE (1,2-dichloroethane; DCM (dichloromethane); DIEA (N,N-diisopropylethylamine); DIBAL-H (diisobutylaluminium hydride); DMA (dimethyl-acetamide); DME (dimethoxyethane); DMF (N,N-dimethylformamide); DMSO (dimethylsulfoxide); Et (ethyl); EtOAc (ethyl acetate); g (gram); h (hour); HATU (O-(7-azabenzotriazol-1-yl)-N,N,N',N'-tetramethyluronium hexafluorophosphate); HRMS (high-resolution mass spectrometry); i-Pr (isopropyl); L (liter); LAH (lithium aluminium hydride); LC/MS (liquid chromatography-mass spectrometry); M (molarity); m (multiplet); Me (methyl); mg (milligram); MHz (megahertz); min (minute); mL (milliliter); μL (microliter); mmol (millimole); N (normal); NBS (N-bromosuccinimide); n-Bu (normal butyl); n-BuLi (n-butyllithium); NMM (N-methylmorpholine); NMR (nuclear magnetic resonance); Ph (phenyl); pH ($-\log_{10}H^+$ concentration); ppm (parts per million); q (quartet); s (singlet); sat. (saturated); t (triplet); t-Bu (tert-butyl); Tf (trifluoromethanesulfonyl); TFA (trifluoroacetic acid); Ts (p-toluenesulfonyl); TsOH (p-toluenesulfonic acid); TBS (tert-butyldimethylsilyl); TEA (triethylamine); THF (tetrahydrofuran); and TMS (trimethylsilyl).

All intermediates required for the preparation of compounds of Formula I can be prepared as described in Scheme 1. Employing intermediates H, K, L, O, P, R, T, U, X and Z provided the synthesis of compounds of Formula I using the transformations described in Scheme 2. In some occasions examples can be converted into additional examples as described in the experimental section.

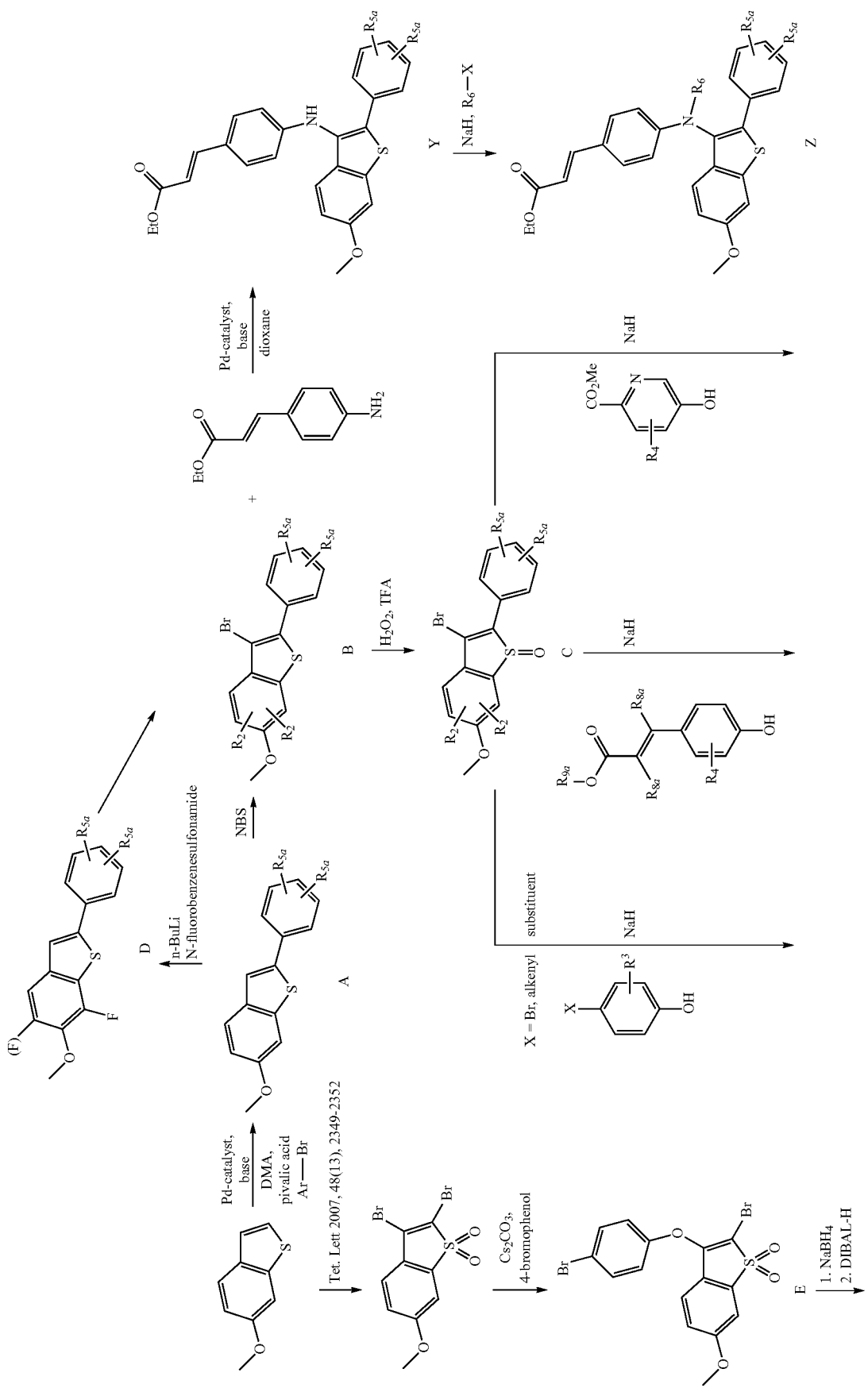
Reaction Scheme I

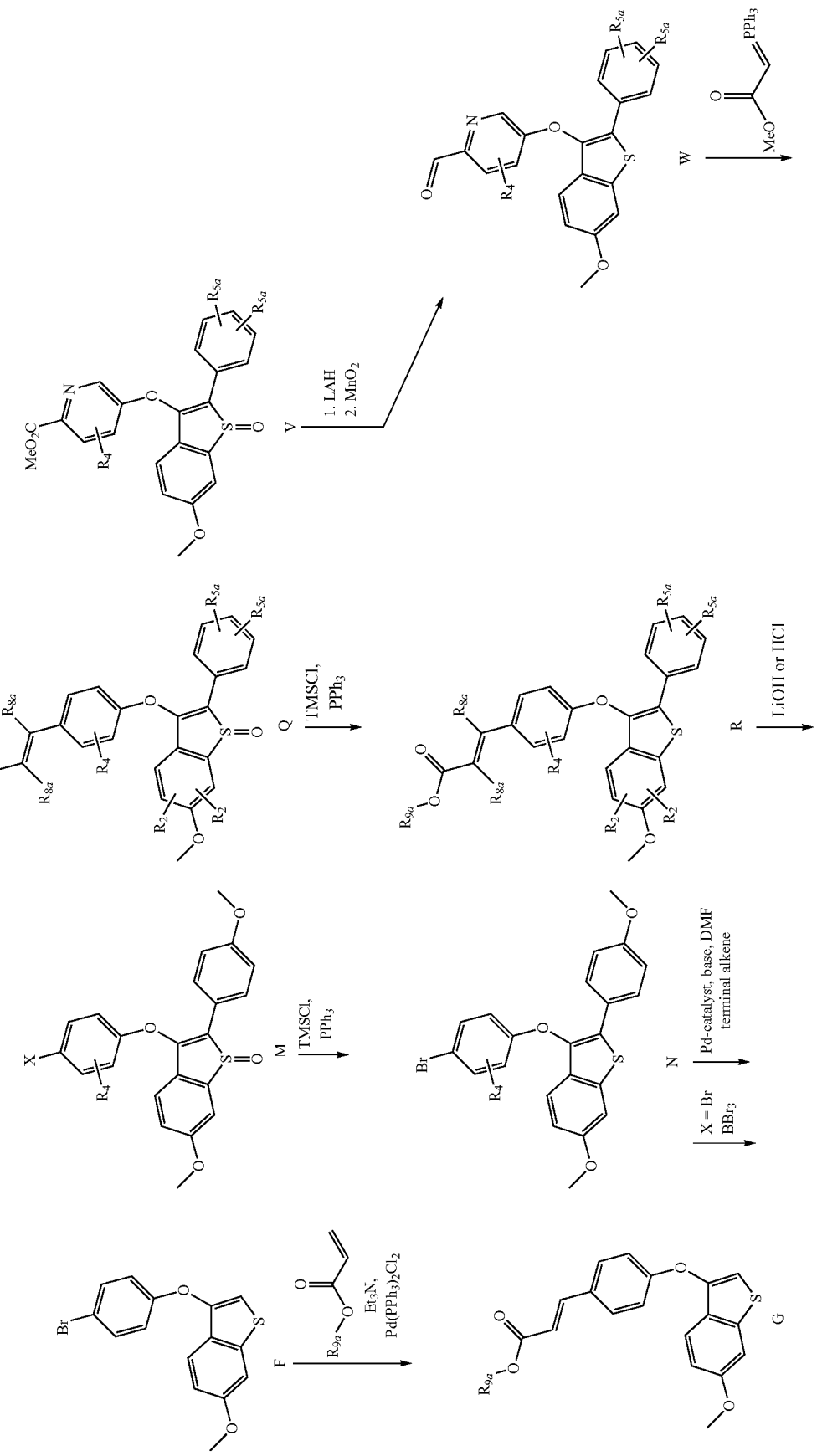

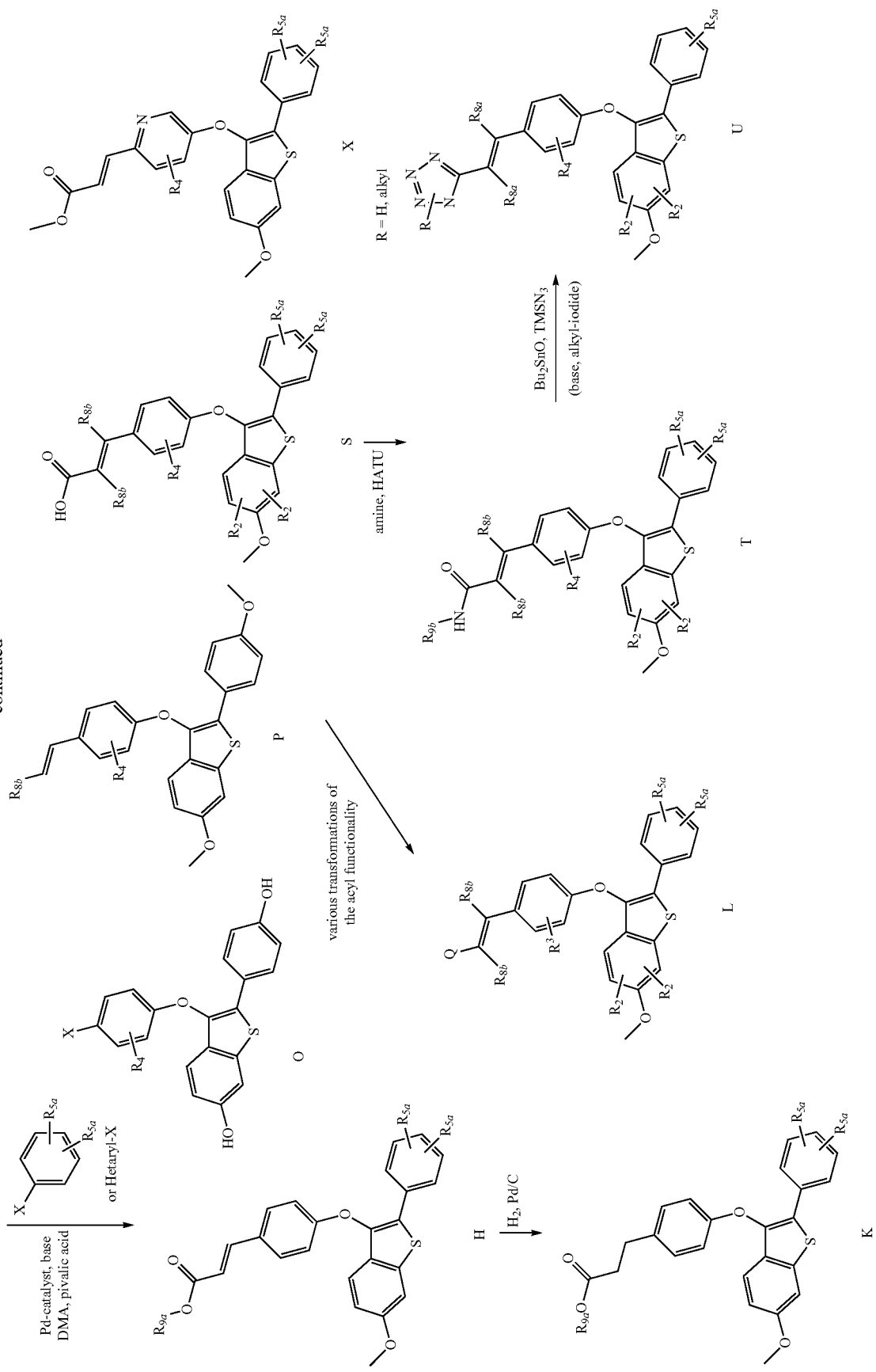

Reaction Scheme 2

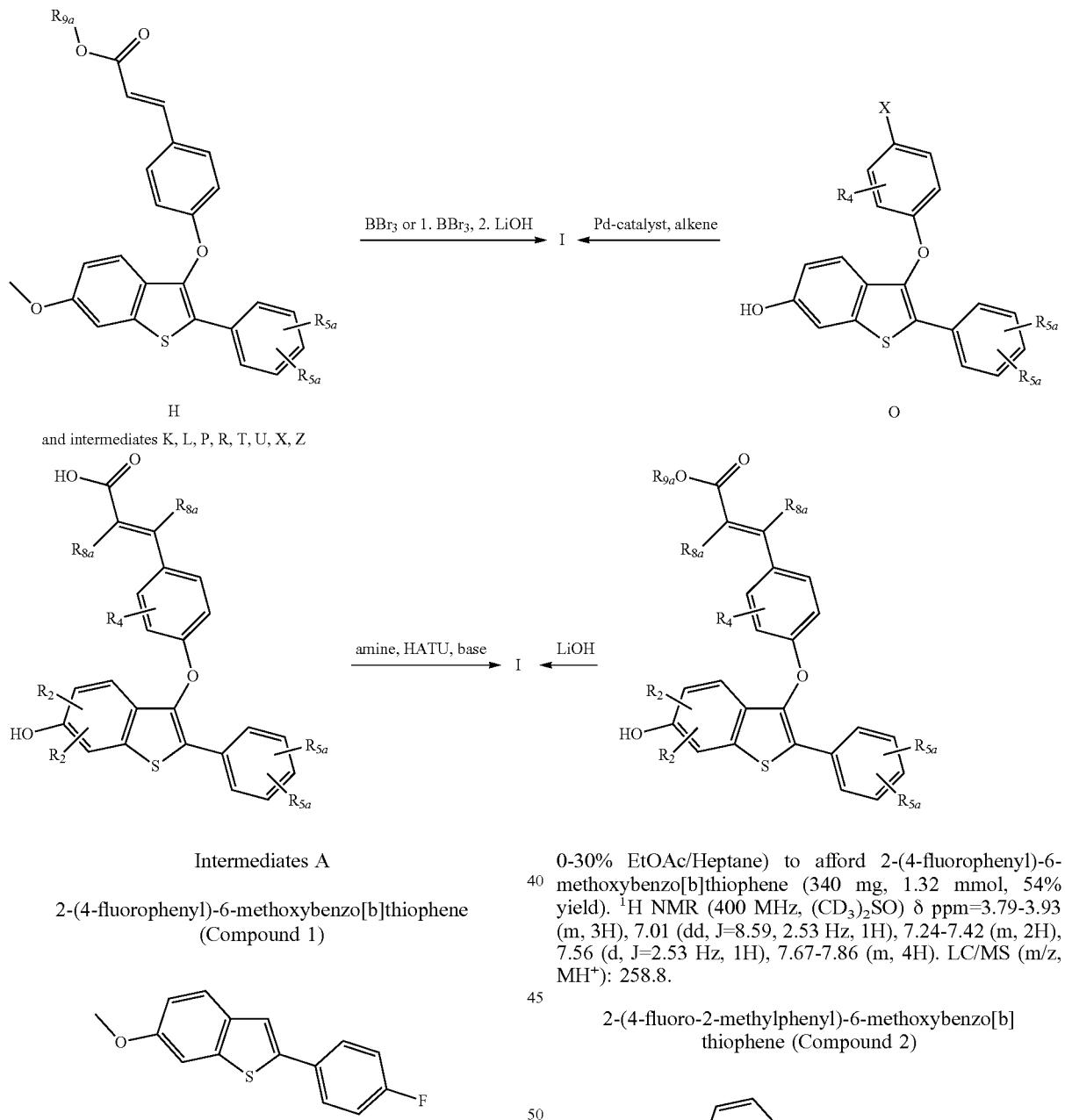

Intermediates A 2-(4-fluorophenyl)-6-methoxybenzo[b]thiophene
(Compound 1)

To a 5 mL microwave vial was added a solution of 6-methoxybenzo[b]thiophene (400 mg, 2.44 mmol) in anhydrous DMA (3 mL) followed by 1-bromo-4-fluorobenzene (448 mg, 2.56 mmol), chloro[2-(dicyclohexylphosphino)-3,6-dimethoxy-2',4',6'-tri-i-propyl-1,1'-biphenyl][2-(2-aminoethyl)phenyl]palladium(II) (BrettPhos palladacycle 1$^{st}$ generation, 97 mg, 0.12 mmol), trimethylacetic acid (746 mg, 7.31 mmol) and potassium carbonate (1.01 g, 7.31 mmol). The microwave vial was sealed, purged with nitrogen and subjected to microwave irradiation at 150° C. for 2 h. Upon completion the reaction mixture was diluted with water and extracted with EtOAc. The combined organic layers were then washed with brine, dried over anhydrous MgSO$_4$, filtered and concentrated in vacuo. The resulting crude material was was purified via trituration 2× with heptane and the remaining triturate (containing some product) was concentrated and purified by column chromatography (SiO$_2$, 0-30% EtOAc/Heptane) to afford 2-(4-fluorophenyl)-6-methoxybenzo[b]thiophene (340 mg, 1.32 mmol, 54% yield). $^1$H NMR (400 MHz, (CD$_3$)$_2$SO) δ ppm=3.79-3.93 (m, 3H), 7.01 (dd, J=8.59, 2.53 Hz, 1H), 7.24-7.42 (m, 2H), 7.56 (d, J=2.53 Hz, 1H), 7.67-7.86 (m, 4H). LC/MS (m/z, MH$^+$): 258.8.

2-(4-fluoro-2-methylphenyl)-6-methoxybenzo[b]thiophene (Compound 2)

To a 20 mL microwave vial, 6-methoxybenzo[b]thiophene (1 g, 6.09 mmol), 2-bromo-5-fluorotoluene (0.808 mL, 6.39 mmol), BrettPhos palladacycle (1st generation) (0.243 g, 0.304 mmol), trimethylacetic acid (1.866 g, 18.27 mmol), and K$_2$CO$_3$ (2.52 g, 18.27 mmol) were suspended in DMA (10 mL). The reaction was heated for 90 min at 150° C. under microwave radiation. The reaction mixture was diluted with DCM and water. The organic layer was collected (phase separator) and concentrated to afford the crude product. The crude material was concentrated onto to silica gel and purified by column chromatography (SiO$_2$, 100% Heptanes) to afford 2-(4-fluoro-2-methylphenyl)-6- methoxybenzo[b]thiophene (730 mg, 2.68 mmol, 44% yield) as a white solid. $^1$H NMR (400 MHz, CDCl$_3$) δ ppm=7.69 (d, J=9.09 Hz, 1H), 7.43 (dd, J=6.06, 8.59 Hz, 1H), 7.35 (d, J=2.53 Hz, 1H), 7.14 (s, 1H), 7.00-7.10 (m, 2H), 6.90-7.00 (m, 1H), 3.92 (s, 3H), 2.47 (s, 3H).

The following compounds were prepared in an analogous fashion utilizing the appropriate bromide:

| Structure | Name | Physical Data |
|---|---|---|
| 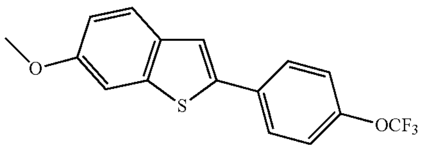 [SMILES: COc1ccc2cc(-c3ccc(OC(F)(F)F)cc3)sc2c1] | 6-methoxy-2-(4-(trifluoromethoxy)phenyl)-benzo[b]thiophene (compound 3) | LC/MS (m/z, MH$^+$): 324.8 |
| 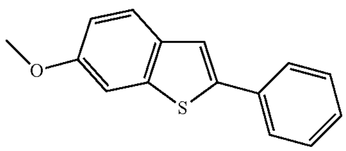 [SMILES: COc1ccc2cc(-c3ccccc3)sc2c1] | 6-methoxy-2-phenylbenzo[b]thiophene (compound 4) | LC/MS (m/z, MH$^+$): 241.3 |
| 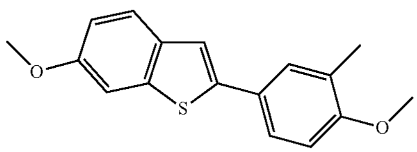 | 6-methoxy-2-(4-methoxy-3-methylphenyl)-benzo[b]thiophene (compound 5) | LC/MS (m/z, MH$^+$): 285.3 |
| 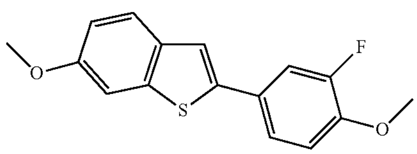 | 2-(3-fluoro-4-methoxyphenyl)-6-methoxybenzo[b]thiophene (compound 6) | LC/MS (m/z, MH$^+$): 289.3 |

Intermediates B

3-bromo-6-methoxy-2-(4-methoxyphenyl)benzo[b]thiophene (Compound 7)

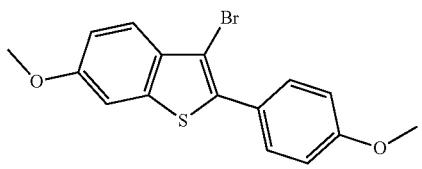

To a 500 mL round bottom flask containing 6-methoxy-2-(4-methoxyphenyl)benzo[b]thiophene (22 g, 81 mmol) in THF (250 mL) at 0° C. was added NBS (15 g, 84 mmol). The reaction mixture was stirred at 0° C. for 60 min and then allowed to warm to room temperature and stirred for an additional 2 h. Upon completion the reaction mixture was concentrated to 50% volume and quenched with sat. aq. sodium thiosulfate solution. The resulting solution was extracted with diethyether 3× and the combined organic solvent was dried over anhydrous MgSO$_4$, filtered and concentrated in vacuo to afford 3-bromo-6-methoxy-2-(4-methoxyphenyl)-benzo[b]thiophene (27.5 g, 79 mmol, 97% yield). $^1$H NMR (400 MHz, CDCl$_3$) δ ppm=7.63 (d, J=9.1 Hz, 1H), 7.55-7.61 (m, 2H), 7.19 (d, J=2.5 Hz, 1H), 6.96-7.02 (m, 1H), 6.87-6.95 (m, 2H), 3.81 (s, 3H), 3.79 (s, 3H).

The following compounds were prepared by bromination from the corresponding starting materials as described above:

| Structure | Name | Physical Data |
|---|---|---|
| 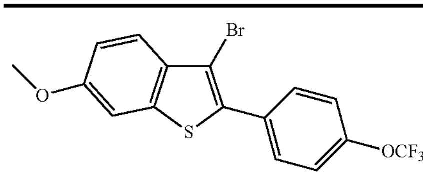 | 3-bromo-6-methoxy-2-(4-(trifluoromethoxy)phenyl)benzo[b]thiophene (compound 8) | LC/MS (m/z, M-H): 403.5 |
| 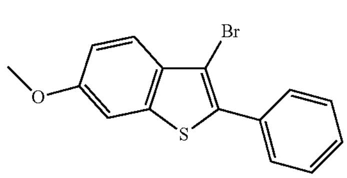 [SMILES: COc1ccc2c(Br)c(-c3ccccc3)sc2c1] | 3-bromo-6-methoxy-2-phenylbenzo[b]thiophene (compound 9) | |

-continued

| Structure | Name | Physical Data |
|---|---|---|
| (structure of compound 10) | 3-bromo-2-(4-fluorophenyl)-6-methoxybenzo[b]thiophene (compound 10) | LC/MS (m/z, MH+): 338.1 |
| (structure of compound 11) | 3-bromo-6-methoxy-2-(4-methoxy-3-methylphenyl)benzo[b]thiophene (compound 11) | |
| (structure of compound 12) | 3-bromo-2-(3-fluoro-4-methoxyphenyl)-6-methoxybenzo[b]thiophene (compound 12) | |

3-bromo-7-fluoro-6-methoxy-2-(4-methoxyphenyl)benzo[b]thiophene and 3-bromo-5,7-difluoro-6-methoxy-2-(4-methoxyphenyl)benzo[b]thiophene (Compounds 13 and 14)

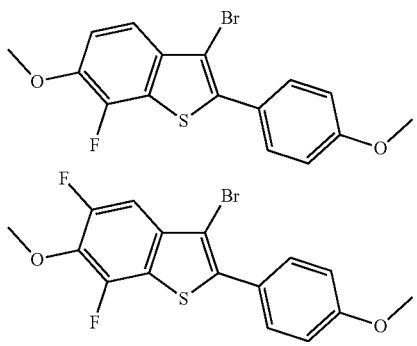

To a round bottom flask, an unseparated mixture of 7-fluoro-6-methoxy-2-(4-methoxyphenyl)benzo[b]thiophene and 5,7-difluoro-6-methoxy-2-(4-methoxyphenyl)benzo[b]thiophene (380 mg, 1.318 mmol) was dissolved in THF (10 mL) and the solution was cooled to 0° C. To the solution was added NBS (237 mg, 1.331 mmol). The reaction mixture was stirred at 0° C. for 1 h then warmed to room temperature and stirred for an additional 2 h. The reaction mixture was concentrated to afford the crude product. The crude product was diluted with DCM and sat. Na₂S₂O₃ (sodium thiosulfate). The organic layer was collected (phase separator) and concentrated. The reaction mixture was diluted with water and DCM. The organic phase was collected (phase separator) and concentrated to afford the crude product. The crude material was purified by column chromatography (SiO₂, 0-5% Heptanes/EtOAc) to afford 3-bromo-7-fluoro-6-methoxy-2-(4-methoxyphenyl)benzo[b]thiophene (211 mg, 0.575 mmol, 43.6% yield) and 3-bromo-5,7-difluoro-6-methoxy-2-(4-methoxyphenyl)benzo[b]thiophene (125 mg, 0.324 mmol, 24.62% yield).

3-bromo-7-fluoro-6-methoxy-2-(4-methoxyphenyl)benzo[b]thiophene: ¹H NMR (400 MHz, CDCl₃) δ ppm=7.56-7.66 (m, 2H), 7.46 (dd, J=1.01, 8.59 Hz, 1H), 7.11 (dd, J=7.58, 8.59 Hz, 1H), 6.90-6.97 (m, 2H), 3.92 (s, 3H), 3.79 (s, 3H). 3-bromo-5,7-difluoro-6-methoxy-2-(4-methoxyphenyl)benzo[b]thiophene: ¹H NMR (400 MHz, CDCl₃) δ ppm=7.53-7.68 (m, 2H), 7.48 (d, J=8.59 Hz, 1H), 7.15-7.27 (m, 1H), 7.07 (dt, J=2.53, 8.59 Hz, 1H), 3.98 (s, 3H), 4.02 (s, 3H).

Intermediates C 3-bromo-6-methoxy-2-(4-methoxyphenyl)benzo[b]thiophene 1-oxide (Compound 15)

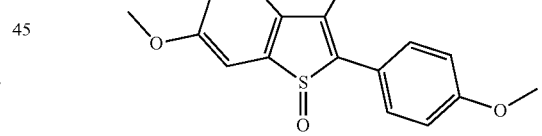

To a solution of 3-bromo-6-methoxy-2-(4-methoxyphenyl)-benzo[b]thiophene (4 g, 11.45 mmol) in DCM (20.02 mL) at room temperature was added trifluoroacetic acid (20.02 mL) dropwise, the reaction went from orange to dark brown in color. Upon addition the resulting mixture was stirred at room temp for 10 min and then hydrogen peroxide (30% wt. aq) (1.583 mL, 16.47 mmol) was added dropwise. After 90 min at room temperature the reaction mixture was quenched with sodium bisulfite (1.714 g, 16.47 mmol) (vigorous bubbling was observed) followed by 3.0 mL of water. The resulting suspension was stirred vigorously for 15 min and then concentrated in vacuo to remove DCM and most of the TFA. The residue was partitioned between DCM (40 mL) and sat. aq. NaHCO₃ solution (40 mL) and separated. The organic layer was collected (phase separator) and concentrated in vacuo to afford the crude product, which was purified by column chromatography (SiO₂, 1-40% EtOAc/

Heptane) to afford 3-bromo-6-methoxy-2-(4-methoxyphenyl)benzo[b]thiophene 1-oxide (4.6 g, 10.08 mmol, 88% yield) as an orange solid. $^1$H NMR (400 MHz, CD$_3$OD) δ ppm=7.51-7.65 (m, 2H), 7.37-7.51 (m, 2H), 7.08 (dd, J=2.27, 8.34 Hz, 1H), 6.79-6.96 (m, 2H), 3.74 (s, 3H), 3.68 (s, 3H).

The following benzo[b]thiophene 1-oxides were prepared in an analogous fashion as described above:

| Structure | Name | Physical Data |
|---|---|---|
| 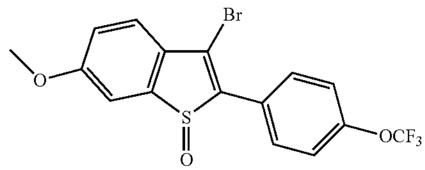 | 3-bromo-6-methoxy-2-(4-(trifluoromethoxy)phenyl)benzo[b]thiophene 1-oxide (compound 16) | LC/MS (m/z, MH$^+$): 422.1 |
| 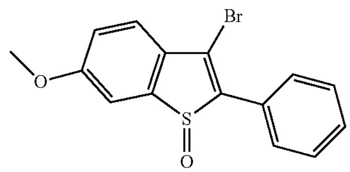 [SMILES: COc1ccc2c(c1)S(=O)C(c1ccccc1)=C2Br] | 3-bromo-6-methoxy-2-phenylbenzo[b]thiophene 1-oxide (compound 17) | LC/MS (m/z, MH$^+$): 337.0 |
| 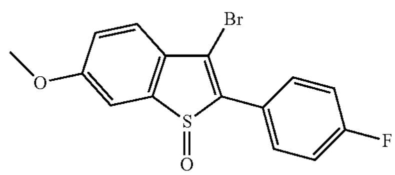 [SMILES: COc1ccc2c(c1)S(=O)C(c1ccc(F)cc1)=C2Br] | 3-bromo-2-(4-fluorophenyl)-6-methoxybenzo[b]thiophene 1-oxide (compound 18) | LC/MS (m/z, MH$^+$): 355.0 |
| 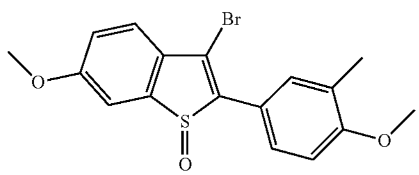 | 3-bromo-6-methoxy-2-(4-methoxy-3-methylphenyl)benzo[b]thiophene 1-oxide (compound 19) | LC/MS (m/z, MH$^+$): 381.1 |
| 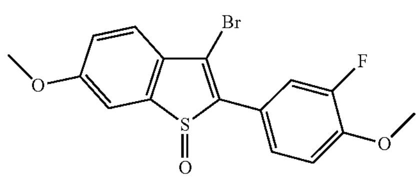 | 3-bromo-2-(3-fluoro-4-methoxyphenyl)-6-methoxybenzo[b]thiophene 1-oxide (compound 20) | LC/MS (m/z, MH$^+$): 385.0 |
| 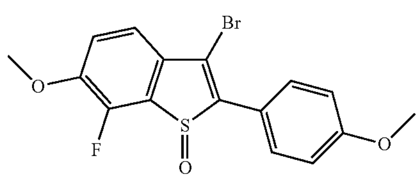 | 3-bromo-7-fluoro-6-methoxy-2-(4-methoxyphenyl)benzo[b]thiophene 1-oxide (compound 21) | $^1$H NMR (400 MHz, CDCl$_3$) δ ppm = 7.71-7.82 (m, J = 8.59 Hz, 2H), 7.35 (d, J = 8.08 Hz, 1H), 7.17 (t, J = 8.08 Hz, 1H), 6.97-7.09 (m, J = 9.09 Hz, 2H), 3.98 (s, 3H), 3.87 (s, 3H) |
| 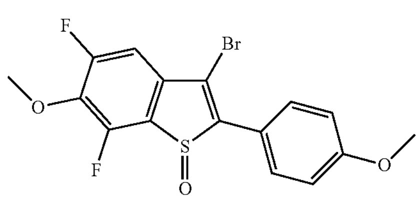 | 3-bromo-5,7-difluoro-6-methoxy-2-(4-methoxyphenyl)benzo[b]thiophene 1-oxide (compound 22) | $^1$H NMR (400 MHz, CDCl$_3$) δ ppm = 7.55-7.72 (m, 2H), 7.36-7.43 (m, 1H), 7.21 (t, J = 7.83 Hz, 1H), 7.11 (t, J = 8.59 Hz, 1H), 4.01 (s, 3H), 3.98 (s, 3H) |
| 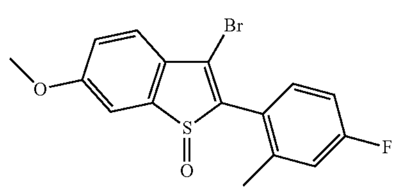 [SMILES: COc1ccc2c(c1)S(=O)C(c1ccc(F)cc1C)=C2Br] | 3-bromo-2-(4-fluoro-2-methylphenyl)-6-methoxybenzo[b]thiophene 1-oxide (compound 23) | $^1$H NMR (400 MHz, CDCl$_3$) δ ppm = 7.49-7.70 (m, 2H), 7.33-7.45 (m, 1H), 7.17 (dd, J = 2.53, 8.59 Hz, 1H), 6.92-7.12 (m, 2H), 3.95 (s, 3H), 2.41 (s, 3H) |

Intermediates D 7-fluoro-6-methoxy-2-(4-methoxyphenyl)benzo[b]thiophene and 5,7-difluoro-6-methoxy-2-(4-methoxyphenyl)benzo[b]thiophene (Compounds 24 and 25)

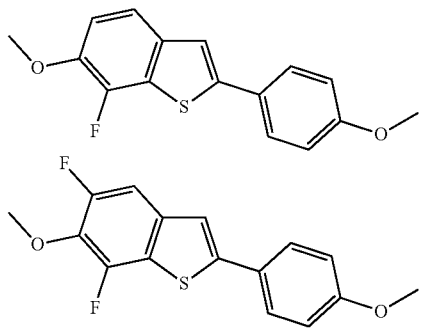

To a 200 mL round bottom flask, 6-methoxy-2-(4-methoxyphenyl)benzo[b]thiophene (4.5 g, 16.7 mmol) was suspended in THF (60 mL) and the solution was cooled to −78° C. To the cooled solution was added n-BuLi (2.5 M in hexanes, 11.65 mL, 29.1 mmol) dropwise. After 30 min, the reaction mixture was warmed to 0° C. and stirred for an additional 1 h causing the reaction mixture to go into solution and turn black. The reaction mixture was cooled to −78° C. and N-fluorobenzenesulfonimide (9.19 g, 29.1 mmol) was added causing the reaction mixture to turn a clear orange. After 20 min at −78° C., the reaction mixture was allowed to gradually warm to room temperature over 1 h. The reaction was quenched with MeOH and diluted with DCM and 1 N NaOH. The organic phase was collected (phase separator) and concentrated to afford the crude product. The crude material was purified by column chromatography (SiO$_2$, 100% Heptane). The fractions were concentrated to a white solid and triturated with cold MeOH. The precipitate was discarded and the filtrate was concentrated to afford 7-fluoro-6-methoxy-2-(4-methoxyphenyl)benzo[b]thiophene and 5,7-difluoro-6-methoxy-2-(4-methoxyphenyl)benzo[b]thiophene as an unseparable mixture (1.8 g, ~35% yield).

Intermediates E 2-bromo-3-(4-bromophenoxy)-6-methoxybenzo[b]thiophene 1,1-dioxide (Compound 26)

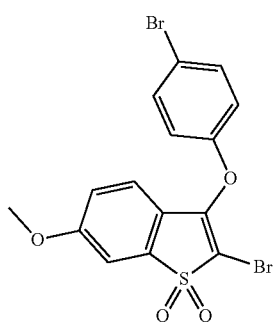 [SMILES: COc1ccc2c(c1)S(=O)(=O)C(Br)=C2Oc1ccc(Br)cc1]

To a solution of 2,3-dibromo-6-methoxybenzo[b]thiophene 1,1-dioxide (2.50 g, 7.06 mmol) in THF (100 mL) at room temperature was added 4-bromophenol (1.344 g, 7.77 mmol) and Cs$_2$CO$_3$ (6.90 g, 21.19 mmol). The reaction mixture turned green after ~1 min of stirring. The mixture was stirred at room temperature for 18 h after which time the reaction was quenched with water and diluted with DCM. The organic layer was collected (phase separator) and concentrated to provide 2-bromo-3-(4-bromophenoxy)-6-methoxybenzo[b]thiophene 1,1-dioxide (3.10 g, 6.95 mmol, 98% yield) as a white solid which was used without further purification. $^1$H NMR (400 MHz, CDCl$_3$) δ ppm=3.83 (s, 3H), 6.92-7.03 (m, 3H), 7.25-7.35 (m, 2H), 7.39-7.50 (m, 2H).

Intermediates F 3-(4-bromophenoxy)-6-methoxybenzo[b]thiophene 1,1-dioxide (Compound 27)

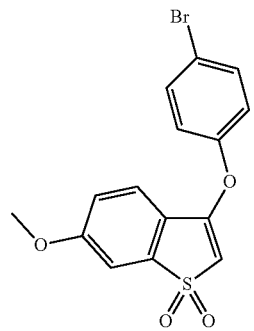 [SMILES: COc1ccc2c(c1)S(=O)(=O)C=C2Oc1ccc(Br)cc1]

Step 1: To a solution of 2-bromo-3-(4-bromophenoxy)-6-methoxy-benzo[b]thiophene 1,1-dioxide (3.10 g, 6.95 mmol) in MeOH (10 mL) and DMSO (30 mL) was added NaBH$_4$ (0.789 g, 20.85 mmol). The mixture was stirred at room temperature for 3 h after which time the reaction was quenched with water and diluted with DCM. The organic layer was collected (phase separator) and concentrated to provide 3-(4-bromophenoxy)-6-methoxybenzo[b]thiophene 1,1-dioxide (2.47 g, 6.73 mmol, 97% yield) as an off white solid which was used without further purification. $^1$H NMR (400 MHz, CDCl$_3$) δ ppm=3.85 (s, 3H), 5.38 (s, 1H), 7.02-7.08 (m, 3H), 7.22 (d, J=2.53 Hz, 1H), 7.47-7.60 (m, 3H).

3-(4-bromophenoxy)-6-methoxybenzo[b]thiophene (Compound 28)

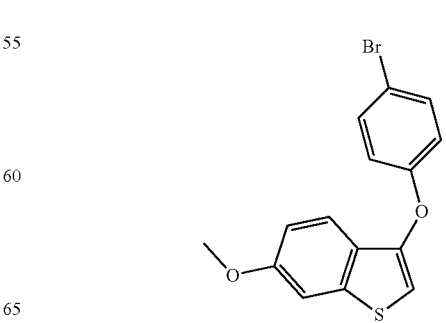

Step 2: To a solution of 3-(4-bromophenoxy)-6-methoxybenzo[b]thiophene 1,1-dioxide (2.47 g, 6.73 mmol) in THF (90 mL) was added DIBAL-H (1.0 M in DCM, 33.6 mL, 33.6 mmol) in one portion. The mixture was heated to 75° C. for 2 h after which time the reaction was cooled to room temperature and quenched with EtOAc (32.9 mL, 336 mmol). The resulting solution was stirred for 10 min before carefully adding 75 mL of water and potassium sodium tartrate (33.100 g, 117 mmol). The mixture was vigorously stirred for 10 min and diluted with 75 mL EtOAc. The organic layer was collected, dried with anhydrous MgSO$_4$ and concentrated in vacuo to afford 3-(4-bromophenoxy)-6-methoxybenzo[b]thiophene (1.9 g, 5.67 mmol, 84% yield) as a white solid which was used without further purification. $^1$H NMR (400 MHz, CDCl$_3$) δ ppm=3.81 (s, 3H), 6.46 (s, 1H), 6.90 (d, J=9.09 Hz, 3H), 7.16-7.22 (m, 1H), 7.31-7.40 (m, 2H), 7.46 (d, J=9.09 Hz, 1H). LC/MS (m/z, MH$^+$): 336.8.

Intermediates G (E)-methyl 3-(4-((6-methoxybenzo[b]thiophen-3-yl)oxy)phenyl)acrylate (Compound 29)

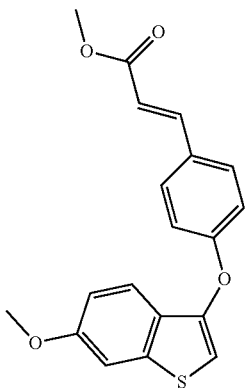 [SMILES: COC(=O)/C=C/c1ccc(Oc2csc3cc(OC)ccc23)cc1]

To a microwave vial, 3-(4-bromophenoxy)-6-methoxybenzo[b]thiophene (500 mg, 1.49 mmol), methyl acrylate (770 mg, 8.95 mmol), and Pd(PPh$_3$)$_2$Cl$_2$ (157 mg, 0.22 mmol) were suspended in DMF (12 mL) and triethylamine (1.039 mL, 7.46 mmol). The reaction was heated for 60 min at 120° C. under microwave irradiation. The reaction mixture was diluted with DCM and water. The organic layer was collected (phase separator) and concentrated to obtain the crude product. The crude material was purified by column chromatography (SiO$_2$, 1-20% EtOAc/Heptane) to afford (E)-methyl 3-(4-((6-methoxybenzo[b]thiophen-3-yl)oxy)phenyl)acrylate (311 mg, 0.91 mmol, 61% yield) as a white solid. $^1$H NMR (400 MHz, CDCl$_3$) δ ppm=1.46 (s, 3H), 3.73 (s, 3H), 6.28 (d, J=16.17 Hz, 1H), 6.59 (s, 1H), 6.90 (dd, J=8.59, 2.02 Hz, 1H), 7.00 (d, J=8.59 Hz, 2H), 7.21 (d, J=2.02 Hz, 1H), 7.37-7.48 (m, 3H), 7.59 (d, J=16.17 Hz, 1H). LC/MS (m/z, MH$^+$): 341.1.

(E)-tert-butyl 3-(4-((6-methoxybenzo[b]thiophen-3-yl)oxy)phenyl)acrylate (Compound 30)

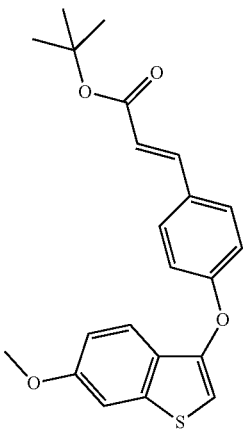 [SMILES: COc1ccc2c(Oc3ccc(/C=C/C(=O)OC(C)(C)C)cc3)csc2c1]

To a microwave vial, 3-(4-bromophenoxy)-6-methoxybenzo[b]thiophene (4 g, 11.93 mmol), tert-butyl acrylate (10.49 mL, 71.6 mmol), and Pd(PPh$_3$)$_2$Cl$_2$ (1.256 g, 1.79 mmol) were suspended in DMF (12 mL) and triethylamine (8.32 mL, 59.7 mmol). The reaction was heated for 60 min at 120° C. under microwave irradiation. The reaction mixture was diluted with DCM and water. The organic layer was collected (phase separator) and concentrated to obtain the crude product. The crude material was purified by column chromatography (SiO$_2$, 1-20% EtOAc/Heptane) to afford (E)-tert-butyl 3-(4-((6-methoxybenzo[b]thiophen-3-yl)oxy)phenyl)acrylate (3 g, 7.84 mmol, 66% yield) as a white solid. $^1$H NMR (CDCl$_3$) δ ppm=7.45-7.63 (m, 4H), 7.27-7.33 (m, 1H), 7.03-7.13 (m, 2H), 6.99 (dd, J=8.8, 2.3 Hz, 1H), 6.66 (s, 1H), 6.30 (d, J=16.2 Hz, 1H), 3.90 (s, 3H), 1.55 (s, 9H).

Intermediates H (E)-tert-butyl 3-(4-((6-methoxy-2-(4-(trifluoromethyl)phenyl)benzo[b]thiophen-3 yl)oxy)phenyl)acrylate (Compound 31)

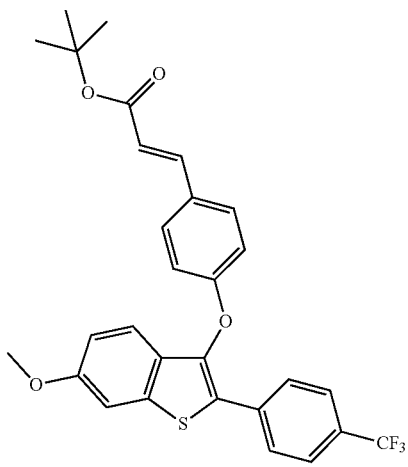 [SMILES: COc1ccc2c(Oc3ccc(/C=C/C(=O)OC(C)(C)C)cc3)c(-c3ccc(C(F)(F)F)cc3)sc2c1]

To a 5 mL microwave vial, added a solution of (E)-tert-butyl 3-(4-((6-methoxybenzo[b]thiophen-3-yl)oxy)phenyl)acrylate (50 mg, 0.13 mmol) in anhydrous DMA (1.5 mL), followed by 1-bromo-4-(trifluoromethyl)benzene (35.3 mg, 0.16 mmol), chloro[2-(dicyclohexylphosphino)-3,6-dimethoxy-2',4',6'-tri-i-propyl-1,1'-biphenyl][2-(2-aminoethyl)phenyl]palladium(II) (BrettPhos palladacycle 1$^{st}$ generation, 10.4 mg, 0.013 mmol), trimethylacetic acid (40.1 mg, 0.392 mmol) and potassium carbonate (54.2 mg, 0.392 mmol). The microwave vial was sealed, purged and back-filled with nitrogen. The reaction mixture subjected to microwave irradiation for 2 h at 150° C. Upon completion the reaction was diluted with EtOAc, and washed with water and brine. The combined organic layer was dried over anhydrous MgSO$_4$, filtered and concentrated in vacuo to give a red brown residue which was purified by column chromatography (SiO$_2$, 0-30% EtOAc/heptane) to afford (E)-tert-butyl 3-(4-((6-methoxy-2-(4-(trifluoromethyl)phenyl)benzo[b]thiophen-3 yl)oxy)phenyl)acrylate (59.4 mg, 0.11 mmol, 86% yield). $^1$H NMR (400 MHz, CD$_3$OD) δ ppm=1.42-1.61 (m, 9H), 3.77-3.98 (m, 3H), 6.31 (d, J=15.66 Hz, 1H), 6.87-7.04 (m, 3H), 7.28 (d, J=9.09 Hz, 1H), 7.46 (d, J=2.53 Hz, 1H), 7.47-7.57 (m, 3H), 7.65 (d, J=8.08 Hz, 2H), 7.89 (d, J=8.08 Hz, 2H). LC/MS (m/z, MH$^+$): 471.40.

(E)-methyl 3-(4-((2-(2-isopropylphenyl)-6-methoxy-benzo[b]thiophen-3-yl)oxy)phenyl)acrylate (Compound 32)

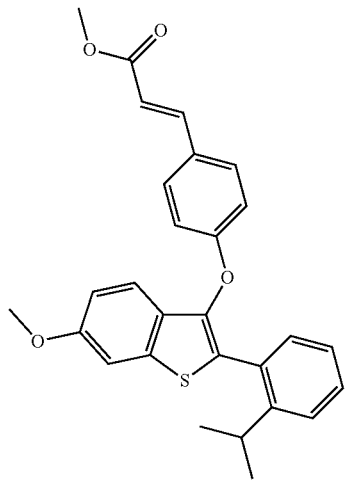 [SMILES: COC(=O)/C=C/c1ccc(Oc2c(-c3ccccc3C(C)C)sc3cc(OC)ccc23)cc1]

To a flask containing (E)-methyl 3-(4-((6-methoxybenzo[b]thiophen-3-yl)oxy)phenyl)acrylate (800 mg, 2.35 mmol) in anhydrous DMA (3.0 mL) was added 1-iodo-2-isopropylbenzene (0.751 mL, 4.70 mmol) followed by chloro[2-(dicyclohexylphosphino)-3,6-dimethoxy-2',4',6'-tri-i-propyl-1,1'-biphenyl][2-(2-aminoethyl)phenyl]palladium(II) (BrettPhos palladacycle 1$^{st}$ generation, 188 mg, 0.24 mmol), trimethylacetic acid (0.818 mL, 7.05 mmol) and potassium carbonate (974 mg, 7.05 mmol). The flask was sealed, purged and back-filled with nitrogen and the resulting mixture was heated to 150° C. for 2 h after which time the reaction was diluted with EtOAc, and washed with water and brine. The combined organic layer was dried over anhydrous MgSO$_4$, filtered and concentrated in vacuo to give a red brown residue which was purified by column chromatography (SiO$_2$, 0-30% EtOAc/heptane) to afford (E)-methyl 3-(4-((2-(2-isopropylphenyl)-6-methoxybenzo[b]thiophen-3-yl)oxy)phenyl)acrylate (675 mg, 1.48 mmol, 63% yield).). $^1$H NMR (400 MHz, CDCl$_3$) δ ppm=7.61 (d, J=15.9 Hz, 1H), 7.42-7.29 (m, 7H), 7.15 (ddd, J=8.1, 5.7, 2.8 Hz, 1H), 6.97 (dd, J=8.8, 2.3 Hz, 1H), 6.91-6.85 (m, 2H), 6.29 (d, J=16.0 Hz, 1H), 3.91 (s, 3H), 3.80 (s, 3H), 3.26 (p, J=6.8 Hz, 1H), 1.19 (d, J=6.9 Hz, 6H). LC/MS (m/z, MH$^+$): 459.0.

The following intermediates H were prepared in a similar fashion to compound 31 using the appropriate intermediates G and the corresponding aryl bromide as starting materials:

| Structure | Name | Physical Data |
| --- | --- | --- |
| ![structure] | (E)-tert-butyl 3-(4-((6-methoxy-2-(o-tolyl)benzo[b]thiophen-3-yl)oxy)phenyl)acrylate (compound 33) | LC/MS (m/z, MH$^+$-C$_4$H$_9$): 417.3 |

| Structure | Name | Physical Data |
|---|---|---|
| 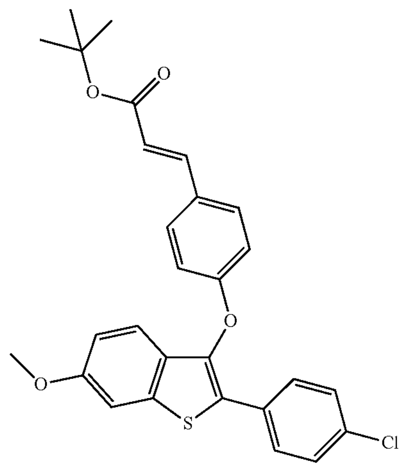 [SMILES: COc1ccc2c(Oc3ccc(/C=C/C(=O)OC(C)(C)C)cc3)c(-c3ccc(Cl)cc3)sc2c1] | (E)-tert-butyl 3-(4-((2-(4-chlorophenyl)-6-methoxybenzo[b]thiophen-3-yl)oxy)phenyl)acrylate (compound 34) | LC/MS (m/z, MH$^+$): 494.4 |
| 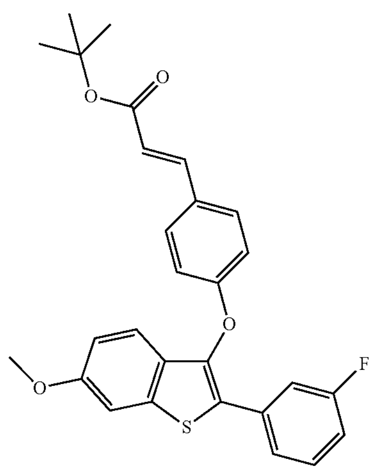 [SMILES: COc1ccc2c(Oc3ccc(/C=C/C(=O)OC(C)(C)C)cc3)c(-c3cccc(F)c3)sc2c1] | (E)-tert-butyl 3-(4-((2-(3-fluorophenyl)-6-methoxybenzo[b]thiophen-3-yl)oxy)phenyl)acrylate (compound 35) | LC/MS (m/z, MH$^+$): 477.6 |
| 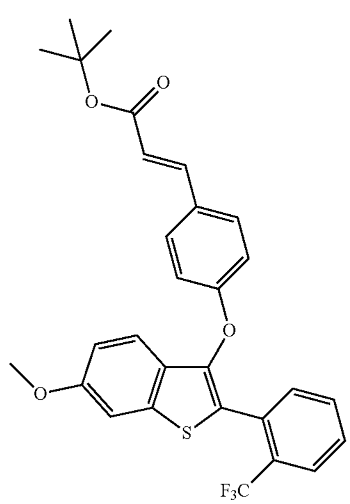 [SMILES: COc1ccc2c(Oc3ccc(/C=C/C(=O)OC(C)(C)C)cc3)c(-c3ccccc3C(F)(F)F)sc2c1] | (E)-tert-butyl 3-(4-((6-methoxy-2-(2-(trifluoromethyl)phenyl)benzo[b]thiophen-3-yl)oxy)phenyl)acrylate (compound 36) | LC/MS (m/z, MH$^+$-C$_4$H$_9$): 471.4 |

| Structure | Name | Physical Data |
|---|---|---|
| 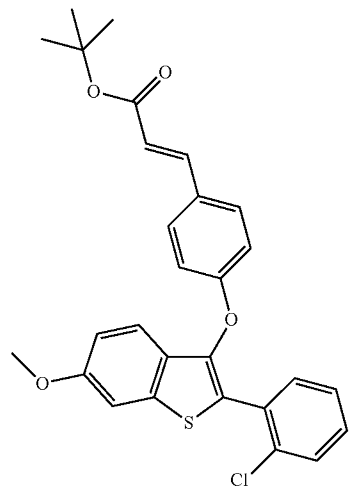 [SMILES: COc1ccc2c(Oc3ccc(/C=C/C(=O)OC(C)(C)C)cc3)c(-c3ccccc3Cl)sc2c1] | (E)-tert-butyl 3-(4-((2-(2-chlorophenyl)-6-methoxybenzo[b]thiophen-3-yl)oxy)phenyl)acrylate (compound 37) | LC/MS (m/z, MH$^+$-C$_4$H$_9$): 437.3 |
| 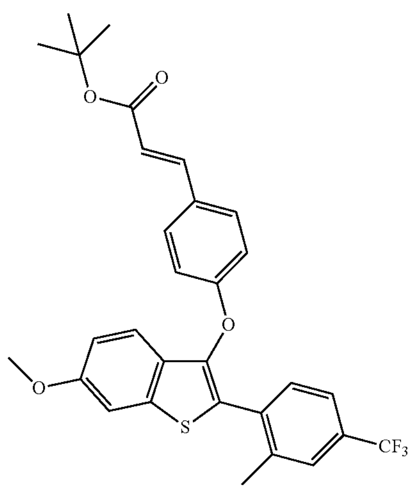 [SMILES: COc1ccc2c(Oc3ccc(/C=C/C(=O)OC(C)(C)C)cc3)c(-c3ccc(C(F)(F)F)cc3C)sc2c1] | (E)-tert-butyl 3-(4-((6-methoxy-2-(2-methyl-4-(trifluoromethyl)phenyl)benzo[b]thiophen-3-yl)oxy)phenyl)acrylate (compound 38) |  |
| 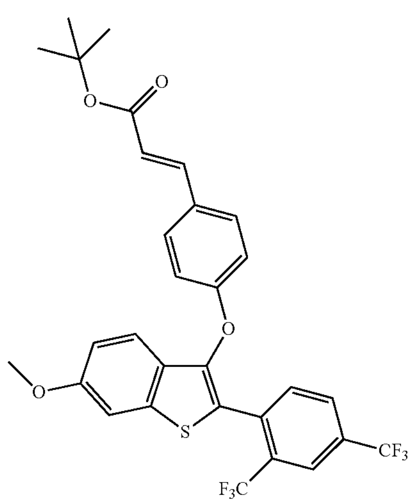 [SMILES: COc1ccc2c(Oc3ccc(/C=C/C(=O)OC(C)(C)C)cc3)c(-c3ccc(C(F)(F)F)cc3C(F)(F)F)sc2c1] | (E)-tert-butyl 3-(4-((2-(2,4-bis(trifluoromethyl)phenyl)-6-methoxybenzo[b]thiophen-3-yl)oxy)phenyl)acrylate (compound 39) |  |

| Structure | Name | Physical Data |
|---|---|---|
| 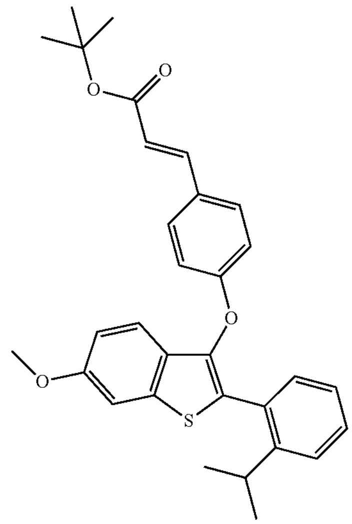 [SMILES: COc1ccc2c(Oc3ccc(/C=C/C(=O)OC(C)(C)C)cc3)c(-c3ccccc3C(C)C)sc2c1] | (E)-tert-butyl 3-(4-((2-(2-isopropylphenyl)-6-methoxybenzo[b]thiophen-3-yl)oxy)phenyl)acrylate (compound 40) | LC/MS (m/z, MH$^+$-C$_4$H$_9$): 445.0 |
| 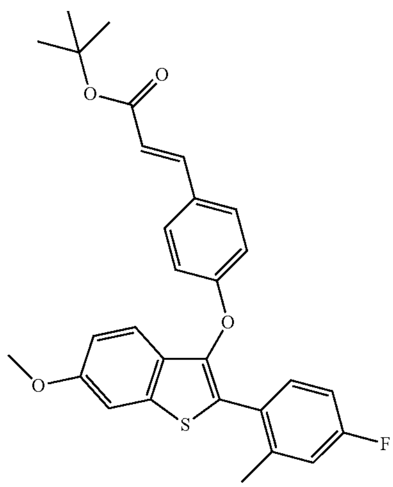 [SMILES: COc1ccc2c(Oc3ccc(/C=C/C(=O)OC(C)(C)C)cc3)c(-c3ccc(F)cc3C)sc2c1] | (E)-tert-butyl 3-(4-((2-(4-fluoro-2-methylphenyl)-6-methoxybenzo[b]thiophen-3-yl)oxy)phenyl)acrylate (compound 41) | LC/MS (m/z, MH$^+$-C$_4$H$_9$): 435.5 |
| 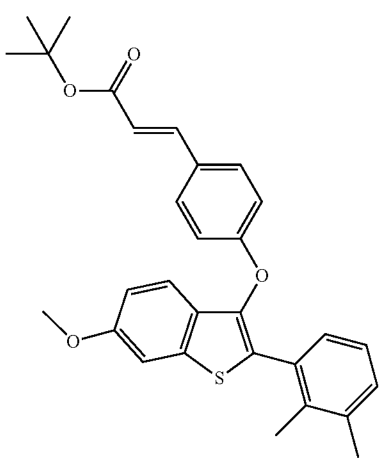 [SMILES: COc1ccc2c(Oc3ccc(/C=C/C(=O)OC(C)(C)C)cc3)c(-c3cccc(C)c3C)sc2c1] | (E)-tert-butyl 3-(4-((2-(2,3-dimethylphenyl)-6-methoxybenzo[b]thiophen-3-yl)oxy)phenyl)acrylate (compound 42) | LC/MS (m/z, MH$^+$-C$_4$H$_9$): 431.3 |

| Structure | Name | Physical Data |
|---|---|---|
| 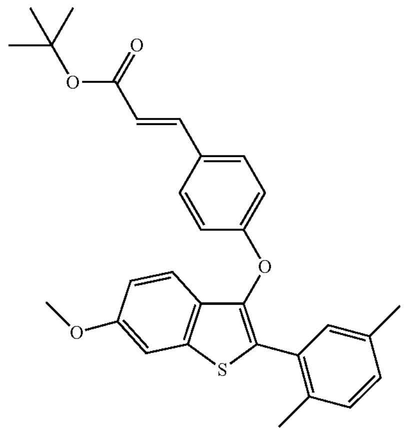 [SMILES: COc1ccc2c(Oc3ccc(/C=C/C(=O)OC(C)(C)C)cc3)c(-c3cc(C)ccc3C)sc2c1] | (E)-tert-butyl 3-(4-((2-(2,5-dimethylphenyl)-6-methoxybenzo[b]thiophen-3-yl)oxy)phenyl)acrylate (compound 43) | LC/MS (m/z, MH$^+$-C$_4$H$_9$): 431.4 |
| 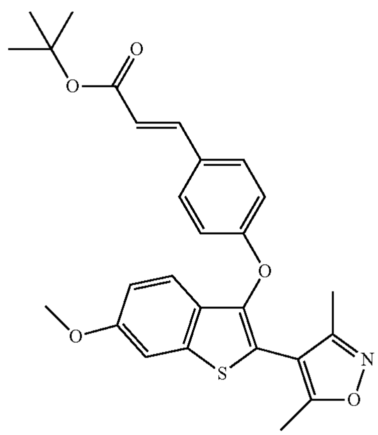 [SMILES: COc1ccc2c(Oc3ccc(/C=C/C(=O)OC(C)(C)C)cc3)c(-c3c(C)noc3C)sc2c1] | (E)-tert-butyl 3-(4-((2-(3,5-dimethylisoxazol-4-yl)-6-methoxybenzo[b]thiophen-3-yl)oxy)phenyl)acrylate (compound 44) | LC/MS (m/z, MH$^+$-C$_4$H$_9$): 422.3 |
| 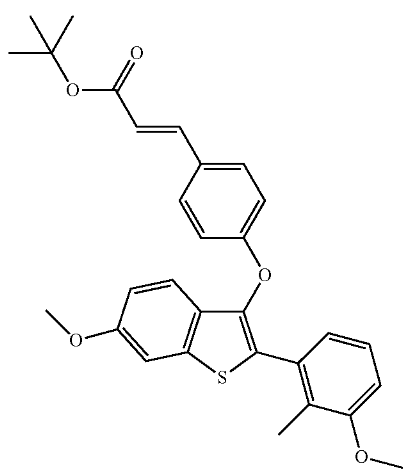 | (E)-tert-butyl 3-(4-((6-methoxy-2-(3-methoxy-2-methylphenyl)benzo[b]thiophen-3-yl)oxy)phenyl)acrylate (compound 45) | LC/MS (m/z, MH$^+$-C$_4$H$_9$): 448.3 |

-continued

| Structure | Name | Physical Data |
|---|---|---|
| 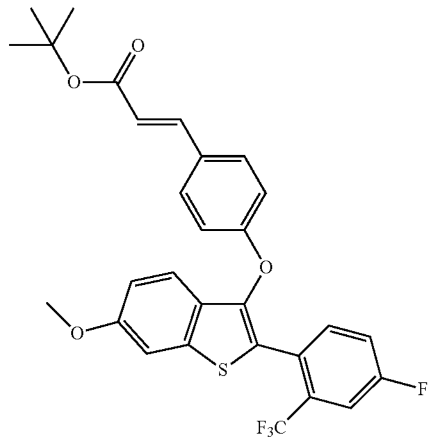 [SMILES: COc1ccc2c(Oc3ccc(/C=C/C(=O)OC(C)(C)C)cc3)c(-c3ccc(F)cc3C(F)(F)F)sc2c1] | (E)-tert-butyl 3-(4-((2-(4-fluoro-2-(trifluoromethyl)phenyl)-6-methoxybenzo[b]thiophen-3-yl)oxy)phenyl)acrylate (compound 46) | LC/MS (m/z, MH$^+$-C$_4$H$_9$): 489.3 |
| 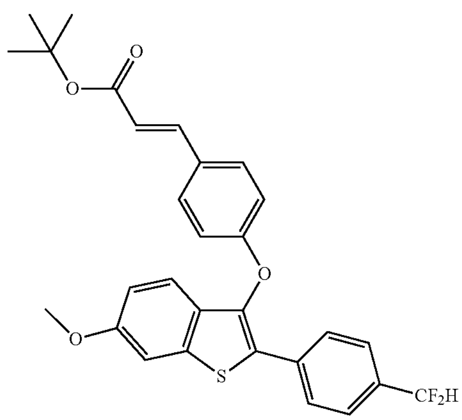 [SMILES: COc1ccc2c(Oc3ccc(/C=C/C(=O)OC(C)(C)C)cc3)c(-c3ccc(C(F)F)cc3)sc2c1] | (E)-tert-butyl 3-(4-((2-(4-(difluoromethyl)phenyl)-6-methoxybenzo[b]thiophen-3-yl)oxy)phenyl)acrylate (compound 47) | LC/MS (m/z, M+NH$^+$4): 526.4 |
| 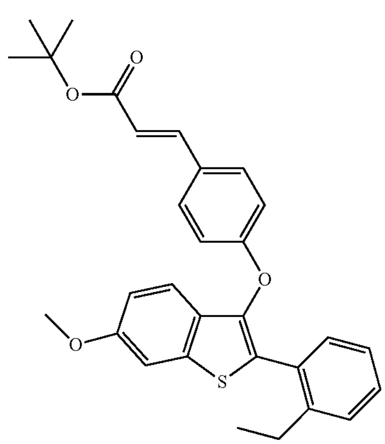 [SMILES: CCc1ccccc1-c1sc2cc(OC)ccc2c1Oc1ccc(/C=C/C(=O)OC(C)(C)C)cc1] | (E)-tert-butyl 3-(4-((2-(2-ethylphenyl)-6-methoxybenzo[b]thiophen-3-yl)oxy)phenyl)acrylate (compound 48) | LC/MS (m/z, MH$^+$-C$_4$H$_9$): 431.4 |

| Structure | Name | Physical Data |
|---|---|---|
| 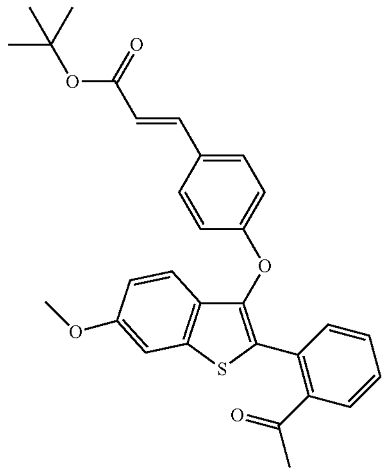 [SMILES: COc1ccc2c(Oc3ccc(/C=C/C(=O)OC(C)(C)C)cc3)c(-c3ccccc3C(C)=O)sc2c1] | (E)-tert-butyl 3-(4-((2-(2-acetylphenyl)-6-methoxybenzo[b]thiophen-3-yl)oxy)phenyl)acrylate (compound 49) | LC/MS (m/z, MH$^+$-C$_4$H$_9$): 445.3 |
| 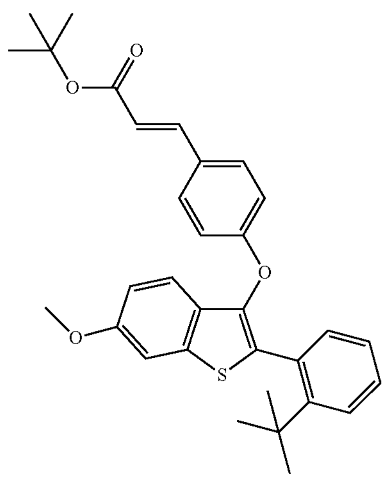 [SMILES: COc1ccc2c(Oc3ccc(/C=C/C(=O)OC(C)(C)C)cc3)c(-c3ccccc3C(C)(C)C)sc2c1] | (E)-tert-butyl 3-(4-((2-(2-(tert-butyl)phenyl)-6-methoxybenzo[b]thiophen-3-yl)oxy)phenyl)acrylate (compound 50) | |
| 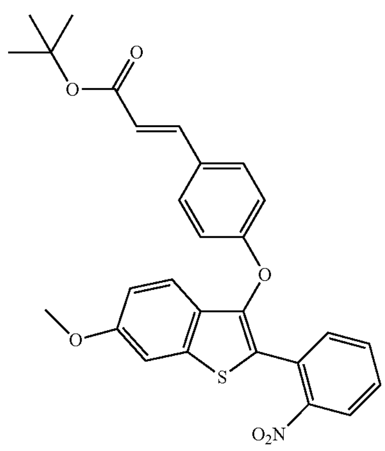 [SMILES: COc1ccc2c(Oc3ccc(/C=C/C(=O)OC(C)(C)C)cc3)c(-c3ccccc3[N+](=O)[O-])sc2c1] | (E)-tert-butyl 3-(4-((6-methoxy-2-(2-nitrophenyl)benzo[b]thiophen-3-yl)oxy)phenyl)acrylate (compound 51) | LC/MS (m/z, MH$^+$-C$_4$H$_9$): 448.3 |

-continued

| Structure | Name | Physical Data |
|---|---|---|
| 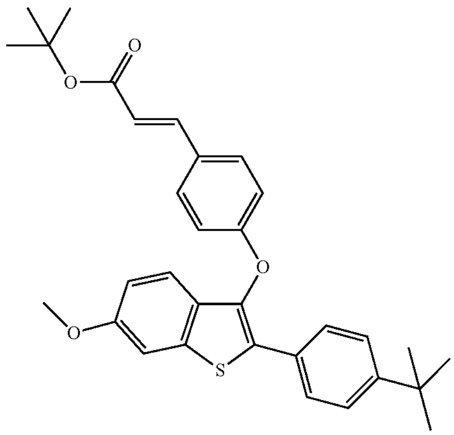 [SMILES: COc1ccc2c(Oc3ccc(/C=C/C(=O)OC(C)(C)C)cc3)c(-c3ccc(C(C)(C)C)cc3)sc2c1] | (E)-tert-butyl 3-(4-((2-(4-(tert-butyl)phenyl)-6-methoxybenzo[b]thiophen-3-yl)oxy)phenyl)acrylate (compound 52) | LC/MS (m/z, M-H): 513.6 |
| 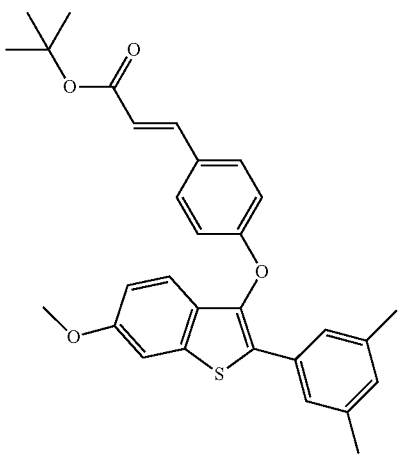 [SMILES: COc1ccc2c(Oc3ccc(/C=C/C(=O)OC(C)(C)C)cc3)c(-c3cc(C)cc(C)c3)sc2c1] | (E)-tert-butyl 3-(4-((2-(3,5-dimethylphenyl)-6-methoxybenzo[b]thiophen-3-yl)oxy)phenyl)acrylate (compound 53) | LC/MS (m/z, MH$^+$): 487.5 |
| 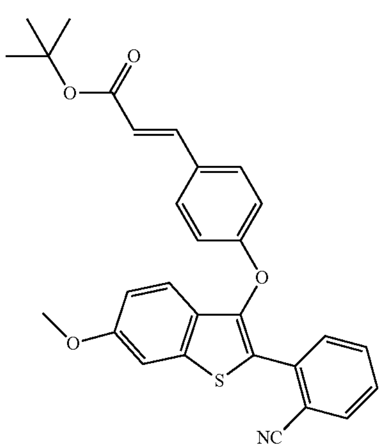 [SMILES: COc1ccc2c(Oc3ccc(/C=C/C(=O)OC(C)(C)C)cc3)c(-c3ccccc3C#N)sc2c1] | (E)-tert-butyl 3-(4-((2-(2-isocyanophenyl)-6-methoxybenzo[b]thiophen-3-yl)oxy)phenyl)acrylate (compound 54) | LC/MS (m/z, MH$^+$): 484.4 |

| Structure | Name | Physical Data |
|---|---|---|
| 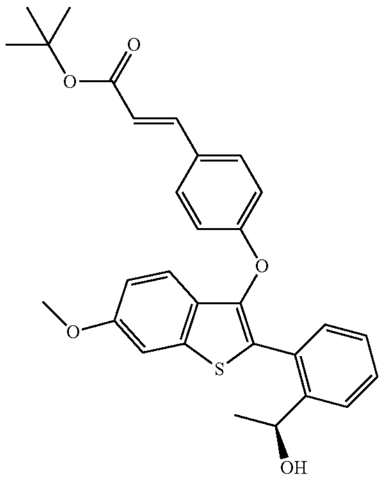 [SMILES: COc1ccc2c(Oc3ccc(/C=C/C(=O)OC(C)(C)C)cc3)c(-c3ccccc3[C@H](C)O)sc2c1] | (S,E)-tert-butyl 3-(4-((2-(2-(1-hydroxyethyl)phenyl)-6-methoxybenzo[b]thiophen-3-yl)oxy)phenyl)acrylate (compound 55) | |

Intermediates K tert-butyl 3-(4-((6-methoxy-2-(4-methoxyphenyl)benzo[b]thiophen-3-yl)oxy)phenyl)propanoate (Compound 56)

Intermediates L (E)-2-(4-((2-(4-fluoro-2-methylphenyl)-6-methoxybenzo[b]thiophen-3-yl)oxy)styryl)-5-methyl-1,3,4-oxadiazole (Compound 57)

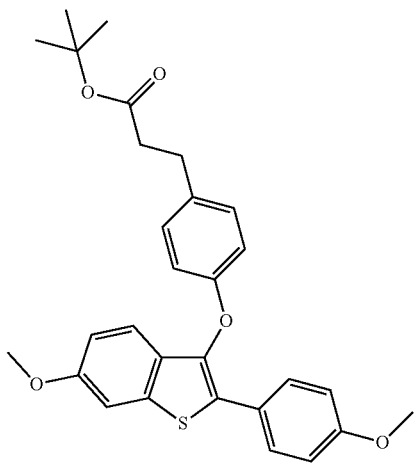

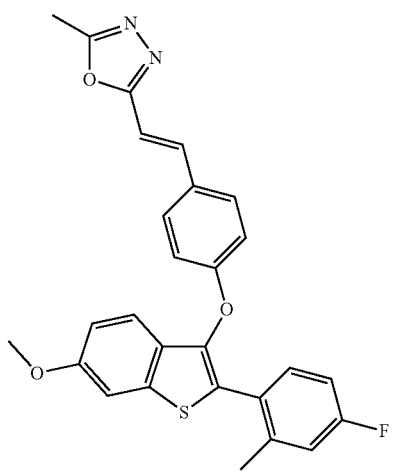 [SMILES: COc1ccc2c(Oc3ccc(/C=C/c4nnc(C)o4)cc3)c(-c3ccc(F)cc3C)sc2c1]

To a solution of (E)-tert-butyl 3-(4-((6-methoxy-2-(4-methoxyphenyl)benzo[b]thiophen-3-yl)oxy)phenyl)acrylate (27 mg, 0.06 mmol) in 4:1 MeOH:DCM (2.5 mL) was added palladium on carbon (10% wt., 0.59 mg, 5.53 μmol). The reaction was stirred at room temperature under a hydrogen balloon for 12 h after which the reaction was purged with nitrogen and filtered through Celite™. The remaining palladium was washed with DCM (30 mL) and the resulting solution was concentrated in vacuo to afford tert-butyl 3-(4-((6-methoxy-2-(4-methoxyphenyl)benzo[b]thiophen-3-yl)oxy)phenyl)propanoate (27 mg, 0.06 mmol, 100% yield) which was used without further purification. LC/MS (m/z, MH+): 491.3.

To a 30 mL vial, (E)-3-(4-((2-(4-fluoro-2-methylphenyl)-6-methoxybenzo[b]thiophen-3-yl)oxy)phenyl)acrylic acid (100 mg, 0.230 mmol) and acetohydrazide (85 mg, 1.151 mmol) were dissolved in POCl₃ (2 mL, 21.46 mmol) and the mixture was heated to 100° C. for 18 h. The reaction mixture was cooled to room temperature poured into ice. The solution was quenched with sat. sodium bicarb and diluted with DCM. The organic layer was collected (phase separator) and concentrated to provide the crude material. The crude product was purified by reverse phase HPLC (acidic condition, 0.1% TFA in 30-100% CH₃CN/H₂O) to afford (E)-2-(4-((2-fluoro-2-methylphenyl)-6-methoxybenzo[b]thiophen-3-yl)oxy)styryl)-5-methyl-1,3,4-oxadiazole (83 mg, 0.176 mmol, 76% yield) as a white solid. $^1$H NMR (400 MHz, CD$_3$OD) δ ppm=2.38 (s, 3H), 2.57 (s, 3H), 3.90 (s, 3H), 6.81-6.98 (m, 4H), 6.98-7.08 (m, 2H), 7.28-7.42 (m, 2H), 7.44-7.58 (m, 4H). LC/MS (m/z, MH$^+$): 473.4.

The following intermediates were prepared in a similar fashion to intermediates above using the appropriate starting materials:

C. under microwave irradiation. The reaction mixture was concentrated and the crude product was purified by reverse phase HPLC (neutral condition, 0.1% TFA in 20-100% CH$_3$CN/H$_2$O) to afford (E)-3-(4-((2-(4-fluoro-2-methylphenyl)-6-methoxybenzo[b]thiophen-3-yl)oxy)styryl)-5-methyl-4H-1,2,4-triazole (15 mg, 0.032 mmol, 65% yield) as a white solid. LC/MS (m/z, MH$^+$): 472.1.

| Structure | Name | Physical Data |
|---|---|---|
| 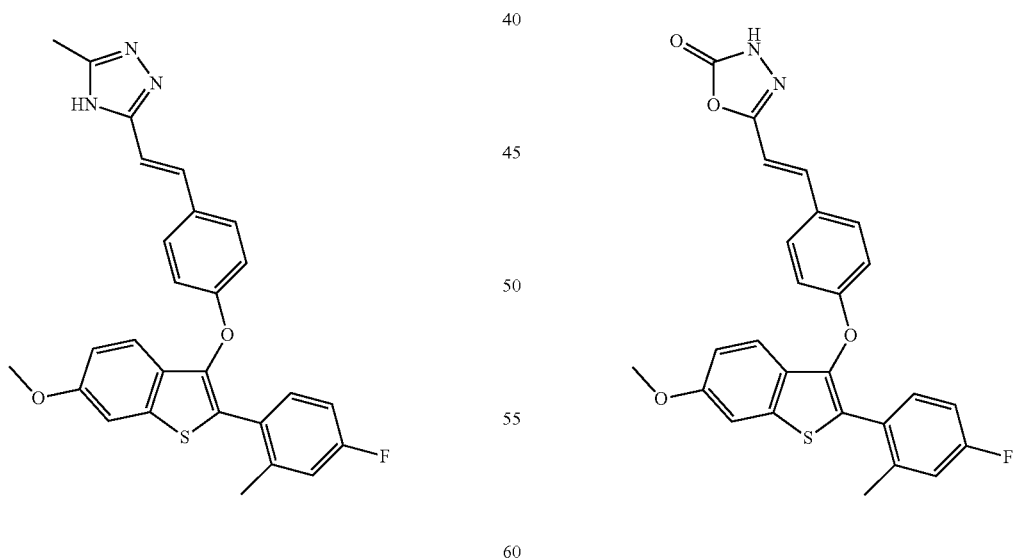 | (E)-2-(4-((2-(4-fluoro-2-methylphenyl)-6-methoxybenzo[b]thiophen-3-yl)oxy)styryl)-5-propyl-1,3,4-oxadiazole (compound 58) | LC/MS (m/z, MH$^+$): 501.0 |

(E)-3-(4-((2-(4-fluoro-2-methylphenyl)-6-methoxy-benzo[b]thiophen-3-yl)oxy)styryl)-5-methyl-4H-1,2,4-triazole (Compound 59)

(E)-5-(4-((2-(4-fluoro-2-methylphenyl)-6-methoxy-benzo[b]thiophen-3-yl)oxy)styryl)-1,3,4-oxadiazol-2(3H)-one (Compound 60)

To a microwave vial, (E)-2-(4-((2-(4-fluoro-2-methylphenyl)-6-methoxybenzo[b]thiophen-3-yl)oxy)styryl)-5-methyl-1,3,4-oxadiazole (23 mg, 0.049 mmol) and ammonium trifluoroacetate (128 mg, 0.973 mmol) were suspended in toluene (2 mL). The reaction was heated for 18 h at 180°

Step 1: To a 30 mL screw cap vial, (E)-3-(4-((2-(4-fluoro-2-methylphenyl)-6-methoxybenzo[b]thiophen-3-yl)oxy)phenyl)acrylic acid (40 mg, 0.092 mmol) was dissolved in DMF (1 mL). The vial was charged with hydrazine (5.90 mg, 0.184 mmol), HATU (52.5 mg, 0.138 mmol), and DIEA (0.048 mL, 0.276 mmol). The reaction mixture was stirred for 10 min at room temperature. The reaction was quenched with sat. aq. NH₄Cl and diluted with DCM. The organic phase was collected (phase separator) and concentrated by vacuum to afford to crude product. The crude material was purified by column chromatography (SiO₂, 1-20% MeOH/DCM) to afford (E)-5-(4-((2-(4-fluoro-2-methylphenyl)-6-methoxybenzo[b]thiophen-3-yl)oxy)styryl)-1,3,4-oxadiazol-2(3H)-one (38 mg, 0.085 mmol, 92% yield). LC/MS (m/z, MH⁺): 449.1

Step 2: To a 30 mL screw cap vial, (E)-3-(4-((2-(4-fluoro-2-methylphenyl)-6-methoxybenzo[b]thiophen-3-yl)oxy)phenyl)acrylohydrazide (38 mg, 0.085 mmol) was dissolved in THF (2 mL). The vial was charged with 1,1'-carbonyldiimidazole (16.49 mg, 0.102 mmol) and the reaction was stirred at room temperature for 1 h. The reaction mixture was acidified with 6 N HCl which caused a precipitate to form. The mixture was diluted with DCM to dissolve the precipitate. The organic phase was collected (phase separator) and concentrated to afford (E)-5-(4-((2-(4-fluoro-2-methylphenyl)-6-methoxybenzo[b]thiophen-3-yl)oxy)styryl)-1,3,4-oxadiazol-2(3H)-one (31 mg, 0.065 mmol, 77% yield) as an off white solid which was used without further purification. LC/MS (m/z, M−H): 473.0

(E)-3-(4-((2-(4-fluoro-2-methylphenyl)-6-methoxybenzo[b]thiophen-3-yl)oxy)phenyl)-N-((tetrahydro-2H-pyran-2-yl)oxy)acrylamide (Compound 61)

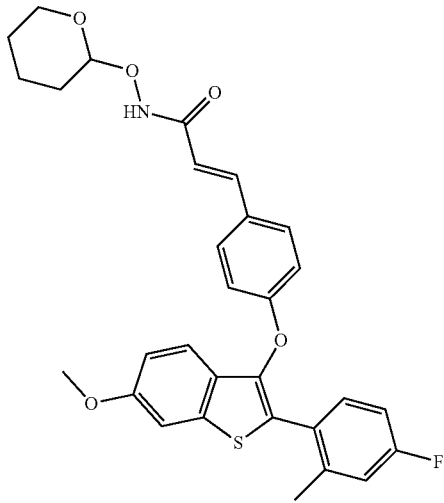 [SMILES: COc1ccc2c(Oc3ccc(/C=C/C(=O)NOC4CCCCO4)cc3)c(-c3ccc(F)cc3C)sc2c1]

To a 30 mL screw cap vial, (E)-3-(4-((2-(4-fluoro-2-methylphenyl)-6-methoxybenzo[b]thiophen-3-yl)oxy)phenyl)acrylic acid (50 mg, 0.115 mmol) was dissolved in DMF (2 mL). The vial was charged with O-(tetrahydro-2H-pyran-2-yl)hydroxylamine (27.0 mg, 0.230 mmol), HATU (65.6 mg, 0.173 mmol), and DIEA (0.060 mL, 0.345 mmol). The reaction mixture was stirred for 30 min at room temperature. The reaction was quenched with sat. NH₄Cl and diluted with DCM. The organic phase was collected (phase separator) and concentrated by vacuum to afford to crude product. The crude material was purified by column chromatography (SiO₂, 1-80% Heptanes/EtOAc) to afford (E)-3-(4-((2-(4-fluoro-2-methylphenyl)-6-methoxybenzo[b]thiophen-3-yl)oxy)phenyl)-N-((tetrahydro-2H-pyran-2-yl)oxy)acrylamide (53 mg, 0.099 mmol, 86% yield). ¹H NMR (400 MHz, CD₃OD) δ ppm=1.48-1.73 (m, 3H), 1.73-1.96 (m, 3H), 2.36 (s, 3H), 3.56-3.70 (m, 1H), 3.89 (s, 3H), 3.98-4.14 (m, 1H), 4.96 (br. s., 1H), 6.35 (d, J=15.66 Hz, 1H), 6.79-6.95 (m, 3H), 6.95-7.07 (m, 2H), 7.26-7.39 (m, 2H), 7.39-7.48 (m, 3H), 7.52 (d, J=16.17 Hz, 1H). LC/MS (m/z, MH⁺): 534.1.

Intermediates M 3-(4-bromophenoxy)-6-methoxy-2-(4-methoxyphenyl)benzo[b]thiophene 1-oxide (Compound 62)

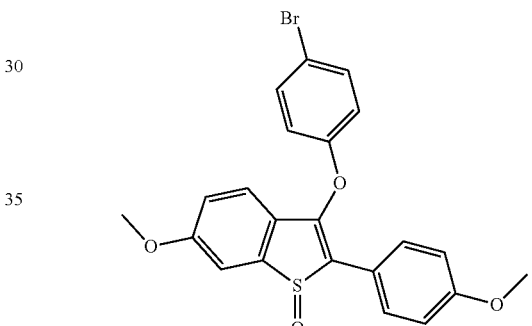

To a solution of 4-bromophenol (469 mg, 2.71 mmol) in DMF (3 mL) was added sodium hydride (60% suspension in oil, 108 mg, 2.71 mmol), the resulting mixture was allowed to stir for 10 min at room temperature. To the solution was added 3-bromo-6-methoxy-2-(4-methoxyphenyl)benzo[b]thiophene 1-oxide (900 mg, 2.46 mmol) as a solid. The reaction was heated to 80° C. for 18 h. Upon completing the reaction was cooled to room temperature, quenched with water and diluted with DCM. The organic phase was collected (phase separator) and concentrated in vacuo to afford the crude product. The crude material was purified by column chromatography (SiO₂, 0-60% EtOAc/Heptane) to afford 3-(4-bromophenoxy)-6-methoxy-2-(4-methoxyphenyl)benzo[b]thiophene 1-oxide (980 mg, 2.14 mmol, 87% yield) as a yellow solid. ¹H NMR (400 MHz, CDCl₃) δ ppm=7.70-7.78 (m, 2H), 7.53 (d, J=2.02 Hz, 1H), 7.41 (d, J=8.59 Hz, 2H), 6.90-7.06 (m, 6H), 3.91 (s, 3H), 3.83 (s, 3H).

The following intermediates were prepared in a similar fashion to intermediates above using the appropriate starting materials:

| Structure | Name | Physical Data |
|---|---|---|
| 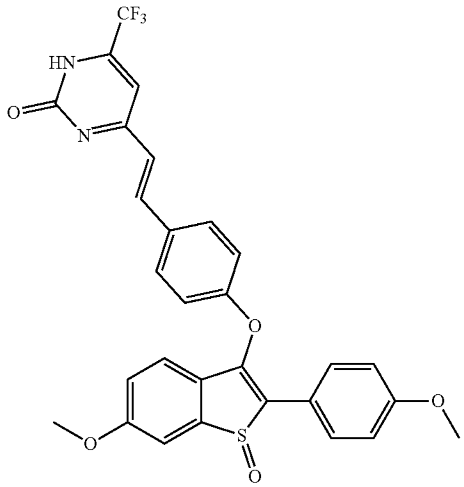 [SMILES: COc1ccc(C2=C(Oc3ccc(/C=C/c4cc(C(F)(F)F)[nH]c(=O)n4)cc3)c3ccc(OC)cc3S2=O)cc1] | (E)-4-(4-((6-methoxy-2-(4-methoxyphenyl)-1-oxidobenzo[b]thiophen-3-yl)oxy)styryl)-6-(trifluoromethyl)pyrimidin-2(1H)-one (compound 63) | $^1$H NMR (400 MHz, CDCl$_3$) δ ppm = 7.86 (d, J = 16.17 Hz, 1H), 7.72-7.80 (m, 2H), 7.58-7.66 (m, J = 8.59 Hz, 2H), 7.56 (d, J = 2.53 Hz, 1H), 7.13-7.21 (m, J = 9.09 Hz, 2H), 7.05-7.11 (m, 1H), 6.90-7.01 (m, 3H), 6.79-6.90 (m, 2H), 3.92 (s, 3H), 3.83 (s, 3H) |
| 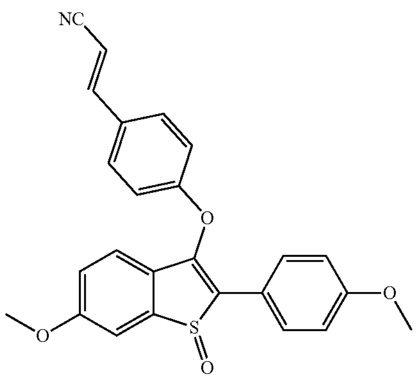 | (E)-3-(4-((2-(4-fluoro-2-methylphenyl)-6-methoxy-1-oxidobenzo[b]thiophen-3-yl)oxy)phenyl)acrylonitrile (compound 64) | $^1$H NMR (400 MHz, CDCl$_3$) δ ppm = 7.46 (d, J = 2.53 Hz, 1H), 7.13-7.27 (m, 5H), 6.86-6.99 (m, 3H), 6.67-6.85 (m, 2H), 5.64 (d, J = 16.67 Hz, 1H), 3.83 (s, 3H), 2.24 (s, 3H) |

Intermediates N 3-(4-bromophenoxy)-6-methoxy-2-(4-methoxyphenyl)benzo[b]thiophene (Compound 65)

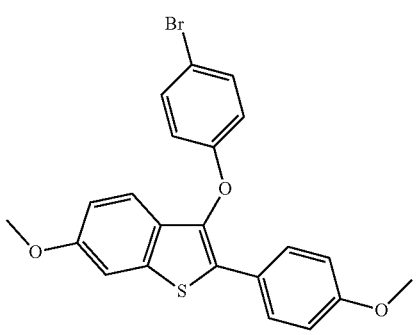

A solution of 3-(4-bromophenoxy)-6-methoxy-2-(4-methoxyphenyl)benzo[b]thiophene 1-oxide (970 mg, 2.12 mmol) in THF (5 mL) was cooled to 0° C. To the cooled solution was added LAH (129 mg, 3.39 mmol) in one portion. The reaction mixture was stirred at 0° C. for 30 min after which the mixture was poured into 1 M aq. NaHSO$_4$ solution and extracted with DCM. The organic layer was collected (phase separator) and concentrated in vacuo to afford the crude product which was purified by column chromatography (SiO$_2$, 0-30% EtOAc/Heptane) to afford 3-(4-bromophenoxy)-6-methoxy-2-(4-methoxyphenyl) benzo[b]thiophene (850 mg, 1.93 mmol, 91% yield) as a white solid. $^1$H NMR (400 MHz, CDCl$_3$) δ ppm=3.83 (s, 3H), 3.90 (s, 3H), 6.80-6.99 (m, 5H), 7.22-7.32 (m, 2H), 7.32-7.44 (m, 2H), 7.65 (d, J=9.09 Hz, 2H).

The following intermediates were prepared in a similar fashion to intermediates above using the appropriate starting materials:

| Structure | Name | Physical Data |
|---|---|---|
| 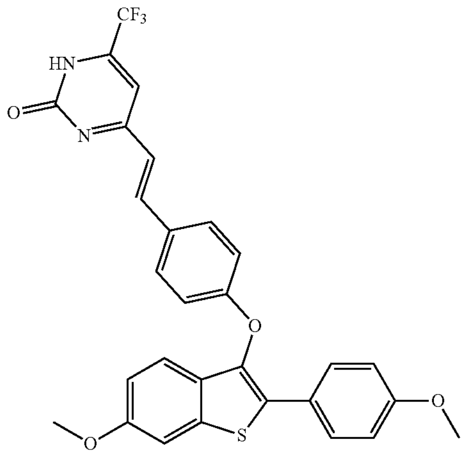 [SMILES: COc1ccc(-c2sc3cc(OC)ccc3c2Oc2ccc(/C=C/c3cc(C(F)(F)F)[nH]c(=O)n3)cc2)cc1] | (E)-4-(4-((6-methoxy-2-(4-methoxyphenyl)benzo[b]thiophen-3-yl)oxy)styryl)-6-(trifluoromethyl)pyrimidin-2(1H)-one (compound 66) | LC/MS (m/z, MH+): 551.4 |
| 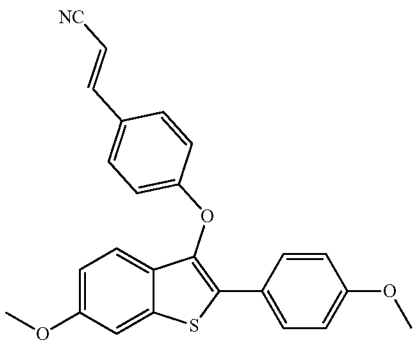 | (E)-3-(4-((2-(4-fluoro-2-methylphenyl)-6-methoxybenzo[b]thiophen-3-yl)oxy)phenyl)acrylonitrile (compound 67) | $^1$H NMR (400 MHz, CDCl$_3$) δ ppm = 7.21-7.39 (m, 6H), 6.78-7.01 (m, 5H), 5.68 (d, J = 16.67 Hz, 1H), 3.89 (s, 3H), 2.35 (s, 3H) |

Intermediates O

3-(4-bromophenoxy)-2-(4-hydroxyphenyl)benzo[b]thiophen-6-ol (Compound 68)

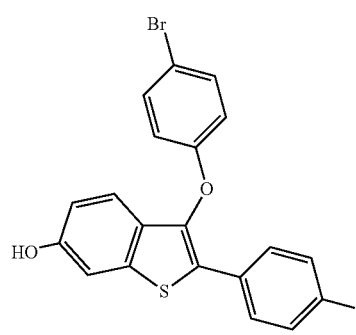

To a 30 mL vial containing 3-(4-bromophenoxy)-6-methoxy-2-(4-methoxyphenyl)benzo[b]thiophene (100 mg, 0.23 mmol) in DCM (1 mL) was added BBr$_3$ (1 M in hexanes, 0.680 mL, 0.68 mmol) and the reaction mixture was stirred for 1 h at room temperature. Upon completion the reaction was quenched with 4 mL MeOH and stirred for 10 min. The mixture was the concentrated in vacuo onto silica gel and the crude material was purified by column chromatography (SiO$_2$, 1-100% EtOAc/Heptane) to afford 3-(4-bromophenoxy)-2-(4-hydroxyphenyl)benzo[b]thiophen-6-ol (72 mg, 0.17 mmol, 77% yield) as a white solid.

$^1$H NMR (400 MHz, CD$_3$OD) δ ppm=7.47-7.57 (m, 2H), 7.35-7.45 (m, 2H), 7.20 (d, J=2.02 Hz, 1H), 7.16 (d, J=8.59 Hz, 1H), 6.73-6.90 (m, 5H).

Intermediates P

(E)-tert-butyl 3-(4-((6-methoxy-2-(4-methoxyphenyl)benzo[b]thiophen-3-yl)oxy)phenyl)acrylate (Compound 69)

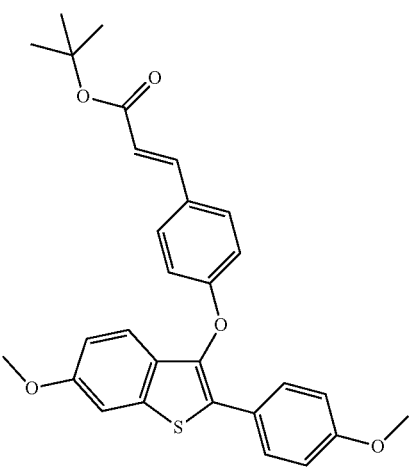

To a solution of 3-(4-bromophenoxy)-6-methoxy-2-(4-methoxyphenyl)benzo[b]thiophene (79 mg, 0.18 mmol) in DMF (1.7 mL) was added triethylamine (0.125 mL, 0.90 mmol) followed by tert-butyl acrylate (0.184 mL, 1.25 mmol) and Pd(PPh$_3$)$_2$Cl$_2$ (18.9 mg, 0.03 mmol). The mixture was then subjected to microwave irradiation for 1 h at 120° C. after which the reaction was diluted with water (15 mL) and extracted with EtOAc (4×10 mL). The combined organic layers were washed with brine (30 mL), passed through a phase separator to remove water and concentrated in vacuo to give the crude product as an orange oil which was purified by column chromatography (SiO$_2$, 0-50% EtOAc/Heptane) to give (E)-tert-butyl 3-(4-((6-methoxy-2-(4-methoxyphenyl)benzo[b]thiophen-3-yl)oxy)phenyl)acrylate as a pale yellow oil (55 mg, 0.11 mmol, 63% yield). $^1$H NMR (400 MHz, CDCl$_3$) δ ppm=1.44 (s, 9H), 3.71 (s, 3H), 3.78 (s, 3H), 6.13 (d, J=15.66 Hz, 1H), 6.76-6.83 (m, 3H), 6.86 (m, J=8.59 Hz, 2H), 7.14-7.19 (m, 2H), 7.31 (m, J=8.59 Hz, 2H), 7.42 (d, J=16.17 Hz, 1H), 7.54 (d, J=8.59 Hz, 2H).

(E)-4-(4-((6-methoxy-2-(4-methoxyphenyl)benzo[b]thiophen-3-yl)oxy)styryl)-1H-imidazole (Compound 70)

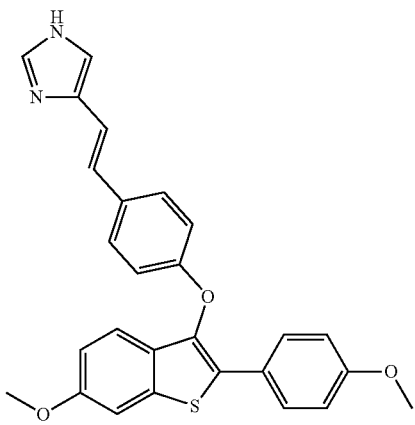

To a microwave vial, 3-(4-bromophenoxy)-6-methoxy-2-(4-methoxyphenyl)benzo[b]thiophene (50 mg, 0.113 mmol) was dissolved in DMF (2 mL) and triethyl amine (0.474 mL, 3.40 mmol). To the solution was added tert-butyl 4-vinyl-1H-imidazole-1-carboxylate (66.0 mg, 0.340 mmol) and Pd(PPh$_3$)$_2$Cl$_2$ (7.95 mg, 0.011 mmol). The system was flushed with nitrogen and heated at 150° C. for 1 h under microwave radiation. The mixture was cooled to room temperature and diluted with DCM and sat. NH4Cl. The organic layer was collected (phase separator) and concentrated onto silica gel and the material was purified by column chromatography (SiO2, 0-30% DCM/MeOH) to afford (E)-4-(4-((6-methoxy-2-(4-methoxyphenyl)benzo[b]thiophen-3-yl)oxy)styryl)-1H-imidazole (41 mg, 0.090 mmol, 80% yield) as a white solid. $^1$H NMR (400 MHz, CD$_3$OD) δ 8.78 (d, J=1.52 Hz, 1H), 7.51-7.62 (m, 2H), 7.46-7.51 (m, 1H), 7.39 (d, J=9.09 Hz, 2H), 7.32 (d, J=2.53 Hz, 1H), 7.15 (d, J=9.09 Hz, 1H), 7.08 (d, J=16.67 Hz, 1H), 6.76-6.95 (m, 6H), 3.77 (s, 3H), 3.69 (s, 3H).

Intermediates Q (E)-methyl 3-(4-((6-methoxy-2-(4-methoxyphenyl)-1-oxidobenzo[b]thiophen-3-yl)oxy)phenyl)acrylate (Compound 71)

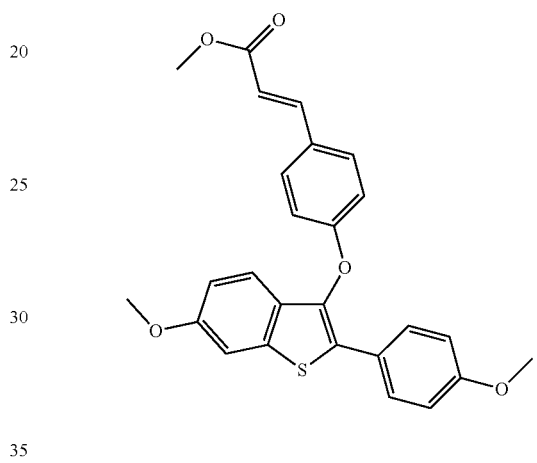

To a solution of (E)-methyl 3-(4-hydroxyphenyl)acrylate (190 mg, 1.07 mmol) in DMF (5 mL) was added sodium hydride (60% suspension in oil, 42.7 mg, 1.07 mmol). The resulting mixture was allowed to stir for 10 min at room temperature after which 3-bromo-6-methoxy-2-(4-methoxyphenyl)benzo[b]thiophene 1-oxide (300 mg, 0.82 mmol) was added, as a solid. The reaction was heated to 80° C. for 18 h and upon completion was cooled to room temperature, quenched with water and diluted with DCM. The organic phase was collected (phase separator) and concentrated in vacuo to afford the crude product which was purified by column chromatography (SiO$_2$, 0-80% EtOAc/Heptane) to afford (E)-methyl 3-(4-((6-methoxy-2-(4-methoxyphenyl)-1-oxidobenzo[b]thiophen-3-yl)oxy)phenyl)acrylate (370 mg, 0.80 mmol, 97% yield) as a yellow solid. $^1$H NMR (400 MHz, CDCl$_3$) δ ppm=7.75 (d, J=9.09 Hz, 2H), 7.65 (d, J=15.66 Hz, 1H), 7.54 (d, J=2.02 Hz, 1H), 7.43-7.52 (m, J=9.09 Hz, 2H), 7.07-7.16 (m, J=8.59 Hz, 2H), 6.98-7.07 (m, 1H), 6.93 (d, J=9.09 Hz, 3H), 6.35 (d, J=16.17 Hz, 1H), 3.91 (s, 3H), 3.82 (d, J=1.52 Hz, 6H). LC/MS (m/z, MH$^+$): 463.4.

The following intermediates were prepared in a similar fashion to intermediates above using the appropriate starting materials:

| Structure | Name | Physical Data |
|---|---|---|
| 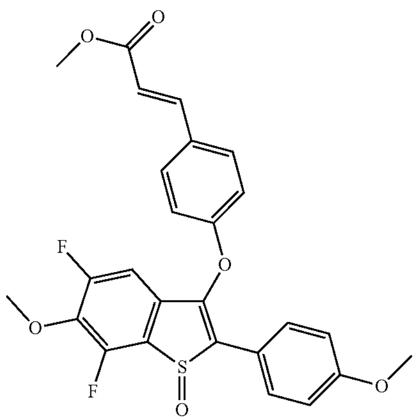 | (E)-methyl 3-(4-((5,7-difluoro-6-methoxy-2-(4-methoxyphenyl)-1-oxidobenzo[b]thiophen-3-yl)oxy)phenyl)acrylate (compound 72) | $^1$H NMR (400 MHz, CDCl$_3$) δ ppm = 7.62 (d, J = 16.17 Hz, 1H), 7.40-7.58 (m, 4H), 7.03-7.19 (m, 2H), 6.92-7.03 (m, 2H), 6.83 (d, J = 8.08 Hz, 1H), 6.34 (d, J = 16.17 Hz, 1H), 3.92 (s, 3H), 3.89 (s, 3H), 3.80 (s, 3H) |
| 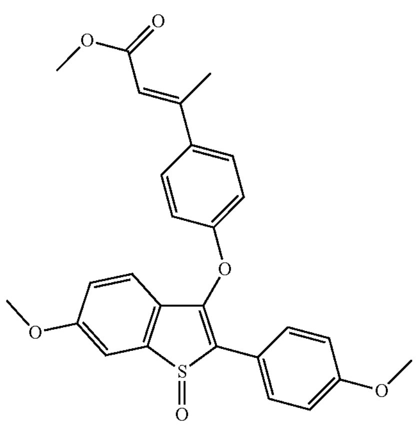 | (E) Methyl-3-(4-((6-methoxy-2-(4-methoxyphenyl)-1-oxidobenzo[b]thiophen-3-yl)oxy)phenyl)but-2-enoic acid (compound 73) | $^1$H NMR (400 MHz, CD$_3$OD) δ ppm = 7.48-7.61 (m, 3H), 7.34-7.45 (m, 2H), 6.94-7.16 (m, 4H), 6.77-6.89 (m, 2H), 6.00 (d, J = 1.52 Hz, 1H), 3.81 (s, 3H), 3.69 (s, 3H), 3.62 (s, 3H), 2.42 (s, 3H) |
| 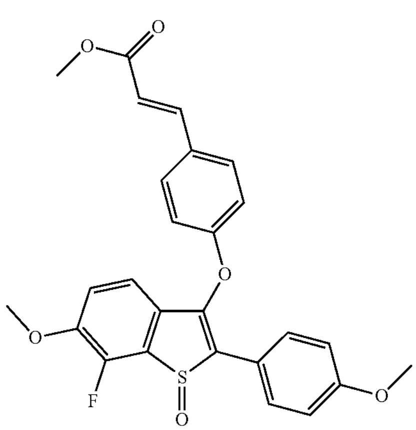 | (E)-methyl 3-(4-((7-fluoro-6-methoxy-2-(4-methoxyphenyl)-1-oxidobenzo[b]thiophen-3-yl)oxy)phenyl)acrylate (compound 74) | LC/MS (m/z, MH$^+$): 481.3 |

(E)-ethyl 3-(4-((6-methoxy-2-(4-methoxyphenyl)-1-oxidobenzo[b]thiophen-3-yl)oxy)phenyl)-2-methylacrylate (Compound 75)

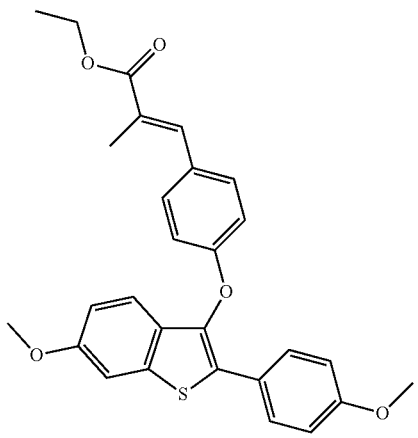

To a solution of (E)-ethyl 3-(4-hydroxyphenyl)-2-methylacrylate (92 mg, 0.445 mmol) in DMF (2.0 mL) was added sodium hydride (60% suspension in oil, 17.79 mg, 0.445 mmol), the resulting mixture was allowed to stir for 30 min at room temperature. To the solution was added 3-bromo-6-methoxy-2-(4-methoxyphenyl)benzo[b]thiophene 1-oxide (125 mg, 0.342 mmol) as a suspension in DMF (2.0 mL). The reaction was heated to 80° C. for 15 h. Upon completion the reaction was cooled to room temperature, quenched with water and extracted with EtOAc. The combined organic layers were then washed with water, sat. aq. NaHCO3, brine and then collected (phase separator) and concentrated in vacuo to afford the crude product. The crude material was purified by column chromatography (SiO$_2$, 0-70% EtOAc/Heptane) to afford (E)-ethyl 3-(4-((6-methoxy-2-(4-methoxyphenyl)-1-oxidobenzo[b]thiophen-3-yl)oxy)phenyl)-2-methylacrylate (144 mg, 0.294 mmol, 86% yield). LC/MS (m/z, MH$^+$): 491.3

(E)-ethyl 3-(4-hydroxy-2-methylphenyl)acrylate (Compound 76)

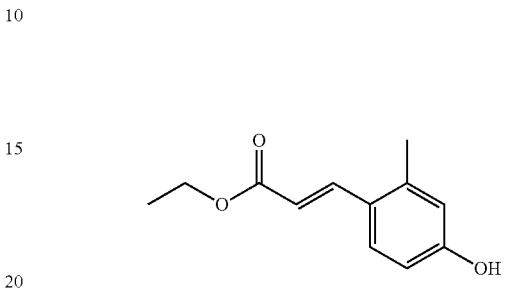

To a microwave vial containing 4-bromo-3-methylphenol (600 mg, 3.21 mmol) in anhydrous DMF (3.0 mL) was added ethyl acrylate (996 mg, 9.94 mmol), palladium (II) acetate (72.0 mg, 0.321 mmol), tri(o-tolyl)phosphine (146 mg, 0.481 mmol) and triethylamine (1.57 mL, 11.23 mmol). The resulting mixture was sealed and subjected to microwave irradiation at 120° C. for 2 h after which time the reaction was diluted with EtOAc and filtered through Celite™. The filtrate was then washed with water, brine and dried over anhydrous Na$_2$SO$_4$, filtered and concentrated in vacuo to give the crude product as a brown oil which was purified by column chromatography (SiO$_2$, 0-30% EtOAc/Heptane) to afford (E)-ethyl 3-(4-hydroxy-2-methylphenyl)acrylate (289.8 mg, 1.405 mmol, 44% yield). LC/MS (m/z, MH$^+$): 207.2.

The following intermediates were prepared in a similar fashion to intermediates above using the appropriate starting materials:

| Structure | Name | Physical Data |
|---|---|---|
| 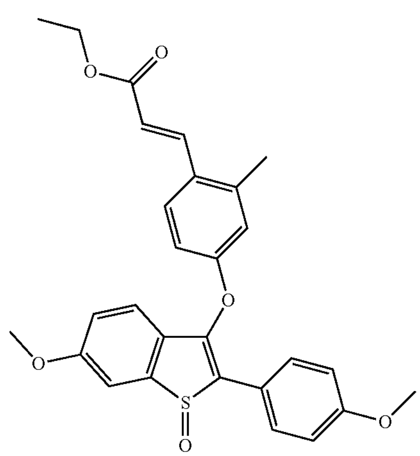 | (E)-ethyl 3-(4-((6-methoxy-2-(4-methoxyphenyl)-1-oxidobenzo[b]thiophen-3-yl)oxy)-2-methylphenyl)acrylate (compound 77) | LC/MS (m/z, MH$^+$): 491.3 |

-continued

| Structure | Name | Physical Data |
|---|---|---|
| 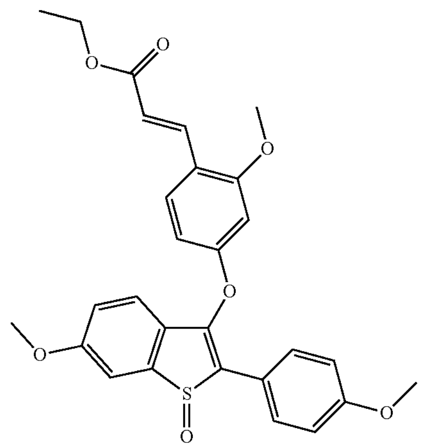 | (E)-ethyl 3-(2-methoxy-4-((6-methoxy-2-(4-methoxyphenyl)-1-oxidobenzo[b]thiophen-3-yl)oxy)phenyl)acrylate (compound 78) | LC/MS (m/z, MH$^+$): 507.3 |
| 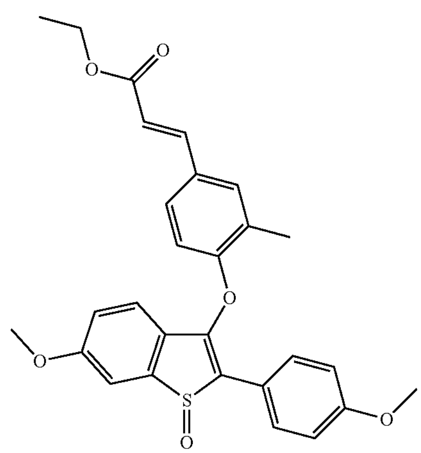 | (E)-ethyl 3-(4-((6-methoxy-2-(4-methoxyphenyl)-1-oxidobenzo[b]thiophen-3-yl)oxy)-3-methylphenyl)acrylate (compound 79) | LC/MS (m/z, MH$^+$): 491.3 |
| | (E)-methyl 3-(4-((6-methoxy-1-oxido-2-(4-(trifluoromethoxy)phenyl)benzo[b]thiophen-3-yl)oxy)phenyl)acrylate (compound 80) | LC/MS (m/z, MH$^+$): 517.3 |

| Structure | Name | Physical Data |
|---|---|---|
| 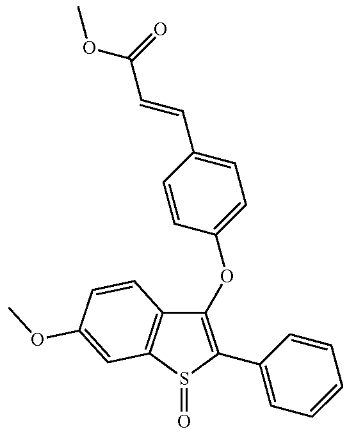 [SMILES: COC(=O)/C=C/c1ccc(OC2=C(c3ccccc3)S(=O)c3cc(OC)ccc32)cc1] | (E)-methyl 3-(4-((6-methoxy-1-oxido-2-phenylbenzo[b]thiophen-3-yl)oxy)phenyl)acrylate (compound 81) | LC/MS (m/z, MH$^+$): 433.3 |
| 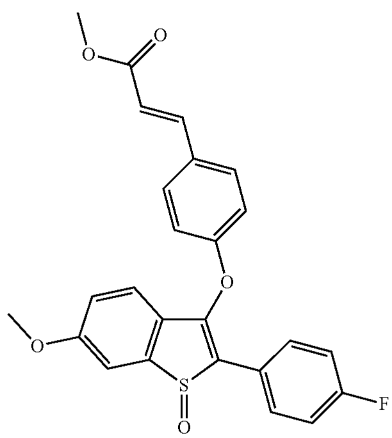 [SMILES: COC(=O)/C=C/c1ccc(OC2=C(c3ccc(F)cc3)S(=O)c3cc(OC)ccc32)cc1] | (E)-methyl 3-(4-((2-(4-fluorophenyl)-6-methoxy-1-oxidobenzo[b]thiophen-3-yl)oxy)phenyl)acrylate (compound 82) | LC/MS (m/z, MH$^+$): 451.3 |
| 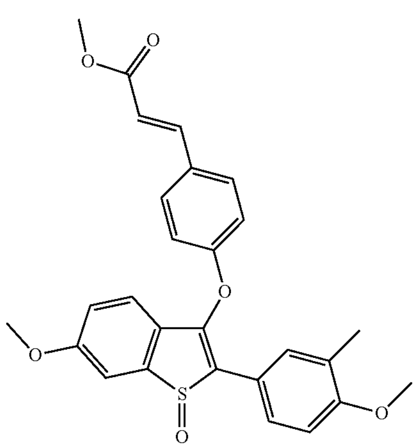 | (E)-methyl 3-(4-((6-methoxy-2-(4-methoxy-3-methylphenyl)-1-oxidobenzo[b]thiophen-3-yl)oxy)phenyl)acrylate (compound 83) | LC/MS (m/z, MH$^+$): 477.4 |

| Structure | Name | Physical Data |
|---|---|---|
| 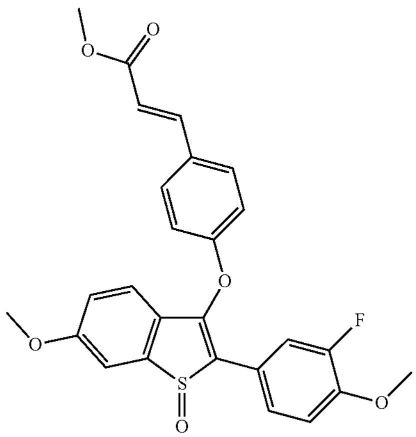 | (E)-methyl 3-(4-((2-(3-fluoro-4-methoxyphenyl)-6-methoxy-1-oxidobenzo[b]thiophen-3-yl)oxy)phenyl)acrylate (compound 84) | LC/MS (m/z, MH+): 481.4 |

Intermediates R (E)-methyl 3-(4-((6-methoxy-2-(4-methoxyphenyl)benzo[b]thiophen-3-yl)oxy)phenyl)acrylate (Compound 85)

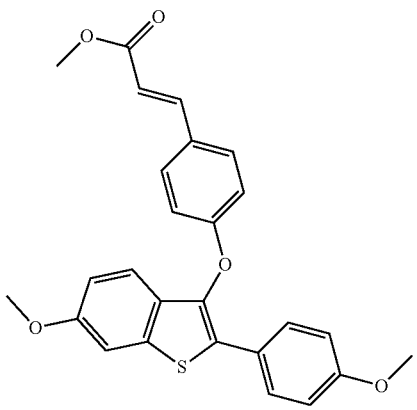

To a 30 mL vial containing (E)-methyl 3-(4-((6-methoxy-2-(4-methoxyphenyl)-1-oxidobenzo[b]thiophen-3-yl)oxy)phenyl)acrylate (200 mg, 0.43 mmol) was added THF (5 mL), triphenylphosphine (420 mg, 1.60 mmol) and TMS-Cl (0.553 mL, 4.32 mmol). The reaction was heated to 75° C. for 18 h after which time the mixture was cooled to room temperature, quenched with sat. aq. NaHCO$_3$ and diluted with DCM. The organic phase was collected (phase separator) and concentrated in vacuo to afford the crude product which was purified by column chromatography (SiO$_2$, 0-60% EtOAc/Heptane) to afford (E)-methyl 3-(4-((6-methoxy-2-(4-methoxyphenyl)benzo[b]thiophen-3-yl)oxy)phenyl)acrylate (110 mg, 0.25 mmol, 57% yield) as a white solid. $^1$H NMR (400 MHz, CDCl$_3$) δ ppm=7.58-7.73 (m, 3H), 7.38-7.50 (m, J=8.59 Hz, 2H), 7.28 (t, J=2.27 Hz, 2H), 6.96-7.05 (m, J=8.59 Hz, 2H), 6.85-6.96 (m, 3H), 6.32 (d, J=15.66 Hz, 1H), 3.90 (s, 3H), 3.81 (s, 3H), 3.82 (s, 3H).

The following intermediates were prepared in a similar fashion to intermediates above using the appropriate starting materials:

| Structure | Name | Physical Data |
|---|---|---|
| 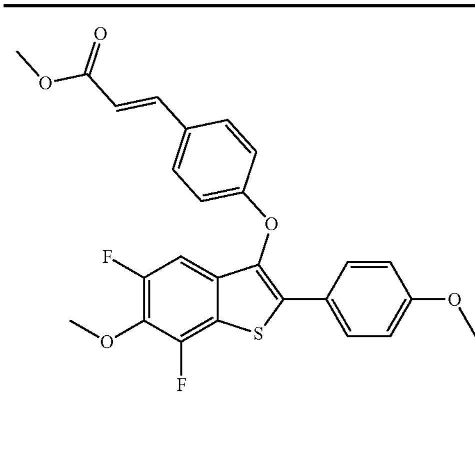 | (E)-methyl 3-(4-((5,7-difluoro-6-methoxy-2-(4-methoxyphenyl)benzo[b]thiophen-3-yl)oxy)phenyl)acrylate (compound 86) | $^1$H NMR (400 MHz, CDCl$_3$) δ ppm = 7.54 (d, J = 15.66 Hz, 1H), 7.28-7.46 (m, 4H), 6.95-7.02 (m, 1H), 6.80-6.95 (m, 4H), 6.23 (d, J = 15.66 Hz, 1H), 3.86 (s, 3H), 3.80 (s, 3H), 3.70 (s, 3H) |

| Structure | Name | Physical Data |
|---|---|---|
| 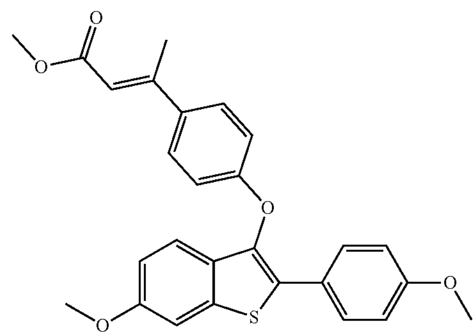 | (E)-methyl 3-(4-((6-methoxy-2-(4-methoxyphenyl)benzo[b]thiophen-3-yl)oxy)phenyl)but-2-enoate (compound 87) | $^1$H NMR (400 MHz, CDCl$_3$) δ ppm = 7.52-7.65 (m, 2H), 7.27-7.38 (m, 2H), 7.13-7.23 (m, 2H), 6.84-6.93 (m, 2H), 6.75-6.84 (m, 3H), 6.01 (d, J = 1.52 Hz, 1H), 3.80 (s, 3H), 3.72 (s, 3H), 3.66 (s, 3H), 2.46 (d, J = 1.01 Hz, 3H) |
| 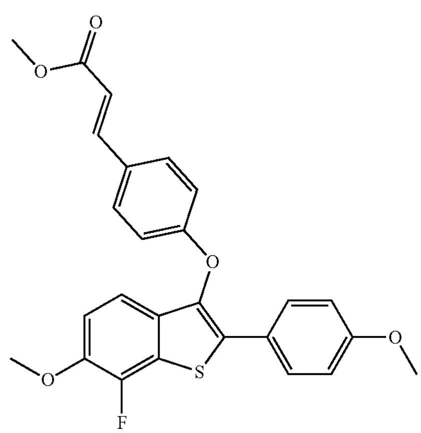 | (E)-methyl 3-(4-((7-fluoro-6-methoxy-2-(4-methoxyphenyl)benzo[b]thiophen-3-yl)oxy)phenyl)acrylate (compound 88) | $^1$H NMR (400 MHz, CDCl$_3$) δ ppm = 7.40-7.58 (m, 3H), 7.21-7.30 (m, 2H), 6.87-6.95 (m, 1H), 6.75-6.87 (m, 3H), 6.66-6.75 (m, 2H), 6.13 (d, J = 16.17 Hz, 1H), 3.78 (s, 3H), 3.61 (s, 3H), 3.63 (s, 3H) |

(E)-ethyl 3-(4-((6-methoxy-2-(4-methoxyphenyl)benzo[b]thiophen-3-yl)oxy)phenyl)-2-methylacrylate (Compound 89)

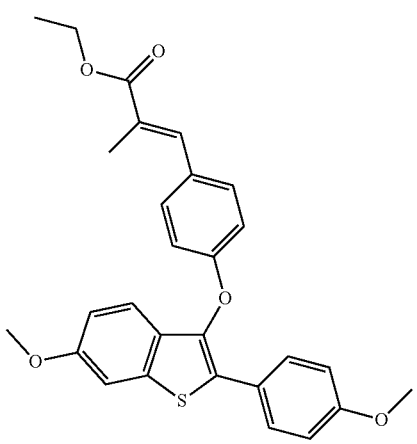

To a solution of (E)-ethyl 3-(4-((6-methoxy-2-(4-methoxyphenyl)-1-oxidobenzo[b]thiophen-3-yl)oxy)phenyl)-2-methylacrylate (144 mg, 0.294 mmol) in THF (6.0 mL) was added triphenylphosphine (285 mg, 1.086 mmol) and TMS-Cl (0.375 mL, 2.94 mmol). The reaction was heated to 75° C. for 7 h after which time the mixture was cooled to room temperature, quenched with sat. aq. NaHCO$_3$ and extracted with EtOAc, the combined organic layers were collected (phase separator) and concentrated in vacuo to afford the crude product which was purified by column chromatography (SiO$_2$, 0-40% EtOAc/Heptane) to afford (E)-ethyl 3-(4-((6-methoxy-2-(4-methoxyphenyl)benzo[b]thiophen-3-yl)oxy)phenyl)-2-methylacrylate (107 mg, 0.225 mmol, 77% yield). LC/MS (m/z, MH$^+$): 475.3.

The following intermediates were prepared in a similar fashion to intermediates above using the appropriate starting materials:

| Structure | Name | Physical Data |
|---|---|---|
| 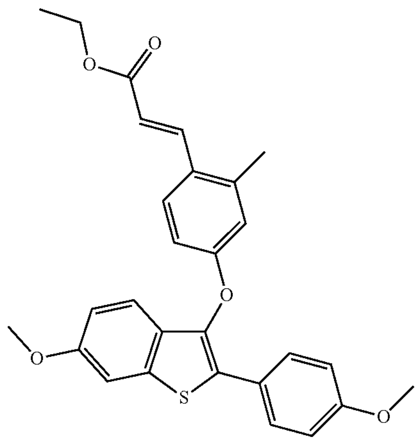 | (E)-ethyl 3-(4-((6-methoxy-2-(4-methoxyphenyl)benzo[b]thiophen-3-yl)oxy)-2-methylphenyl)acrylate (compound 90) | |
| 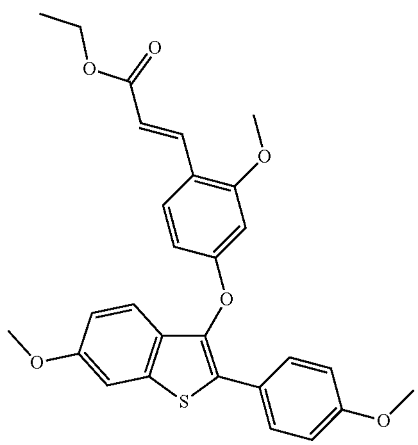 | (E)-ethyl 3-(2-methoxy-4-((6-methoxy-2-(4-methoxyphenyl)benzo[b]thiophen-3-yl)oxy)phenyl)acrylate (compound 91) | LC/MS (m/z, MH$^+$): 491.3 |
| 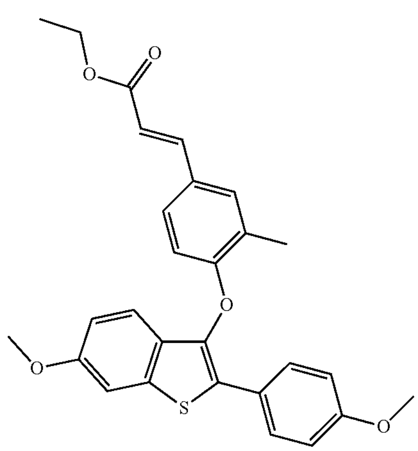 | (E)-ethyl 3-(4-((6-methoxy-2-(4-methoxyphenyl)benzo[b]thiophen-3-yl)oxy)-3-methylphenyl)acrylate (compound 92) | LC/MS (m/z, MH$^+$): 475.3 |

| Structure | Name | Physical Data |
|---|---|---|
| | (E)-methyl 3-(4-((6-methoxy-2-(4-(trifluoromethoxy)phenyl)benzo[b]thiophen-3-yl)oxy)phenyl)acrylate (compound 93) | LC/MS (m/z, MH$^+$): 501.2 |
| 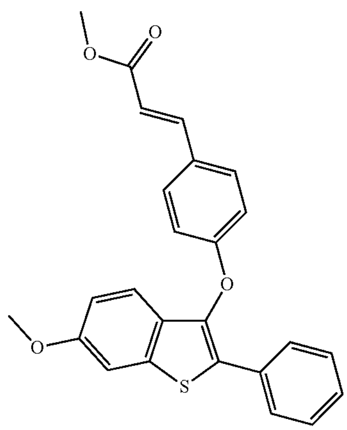 [SMILES: COC(=O)/C=C/c1ccc(Oc2c(-c3ccccc3)sc3cc(OC)ccc23)cc1] | (E)-methyl 3-(4-((6-methoxy-2-phenylbenzo[b]thiophen-3-yl)oxy)phenyl)acrylate (compound 94) | LC/MS (m/z, MH$^+$): 417.3 |
| 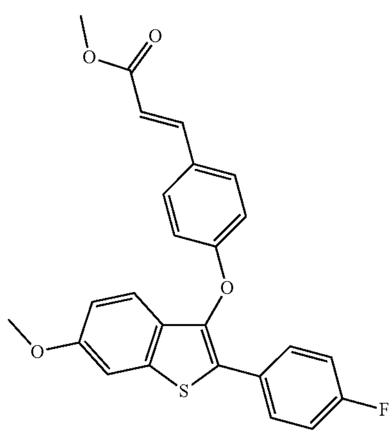 [SMILES: COC(=O)/C=C/c1ccc(Oc2c(-c3ccc(F)cc3)sc3cc(OC)ccc23)cc1] | (E)-methyl 3-(4-((2-(4-fluorophenyl)-6-methoxybenzo[b]thiophen-3-yl)oxy)phenyl)acrylate (compound 95) | |

-continued

| Structure | Name | Physical Data |
|---|---|---|
| 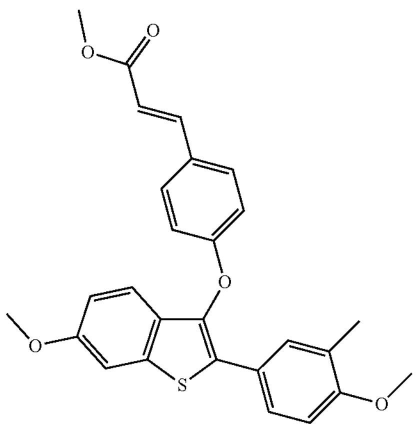 | (E)-methyl 3-(4-((6-methoxy-2-(4-methoxy-3-methylphenyl)benzo[b]thiophen-3-yl)oxy)phenyl)acrylate (compound 96) | |
| 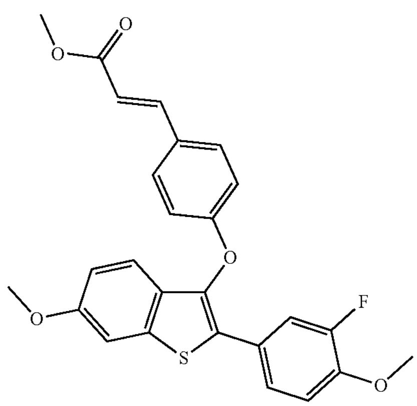 | (E)-methyl 3-(4-((2-(3-fluoro-4-methoxyphenyl)-6-methoxybenzo[b]thiophen-3-yl)oxy)phenyl)acrylate (compound 97) | |

Intermediates S (E)-3-(4-((6-methoxy-2-(4-methoxyphenyl)benzo[b]thiophen-3-yl)oxy)phenyl)acrylic acid (Compound 98)

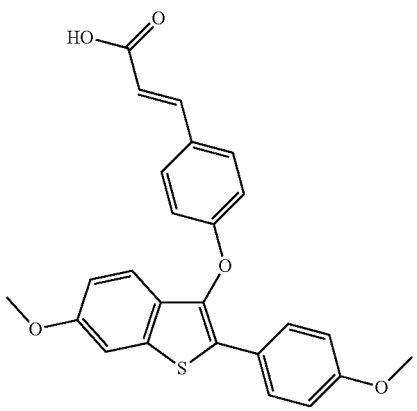

To a 30 mL vial containing (E)-methyl 3-(4-((6-methoxy-2-(4-methoxyphenyl)benzo[b]thiophen-3-yl)oxy)phenyl) acrylate (110 mg, 0.25 mmol) was added THF (2.00 mL), MeOH (1.00 mL), H$_2$O (1.00 mL) and LiOH (29.5 mg, 1.23 mmol). The resulting mixture was stirred at room temperature for 60 min after which the reaction was concentrated in vacuo, diluted with water, and acidified to pH 2 with 6 M HCl causing a precipitate to form. The mixture was diluted with 20 mL DCM and 2 mL MeOH and the organic layer was collected (phase separator) and concentrated in vacuo to afford (E)-3-(4-((6-methoxy-2-(4-methoxyphenyl)benzo[b]thiophen-3-yl)oxy)phenyl)acrylic acid (98 mg, 0.23 mmol, 92% yield) as a yellow solid. $^1$H NMR (400 MHz, CD$_3$OD) δ ppm=7.51-7.69 (m, 5H), 7.43 (d, J=2.02 Hz, 1H), 7.25 (d, J=9.09 Hz, 1H), 6.88-7.02 (m, 5H), 6.37 (d, J=15.66 Hz, 1H), 3.89 (s, 3H), 3.80 (s, 3H). LC/MS (m/z, MH$^+$): 433.0.

The following intermediates were prepared in a similar fashion to intermediates above using the appropriate starting materials:

| Structure | Name | Physical Data |
|---|---|---|
| 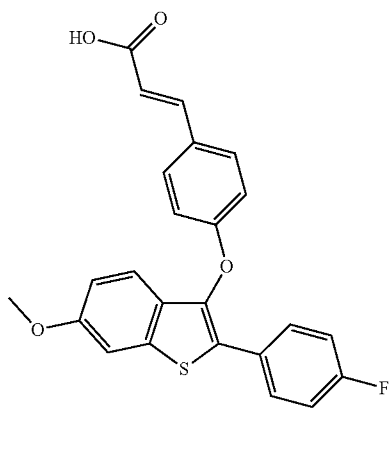 [SMILES: COc1ccc2c(Oc3ccc(/C=C/C(=O)O)cc3)c(-c3ccc(F)cc3)sc2c1] | (E)-3-(4-((2-(4-fluorophenyl)-6-methoxybenzo[b]thiophen-3-yl)oxy)phenyl)acrylic acid (compound 99) | LC/MS (m/z, MH+): 421.2 |

(E)-3-(4-((2-(4-fluoro-2-methylphenyl)-6-methoxy-benzo[b]thiophen-3-yl)oxy)phenyl)acrylic acid (Compound 100)

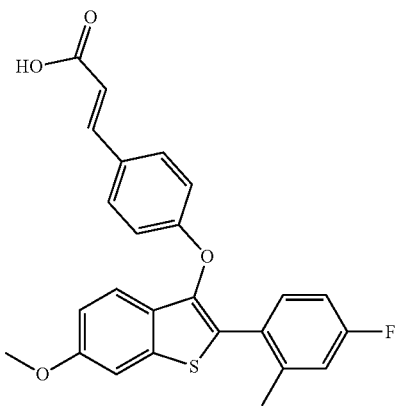 [SMILES: COc1ccc2c(Oc3ccc(/C=C/C(=O)O)cc3)c(-c3ccc(F)cc3C)sc2c1]

To a 30 mL screw cap vial, (E)-tert-butyl 3-(4-((2-(4-fluoro-2-methylphenyl)-6-methoxybenzo[b]thiophen-3-yl)oxy)phenyl)acrylate (100 mg, 0.204 mmol) was dissolved in 4M HCl in dioxane (153 μl 0.612 mmol) and the reaction mixture was stirred for 10 min at room temperature. The reaction mixture was concentrated to dryness to afford (E)-3-(4-((2-(4-fluoro-2-methylphenyl)-6-methoxybenzo[b]thiophen-3-yl)oxy)phenyl)acrylic acid (88 mg, 0.202 mmol, 99% yield). $^1$H NMR (400 MHz, CD$_3$OD) δ ppm=2.25 (s, 3H) 3.78 (s, 3H) 6.21 (d, J=15.66 Hz, 1H) 6.68-6.84 (m, 3H) 6.84-6.92 (m, 2H) 7.16-7.29 (m, 2H) 7.31-7.41 (m, 3H) 7.46 (d, J=16.17 Hz, 1H).

Intermediates T (E)-3-(4-((6-methoxy-2-(4-methoxyphenyl)benzo[b]thiophen-3-yl)oxy)phenyl)acrylamide (Compound 101)

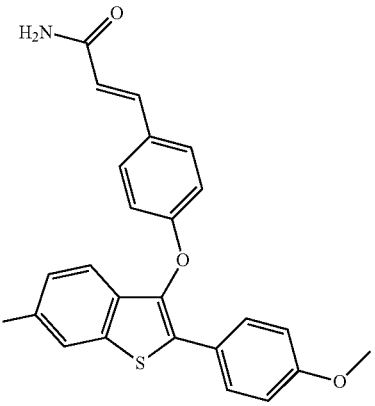

To a 30 mL vial, (E)-3-(4-((6-methoxy-2-(4-methoxyphenyl)benzo[b]thiophen-3-yl)oxy)phenyl)acrylic acid (98 mg, 0.23 mmol) was dissolved in DMF (2 mL). The vial was charged with HATU (129 mg, 0.34 mmol) and DIEA (0.119 mL, 0.68 mmol) and the mixture was stirred for 10 min. A color change from pale orange to a dark orange was observed. To the solution was added NH$_4$Cl (24.24 mg, 0.45 mmol) and the reaction mixture was stirred for 30 min at room temperature. The reaction was quenched with sat. aq. NH$_4$Cl and diluted with DCM. The organic phase was collected (phase separator) and concentrated to afford the crude product. The crude material was purified by column chromatography (SiO$_2$, 1-10% MeOH/DCM) to afford (E)-3-(4-((6-methoxy-2-(4-methoxyphenyl)benzo[b]thiophen-3-yl)oxy)phenyl)acrylamide (77 mg, 0.18 mmol, 79% yield) as an off white solid. $^1$H NMR (400 MHz, CD$_3$OD) δ ppm=8.00 (s, 4H), 7.59-7.70 (m, 2H), 7.45-7.55 (m, 2H), 7.42 (d, J=2.02 Hz, 1H), 7.24 (d, J=8.59 Hz, 1H), 6.84-7.02 (m, 4H), 6.52 (d, J=15.66 Hz, 1H), 3.88 (s, 3H), 3.79 (s, 3H). LC/MS (m/z, MH+): 432.3.

(E)-3-(4-((6-methoxy-2-(4-methoxyphenyl)benzo[b]thiophen-3-yl)oxy)phenyl)-N-(3,3,3-trifluoropropyl)acrylamide (Compound 102)

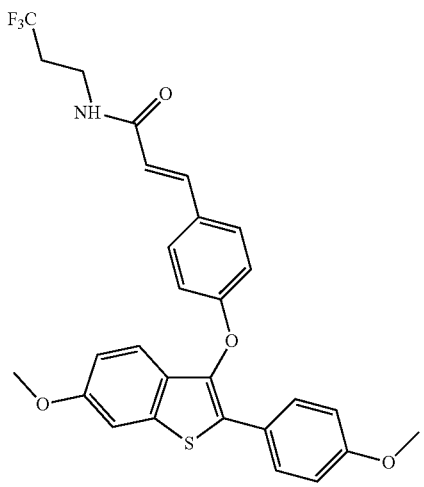

To a 30 mL vial containing (E)-3-(4-((6-methoxy-2-(4-methoxyphenyl)benzo[b]thiophen-3-yl)oxy)phenyl)acrylic acid (41 mg, 0.10 mmol) was added DMF (3 mL), followed by 3,3,3-trifluoropropan-1-amine (13.94 mg, 0.12 mmol), HATU (54.1 mg, 0.14 mmol), and DIEA (0.050 mL, 0.28 mmol). The mixture was stirred at room temperature for 30 min after which the reaction was quenched with sat. aq. $NH_4Cl$ and diluted with DCM. The organic phase was collected (phase separator) and concentrated in vacuo onto silica gel. The crude material was purified by column chromatography ($SiO_2$, 0-30% EtOAc/heptane) to afford (E)-3-(4-((6-methoxy-2-(4-methoxyphenyl)benzo[b]thiophen-3-yl)oxy)phenyl)-N-(3,3,3-trifluoropropyl)acrylamide (38 mg, 0.07 mmol, 72% yield) as a white solid. $^1$H NMR (400 MHz, $CD_3OD$) δ ppm=7.64 (d, J=9.09 Hz, 2H), 7.45-7.56 (m, 3H), 7.42 (d, J=2.02 Hz, 1H), 7.25 (d, J=8.59 Hz, 1H), 6.90-7.02 (m, 5H), 6.47 (d, J=15.66 Hz, 1H), 3.88 (s, 3H), 3.74-3.85 (m, 3H), 3.54 (t, J=7.07 Hz, 2H), 2.34-2.56 (m, 2H). LC/MS (m/z, $MH^+$): 528.3.

The following intermediates were prepared in a similar fashion to intermediates above using the appropriate starting materials:

| Structure | Name | Physical Data |
|---|---|---|
| 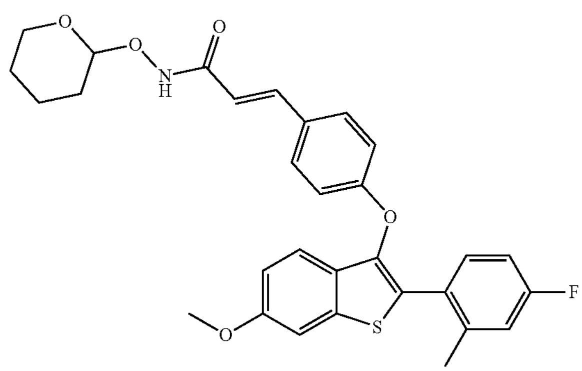 [SMILES: COc1ccc2c(Oc3ccc(/C=C/C(=O)NOC4CCCCO4)cc3)c(-c3ccc(F)cc3C)sc2c1] | (E)-3-(4-((2-(4-fluoro-2-methylphenyl)-6-methoxybenzo[b]thiophen-3-yl)oxy)phenyl)-N-((tetrahydro-2H-pyran-2-yl)oxy)acrylamide (compound 103) | $^1$H NMR (400 MHz, $CD_3OD$) δ ppm = 1.48-1.73 (m, 3H) 1.73-1.96 (m, 3H) 2.36 (s, 3H) 3.56-3.70 (m, 1H) 3.89 (s, 3H), 3.98-4.14 (m, 1H) 4.96 (br. s., 1H) 6.35 (d, J = 15.66 Hz, 1H) 6.79-6.95 (m, 3H) 6.95-7.07 (m, 2H) 7.26-7.39 (m, 2H) 7.39-7.48 (m, 3H) 7.52 (d, J = 16.17 Hz, 1H) |
| 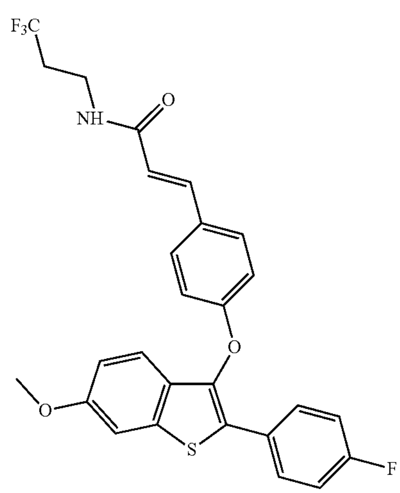 [SMILES: COc1ccc2c(Oc3ccc(/C=C/C(=O)NCCC(F)(F)F)cc3)c(-c3ccc(F)cc3)sc2c1] | (E)-3-(4-((2-(4-fluorophenyl)-6-methoxybenzo[b]thiophen-3-yl)oxy)phenyl)-N-(3,3,3-trifluoropropyl)acrylamide (compound 104) | $^1$H NMR (400 MHz, $CD_3OD$) δ ppm = 7.74 (dd, J = 5.31, 8.84 Hz, 2H), 7.43-7.55 (m, 4H), 7.28 (d, J = 9.09 Hz, 1H), 7.13 (t, J = 8.84 Hz, 2H), 6.91-7.03 (m, 3H), 6.47 (d, J = 15.66 Hz, 1H), 3.89 (s, 3H), 3.54 (t, J = 6.82 Hz, 2H), 2.37-2.57 (m, 2H) |

151

(E)-3-(4-((2-(4-fluorophenyl)-6-methoxybenzo[b]thiophen-3-yl)oxy)phenyl)acrylamide (Compound 105)

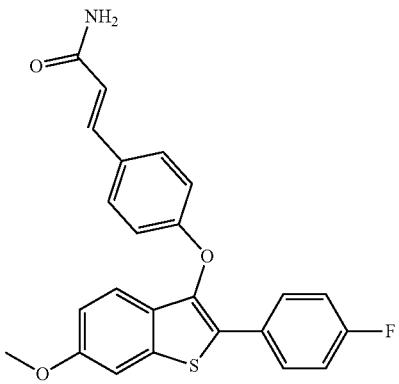 [SMILES: COc1ccc2c(Oc3ccc(/C=C/C(N)=O)cc3)c(-c3ccc(F)cc3)sc2c1]

(E)-3-(4-((2-(4-fluorophenyl)-6-methoxybenzo[b]thiophen-3-yl)oxy)phenyl)acrylic acid (48 mg, 0.115 mmol) was dissolved in DMF (3.00 mL). The vial was charged with HATU (65.6 mg, 0.173 mmol), DIEA (0.060 mL, 0.345 mmol), and NH$_4$Cl (6.16 mg, 0.115 mmol). The reaction mixture was stirred for 10 min at room temperature. The reaction was quenched with sat. NH$_4$Cl and diluted with DCM. The organic phase was collected (phase separator) and concentrated by vacuum to afford to crude product. The crude material was purified by reverse phase HPLC (neutral condition, 3% 1-propanol in 1-100% CH$_3$CN/H$_2$O) to afford (E)-3-(4-((2-(4-fluorophenyl)-6-methoxybenzo[b]thiophen-3-yl)oxy)phenyl)acrylamide (41 mg, 0.098 mmol, 85% yield) as a pale orange solid. $^1$H NMR (400 MHz, CD$_3$OD) δ ppm=3.77 (s, 3H) 6.40 (d, J=15.66 Hz, 1H) 6.78-6.90 (m, 3H) 6.95-7.06 (m, 2H) 7.16 (d, J=8.59 Hz, 1H) 7.29-7.49 (m, 4H) 7.55-7.69 (m, 2H).

Intermediates U (E)-5-(4-((6-methoxy-2-(4-methoxyphenyl)benzo[b]thiophen-3-yl)oxy)styryl)-1H-tetrazole (Compound 106)

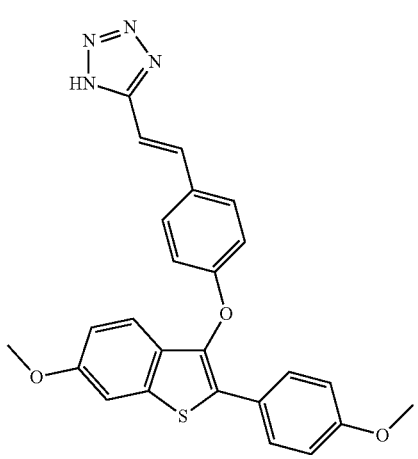

To a microwave vial, (E)-3-(4-((6-methoxy-2-(4-methoxyphenyl)benzo[b]thiophen-3-yl)oxy)phenyl)acrylamide (75 mg, 0.174 mmol) and Bu$_2$SnO (4.33 mg, 0.02 mmol) were suspended in DME (3 mL). The vial was charged with TMSN$_3$ (0.023 mL, 0.17 mmol) and the reaction was heated for 60 min at 180° C. under microwave irradiation. The reaction mixture was filtered to remove solids and concentrated onto silica gel. The crude material was purified by column chromatography (SiO$_2$, 1-20% MeOH/DCM) to afford (E)-5-(4-((6-methoxy-2-(4-methoxyphenyl)benzo[b]thiophen-3-yl)oxy)styryl)-1H-tetrazole (66 mg, 0.15 mmol, 83% yield) as a white solid. $^1$H NMR (400 MHz, CD$_3$OD) δ ppm=7.45-7.61 (m, 5H), 7.32 (d, J=2.02 Hz, 1H), 7.15 (d, J=9.09 Hz, 1H), 6.98 (d, J=16.67 Hz, 1H), 6.86-6.93 (m, 2H), 6.78-6.86 (m, 3H), 3.78 (s, 3H), 3.69 (s, 3H). LC/MS (m/z, MH$^+$): 457.4.

(E)-5-(4-((2-(4-fluorophenyl)-6-methoxybenzo[b]thiophen-3-yl)oxy)styryl)-1H-tetrazole (Compound 107)

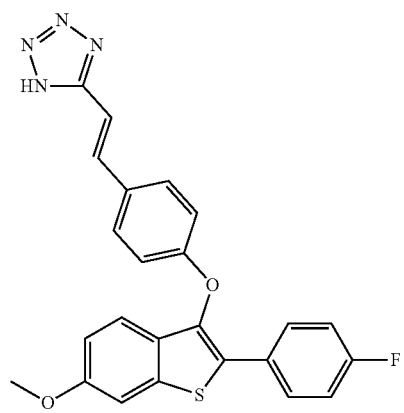 [SMILES: COc1ccc2c(Oc3ccc(/C=C/c4nnn[nH]4)cc3)c(-c3ccc(F)cc3)sc2c1]

To a microwave vial, (E)-3-(4-((2-(4-fluorophenyl)-6-methoxybenzo[b]thiophen-3-yl)oxy)phenyl)acrylamide (41 mg, 0.098 mmol) and Bu$_2$SnO (2.433 mg, 9.77 μmol) were suspended in DME (3 mL). The vial was charged with TMSN$_3$ (0.013 mL, 0.098 mmol) and the reaction was heated for 60 min at 180° C. under microwave radiation. The reaction mixture was filtered to remove solids and concentrated onto silica gel. The crude material was purified by column chromatography (SiO$_2$, 1-20% DCM/MeOH) to afford (E)-5-(4-((2-(4-fluorophenyl)-6-methoxybenzo[b]thiophen-3-yl)oxy)styryl)-1H-tetrazole (31 mg, 0.070 mmol, 71.4% yield) as an orange solid. $^1$H NMR (400 MHz, CD$_3$OD) δ ppm=3.78 (s, 3H) 6.80-6.91 (m, 3H) 6.96-7.07 (m, 3H) 7.19 (d, J=8.59 Hz, 1H) 7.34 (d, J=2.53 Hz, 1H) 7.35-7.52 (m, 3H) 7.58-7.74 (m, 2H).

(E)-5-(4-((6-methoxy-2-(4-methoxyphenyl)benzo[b]thiophen-3-yl)oxy)styryl)-1-methyl-1H-tetrazole and (E)-5-(4-((6-methoxy-2-(4-methoxyphenyl)benzo[b]thiophen-3-yl)oxy)styryl)-2-methyl-2H-tetrazole (Compounds 108 and 109)

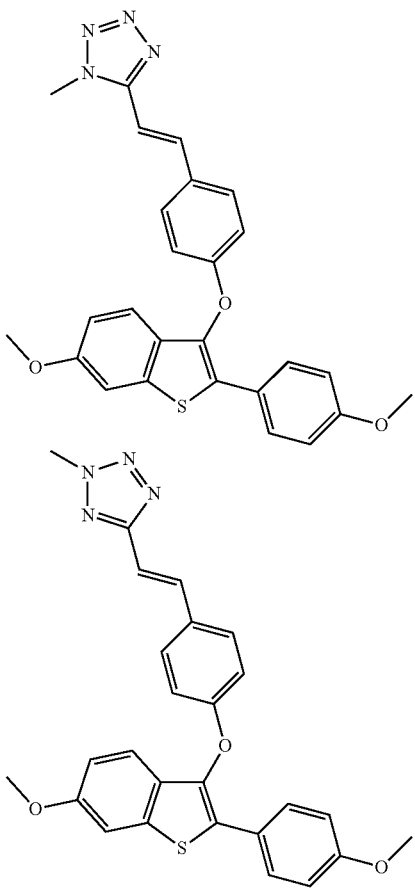

To a 30 mL vial containing (E)-5-(4-((6-methoxy-2-(4-methoxyphenyl)benzo[b]thiophen-3-yl)oxy)styryl)-2H-tetrazole (15 mg, 0.03 mmol) in DMF (2 mL) was added with iodomethane (2.260 μL, 0.04 mmol) and $K_2CO_3$ (13.62 mg, 0.10 mmol) and the reaction was stirred at room temperature for 18 h. The reaction was quenched with sat. aq. $NH_4Cl$ (15 mL) and extracted with DCM (25 mL). The organic phase was collected (phase separator) and concentrated in vacuo to afford the crude product. The crude product was purified by reverse phase HPLC (neutral condition, 3% 1-propanol in 1-100% $CH_3CN/H_2O$) to afford (E)-5-(4-((6-methoxy-2-(4-methoxyphenyl)benzo[b]thiophen-3-yl)oxy)styryl)-1-methyl-1H-tetrazole (8 mg, 0.08 mmol, 52% yield) and (E)-5-(4-(6-methoxy-2-(4-methoxyphenyl)benzo[b]thiophen-3-yl)oxy)styryl)-2-methyl-2H-tetrazole (6 mg, 0.01 mmol, 39% yield) both as a white solids.

(E)-5-(4-((6-methoxy-2-(4-methoxyphenyl)benzo[b]thiophen-3-yl)oxy)styryl)-1-methyl-1H-tetrazole: 1H NMR (400 MHz, $CD_3OD$) δ ppm=7.48-7.60 (m, 3H), 7.39-7.48 (m, 2H), 7.30 (d, J=2.02 Hz, 1H), 7.14 (d, J=9.09 Hz, 1H), 6.95 (d, J=16.67 Hz, 1H), 6.77-6.90 (m, 5H), 4.24 (s, 3H), 3.76 (s, 3H), 3.68 (s, 3H). LC/MS (m/z, $MH^+$): 471.4.

(E)-5-(4-((6-methoxy-2-(4-methoxyphenyl)benzo[b]thiophen-3-yl)oxy)styryl)-2-methyl-2H-tetrazole: 1H NMR (400 MHz, $CD_3OD$) δ ppm=7.75 (d, J=16.17 Hz, 1H), 7.59-7.70 (m, 4H), 7.43 (d, J=2.02 Hz, 1H), 7.27 (d, J=8.59 Hz, 1H), 7.09 (d, J=16.17 Hz, 1H), 6.97-7.05 (m, 2H), 6.90-6.97 (m, 3H), 4.14 (s, 3H), 3.89 (s, 3H), 3.80 (s, 3H). LC/MS (m/z, $MH^+$): 471.4.

The following intermediates were prepared in a similar fashion to intermediates above using the appropriate starting materials:

| Structure | Name | Physical Data |
|---|---|---|
| 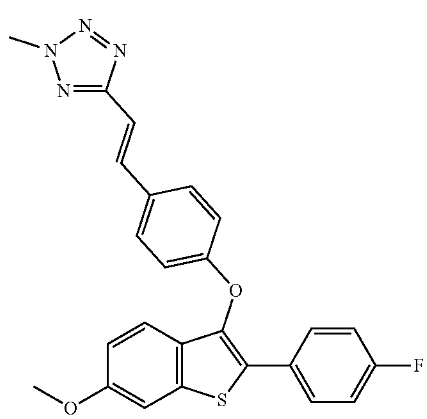 [SMILES: COc1ccc2c(Oc3ccc(/C=C/c4nnn(C)n4)cc3)c(-c3ccc(F)cc3)sc2c1] | (E)-5-(4-((2-(4-fluorophenyl)-6-methoxybenzo[b]thiophen-3-yl)oxy)styryl)-2-methyl-2H-tetrazole (compound 110) | 1H NMR (400 MHz, $CD_3OD$) δ ppm = 3.78 (s, 3H) 4.03 (s, 3H) 6.81-6.87 (m, 1H) 6.87-6.93 (m, 2H) 6.95-7.06 (m, 3H) 7.18 (d, J = 8.59 Hz, 1H) 7.35 (d, J = 2.53 Hz, 1H) 7.55 (m, J = 9.09 Hz, 2H) 7.59-7.69 (m, 3H) |

| Structure | Name | Physical Data |
|---|---|---|
| 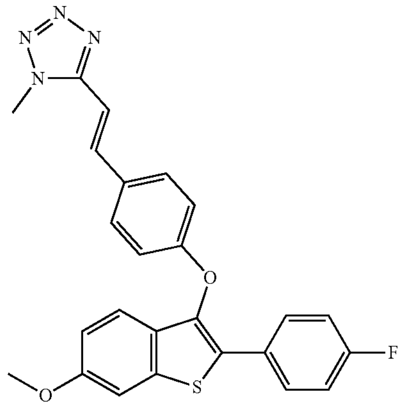 [SMILES: COc1ccc2c(Oc3ccc(/C=C/c4nnnn4C)cc3)c(-c3ccc(F)cc3)sc2c1] | (E)-5-(4-((2-(4-fluorophenyl)-6-methoxybenzo[b]thiophen-3-yl)oxy)styryl)-1-methyl-1H-tetrazole (compound 111) | $^1$H NMR (400 MHz, CD$_3$OD) δ ppm = 3.77 (s, 3H) 4.24 (s, 3H) 6.81-6.91 (m, 3H) 6.97-7.07 (m, 3H) 7.18 (d, J = 9.09 Hz, 1H) 7.33 (d, J = 2.53 Hz, 1H) 7.41-7.48 (m, 2H) 7.52 (d, J = 16.67 Hz, 1H) 7.60-7.69 (m, 2H) |
| 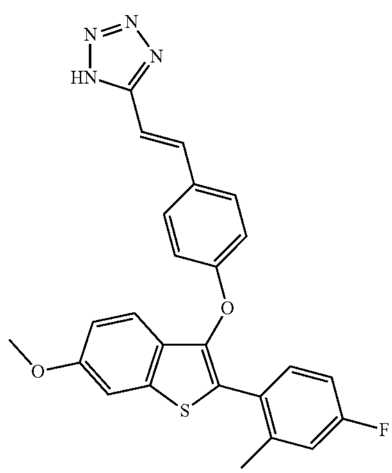 [SMILES: COc1ccc2c(Oc3ccc(/C=C/c4nnn[nH]4)cc3)c(-c3ccc(F)cc3C)sc2c1] | (E)-5-(4-((2-(4-fluoro-2-methylphenyl)-6-methoxybenzo[b]thiophen-3-yl)oxy)styryl)-1H-tetrazole (compound 112) | $^1$H NMR (400 MHz, CD$_3$Cl) δ ppm = 7.71 (d, J = 16.67 Hz, 1H), 7.32-7.44 (m, 2H), 7.22-7.32 (m, 3H), 7.00 (d, J = 16.67 Hz, 1H), 6.72-6.95 (m, 5H), 3.85 (s, 3H), 2.33 (s, 3H) |
| 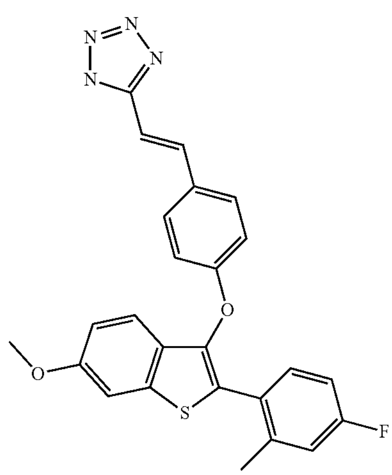 [SMILES: COc1ccc2c(Oc3ccc(/C=C/c4nnn[nH]4)cc3)c(-c3ccc(F)cc3C)sc2c1] | (E)-5-(4-((2-(4-fluoro-2-methylphenyl)-6-methoxybenzo[b]thiophen-3-yl)oxy)styryl)-2-methyl-2H-tetrazole (compound 113) | $^1$H NMR (400 MHz, CD$_3$OD) δ ppm = 2.26 (s, 3H), 3.79 (s, 3H) 4.02 (s, 3H) 6.74-6.84 (m, 3H) 6.86-6.92 (m, 2H) 6.94 (d, J = 16.17 Hz, 1H) 7.20-7.29 (m, 2H) 7.35 (d, J = 2.02 Hz, 1H) 7.47 (d, J = 8.59 Hz, 2H) 7.60 (d, J = 16.17 Hz, 1H) |

| Structure | Name | Physical Data |
|---|---|---|
| 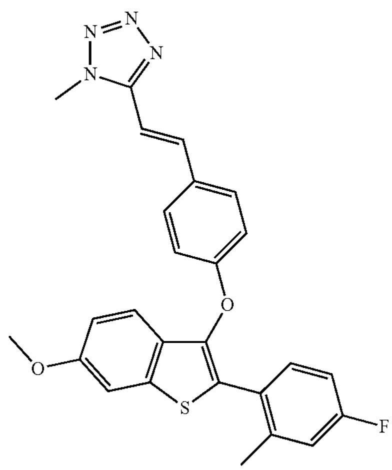 [SMILES: COc1ccc2c(Oc3ccc(/C=C/c4nnnn4C)cc3)c(-c3ccc(F)cc3C)sc2c1] | (E)-5-(4-((2-(4-fluoro-2-methylphenyl)-6-methoxybenzo[b]thiophen-3-yl)oxy)styryl)-1-methyl-1H-tetrazole (compound 114) | $^1$H NMR (400 MHz, CD$_3$OD) δ ppm = 2.26 (s, 3H) 3.78 (s, 3H) 4.24 (s, 3H) 6.72-6.84 (m, 3H) 6.85-6.98 (m, 3H) 7.18-7.30 (m, 2H) 7.31-7.40 (m, 3H) 7.47 (d, J = 16.67 Hz, 1H) |
| 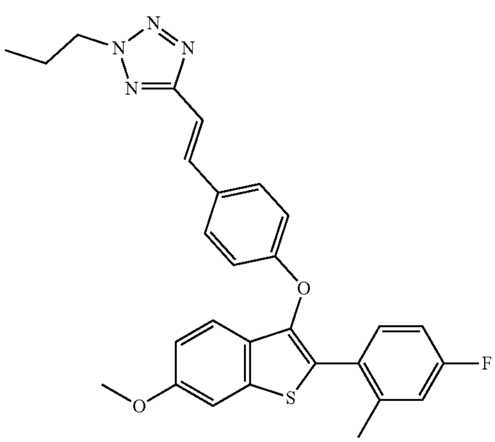 [SMILES: CCCn1nnc(/C=C/c2ccc(Oc3c(-c4ccc(F)cc4C)sc4cc(OC)ccc34)cc2)n1] | (E)-5-(4-((2-(4-fluoro-2-methylphenyl)-6-methoxybenzo[b]thiophen-3-yl)oxy)styryl)-2-propyl-2H-tetrazole (compound 115) | LC/MS (m/z, MH$^+$): 501.4 |
| 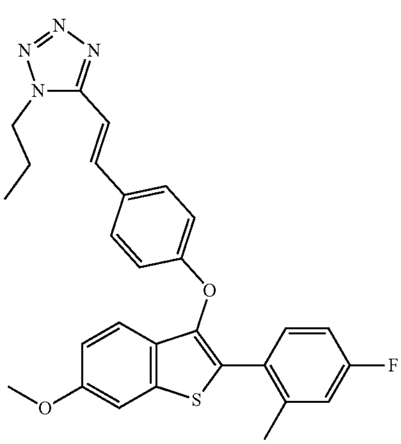 [SMILES: CCCn1nnnc1/C=C/c1ccc(Oc2c(-c3ccc(F)cc3C)sc3cc(OC)ccc23)cc1] | (E)-5-(4-((2-(4-fluoro-2-methylphenyl)-6-methoxybenzo[b]thiophen-3-yl)oxy)styryl)-1-propyl-1H-tetrazole (compound 116) | LC/MS (m/z, MH$^+$): 501.4 |

Intermediates V methyl 5-((6-methoxy-2-(4-methoxyphenyl)-1-oxidobenzo[b]thiophen-3-yl)oxy)picolinate (Compound 117)

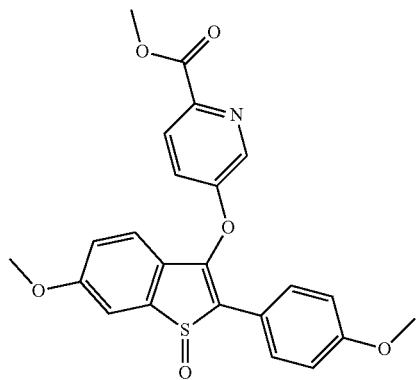

To a solution of methyl 5-hydroxypyridine-2-carboxylate (0.273 g, 1.78 mmol) in DMF (6.84 mL) at room temperature was added sodium hydride (60% suspension in oil, 0.043 g, 1.78 mmol) and the resulting mixture was stirred at room temperature for 30 mins. After 30 min at room temperature 3-bromo-6-methoxy-2-(4-methoxyphenyl)benzothiophene 1-oxide (0.5 g, 1.37 mmol) was added and the reaction was heated to 80° C. for 18 h. Upon completion the reaction was cooled to room temperature, quenched with water and extracted with DCM. The organic layers were combined, passed through a phase separator and concentrated in vacuo to give the crude product, which was purified by column chromatography (SiO$_2$, 0-75% EtOAc/heptane) to afford methyl 5-((6-methoxy-2-(4-methoxyphenyl)-1-oxidobenzo[b]thiophen-3-yl)oxy)picolinate (314 mg, 0.72 mmol, 52% yield). $^1$H NMR (400 MHz, CDCl$_3$) δ ppm=3.73 (s, 3H), 3.84 (s, 3H), 3.90-3.92 (m, 3H), 6.79-6.86 (m, 2H), 6.91 (dd, J=8.59, 2.53 Hz, 1H), 7.03 (d, J=8.59 Hz, 1H), 7.30 (dd, J=8.59, 3.03 Hz, 1H), 7.48 (d, J=2.53 Hz, 1H), 7.55-7.60 (m, 2H), 7.95 (d, J=8.59 Hz, 1H), 8.55 (d, J=2.02 Hz, 1H). LC/MS (m/z, MH$^+$): 438.2.

Intermediates W (5-((6-methoxy-2-(4-methoxyphenyl)benzo[b]thiophen-3-yl)oxy)pyridin-2-yl)methanol (Compound 118)

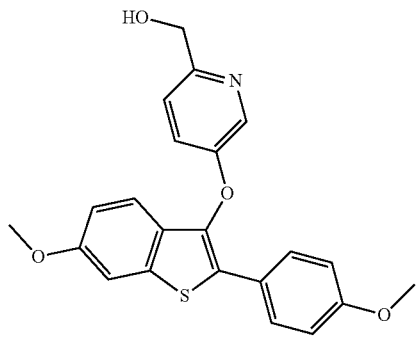

Step 1: To a solution of methyl 5-((6-methoxy-2-(4-methoxyphenyl)-1-oxidobenzo[b]thiophen-3-yl)oxy)picolinate (0.314 g, 0.718 mmol) in THF (5.98 mL) at 0° C. was added LAH (1.0 M in THF, 2.153 mL, 2.15 mmol) dropwise and the reaction was stirred at 0° C. for 1 h. Upon completion the reaction was quenched with water and sat. aq. potassium sodium tartrate and the resulting mixture was stirred for 30 min and then extracted with EtOAc (3×). The organic layers were combined, passed through a phase separator and concentrated in vacuo to afford crude (5-((6-methoxy-2-(4-methoxyphenyl)benzo[b]thiophen-3-yl)oxy)pyridin-2-yl)methanol which was used without further purification. LC/MS (m/z, MH$^+$): 394.2.

5-((6-methoxy-2-(4-methoxyphenyl)benzo[b]thiophen-3-yl)oxy)picolinaldehyde (Compound 119)

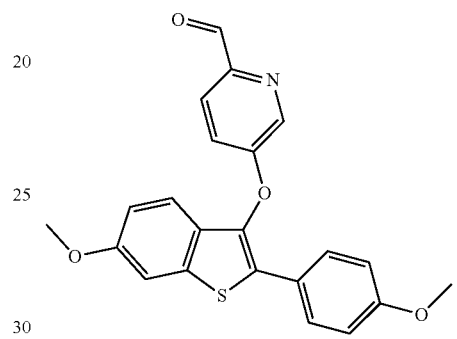

Step 2: To a solution of (5-((6-methoxy-2-(4-methoxyphenyl)-benzo[b]thiophen-3-yl)oxy)pyridin-2-yl)methanol (0.266 g, 0.676 mmol) in DCM (3.38 mL) was added manganese dioxide (1.176 g, 13.52 mmol) and the reaction was stirred at room temperature for 48 h. Upon completion the reaction was was filtered over Celite™ and concentrated in vacuo to afford crude 5-((6-methoxy-2-(4-methoxyphenyl)benzo[b]thiophen-3-yl)oxy)picolinaldehyde which was used without further purification. LC/MS (m/z, MH$^+$): 392.2.

Intermediates X (E)-methyl 3-(5-((6-methoxy-2-(4-methoxyphenyl)benzo[b]thiophen-3-yl)oxy)pyridin-2-yl)acrylate (Compound 120)

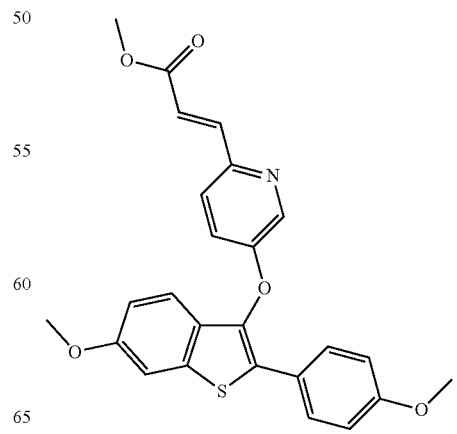

To a solution of 5-((6-methoxy-2-(4-methoxyphenyl)benzo[b]thiophen-3-yl)oxy)picolinaldehyde (0.265 g, 0.68 mmol) in DCM (3.38 mL) at 0° C. was added methyl 2-(triphenylphosphoranylidene)acetate (0.543 g, 1.63 mmol) and the reaction was stirred at room temperature for 18 h. Upon completion the mixture was concentrated in vacuo to afford crude material which was purified by column chromatography (SiO$_2$, 0-25% EtOAc/heptanes) to afford (E)-methyl 3-(5-((6-methoxy-2-(4-methoxyphenyl)benzo[b]thiophen-3-yl)oxy)pyridin-2-yl)acrylate (96 mg, 0.22 mmol, 32% yield). $^1$H NMR (400 MHz, CDCl$_3$) δ ppm=3.70-3.75 (m, 6H), 3.79-3.83 (m, 3H), 6.70 (d, J=15.66 Hz, 1H), 6.77-6.88 (m, 3H), 7.02 (dd, J=8.59, 3.03 Hz, 1H), 7.17 (s, 1H), 7.18-7.22 (m, 2H), 7.48-7.59 (m, 3H), 8.42 (d, J=2.53 Hz, 1H). LC/MS (m/z, MH$^+$): 448.3.

Intermediates Y (E)-ethyl 3-(4-((6-methoxy-2-(4-methoxyphenyl)benzo[b]thiophen-3-yl)amino)phenyl)acrylate (Compound 121)

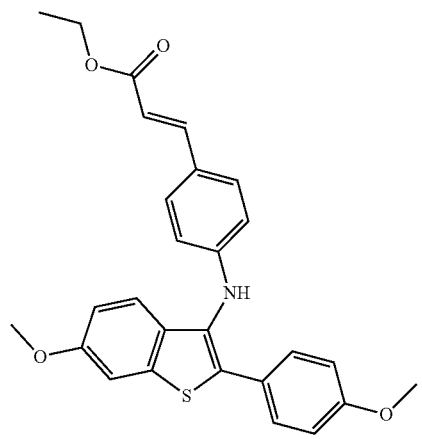

To a large microwave vial (10-20 mL) was added 3-bromo-6-methoxy-2-(4-methoxyphenyl)benzo[b]thiophene (350 mg, 1.00 mmol), ethyl 4-aminocinnamate (383 mg, 2.00 mmol) and K$_3$PO$_4$ (425 mg, 2.00 mmol). 1,4-dioxane (6.0 mL) was then added followed by chloro-(2-dicyclohexylphosphino-2',6'-diisopropoxy-1,1'-biphenyl)[2-(2-aminoethyl)phenyl]palladium(II) methyl-t-butyl ether adduct (RuPhos palladacycle, 73.0 mg, 0.10 mmol) and the reaction was subjected to microwave irradiation at 120° C. for 3 h. Upon completion the reaction mixture was transferred to round bottom flask with EtOAc and concentrated in vacuo. The resulting material was partitioned between water and EtOAc and separated, the aqueous layer was then further extracted with EtOAc (3×) and the combined organic layers were passed through a phase separator to remove water and concentrated in vacuo. The crude material was purified by column chromatography (SiO$_2$, 0-30% EtOAc/heptane) to afford (E)-ethyl 3-(4-((6-methoxy-2-(4-methoxyphenyl)benzo[b]thiophen-3-yl)amino)phenyl)acrylate (69.0 mg, 0.15 mmol, 15% yield) as a white solid. LC/MS (m/z, MH$^+$): 460.3.

Intermediates Z (E)-ethyl 3-(4-((6-methoxy-2-(4-methoxyphenyl)benzo[b]thiophen-3-yl)(methyl)amino)phenyl)acrylate (Compound 122)

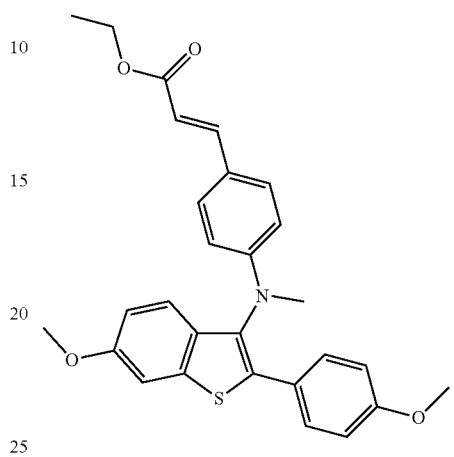

To a solution of (E)-ethyl 3-(4-((6-methoxy-2-(4-methoxyphenyl)benzo[b]thiophen-3-yl)amino)phenyl)acrylate (69.0 mg, 0.15 mmol) in DMF (6.0 mL) at room temperature was added NaH (60% suspension in oil, 139 mg, 3.48 mmol). After 15 min, methyl iodide (0.272 mL, 4.35 mmol) was added and the resulting solution was allowed to stir at room temperature for 45 min after which time the reaction was quenched with brine and diluted with water. The resulting solution was then extracted with EtOAc (3×) and the combined organic layers were washed with brine (2×), passed through a phase separator and concentrated in vacuo to afford the crude product which was purified by reverse phase HPLC (neutral condition, 3% 1-propanol in 1-100% CH$_3$CN/H$_2$O) to afford ((E)-ethyl 3-(4-((6-methoxy-2-(4-methoxyphenyl)benzo[b]thiophen-3-yl)(methyl)amino)phenyl)acrylate (25.5 mg, 0.05 mmol, 36% yield) as a white solid. LC/MS (m/z, MH$^+$): 474.3.

Additional Intermediates 2-bromo-5-fluoro-N-methoxy-N-methylbenzamide (Compound 123)

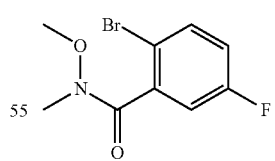

To a suspension of 2-bromo-5-fluorobenzoic acid (2.0 g, 9.13 mmol) in DCM (90 mL) at room temperature was added N,O-dimethylhydroxylamine hydrochloride (1.069 g, 10.96 mmol), N-(3-dimethylaminopropyl)-N'-ethylcarbodiimide hydrochloride (2.276 g, 11.87 mmol), hydroxybenzotriazole (1.818 g, 11.87 mmol) and triethylamine (2.55 mL, 18.26 mmol). The resulting mixture was stirred at room temperature for 5.5 h after which time the reaction was quenched by addition of sat. aq. NaHCO$_3$ solution and the layers separated. The organic layer was then washed with brine, dried over anhydrous MgSO$_4$, filtered and concentrated in vacuo. The resulting crude material was purified by column chromatography (SiO$_2$, 0-40% EtOAc/Hexanes) to afford 2-bromo-5-fluoro-N-methoxy-N-methylbenzamide as a white solid. $^1$H NMR (400 MHz, CDCl$_3$) δ ppm 7.54 (dd, J=8.8, 4.9 Hz, 1H), 7.05 (dd, J=8.2, 3.0 Hz, 1H), 7.00 (td, J=8.4, 3.0 Hz, 1H), 3.50 (s, 2H), 3.38 (s, 3H).

1-(2-bromo-5-fluorophenyl)ethanone (Compound 124)

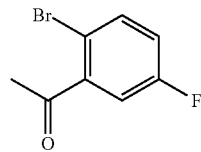

To a solution of 2-bromo-5-fluoro-N-methoxy-N-methylbenzamide (1.54 g, 5.88 mmol) in THF (60 mL) at 0° C. was added MeMgI (3.0 M in diethyl ether, 1.998 mL, 5.99 mmol) dropwise over 5 min, the reaction immediately turned bright yellow after a few drops and then after continued addition the reaction lost the yellow color and a significant amount of white precipitate crashed out. After 15 min the reaction was warmed to room temperature and stirred for 15 h after which an additional 3×0.5 equiv. MeMgI (1.0 mL) was added every 3 h until after 23 h the reaction was quenched by addition of sat. aq. NH$_4$Cl solution and extracted with diethy ether (3×). The combined organic layers were dried over anhydrous MgSO$_4$, filtered and concentrated in vacuo and the resulting crude material was purified by column chromatography (SiO$_2$, 0-20% EtOAc/Hexanes) to afford 1-(2-bromo-5-fluorophenyl)ethanone (1.038 g, 4.78 mmol, 81% yield). $^1$H NMR (400 MHz, CDCl$_3$) δ ppm 7.57 (dd, J=8.8, 4.9 Hz, 1H), 7.18 (dd, J=8.4, 3.1 Hz, 1H), 7.07-6.99 (m, 1H), 2.63 (s, 3H).

1-bromo-4-fluoro-2-(prop-1-en-2-yl)benzene (Compound 125)

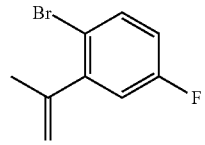

To a suspension of methyltriphenylphosphonium bromide (5.69 g, 15.91 mmol) in diethyl ether (80 mL) at room temperature was added n-BuLi (2.5 M in hexanes, 6.37 mL, 15.91 mmol) dropwise. The reaction immediately turned bright orange and the resulting solution was stirred for 35 min at room temperature after which time a solution of 1-(2-bromo-5-fluorophenyl)ethanone (3.14 g, 14.47 mmol) in diethyl ether (20 mL) was added dropwise. The reaction lost the bright yellow color and became almost completely white with a significant amount of white precipitate, the reaction was stirred for 89 h after it was quenched by addition of water and extracted with diethyl ether (3×), the combined organic layers were dried over anhydrous MgSO$_4$, filtered and concentrated in vacuo. The resulting crude material was purified by column chromatography (SiO$_2$, 0-5% Diethyl Ether/Hexanes) to afford 1-bromo-4-fluoro-2-(prop-1-en-2-yl)benzene. $^1$H NMR (400 MHz, CDCl$_3$) δ ppm 7.49 (dd, J=8.8, 5.3 Hz, 1H), 6.92 (dd, J=9.0, 3.1 Hz, 1H), 6.85 (td, J=8.3, 3.1 Hz, 1H), 5.24 (t, J=1.7 Hz, 1H), 4.96 (s, 1H), 2.08 (d, J=1.4 Hz, 3H).

1-bromo-4-fluoro-2-isopropylbenzene (Compound 126)

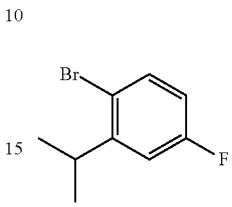

To a solution of 1-bromo-4-fluoro-2-(prop-1-en-2-yl)benzene (200 mg, 0.930 mmol) in DCM (5 mL) was added 5% Rhodium on Alumina (30 mg, 0.015 mmol). The resulting mixture was stirred under hydrogen atmosphere (50 psi) for 18 h after which time the reaction was filtered through Celite™ and concentrated in vacuo to afford 1-bromo-4-fluoro-2-isopropylbenzene. $^1$H NMR (400 MHz, CD$_2$Cl$_2$) δ ppm 7.48 (dd, J=8.6, 5.7 Hz, 1H), 7.01 (dd, J=10.3, 3.1 Hz, 1H), 6.82-6.75 (m, 1H), 3.38-3.25 (m, 1H), 1.21 (d, J=6.9 Hz, 6H).

1-bromo-2-(1-fluoroethyl)benzene (Compound 127)

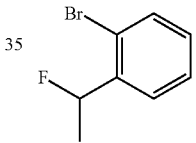

To a solution of 1-(2-bromophenyl)ethanol (1 g, 4.97 mmol) in DCM (12 mL) was added triethylamine trihydrofluoride (1.621 mL, 9.95 mmol) and XtalFluor-E® (1.708 g, 7.46 mmol) dropwise over 5 min. After addition the resulting mixture was stirred at room temperature for 1 h and then cooled to 0° C. and quenched by addition of sat. aq. NaHCO$_3$. The layers were separated and the aqueous was extracted with DCM (2×). The combined organic layers were dried over anhydrous MgSO$_4$, filtered and concentrated in vacuo to afford 1-bromo-2-(1-fluoroethyl)benzene. $^1$H NMR (400 MHz, CD$_2$Cl$_2$) δ ppm 7.54 (dt, J=8.0, 1.2 Hz, 1H), 7.50 (dd, J=7.8, 1.8 Hz, 1H), 7.38 (td, J=7.6, 1.3 Hz, 1H), 7.19 (td, J=7.7, 1.7 Hz, 1H), 5.90 (dq, J=46.6, 6.4 Hz, 1H), 1.60 (dd, J=24.2, 6.5 Hz, 3H).

(E)-ethyl 2-(4-hydroxybenzylidene)butanoate (Compound 128)

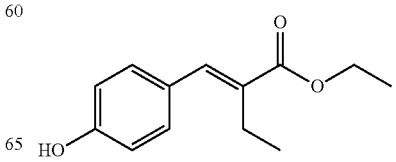

To a solution ethyl 2-bromobutanoate (2.75 mL, 19.65 mmol) in DMF (15 mL) were added PPh3 (3.87 g, 14.74 mmol) and Zinc (1.285 g, 19.65 mmol). The resulting mixture was heated to 140° C. for 3 h after which time the reaction was cooled to room temperature and filtered to remove solid. The filtrate was concentrated in vacuo and the resulting crude material was purified by column chromatography (SiO$_2$, 0-30% EtOAc/Heptane) to afford (E)-ethyl 2-(4-hydroxybenzylidene)butanoate (820 mg, 3.72 mmol, 38% yield) as a white solid. $^1$H NMR (400 MHz, CD$_3$OD) δ ppm 0.95 (t, J=7.33 Hz, 3H), 1.12 (t, J=7.07 Hz, 3H), 2.36 (q, J=7.58 Hz, 2H), 4.03 (q, J=7.07 Hz, 2H), 6.61 (m, J=8.59 Hz, 2H), 7.08 (m, J=8.59 Hz, 2H), 7.35 (s, 1H). LC/MS (m/z, MH$^+$): 221.2.

1-((1-isocyano-2-methylpropyl)sulfonyl)-4-methylbenzene (Compound 129)

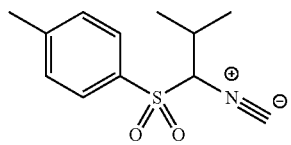

To a solution toluenesulfonylmethyl isocyanide (53 mg, 0.271 mmol) in DMSO (0.27 mL) and diethyl ether (0.27 mL) at room temperature was added NaH (60% suspension in oil, 21.71 mg, 0.543 mmol) in one portion as a solid. The resulting mixture was stirred for 20 min at room temperature after which time 2-bromopropane (0.038 mL, 0.407 mmol) was added and the reaction was stirred at for 1 h and then quenched by addition of water (8 mL) and extracted with EtOAc (8 mL). The organic layer was dried over anhydrous MgSO$_4$, filtered and concentrated in vacuo. The resulting crude material was purified by column chromatography (SiO$_2$, 0-30% EtOAc/Heptane) to afford 1-(1-isocyano-2-methylpropyl)sulfonyl)-4-methylbenzene (41 mg, 0.173 mmol, 64% yield). $^1$H NMR (400 MHz, CDCl$_3$) δ ppm 7.87 (d, J=7.1 Hz, 2H), 7.42 (d, J=7.1 Hz, 2H), 4.34 (s, 1H), 2.74 (s, 1H), 2.48 (s, 3H), 1.19 (dd, J=19.1, 6.6 Hz, 6H).

(E)-methyl 3-(4-((2-formyl-6-methoxybenzo[b]thiophen-3-yl)oxy)phenyl)acrylate (Compound 130)

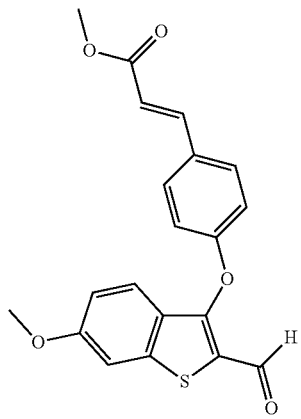 [SMILES: COC(=O)/C=C/c1ccc(Oc2c(C=O)sc3cc(OC)ccc23)cc1]

To a solution of (E)-methyl 3-(4-((6-methoxybenzo[b]thiophen-3-yl)oxy)phenyl)acrylate (30 mg, 0.088 mmol) in CHCl$_3$ (1.5 mL) at 0° C. was added POCl$_3$ (0.5 mL, 5.36 mmol) followed by DMF (0.5 mL, 6.46 mmol). The resulting mixture was stirred at 0° C. for 5 min and then allowed to warm to room temperature for 2 h after which time the reaction was again cooled to 0° C. and quenched by dropwise addition of water. The mixture was then partitioned between 1N aqueous NaOH and CH$_2$Cl$_2$. The layers were separated and the organic layer was dried over anhydrous Na$_2$SO$_4$, filtered and concentrated in vacuo to afford (E)-methyl 3-(4-((2-formyl-6-methoxybenzo[b]thiophen-3-yl)oxy)phenyl)acrylate (31 mg, 0.084 mmol, 95% yield) which was used without further purification. LC/MS (m/z, MH$^+$): 369.0.

(E)-methyl 3-(4-((2-(4-isopropyloxazol-5-yl)-6-methoxybenzo[b]thiophen-3-yl)oxy)phenyl)acrylate (Compound 131)

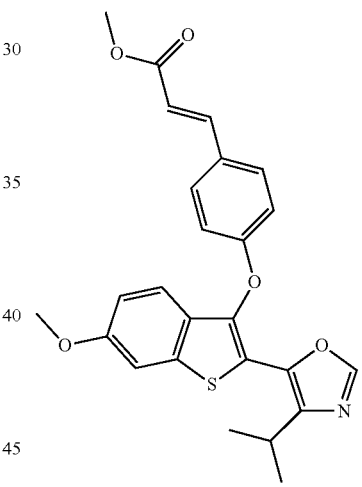

To a solution of (E)-methyl 3-(4-((2-formyl-6-methoxybenzo[b]thiophen-3-yl)oxy)phenyl)acrylate (30 mg, 0.081 mmol) and 1-(1-isocyano-2-methylpropyl)sulfonyl)-4-methylbenzene (38.7 mg, 0.163 mmol) in MeOH (1.5 mL) at room temperature was added NaOMe (13.20 mg, 0.244 mmol) as a solid. The resulting mixture was warmed to 80° C. for 3 h after which time the reaction was quenched by addition of brine and extracted with EtOAc (2×). The combined organic layers were dried over anhydrous Na2SO4, filtered and concentrated in vacuo. The resulting crude material was purified by column chromatography (SiO$_2$, 0-20% EtOAc/Heptane) to afford (E)-methyl 3-(4-((2-(4-isopropyloxazol-5-yl)-6-methoxybenzo[b]thiophen-3-yl)oxy)phenyl)acrylate (10 mg, 0.022 mmol, 27% yield) as a yellow oil. LC/MS (m/z, MH$^+$): 450.0.

(E)-4-(4-((6-methoxybenzo[b]thiophen-3-yl)oxy)phenyl)but-3-en-2-one (Compound 132)

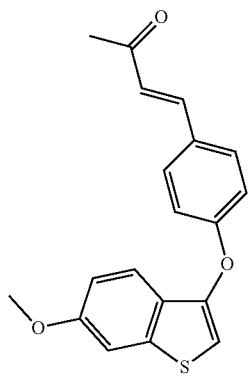 [SMILES: COc1ccc2c(Oc3ccc(/C=C/C(C)=O)cc3)csc2c1]

To a microwave vial, 3-(4-bromophenoxy)-6-methoxybenzo[b]thiophene (1.0 g, 2.98 mmol), but-3-en-2-one (0.483 mL, 8.95 mmol), and Pd(PPh$_3$)$_2$Cl$_2$ (209 mg, 0.298 mmol) were suspended in DMF (10 mL) and triethylamine (2.079 mL, 14.92 mmol). The reaction was heated for 60 min at 120° C. under microwave irradiation. The reaction mixture was diluted with EtOAc and brine and the layers were separated. The aqueous layer was then further extracted with EtOAc (2×), the combined organic layers were dried over anhydrous Na$_2$SO$_4$, filtered and concentrated in vacuo. The resulting crude material was purified by column chromatography (SiO$_2$, 0-20% EtOAc/Heptane) to afford (E)-4-(4-((6-methoxybenzo[b]thiophen-3-yl)oxy)phenyl)but-3-en-2-one (584 mg, 1.800 mmol, 60% yield) as a light brown solid. LC/MS (m/z, MH$^+$): 325.0.

(E)-4-(4-((2-(2-isopropylphenyl)-6-methoxybenzo[b]thiophen-3-yl)oxy)phenyl)but-3-en-2-one (Compound 133)

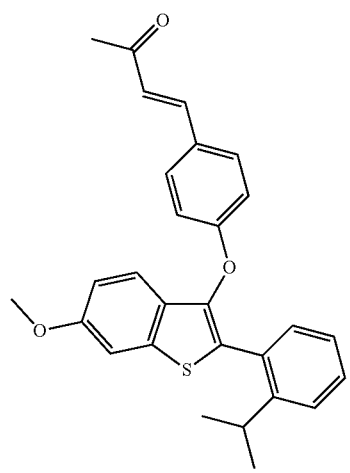 [SMILES: COc1ccc2c(Oc3ccc(/C=C/C(C)=O)cc3)c(-c3ccccc3C(C)C)sc2c1]

To a 5 mL microwave vial, added a solution of (E)-4-(4-((6-methoxybenzo[b]thiophen-3-yl)oxy)phenyl)but-3-en-2-one (90 mg, 0.277 mmol) in anhydrous DMA (3.0 mL), followed by 1-iodo-2-isopropylbenzene (137 mg, 0.555 mmol), chloro[2-(dicyclohexylphosphino)-3,6-dimethoxy-2',4',6'-tri-i-propyl-1,1'-biphenyl][2-(2-aminoethyl)phenyl]palladium(II) (BrettPhos Palladacycle 1$^{st}$ generation, 22.16 mg, 0.028 mmol), trimethylacetic acid (85 mg, 0.832 mmol) and potassium carbonate (115 mg, 0.832 mmol). The microwave vial was sealed, purged and back-filled with nitrogen. The reaction mixture subjected to microwave irradiation for 2 h at 150° C. Upon completion the reaction was diluted with EtOAc, and washed with water (2×) and brine (1×). The combined organic layer was dried over anhydrous Na$_2$SO$_4$, filtered and concentrated in vacuo to give the crude product, which was purified by column chromatography (SiO$_2$, 0-20% EtOAc/heptane) to afford (E)-4-(4-((2-(2-isopropylphenyl)-6-methoxybenzo[b]thiophen-3-yl)oxy)phenyl)but-3-en-2-one (71.3 mg, 0.161 mmol, 58% yield). LC/MS (m/z, MH$^+$): 443.0.

(E)-methyl 3-(4-((2-bromo-6-methoxybenzo[b]thiophen-3-yl)oxy)phenyl)acrylate (Compound 134)

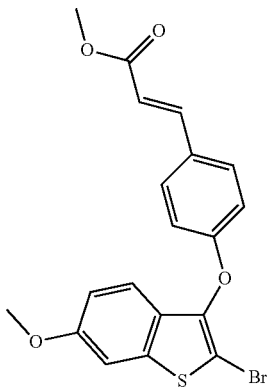 [SMILES: COC(=O)/C=C/c1ccc(Oc2c(Br)sc3cc(OC)ccc23)cc1]

To a solution (E)-methyl 3-(4-((6-methoxybenzo[b]thiophen-3-yl)oxy)phenyl)acrylate (2.1 g, 6.17 mmol) in THF 201 mL) at room temperature was added N-bromosuccinimide (1.208 g, 6.79 mmol). The resulting solution was stirred vigorously at room temperature for 2 h after which time the reaction was quenched by addition of sat. aq. Sodium Thiosulfate solution and extracted with EtOAc (3×). The combined organic layers were dried over anhydrous MgSO$_4$, filtered and concentrated in vacuo. The resulting crude material was purified by column chromatography (SiO$_2$, 0-40% EtOAc/Heptane) to afford (E)-methyl 3-(4-((2-bromo-6-methoxybenzo[b]thiophen-3-yl)oxy)phenyl)acrylate (2.4 g, 5.72 mmol, 93% yield). $^1$H NMR (400 MHz, CDCl$_3$) δ ppm 7.65 (d, J=16.0 Hz, 1H), 7.46 (d, J=8.7 Hz, 2H), 7.32 (d, J=8.9 Hz, 1H), 7.20 (d, J=2.2 Hz, 1H), 6.95 (d, J=8.7 Hz, 2H), 6.91 (dd, J=8.8, 2.2 Hz, 1H), 6.31 (s, 1H), 3.86 (s, 3H), 3.79 (s, 3H). LC/MS (m/z, MH$^+$): 420.9.

(E)-methyl 3-(4-((2-bromo-6-hydroxybenzo[b]thiophen-3-yl)oxy)phenyl)acrylate & (E)-3-(4-((2-bromo-6-hydroxybenzo[b]thiophen-3-yl)oxy)phenyl)acrylic acid (Compounds 135 and 136)

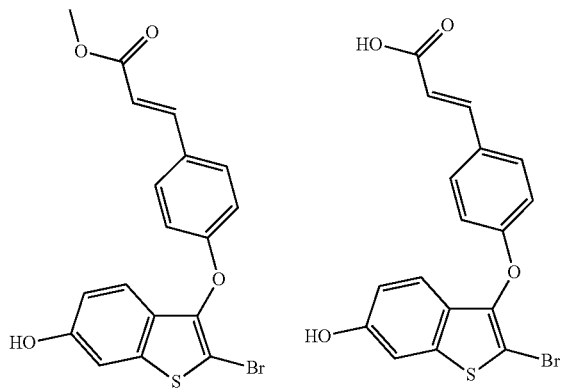 [SMILES: COC(=O)/C=C/c1ccc(Oc2c(Br)sc3cc(O)ccc23)cc1 ; O=C(O)/C=C/c1ccc(Oc2c(Br)sc3cc(O)ccc23)cc1]

To a solution of (E)-methyl 3-(4-((2-bromo-6-methoxybenzo[b]thiophen-3-yl)oxy)phenyl)acrylate (2.4 g, 5.72 mmol) in DCM (20 mL) at room temperature was added BBr$_3$ (1.0 M in Heptane, 17.17 mL, 17.17 mmol) dropwise. The resulting mixture was stirred at room temperature for 2 h after which time an aqueous buffer (pH 7.4, made from citric acid and dibasic sodium phophate, 10 mL), cooled to 0° C., was slowly added into the reaction. The resulting mixture was then diluted with DCM (30 mL) and stirred at room temperature for 1 h. The phases were then separated and the organic phase was dried over anhydrous Na$_2$SO$_4$, filtered and concentrated in vacuo. The crude material was purified by column chromatography (SiO$_2$, 0-100% EtOAc/Heptane) to afford (E)-methyl 3-(4-((2-bromo-6-hydroxybenzo[b]thiophen-3-yl)oxy)phenyl)acrylate (1.6 g, 3.95 mmol, 69% yield) as a pale yellow solid and (E)-3-(4-((2-bromo-6-hydroxybenzo[b]thiophen-3-yl)oxy)phenyl)acrylic acid (370 mg, 0.946 mmol, 17% yield) as a yellow solid.

(E)-methyl 3-(4-((2-bromo-6-hydroxybenzo[b]thiophen-3-yl)oxy)phenyl)acrylate: $^1$H NMR (400 MHz, CD$_3$OD) δ ppm 3.76 (s, 3H), 6.43 (d, J=16.17 Hz, 1H), 6.82 (dd, J=8.84, 2.27 Hz, 1H), 6.90-6.97 (m, 2H), 7.17 (d, J=2.02 Hz, 1H), 7.22 (d, J=8.59 Hz, 1H), 7.53-7.62 (m, 2H), 7.65 (d, J=15.66 Hz, 1H). LC/MS (m/z, MH$^+$): 406.8.

(E)-3-(4-((2-bromo-6-hydroxybenzo[b]thiophen-3-yl)oxy)phenyl)acrylic acid: $^1$H NMR (400 MHz, CD$_3$OD) δ ppm 6.38 (d, J=16.17 Hz, 1H), 6.82 (dd, J=8.59, 2.02 Hz, 1H), 6.89-6.97 (m, 2H), 7.17 (d, J=2.02 Hz, 1H), 7.23 (d, J=8.59 Hz, 1H), 7.53-7.60 (m, 2H), 7.63 (d, J=15.66 Hz, 1H). LC/MS (m/z, MH$^+$): 392.8.

(E)-methyl 3-(4-((2-(2-isopropyl-6-methylphenyl)-6-methoxybenzo[b]thiophen-3-yl)oxy)phenyl)acrylate (Compound 137)

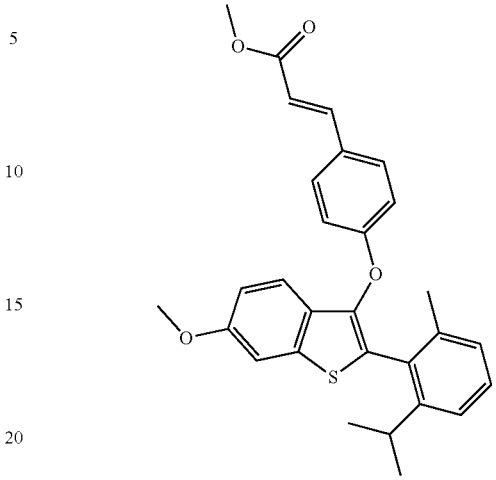

To a solution of (E)-methyl 3-(4-((2-bromo-6-methoxybenzo[b]thiophen-3-yl)oxy)phenyl)acrylate (150 mg, 0.358 mmol) in dimethoxyethane (1.7 mL) and water (0.3 mL) was added (2-isopropyl-6-methylphenyl)boronic acid (127 mg, 0.715 mmol), barium hydroxide (123 mg, 0.715 mmol) and tetrakis(triphenylphosphine)palladium(0) (41.3 mg, 0.036 mmol). The mixture was subjected to microwave irradiation at 125° C. for 25 min after which time the reaction was acidified to pH 2 by addition of concentrated HCl. The mixture was then extracted with DCM (3×) and the combined organic layers were dried over anhydrous MgSO4, filtered and concentrated in vacuo. The resulting crude material was purified by column chromatography (SiO$_2$, 0-30% EtOAc/Heptane) to afford (E)-methyl 3-(4-((2-(2-isopropyl-6-methylphenyl)-6-methoxybenzo[b]thiophen-3-yl)oxy)phenyl)acrylate (151 mg, 0.304 mmol, 85% yield).
$^1$H NMR (400 MHz, (CD$_3$)$_2$SO) δ ppm 7.65 (d, J=2.2 Hz, 1H), 7.62 (d, J=8.5 Hz, 2H), 7.56 (d, J=16.0 Hz, 1H), 7.32-7.18 (m, 3H), 7.10 (d, J=7.4 Hz, 1H), 7.00 (dd, J=8.7, 2.3 Hz, 1H), 6.85 (d, J=8.6 Hz, 2H), 6.47 (d, J=16.0 Hz, 1H), 3.84 (s, 3H), 3.69 (s, 3H), 2.94 (p, J=6.8 Hz, 1H), 2.15 (s, 3H), 1.12 (d, J=6.8 Hz, 3H), 0.98 (d, J=6.8 Hz, 3H). LC/MS (m/z, MH$^+$): 473.0.

(E)-tert-butyl 3-(4-((2-(2-(difluoromethyl)phenyl)-6-hydroxybenzo[b]thiophen-3-yl)oxy)phenyl)acrylate (Compound 138)

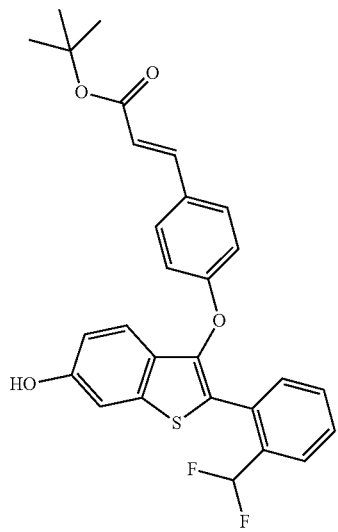 [SMILES: CC(C)(C)OC(=O)/C=C/c1ccc(Oc2c(-c3ccccc3C(F)F)sc3cc(O)ccc23)cc1]

To a solution of (E)-tert-butyl 3-(4-((2-(2-(difluoromethyl)phenyl)-6-methoxybenzo[b]thiophen-3-yl)oxy)phenyl)acrylate (133 mg, 0262 mmol) in N-Methyl-2-pyrrolidone (1.5 mL) was added thiophenol (0.040 mL, 0.392 mmol) and K$_2$CO$_3$ (36.1 mg, 0.262 mmol). The resulting mixture was subjected to microwave irradiation at 200° C. for 1 h after which time the reaction was quenched by addition of water and extracted with EtOAc (2×). The combined organic layers were dried over anhydrous MgSO4, filtered and concentrated in vacuo and the resulting crude material was purified by column chromatography (SiO$_2$, 0-20% EtOAc/Heptane) to afford (E)-tert-butyl 3-(4-((2-(2-(difluoromethyl)phenyl)-6-hydroxybenzo[b]thiophen-3-yl)oxy)phenyl)acrylate (100 mg, 0.202 mmol, 77% yield). LC/MS (m/z, M−H): 493.1.

(E)-methyl 3-(4-((2-(2-(1,1-difluoroethyl)phenyl)-6-hydroxybenzo[b]thiophen-3-yl)oxy)phenyl)acrylate (Compound 139)

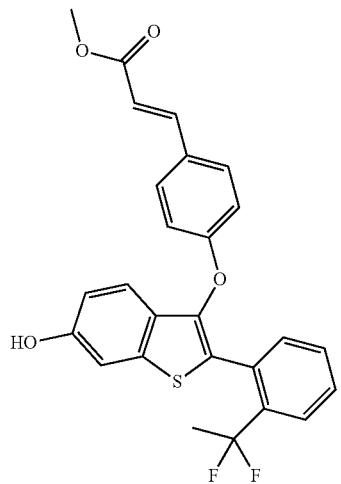 [SMILES: COC(=O)/C=C/c1ccc(Oc2c(-c3ccccc3C(C)(F)F)sc3cc(O)ccc23)cc1]

To a solution of (E)-methyl 3-(4-((2-bromo-6-hydroxybenzo[b]thiophen-3-yl)oxy)phenyl)acrylate (95 mg, 0.234 mmol) in dimethoxyethane (3.0 mL) was added 2-(2-(1,1-difluoroethyl)phenyl)-4,4,5,5-tetramethyl-1,3,2-dioxaborolane (94 mg, 0.352 mmol), [1,1'-Bis(diphenylphosphino)ferrocene]dichloropalladium(II) complex with dichloromethane (19.14 mg, 0.023 mmol) and potassium carbonate (2.0M aqueous solution, 0.469 mL, 0.938 mmol). The resulting mixture was subjected to microwave irradiation at 100° C. for 20 min after which time the reaction was diluted with EtOAc and washed with sat. aq. NH$_4$Cl solution (2×). The combined organic layers were dried over anhydrous MgSO$_4$, filtered and concentrated in vacuo and the resulting crude material was purified by column chromatography (SiO$_2$, 0-40% EtOAc/Heptane) to afford (E)-methyl 3-(4-((2-(2-(1,1-difluoroethyl)phenyl)-6-hydroxybenzo[b]thiophen-3-yl)oxy)phenyl)acrylate (77 mg, 0.165 mmol, 70% yield). $^1$H NMR (400 MHz, CDCl$_3$) δ ppm 7.63-7.56 (m, 2H), 7.44-7.38 (m, 1H), 7.36 (d, J=8.8 Hz, 2H), 7.33 (d, J=4.1 Hz, 2H), 7.28-7.24 (m, 2H), 6.90-6.81 (m, 3H), 6.28 (d, J=16.1 Hz, 1H), 3.78 (s, 3H), 1.91 (t, J=18.4 Hz, 3H).

(E)-methyl 3-(4-((6-methoxy-2-(2-(methoxymethyl)phenyl)benzo[b]thiophen-3-yl)oxy)phenyl)acrylate (Compound 140)

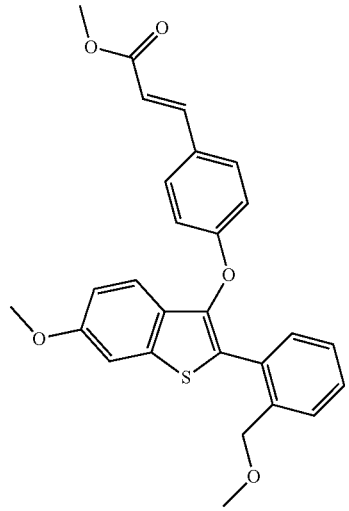 [SMILES: COCc1ccccc1-c1sc2cc(OC)ccc2c1Oc1ccc(/C=C/C(=O)OC)cc1]

To a solution of (E)-methyl 3-(4-((2-bromo-6-methoxybenzo[b]thiophen-3-yl)oxy)phenyl)acrylate (100 mg, 0.238 mmol) in 1,2-dimethoxyethane (3.0 mL) was added (2-(methoxymethyl)phenyl)boronic acid (79 mg, 0.477 mmol), [1,1'-bis(diphenylphosphino)ferrocene]dichloropalladium (II) (17.5 mg, 0.024 mmol) and Na$_2$CO$_3$ (2.0N aqueous, 0.358 mL, 0.715 mmol). The resulting mixture was subjected to microwave irradiation at 100° C. for 20 min after which time the reaction was diluted with EtOAc, added anhydrous Na$_2$SO$_4$, filtered and concentrated in vacuo. The crude material was purified by column chromatography (SiO$_2$, 0-20% EtOAc/Heptane) to afford (E)-methyl 3-(4-((6-methoxy-2-(2-(methoxymethyl)phenyl)benzo[b]thiophen-3-yl)oxy)phenyl)acrylate (86.6 mg, 0.188 mmol, 79% yield). LC/MS (m/z, M+H$_2$O): 478.0.

(E)-3-(4-((6-methoxy-2-(2-(methoxymethyl)phenyl)benzo[b]thiophen-3-yl)oxy)phenyl)acrylic acid (Compound 141)

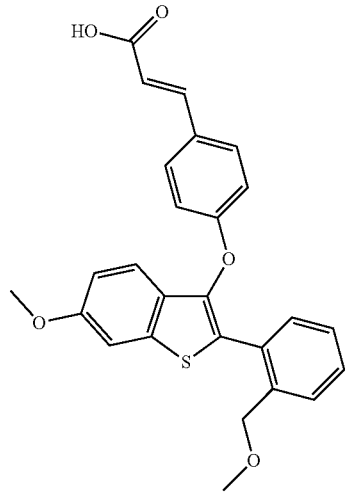 [SMILES: COCc1ccccc1-c1sc2cc(OC)ccc2c1Oc1ccc(/C=C/C(=O)O)cc1]

To a solution of (E)-methyl 3-(4-((6-methoxy-2-(2-(methoxymethyl)phenyl)benzo[b]thiophen-3-yl)oxy)phenyl)acrylate (86.6 mg, 0.188 mmol) in MeOH (3.0 mL) was added LiOH (2.0N aqueous, 0.564 mL, 1.128 mmol). The resulting mixture was stirred at room temperature for 48 h after which time the reaction was brought to pH 7 by addition of 1N HCl, the neutralized reaction was then concentrated in vacuo to afford (E)-3-(4-((6-methoxy-2-(2-(methoxymethyl)phenyl)benzo[b]thiophen-3-yl)oxy)phenyl)acrylic acid (45.9 mg, 0.103 mmol, 55% yield). LC/MS (m/z, MH$^+$): 447.0.

(R,E)-methyl 3-(4-((2-(2-(1-hydroxyethyl)phenyl)-6-methoxybenzo[b]thiophen-3-yl)oxy)phenyl)acrylate (Compound 142)

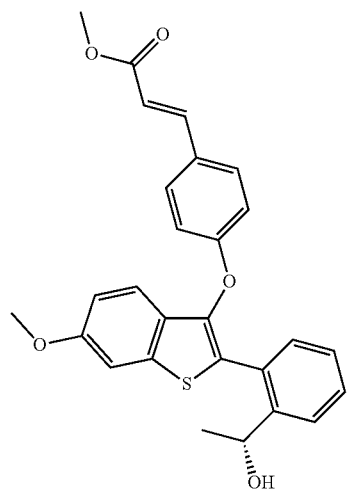 [SMILES: COC(=O)/C=C/c1ccc(Oc2c(-c3ccccc3[C@@H](C)O)sc3cc(OC)ccc23)cc1]

To a microwave vial containing (E)-methyl 3-(4-((6-methoxybenzo[b]thiophen-3-yl)oxy)phenyl)acrylate (100 mg, 0.294 mmol) in DMA (2.5 mL) was added (R)-1-(2-bromophenyl)ethanol (118 mg, 0.588 mmol), chloro[2-(dicyclohexylphosphino)-3,6-dimethoxy-2',4',6'-tri-i-propyl-1,1'-biphenyl][2-(2-aminoethyl)phenyl]palladium(II) (BrettPhos Palladacycle 1$^{st}$ generation, 23.47 mg, 0.029 mmol), trimethylacetic acid (90 mg, 0.881 mmol) and potassium carbonate (122 mg, 0.881 mmol) The microwave vial was sealed, purged and back-filled with nitrogen. The reaction mixture subjected to microwave irradiation for 2 h at 150° C. Upon completion the reaction was diluted with EtOAc, and washed with water and brine. The combined organic layer was dried over anhydrous Na$_2$SO$_4$, filtered and concentrated in vacuo. The resulting crude material was purified by column chromatography (SiO$_2$, 0-30% EtOAc/heptane) to afford (R,E)-methyl 3-(4-((2-(2-(1-hydroxyethyl)phenyl)-6-methoxybenzo[b]thiophen-3-yl)oxy)phenyl)acrylate (27.5 mg, 0.060 mmol, 20% yield). LC/MS (m/z, MH$^+$): 459.0.

(R,E)-methyl 3-(4-((6-hydroxy-2-(2-(1-hydroxyethyl)phenyl)benzo[b]thiophen-3-yl)oxy)phenyl) acrylate (Compound 143)

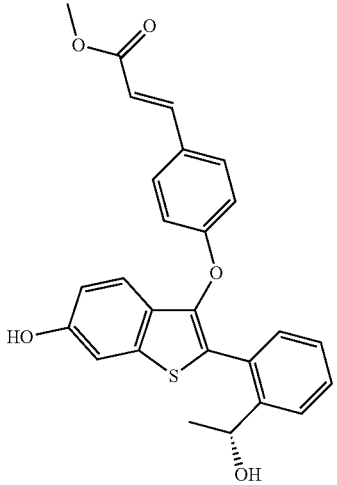 [SMILES: COC(=O)/C=C/c1ccc(Oc2c(-c3ccccc3[C@@H](C)O)sc3cc(O)ccc23)cc1]

To a solution of afford (R,E)-methyl 3-(4-((2-(2-(1-hydroxyethyl)phenyl)-6-methoxybenzo[b]thiophen-3-yl)oxy) phenyl)acrylate (27.5 mg, 0.060 mmol) N-methyl-2-pyrrolidone (1.0 mL) was added thiophenol (0.00922 mL, 0.090 mmol) and K$_2$CO$_3$ (8.25 mg, 0.060 mmol). The resulting mixture was subjected to microwave irradiation at 190° C. for 1 h after which time the reaction was diluted with EtOAc and washed with brine. The layers were separated and the aqueous layer was further extracted with EtOAc, the combined organic layers were dried over anhydrous Na$_2$SO$_4$, filtered and concentrated in vacuo. The resulting crude material was purified by column chromatography (SiO$_2$, 0-30% EtOAc/heptane) to afford (R,E)-methyl 3-(4-((6-hydroxy-2-(2-(1-hydroxyethyl)phenyl)benzo[b]thiophen-3-yl)oxy)phenyl)acrylate (5 mg, 0.011, 19% yield). LC/MS (m/z, MH$^+$): 445.0.

(E)-3-(4-((6-((tert-butyldimethylsilyl)oxy)-2-(2-isopropylphenyl)benzo[b]thiophen-3-yl)oxy)phenyl) acrylic acid (Compound 144)

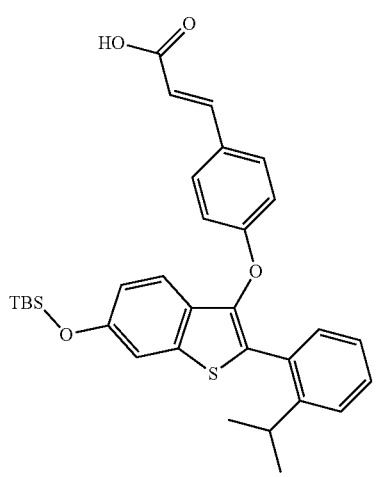

To a solution of (E)-3-(4-((6-hydroxy-2-(2-isopropylphenyl)benzo[b]thiophen-3-yl)oxy)phenyl)acrylic acid (100 mg, 0.232 mmol) in DCM (3 mL) at room temperature were added tert-butyldimethylsilyl chloride (88 mg, 0.581 mmol) and N,N-diisopropylethylamine (0.122 mL, 0.697 mmol). The resulting mixture was stirred at room temperature for 18 h after which time the reaction was quenched by addition of water and extracted with EtOAc (2×). The combined organic layers were dried over anhydrous Na$_2$SO$_4$, filtered and concentrated in vacuo and the resulting crude material was then dissolved in THF (wet) and K$_2$CO$_3$ (32.1 mg, 0.232 mmol) was added and the mixture was stirred at room temperature for 2 h. Upon completion the reaction was quenched by addition of 1N HCl and extracted with EtOAc (2×), the combined organic layers were washed with brine, dried over anhydrous Na$_2$SO$_4$, filtered and concentrated in vacuo to afford (E)-3-(4-((6-((tert-butyldimethylsilyl)oxy)-2-(2-isopropylphenyl)benzo[b]thiophen-3-yl)oxy)phenyl)acrylic acid (120 mg, 0.220 mmol, 95% yield). $^1$H NMR (400 MHz, CDCl$_3$) δ ppm 7.66 (d, J=16.0 Hz, 1H), 7.37 (d, J=8.8 Hz, 2H), 7.34-7.24 (m, 5H), 7.17-7.09 (m, 1H), 6.90-6.82 (m, 3H), 6.26 (d, J=15.9 Hz, 1H), 3.24 (p, J=6.7 Hz, 1H), 1.17 (d, J=6.7 Hz, 6H), 1.01 (s, 9H), 0.24 (s, 6H).

(E)-isopropyl 3-(4-((6-((tert-butyldimethylsilyl)oxy)-2-(2-isopropylphenyl)benzo[b]thiophen-3-yl)oxy)phenyl)acrylate (Compound 145)

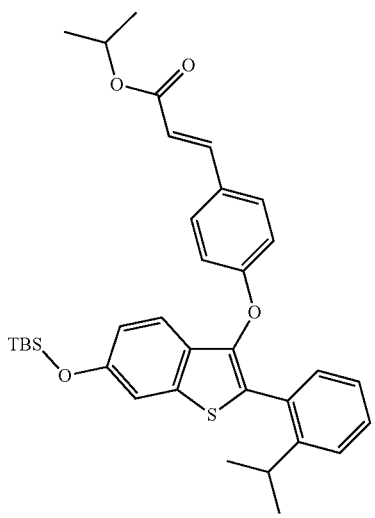

To a solution of (E)-3-(4-((6-((tert-butyldimethylsilyl)oxy)-2-(2-isopropylphenyl)benzo[b]thiophen-3-yl)oxy)phenyl)acrylic acid (59.6 mg, 0.109 mmol) in DCM (2.5 mL) was added i-PrOH (0.034 mL, 0.438 mmol), N-(3-dimethylaminopropyl)-N'-ethylcarbodiimide hydrochloride (84 mg, 0.438 mmol) and 4-dimethylaminopyridine (8.02 mg, 0.066 mmol). The resulting mixture was stirred at room temperature for 75 min after which time the reaction was quenched by addition of water and diluted with DCM. The phases were separated and the aqueous layer was further extracted with DCM (3×). The combined organic layers were dried over anhydrous MgSO$_4$, filtered and concentrated in vacuo. The resulting crude material was purified by column chromatography (SiO$_2$, 0-30% EtOAc/Heptane) to (E)-isopropyl 3-(4-((6-((tert-butyldimethylsilyl)oxy)-2-(2-isopropylphenyl)benzo[b]thiophen-3-yl)oxy)phenyl)acrylate (35 mg, 0.060 mmol, 55% yield). $^1$H NMR (400 MHz, CDCl$_3$) δ ppm 7.49 (d, J=16.0 Hz, 1H), 7.32-7.17 (m, 7H), 7.10-7.03 (m, 1H), 6.79 (d, J=8.8 Hz, 3H), 6.18 (d, J=16.1 Hz, 1H), 5.05 (p, J=6.2 Hz, 1H), 3.18 (p, J=6.8 Hz, 1H), 1.23 (d, J=6.4 Hz, 6H), 1.11 (d, J=6.8 Hz, 6H), 0.95 (s, 9H), 0.18 (s, 6H).

(E)-tert-butyl 3-(4-((6-hydroxy-2-(2-isopropylphenyl)benzo[b]thiophen-3-yl)oxy)phenyl)acrylate (Compound 146)

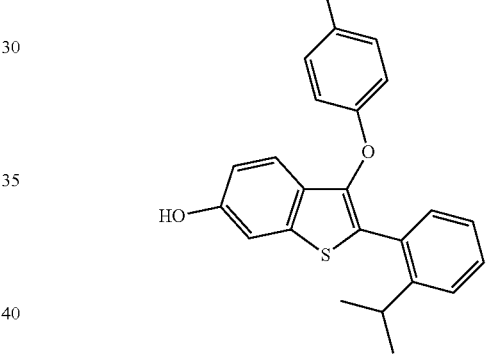

To a solution of (E)-3-(4-((6-hydroxy-2-(2-isopropylphenyl)benzo[b]thiophen-3-yl)oxy)phenyl)acrylic acid (400 mg, 0.929 mmol) in toluene (10 mL) was added N,N-dimethylformamide di-tert-butyl acetal (0.891 mLm 3.72 mmol) dropwise, a large amount of precipitate immediately crashed out. The resulting mixture was heated to 80° C. for 1 h after which time the reaction was cooled to room temperature, diluted with EtOAc, washed with water, sat. aq. NaHCO$_3$ solution and brine. The combined organic layers were dried over anhydrous MgSO4, filtered and concentrated in vacuo and the resulting crude material was purified by column chromatography (SiO$_2$, 0-40% EtOAc/Heptane) to afford (E)-tert-butyl 3-(4-((6-hydroxy-2-(2-isopropylphenyl)benzo[b]thiophen-3-yl)oxy)phenyl)acrylate (149 mg, 0.306 mmol, 88% yield). $^1$H NMR (400 MHz, CDCl$_3$) δ ppm 7.42 (d, J=16.0 Hz, 1H), 7.30-7.18 (m, 7H), 7.10-7.03 (m, 1H), 6.81 (dd, J=8.7, 2.3 Hz, 1H), 6.77 (d, J=8.8 Hz, 2H), 6.14 (d, J=15.9 Hz, 1H), 5.55 (br s, 1H), 3.17 (p, J=6.8 Hz, 1H), 1.46 (s, 9H), 1.10 (d, J=6.9 Hz, 6H). LC/MS (m/z, M–H): 485.1.

(E)-tert-butyl 3-(4-((6-acetoxy-2-(2-isopropylphenyl)benzo[b]thiophen-3-yl)oxy)phenyl)acrylate (Compound 147)

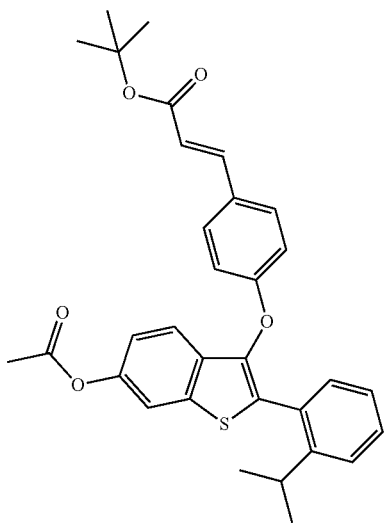 [SMILES: CC(=O)Oc1ccc2c(Oc3ccc(/C=C/C(=O)OC(C)(C)C)cc3)c(-c3ccccc3C(C)C)sc2c1]

To a solution of (E)-tert-butyl 3-(4-((6-hydroxy-2-(2-isopropylphenyl)benzo[b]thiophen-3-yl)oxy)phenyl)acrylate (63 mg, 0.129 mmol) in DCM (2.5 mL) was added acetic acid (0.030 mL, 0.518 mmol), N-(3-dimethylaminopropyl)-N'-ethylcarbodiimide hydrochloride (99 mg, 0.518 mmol) and 4-dimethylaminopyridine (9.49 mg, 0.078 mmol). The resulting mixture was stirred at room temperature for 16 h after which time the reaction was quenched by addition of 0.1N HCl and diluted with DCM. The phases were separated and the aqueous layer was further extracted with DCM (2×). The combined organic layers were dried over anhydrous MgSO4, filtered and concentrated in vacuo. The resulting crude material was purified by column chromatography (SiO$_2$, 0-40% EtOAc/Heptane) to afford (E)-tert-butyl 3-(4-((6-acetoxy-2-(2-isopropylphenyl)benzo[b]thiophen-3-yl)oxy)phenyl)acrylate (65 mg, 0.123 mmol, 95% yield). $^1$H NMR (400 MHz, CDCl$_3$) δ ppm 7.50 (d, J=2.0 Hz, 1H), 7.40 (d, J=12.9 Hz, 1H), 7.37 (d, J=5.9 Hz, 1H), 7.28-7.22 (m, 4H), 7.22-7.18 (m, 1H), 7.11-7.02 (m, 1H), 6.98 (dd, J=8.6, 2.1 Hz, 1H), 6.81-6.72 (m, 2H), 6.12 (d, J=15.9 Hz, 1H), 3.11 (p, J=6.8 Hz, 1H), 2.28 (s, 3H), 1.44 (s, 9H), 1.09 (d, J=6.8 Hz, 6H).

(E)-tert-butyl 3-(4-((6-((1,1-dioxido-3-oxobenzo[d]isothiazol-2(3H)-yl)methoxy)-2-(2-isopropylphenyl)benzo[b]thiophen-3-yl)oxy)phenyl)acrylate (Compound 148)

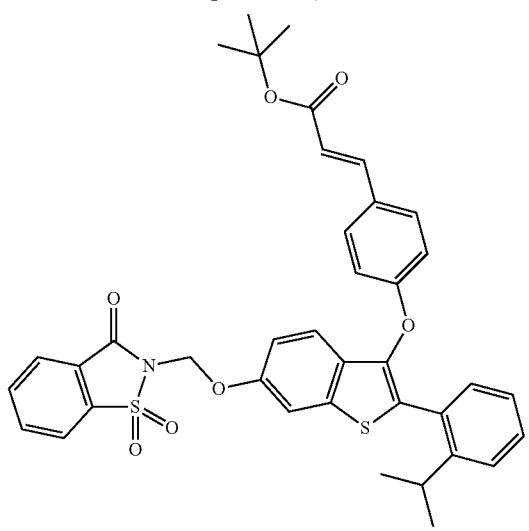

To a solution of (E)-tert-butyl 3-(4-((6-hydroxy-2-(2-isopropylphenyl)benzo[b]thiophen-3-yl)oxy)phenyl)acrylate (68 mg, 0.140 mmol) in acetone (2 mL) was added 2-(chloromethyl)benzo[d]isothiazol-3(2H)-one 1,1-dioxide (32.4 mg, 0.140 mmol), potassium carbonate (19.31 mg, 0.140 mmol) and potassium iodide (23.2 mg, 0.140 mmol). The resulting mixture was stirred at room temperature for 48 hours. The solvent was removed in vacuo. The resulting solid was retaken in ethyl acetate. The organic layer was washed with aqueous saturated ammonium chloride solution followed by brine. The organic layer was dried over anhydrous MgSO$_4$, filtered and concentrated in vacuo to give the crude product, which was purified by flash chromatography (SiO$_2$, 0-30% EtOAc/Heptane) to afford (E)-tert-butyl 3-(4-((6-((1,1-dioxido-3-oxobenzo[d]isothiazol-2(3H)-yl)methoxy)-2-(2-isopropylphenyl)benzo[b]thiophen-3-yl)oxy)phenyl)acrylate (67.4 mg, 0.099 mmol, 71% yield). $^1$H NMR (400 MHz, (CD$_3$)$_2$SO) δ 8.37 (d, J=7.4 Hz, 1H), 8.18 (dd, J=7.4, 1.3 Hz, 1H), 8.11 (td, J=7.7, 1.3 Hz, 1H), 8.04 (t, J=7.6 Hz, 1H), 7.88 (d, J=2.2 Hz, 1H), 7.61-7.54 (m, 2H), 7.48-7.34 (m, 3H), 7.34-7.30 (m, 2H), 7.23-7.15 (m, 2H), 6.89-6.81 (m, 2H), 6.33 (d, J=16.0 Hz, 1H), 5.90 (s, 2H), 3.13 (q, J=6.9 Hz, 1H), 1.45 (s, 9H), 1.13 (d, J=6.8 Hz, 6H).

Examples

For synthesis of examples 1-55: the following examples have been prepared from the corresponding intermediates by removing the methyl group(s) from the phenolic ether(s) and in some cases also removing a tert-butyl group from a carboxylic ester functionality in the same step.

General Method A

To a solution of the above described intermediate in DCM (0.02-0.1 M) at 0° C. was added BBr$_3$ (1 M in DCM, 1.5-3 eq per MeO— group) dropwise. The resulting dark mixture was stirred at 0° C. for 1-3 h after which the reaction was quenched with ice water or sat. aq. NaHCO$_3$ solution. The mixture was allowed to warm up to room temperature and extracted with 5% MeOH in EtOAc. The combined organic phases were concentrated and the crude product dissolved in MeOH and purified by RP-HPLC to provide the example.

General Method B:

To a solution of the above described intermediate in DCM (0.02-0.1 M) at 0° C. added BBr$_3$ (1 M in hexanes, 1.5-3 eq. per MeO— group) dropwise. The resulting dark mixture was stirred at 0° C. for 1-3 h after which the reaction was quenched with methanol. The mixture was concentrated to a small volume and purified by RP-HPLC to provide the example.

Example 1

3-(4-((6-hydroxy-2-(4-hydroxyphenyl)benzo[b]thiophen-3-yl)oxy)phenyl)propanoic acid

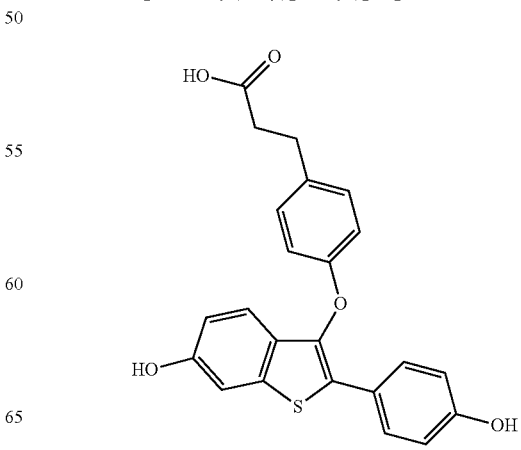

To a solution of tert-butyl 3-(4-((6-methoxy-2-(4-methoxyphenyl)benzo[b]thiophen-3-yl)oxy)phenyl)propanoate (27 mg, 0.055 mmol) in DCM (1.7 mL) at 0° C. was added BBr₃ (1.0 M in DCM, 0.220 mL, 0.220 mmol) dropwise (reaction turned brown in color and a solid immediately precipitated from the solution). The resulting mixture was stirred at 0° C. for 1 h after which the reaction was quenched with ice water (3.0 mL) and allowed to warm to room temperature with vigorous stirring. The resulting mixture was concentrated in vacuo and dissolved in MeOH (2 mL) then purified by reverse phase HPLC (neutral condition, 3% 1-propanol in 1-100% CH₃CN/H₂O) to afford 3-(4-((6-hydroxy-2-(4-hydroxyphenyl)-benzo[b]thiophen-3-yl)oxy)phenyl)propanoic acid (7 mg, 0.02 mmol, 31% yield). LC/MS (m/z, MH⁺): 407.0943.

Example 2

(E)-3-(4-((6-hydroxy-2-(4-hydroxyphenyl)benzo[b]thiophen-3-yl)oxy)phenyl)acrylic acid

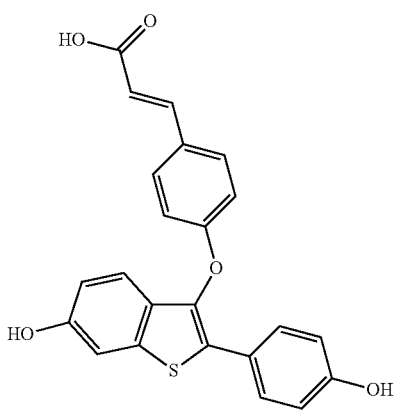 [SMILES: O=C(O)/C=C/c1ccc(Oc2c(-c3ccc(O)cc3)sc3cc(O)ccc23)cc1]

To a solution of (E)-tert-butyl 3-(4-((6-methoxy-2-(4-methoxyphenyl)-benzo[b]thiophen-3-yl)oxy)phenyl)acrylate (40 mg, 0.08 mmol) in DCM (2.5 mL) at 0° C. was added BBr₃ (1.0 M in DCM, 0.33 mL, 0.33 mmol) dropwise, a solid immediately precipitated from the solution. The resulting mixture was stirred at 0° C. for 100 min after which the reaction was quenched by addition of sat. aq. NaHCO₃ (4 mL) solution and a white precipitate was observed. The aqueous layer was then extracted with 5% MeOH/EtOAc (4×12 mL) and the combined organic layers were passed through a phase separator to remove water and concentrated in vacuo to afford the crude product which was dissolved in MeOH (2 mL) and purified by reverse phase HPLC (neutral condition, 3% 1-propanol in 1-100% CH₃CN/H₂O) to afford (E)-3-(4-((6-hydroxy-2-(4-hydroxyphenyl)benzo[b]thiophen-3-yl)oxy)phenyl)acrylic acid (17.5 mg, 0.04 mmol, 53% yield). LC/MS (m/z, MH⁺): 405.0790.

Example 3

(E)-3-(4-((6-hydroxy-2-(4-(trifluoromethyl)phenyl)benzo[b]thiophen-3-yl)oxy)phenyl)acrylic acid

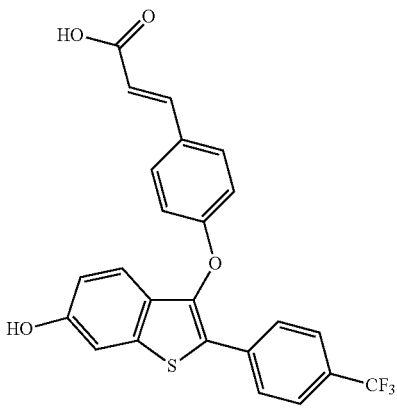 [SMILES: O=C(O)/C=C/c1ccc(Oc2c(-c3ccc(C(F)(F)F)cc3)sc3cc(O)ccc23)cc1]

To a 2-dram vial containing (E)-tert-butyl 3-(4-((6-methoxy-2-(4-(trifluoromethyl)phenyl)benzo[b]thiophen-3-yl)oxy)phenyl)acrylate (59.4 mg, 0.113 mmol) in anhydrous DCM (1.5 mL) at 0° C. was added BBr₃ (1.0 M in DCM, 451 µL, 0.451 mmol) dropwise. The resulting mixture was stirred at 0° C. for 1 h after which the reaction was quenched with 3 drops of water, diluted with DCM, and extracted with sat. aq. NaHCO₃ (added a few drops of 2-propanol). The organic layer was dried over anhydrous MgSO₄, filtered concentrated in vacuo to afford the curde material which was purified by reverse phase HPLC (neutral condition, 3% 1-propanol in 10-100% CH₃CN/H₂O) to afford (E)-3-(4-((6-hydroxy-2-(4-(trifluoromethyl)phenyl)benzo[b]thiophen-3-yl)oxy)phenyl)acrylic acid (33.8 mg, 0.074 mmol, 66% yield) as a white solid. ¹H NMR (400 MHz, CD₃OD) δ ppm=6.36 (d, J=16.17 Hz, 1H), 6.78-6.89 (m, 1H), 6.98 (d, J=8.59 Hz, 2H), 7.17-7.30 (m, 2H), 7.51-7.70 (m, 5H), 7.88 (d, J=8.08 Hz, 2H). HRMS (m/z, MH⁺): 457.0710.

Example 4

(E)-3-(4-((6-hydroxy-2-(2-isopropylphenyl)benzo[b]thiophen-3-yl)oxy)phenyl)acrylic acid

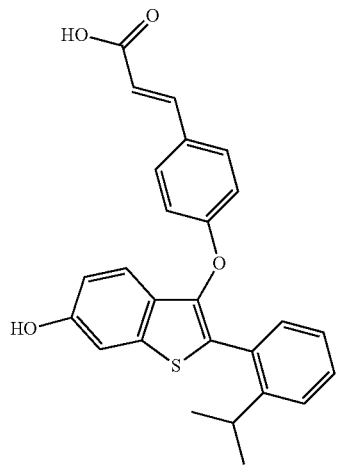

Example 4 was be prepared from the corresponding methylether/tert-butyl ester intermediates using method A. Example 4 was also prepared, using the following hydrolysis reaction: to a solution of (E)-methyl 3-(4-((6-hydroxy-2-(2-isopropylphenyl)benzo[b]thiophen-3-yl)oxy)phenyl) acrylate (25.8 mg, 0.058 mmol) in EtOH (1.5 mL) was added LiOH (2.0 M aqueous, 0.290 mL, 0.580 mmol). After 5 h at room temperature the reaction was acidified to pH 3 by addition of 1.0 N aqueous HCl and extracted with 5% MeOH/EtOAc, the combined organic layers were passed through a phase separator and concentrated in vacuo to afford (E)-3-(4-((6-hydroxy-2-(2-isopropylphenyl)benzo[b] thiophen-3-yl)oxy)phenyl)acrylic acid (24.0 mg, 0.056 mmol, 96% yield). $^1$H NMR (400 MHz, $CD_3OD$) δ ppm=7.57 (d, J=15.9 Hz, 1H), 7.45 (d, J=8.7 Hz, 2H), 7.37-7.21 (m, 5H), 7.15-7.08 (m, 1H), 6.88-6.82 (m, 3H), 6.31 (d, J=15.9 Hz, 1H), 3.27-3.18 (m, 1H), 1.16 (d, J=6.8 Hz, 6H). LC/MS (m/z, M−H): 429.0.

Alternatively, Example 4 can also be prepared according to the following procedure:

Step 1: 2-bromo-3-(4-bromophenoxy)-6-methoxybenzo [b]thiophene 1,1-dioxide (compound 26). To a solution of 2,3-dibromo-6-methoxybenzo[b]thiophene 1,1-dioxide (12.5 g, 35.3 mmol) in THF (175 mL) at room temperature was added 4-bromophenol (6.49 g, 37.1 mmol) and $Cs_2CO_3$ (34.5 g, 106 mmol). The resulting suspension was warmed to 50° C. and the reaction turned faintly yellowish0green after a few minutes and then subsequently faintly pink, the mixture remained a suspension. After 4 h at 50° C. the mixture was cooled to room temperature, diluted with water (175 mL), and stirred for 15 min. The solution was transferred to a separator funnel and the phases were separated. The aqueous layer was extracted with EtOAc (3×100 mL) and the combined organic layers were then washed with brine (100 mL), dried over anhydrous $Na_2SO_4$, filtered and concentrated in vacuo to afford 2-bromo-3-(4-bromophenoxy)-6-methoxybenzo[b]thiophene 1,1-dioxide (14.7 g, 33.0 mmol, 93% yield) as a faintly pink solid which was used without further purification. $^1$H NMR (400 MHz, $CDCl_3$) δ ppm=3.83 (s, 3H), 6.92-7.03 (m, 3H), 7.25-7.35 (m, 2H), 7.39-7.50 (m, 2H).

Step 2: 3-(4-bromophenoxy)-6-methoxybenzo[b]thiophene 1,1-dioxide (compound 27). To a solution of 2-bromo-3-(4-bromophenoxy)-6-methoxy-benzo[b]thiophene 1,1-dioxide (180 g, 403 mmol) in MeOH (150 mL) and DMSO (1300 mL) at 0° C. (internal temperature was at 5° C.) was added the first portion of $NaBH_4$ (15 g, 396.5 mmol). Internal temperature rose quickly to 40° C. and $H_2$ gas release was observed. The mixture was stirred in an ice bath for 30 min (internal temperature cooled down to 10° C.). The second portion of $NaBH_4$ (15.5 g, 409.7 mmol) was added. The resulting mixture was stirred for 30 minutes after which time the reaction was quenched with water (2000 mL) over 1 hour. The resulting precipitate was collected, air dried over 18 hours, then washed with heptane to afford 3-(4-bromophenoxy)-6-methoxybenzo[b]thiophene 1,1-dioxide as an off white solid which was used without further purification. $^1$H NMR (400 MHz, $CDCl_3$) δ ppm=3.85 (s, 3H), 5.38 (s, 1H), 7.02-7.08 (m, 3H), 7.22 (d, J=2.53 Hz, 1H), 7.47-7.60 (m, 3H).

Step 3: 3-(4-bromophenoxy)-6-methoxybenzo[b]thiophene (compound 28). To a solution of 3-(4-bromophenoxy)-6-methoxybenzo[b]thiophene 1,1-dioxide (230 g, 626 mmol) in THF (3450 mL) was added DIBAL-H (1.0 M in DCM, 3132 mL, 3132 mmol). The mixture was heated to 60° C. for 18 hours. The mixture was cooled down to 40° C. DIBAL-H (1.0 M in DCM or Toluene, 500 mL, 500 mmol) was added. The mixture was refluxed for 6 hours. DIBAL-H (1.0 M in DCM, 300 mL, 300 mmol) was added. The mixture was refluxed for 8 hours. after which time the reaction was cooled to 0° C. over 2 hours. EtOAc (1226 mL) was added very slowly. Rochelle salt solution (884 g, 626 mmol in 6000 mL water) was slowly added (over 3 hours). The resulting solution was aged at room temperature for 18 hours. The organic layer was separated from the aqueous layer. The aqueous layer was extracted with EtOAc (1000 mL). The combined organic layer was washed with brined, dried with anhydrous $Na_2SO_4$ and concentrated in vacuo to afford 3-(4-bromophenoxy)-6-methoxybenzo[b]thiophene (149.8 g, 446.9 mmol, 71% yield) as a white solid which was used without further purification. $^1$H NMR (400 MHz, $CDCl_3$) δ ppm=3.81 (s, 3H), 6.46 (s, 1H), 6.90 (d, J=9.09 Hz, 3H), 7.16-7.22 (m, 1H), 7.31-7.40 (m, 2H), 7.46 (d, J=9.09 Hz, 1H). LC/MS (m/z, MH$^+$): 336.8.

Step 4: (E)-methyl 3-(4-((6-methoxybenzo[b]thiophen-3-yl)oxy)phenyl)acrylate (compound 29). To a solution of 3-(4-bromophenoxy)-6-methoxybenzo[b]thiophene (125 g, 373 mmol) and $Pd(PPh_3)_2Cl_2$ (13.09 g, 18.64 mmol) in DMF (2500 mL) and diisopropyl ethylamine (326 mL, 1864 mmol) at room temperature was added (subsurface) methyl acrylate (845 mL, 9322 mmol) over 3-4 hours. As the addition started, the reaction was heated at 120° C. for 13 hours. Methyl acrylate (150 mL, 1654.8 mmol) was added (subsurface). The reaction was heated at 120° C. for 1 hour. The mixture was cooled to RT. Excess methyl acrylate and diisopropyl ethylamine were remove in vacuo. The resulting mixture was filtered through celite pad and the cake was washed with EtOAc (2000 mL). The resulting mixture was washed with water (2×), dried with anhydrous $Na_2SO_4$ and concentrated in vacuo. The crude material was purified by column chromatography ($SiO_2$, 5% to 50% EtOAc/Heptane) to afford (E)-methyl 3-(4-((6-methoxybenzo[b]thiophen-3-yl)oxy)phenyl)acrylate (81 g, 238 mmol, 64% yield) as a white solid. $^1$H NMR (400 MHz, $CDCl_3$) δ ppm=1.46 (s, 3H), 3.73 (s, 3H), 6.28 (d, J=16.17 Hz, 1H), 6.59 (s, 1H), 6.90 (dd, J=8.59, 2.02 Hz, 1H), 7.00 (d, J=8.59 Hz, 2H), 7.21 (d, J=2.02 Hz, 1H), 7.37-7.48 (m, 3H), 7.59 (d, J=16.17 Hz, 1H). LC/MS (m/z, MH$^+$): 341.1.

Step 5: (E)-methyl 3-(4-((2-(2-isopropylphenyl)-6-methoxybenzo[b]thiophen-3-yl)oxy)phenyl)acrylate (compound 32). To a solution of (E)-4-(4-((6-methoxybenzo[b] thiophen-3-yl)oxy)phenyl)but-3-en-2-one (45 g, 132 mmol) in anhydrous DMA (450 mL) at room temperature was added 1-iodo-2-isopropylbenzene (57 g, 231.6 mmol), chloro[2-(dicyclohexylphosphino)-3,6-dimethoxy-2',4',6'-tri-i-propyl-1,1'-biphenyl][2-(2-aminoethyl)phenyl]palladium(II) (BrettPhos Palladacycle 1$^{st}$ generation, 6.34 g, 7.93 mmol), trimethylacetic acid (40.5 g, 397 mmol) and potassium carbonate (55 g, 397 mmol). The resulting mixture was heated at 140° C. for 1.5 hours. The reaction mixture was cooled down to 50° C. The reaction was diluted with EtOAc (400 mL) and let to cool down to room temperature. As the reaction cooled, a precipitate formed and was removed by filtration. The mother liquor was washed with water and brine, dried over anhydrous $Na_2SO_4$, filtered and concentrated in vacuo to give the crude product, which was purified by column chromatography ($SiO_2$, 10-20% EtOAc/heptane) to afford (E)-methyl 3-(4-((2-(2-isopropylphenyl)-6-methoxybenzo[b]thiophen-3-yl)oxy)phenyl)acrylate (47 g, 102.5 mmol). $^1$H NMR (400 MHz, $CDCl_3$) δ ppm=7.61 (d, J=15.9 Hz, 1H), 7.42-7.29 (m, 7H), 7.15 (ddd, J=8.1, 5.7, 2.8 Hz, 1H), 6.97 (dd, J=8.8, 2.3 Hz, 1H), 6.91-6.85 (m, 2H), 6.29 (d, J=16.0 Hz, 1H), 3.91 (s, 3H), 3.80 (s, 3H), 3.26 (p, J=6.8 Hz, 1H), 1.19 (d, J=6.9 Hz, 6H). LC/MS (m/z, MH$^+$): 459.5.

Step 6: (E)-methyl 3-(4-((6-hydroxy-2-(2-isopropylphenyl)benzo[b]thiophen-3-yl)oxy)phenyl)acrylate (example 45). To a solution of (E)-methyl 3-(4-((2-(2-isopropylphenyl)-6-methoxybenzo[b]thiophen-3-yl)oxy)phenyl)acrylate (75 g, 164 mmol) in DCM (1000 mL) at −2° C. (internal temperature) was added tribromoborane (491 mL, 491 mmol) slowly via addition funnel to keep internal temperature below 2° C. The resulting mixture was maintained around 0° C. for 30 minutes. To a solution of sodium bicarbonate (Aqueous, 10%, 347 mL) at 5° C. (internal temperature) was added the reaction mixture over 2 hour. The organic layer was separated from the aqueous layer. The organic layer was dried over Na$_2$SO$_4$, filtered and concentrated in vacuo. The aqueous layer was extracted with EtOAc (500 mL). The organic layer was dried over Na$_2$SO$_4$, filtered and concentrated in vacuo. The crude product was purified by column chromatography (SiO2, 10-30% EtOAc/heptane) to afford (E)-methyl 3-(4-((2-(2-isopropylphenyl)-6-methoxybenzo[b]thiophen-3-yl)oxy)phenyl)acrylate (90% purity). The resultant product can be purified by either slurry in acetonitrile for 1 hour or in EtOAc/Heptane (1:9) for 30 minutes. The solid was filtered and air dried for 18 hours to afford (E)-methyl 3-(4-((6-hydroxy-2-(2-isopropylphenyl)benzo[b]thiophen-3-yl)oxy)phenyl)acrylate (68 g, 130 mmol, 79%). $^1$H NMR (400 MHz, CDCl$_3$) δ ppm=7.60 (d, J=15.9 Hz, 1H), 7.40-7.25 (m, 8H), 7.15 (ddd, J=8.1, 5.5, 3.0 Hz, 1H), 6.91-6.85 (m, 3H), 6.29 (d, J=16.0 Hz, 1H), 3.80 (s, 3H), 3.25 (p, J=6.8 Hz, 1H), 1.19 (d, J=6.8 Hz, 6H). HR-MS (m/z, MH+): 445.1473.

Step 7: (E)-3-(4-((6-hydroxy-2-(2-isopropylphenyl)benzo[b]thiophen-3-yl)oxy)phenyl)acrylic acid (example 4). To a solution of (E)-methyl 3-(4-((6-hydroxy-2-(2-isopropylphenyl)benzo[b]thiophen-3-yl)oxy)phenyl)acrylate (50 g, 112 mmol) in MeOH (1000 mL) at 0° C. was added lithium hydroxide (2N, 281 mL, 562 mmol). The resulting mixture was stirred at room temperature for 5 hours. Lithium hydroxide (2N, 281 mL, 562 mmol) was added. The reaction was stirred at room temperature for 18 hours. The reaction mixture was cooled in an ice bath and HCl (0.5N, 3500 mL, 1750 mmol) was added over 30 minutes. A precipitate formed as HCl was added to the reaction mixture. The precipitate was collected by vacuum filtration and washed with water and heptane. The resulting cake was air dried for 22 hours. The resulting pasty solid was dried in a vacuum over (house vacuum) at 45° C. for 24 hours. The vacuum was switched to high vacuum the temperature was increased to 50° C. A beaker containing molecular and a beaker containing P$_2$O$_5$ was placed in the vacuum oven. After few hours, the beaker containing P$_2$O$_5$ was removed. The product was dried in the vacuum oven (high vacuum) at 50° C. for 18 hours to afford (E)-3-(4-((6-hydroxy-2-(2-isopropylphenyl)benzo[b]thiophen-3-yl)oxy)phenyl)acrylic acid (50 g, 114 mmol). $^1$H NMR (400 MHz, CD$_3$OD) δ ppm=7.57 (d, J=15.9 Hz, 1H), 7.45 (d, J=8.7 Hz, 2H), 7.37-7.21 (m, 5H), 7.15-7.08 (m, 1H), 6.88-6.82 (m, 3H), 6.31 (d, J=15.9 Hz, 1H), 3.27-3.18 (m, 1H), 1.16 (d, J=6.8 Hz, 6H).

The following examples were prepared from the corresponding methylether/tert-butyl ester intermediates using method A:

TABLE 1

| Example | Structure | Name | Physical data |
|---|---|---|---|
| 4 | 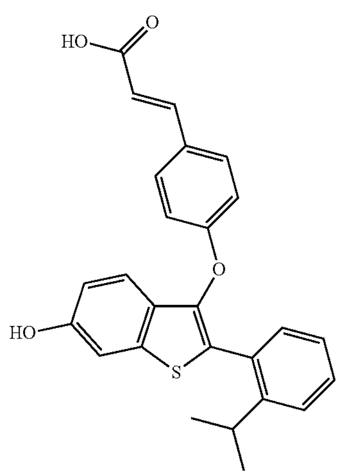 [SMILES: CC(C)c1ccccc1-c1sc2cc(O)ccc2c1Oc1ccc(/C=C/C(=O)O)cc1] | (E)-3-(4-((6-hydroxy-2-(2-isopropylphenyl)-benzo[b]thiophen-3-yl)oxy)phenyl)acrylic acid | $^1$H NMR (400 MHz, CD$_3$OD) δ ppm = 7.57 (d, J = 15.9 Hz, 1H), 7.45 (d, J = 8.7 Hz, 2H), 7.37-7.21 (m, 5H), 7.15-7.08 (m, 1H), 6.88-6.82 (m, 3H), 6.31 (d, J = 15.9 Hz, 1H), 3.27-3.18 1H), 1.16 (d, J = 6.8 Hz, 6H) HRMS (m/z, MH+): 431.1309 |
| 5 | 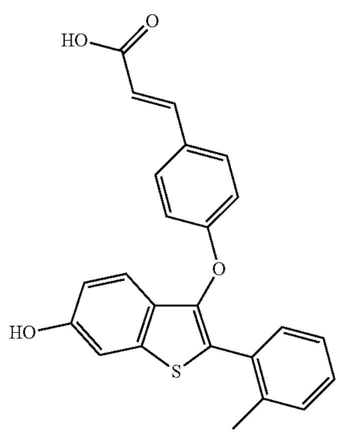 [SMILES: Cc1ccccc1-c1sc2cc(O)ccc2c1Oc1ccc(/C=C/C(=O)O)cc1] | (E)-3-(4-((6-hydroxy-2-(o-tolyl)benzo-[b]thiophen-3-yl)oxy)-phenyl)acrylic acid | $^1$H NMR (400 MHz, CD$_3$OD) δ ppm = 2.35 (s, 3H), 6.34 (d, J = 15.66 Hz, 1H), 6.76-6.82 (m, 2H), 6.84 (dd, J = 8.84, 2.27 Hz, 1H), 7.13 (d, J = 8.08 Hz, 1H), 7.16-7.38 (m, 8H) HRMS (m/z, MH+): 403.0995 |

| Example | Structure | Name | Physical data |
|---------|-----------|------|---------------|
| 6 | 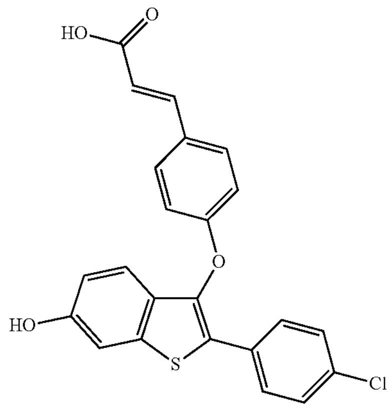 [SMILES: O=C(O)/C=C/c1ccc(Oc2c(-c3ccc(Cl)cc3)sc3cc(O)ccc23)cc1] | (E)-3-(4-((2-(4-chlorophenyl)-6-hydroxybenzo[b]thiophen-3-yl)oxy)phenyl)-acrylic acid | ¹H NMR (400 MHz, CD₃OD) δ ppm = 6.35 (d, J = 16.17 Hz, 1H), 6.77-6.85 (m, 1H), 6.90-7.00 (m, 2H), 7.19 (d, J = 9.09 Hz, 1H), 7.22 (d, J = 2.02 Hz, 1H), 7.29-7.38 (m, 2H), 7.46-7.55 (m, 2H), 7.58 (d, J = 15.66 Hz, 1H), 7.62-7.69 (m, 2H)<br>LC/MS (m/z, MH⁻): 421.40 |
| 7 | 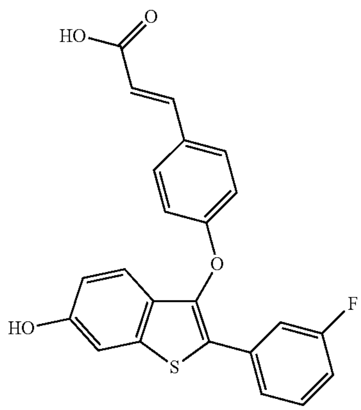 [SMILES: O=C(O)/C=C/c1ccc(Oc2c(-c3cccc(F)c3)sc3cc(O)ccc23)cc1] | (E)-3-(4-((2-(3-fluorophenyl)-6-hydroxybenzo[b]thiophen-3-yl)oxy)phenyl)-acrylic acid | ¹H NMR (400 MHz, CD₃OD) δ ppm = 6.39 (d, J = 16.17 Hz, 1H), 6.82 (dd, J = 8.84, 2.27 Hz, 1H), 6.88-6.94 (m, 2H), 6.95-7.03 (m, 1H), 7.16-7.24 (m, 2H), 7.29-7.39 (m, 2H), 7.40-7.53 (m, 4H)<br>LC/MS (m/z, MH⁻): 405.40 |
| 8 | 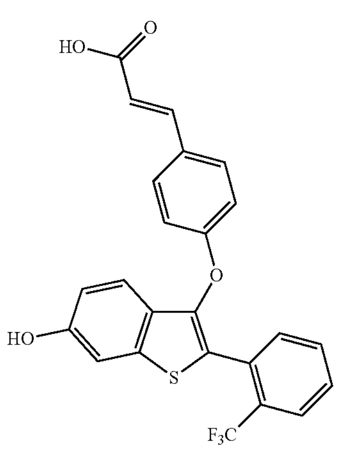 | (E)-3-(4-((6-hydroxy-2-(2-(trifluoromethyl)-phenyl)benzo[b]thiophen-3-yl)oxy)phenyl)-acrylic acid | ¹H NMR (400 MHz, CD₃OD) δ ppm = 6.32 (d, J = 15.66 Hz, 1H), 6.78-6.91 (m, 3H), 7.16-7.28 (m, 2H), 7.45 (d, J = 9.09 Hz, 2H), 7.49-7.62 (m, 4H), 7.70-7.81 (m, 1H)<br>HRMS (m/z, MH⁺): 457.0702 |

TABLE 1-continued

| Example | Structure | Name | Physical data |
|---|---|---|---|
| 9 | 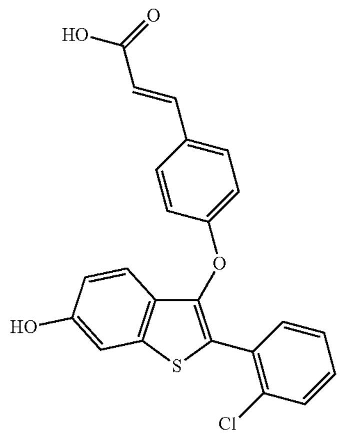 [SMILES: O=C(O)/C=C/c1ccc(Oc2c(-c3ccccc3Cl)sc3cc(O)ccc23)cc1] | (E)-3-(4-((2-(2-chlorophenyl)-6-hydroxybenzo[b]thiophen-3-yl)oxy)phenyl)-acrylic acid | $^1$H NMR (400 MHz, CD$_3$OD) δ ppm = 6.31 (d, J = 16.17 Hz, 1H), 6.84-6.88 (m, 1H), 6.88-6.92 (m, 2H), 7.24 (d, J = 2.02 Hz, 1H), 7.25-7.34 (m, 3H), 7.41-7.49 (m, 4H), 7.56 (d, J = 16.17 Hz, 1H) HRMS (m/z, MH$^+$): 423.0446 |
| 10 | 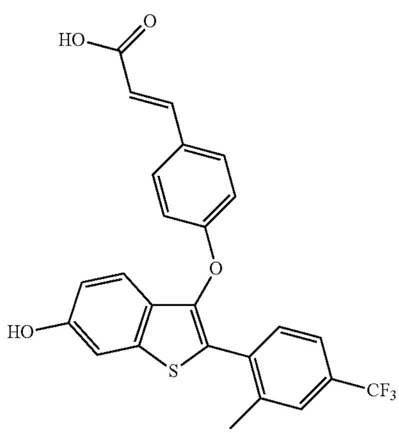 [SMILES: Cc1cc(C(F)(F)F)ccc1-c1sc2cc(O)ccc2c1Oc1ccc(/C=C/C(=O)O)cc1] | (E)-3-(4-((6-hydroxy-2-(2-methyl-4-(trifluoromethyl)phenyl)benzo[b]thiophen-3-yl)oxy)phenyl)acrylic acid | $^1$H NMR (400 MHz, CD$_3$OD) δ ppm = 2.44 (s, 3H), 6.31 (d, J = 15.66 Hz, 1H), 6.82-6.91 (m, 3H), 7.26 (d, J = 2.02 Hz, 1H), 7.29 (d, J = 8.59 Hz, 1H), 7.39-7.48 (m, 3H), 7.48-7.59 (m, 3H) HRMS (m/z, MH$^+$): 471.0851 |
| 11 | 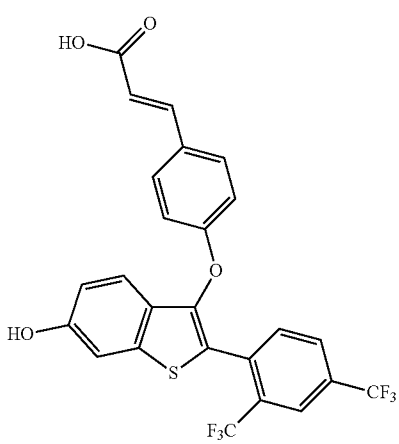 [SMILES: O=C(O)/C=C/c1ccc(Oc2c(-c3ccc(C(F)(F)F)cc3C(F)(F)F)sc3cc(O)ccc23)cc1] | (E)-3-(4-((2-(2,4-bis(trifluoromethyl)phenyl)-6-hydroxy-benzo[b]thiophen-3-yl)oxy)phenyl)-acrylic acid | $^1$H NMR (400 MHz, CD$_3$OD) δ ppm = 6.32 (d, J = 15.66 Hz, 1H), 6.82-6.91 (m, 3H), 7.26 (dd, J = 5.56, 3.03 Hz, 2H), 7.42-7.49 (m, 2H), 7.57 (d, J = 16.17 Hz, 1H), 7.75 (d, J = 8.08 Hz, 1H), 7.89 (d, J = 8.08 Hz, 1H), 8.02 (s, 1H) HRMS (m/z, MH$^+$): 525.0572 |

TABLE 1-continued

| Example | Structure | Name | Physical data |
|---------|-----------|------|---------------|
| 12 | 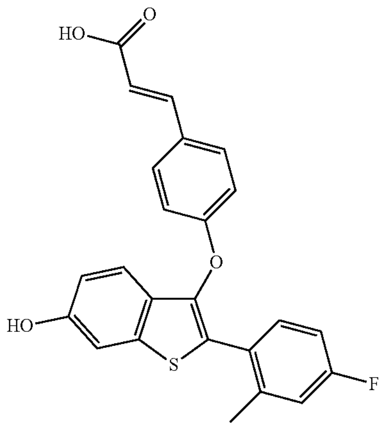 [SMILES: Cc1cc(F)ccc1-c1sc2cc(O)ccc2c1Oc1ccc(/C=C/C(=O)O)cc1] | (E)-3-(4-((2-(4-fluoro-2-methylphenyl)-6-hydroxybenzo[b]thiophen-3-yl)oxy)phenyl)-acrylic acid | $^1$H NMR (400 MHz, CD$_3$OD) δ ppm = 2.35 (s, 3H), 6.32 (d, J = 15.66 Hz, 1H), 6.81-6.92 (m, 4H), 6.98 (dd, J = 9.60, 2.53 Hz, 1H), 7.24 (d, J = 2.02 Hz, 1H), 7.27 (d, J = 8.59 Hz, 1H), 7.31 (dd, J = 8.59, 5.56 Hz, 1H), 7.42-7.49 (m, 2H), 7.56 (d, J = 16.17 Hz, 1H) HRMS (m/z, MH$^+$): 421.0911 |
| 13 | 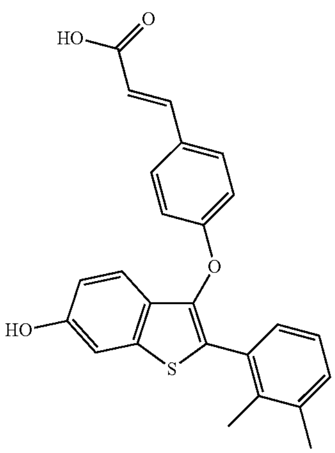 [SMILES: Cc1cccc(-c2sc3cc(O)ccc3c2Oc2ccc(/C=C/C(=O)O)cc2)c1C] | (E)-3-(4-((2-(2,3-dimethylphenyl)-6-hydroxybenzo[b]thiophen-3-yl)oxy)phenyl)-acrylic acid | $^1$H NMR (400 MHz, CD$_3$OD) δ ppm = 2.24 (d, J = 12.63 Hz, 6H), 6.29 (d, J = 16.17 Hz, 1H), 6.79-6.90 (m, 3H), 6.97-7.05 (m, 1H), 7.11 (dd, J = 14.40, 7.33 Hz, 2H), 7.20-7.30 (m, 2H), 7.37-7.46 (m, 2H), 7.55 (d, J = 15.66 Hz, 1H) HRMS (m/z, MH$^+$): 417.1139 |
| 14 | 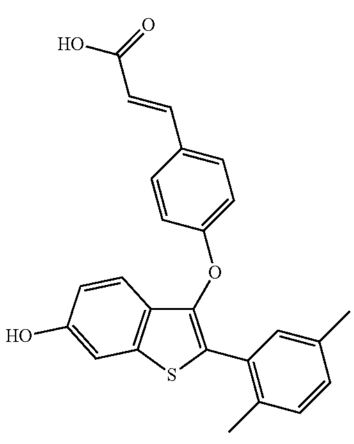 [SMILES: Cc1ccc(C)c(-c2sc3cc(O)ccc3c2Oc2ccc(/C=C/C(=O)O)cc2)c1] | (E)-3-(4-((2-(2,5-dimethylphenyl)-6-hydroxybenzo[b]thiophen-3-yl)oxy)phenyl)-acrylic acid | $^1$H NMR (400 MHz, CD$_3$OD) δ ppm = 2.09-2.44 (m, 6H), 6.30 (d, J = 16.17 Hz, 1H), 6.79-6.89 (m, 3H), 6.98-7.05 (m, 1H), 7.06-7.14 (m, 2H), 7.21-7.27 (m, 2H), 7.39-7.47 (m, 2H), 7.55 (d, J = 15.66 Hz, 1H) HRMS (m/z, MH$^+$): 417.1144 |

TABLE 1-continued

| Example | Structure | Name | Physical data |
|---|---|---|---|
| 15 | 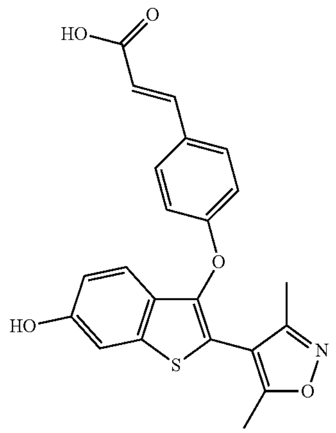 [SMILES: Cc1noc(C)c1-c1sc2cc(O)ccc2c1Oc1ccc(/C=C/C(=O)O)cc1] | (E)-3-(4-((2-(3,5-dimethylisoxazol-4-yl)-6-hydroxybenzo[b]thiophen-3-yl)oxy)phenyl)acrylic acid | $^1$H NMR (400 MHz, CD$_3$OD) δ ppm = 2.20-2.27 (m, 3H), 2.33-2.44 (m, 3H), 6.34 (d, J = 16.17 Hz, 1H), 6.28-6.41 (m, 1H), 6.81-6.95 (m, 3H), 7.25 (d, J = 2.02 Hz, 1H), 7.31 (d, J = 8.59 Hz, 1H), 7.49 (d, J = 8.59 Hz, 2H), 7.57 (d, J = 15.66 Hz, 1H) HRMS (m/z, MH$^+$): 408.0883 |
| 16 | 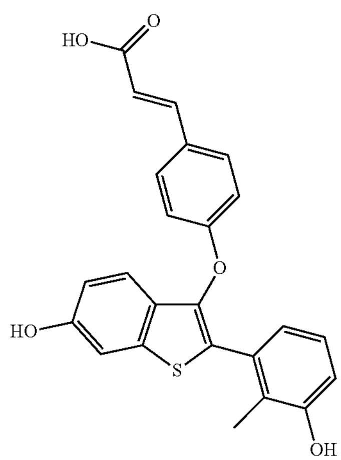 [SMILES: Cc1c(O)cccc1-c1sc2cc(O)ccc2c1Oc1ccc(/C=C/C(=O)O)cc1] | (E)-3-(4-((6-hydroxy-2-(3-hydroxy-2-methylphenyl)benzo[b]thiophen-3-yl)oxy)phenyl)acrylic acid | HRMS (m/z, MH$^+$): 419.0938 |
| 17 | 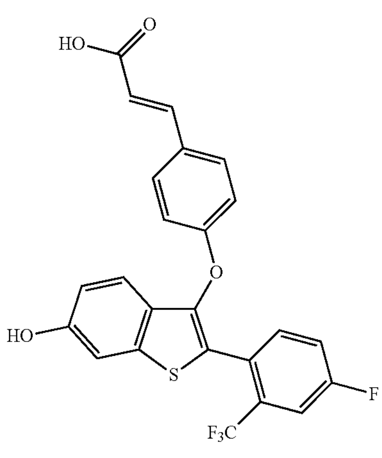 [SMILES: O=C(O)/C=C/c1ccc(Oc2c(-c3ccc(F)cc3C(F)(F)F)sc3cc(O)ccc23)cc1] | (E)-3-(4-((2-(4-fluoro-2-(trifluoromethyl)phenyl)-6-hydroxybenzo[b]thiophen-3-yl)oxy)phenyl)acrylic acid | HRMS (m/z, MH$^+$): 475.0634 |

TABLE 1-continued

| Example | Structure | Name | Physical data |
|---|---|---|---|
| 18 | 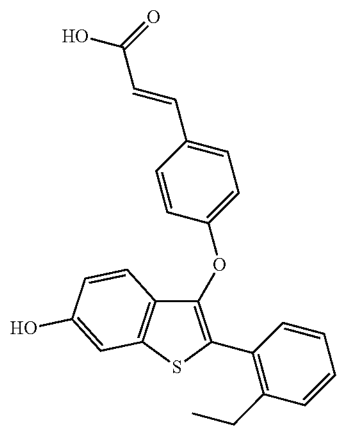 [SMILES: CCc1ccccc1-c1sc2cc(O)ccc2c1Oc1ccc(/C=C/C(=O)O)cc1] | (E)-3-(4-((2-(2-ethylphenyl)-6-hydroxybenzo[b]thiophen-3-yl)oxy)phenyl)-acrylic acid | HRMS (m/z, MH$^+$): 417.1148 |
| 19 | 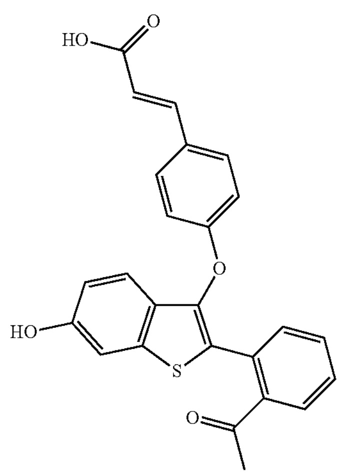 [SMILES: CC(=O)c1ccccc1-c1sc2cc(O)ccc2c1Oc1ccc(/C=C/C(=O)O)cc1] | (E)-3-(4-((2-(2-acetylphenyl)-6-hydroxybenzo[b]thiophen-3-yl)oxy)phenyl)-acrylic acid | HRMS (m/z, MH$^+$): 431.0948 |
| 20 | 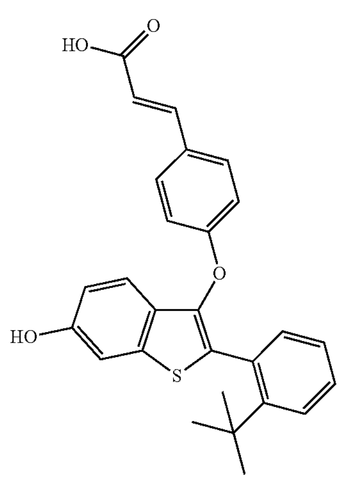 [SMILES: CC(C)(C)c1ccccc1-c1sc2cc(O)ccc2c1Oc1ccc(/C=C/C(=O)O)cc1] | (E)-3-(4-((2-(2-(tert-butyl)phenyl)-6-hydroxybenzo[b]thiophen-3-yl)oxy)phenyl)-acrylic acid | HRMS (m/z, MH$^+$): 445.1465 |

TABLE 1-continued

| Example | Structure | Name | Physical data |
|---|---|---|---|
| 21 | 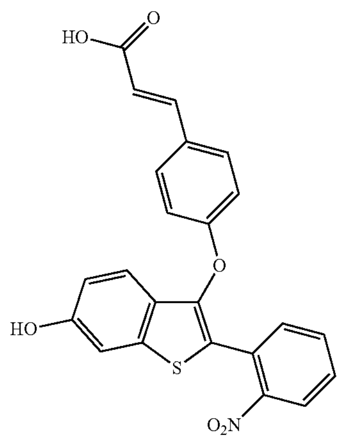 [SMILES: O=C(O)/C=C/c1ccc(Oc2c(-c3ccccc3[N+](=O)[O-])sc3cc(O)ccc23)cc1] | (E)-3-(4-((6-hydroxy-2-(2-nitrophenyl)-benzo[b]thiophen-3-yl)oxy)phenyl)-acrylic acid | HRMS (m/z, MH+): 434.0625 |
| 22 | 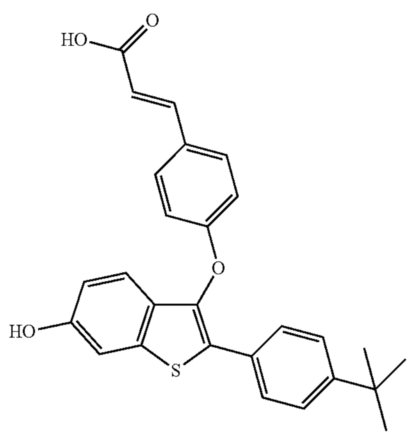 [SMILES: CC(C)(C)c1ccc(-c2sc3cc(O)ccc3c2Oc2ccc(/C=C/C(=O)O)cc2)cc1] | (E)-3-(4-((2-(4-(tert-butyl)phenyl)-6-hydroxybenzo[b]thiophen-3-yl)oxy)phenyl)-acrylic acid | HRMS (m/z, MH+): 445.1465 |
| 23 | 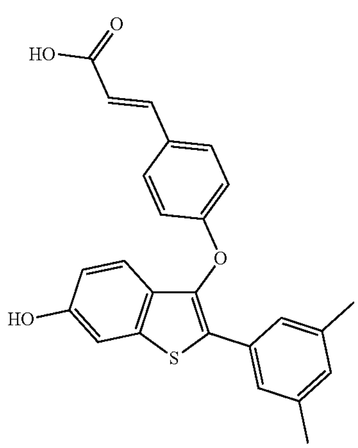 [SMILES: Cc1cc(C)cc(-c2sc3cc(O)ccc3c2Oc2ccc(/C=C/C(=O)O)cc2)c1] | (E)-3-(4-((2-(3,5-dimethylphenyl)-6-hydroxybenzo[b]thiophen-3-yl)oxy)phenyl)-acrylic acid | HRMS (m/z, MH+): 417.1157 |

TABLE 1-continued

| Example | Structure | Name | Physical data |
|---|---|---|---|
| 24 | 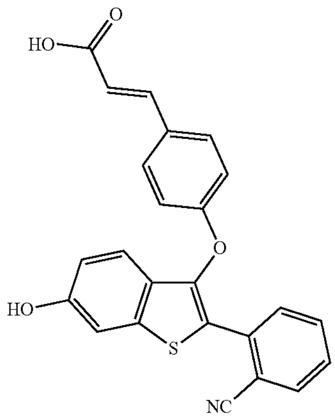 [SMILES: N#Cc1ccccc1-c1sc2cc(O)ccc2c1Oc1ccc(/C=C/C(=O)O)cc1] | (E)-3-(4-((6-hydroxy-2-(2-isocyanophenyl)-benzo[b]thiophen-3-yl)oxy)phenyl)acrylic acid | LC/MS (m/z, MH⁻): 412.4 |
| 25 | 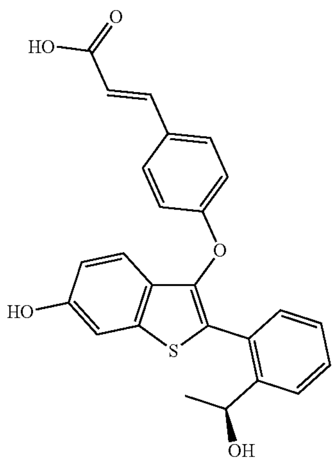 [SMILES: C[C@H](O)c1ccccc1-c1sc2cc(O)ccc2c1Oc1ccc(/C=C/C(=O)O)cc1] | (S,E)-3-(4-((6-hydroxy-2-(2-(1-hydroxy-ethyl)phenyl)benzo[b]thiophen-3-yl)oxy)phenyl)acrylic acid | LC/MS (m/z, M-H): 431.4 |

Example 26

(E)-3-(4-((6-hydroxy-2-(4-methoxyphenyl)benzo[b]thiophen-3-yl)oxy)phenyl)acrylic acid

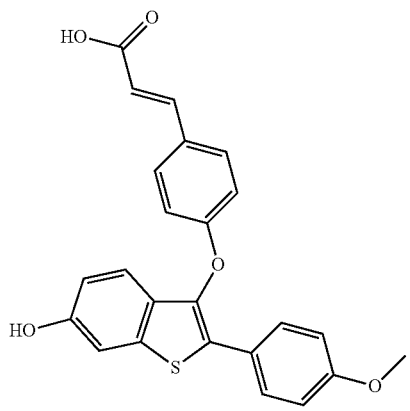 [SMILES: COc1ccc(-c2sc3cc(O)ccc3c2Oc2ccc(/C=C/C(=O)O)cc2)cc1]

Step 1: To a 30 mL vial containing (E)-methyl 3-(4-((6-methoxy-2-(4-methoxyphenyl)benzo[b]thiophen-3-yl)oxy)phenyl)acrylate (100 mg, 0.22 mmol) in DCM (1 mL) was added BBr₃ (1 M in heptane, 0.224 mL, 0.22 mmol) and the reaction was stirred for 1 h at room temperature. The reaction mixture was quenched with 4 mL MeOH and stirred for 10 min at room temperature. The crude material was concentrated onto silica gel and purified by column chromatography (SiO₂, 1-100% EtOAc/Heptane) to afford (E)-methyl 3-(4-((6-hydroxy-2-(4-hydroxyphenyl)benzo[b]thiophen-3-yl)oxy)phenyl)acrylate (11 mg, 0.03 mmol, 12% yield), and a mixture of (E)-methyl 3-(4-((2-(4-hydroxyphenyl)-6-methoxybenzo[b]thiophen-3-yl)oxy)phenyl)acrylate and (E)-methyl 3-(4-((6-hydroxy-2-(4-methoxyphenyl)benzo[b]thiophen-3-yl)oxy)phenyl)acrylate (32 mg, 0.07 mmol, 33% yield). LC/MS (m/z, MH⁺): 433.2.

Step 2: To a 30 mL vial containing a mixture of of (E)-methyl 3-(4-((2-(4-hydroxyphenyl)-6-methoxybenzo[b]thiophen-3-yl)oxy)phenyl)acrylate and (E)-methyl 3-(4-((6-hydroxy-2-(4-methoxyphenyl)benzo[b]thiophen-3-yl)oxy)phenyl)acrylate (32 mg, 0.07 mmol) in THF (3 mL), MeOH (1 mL), and H₂O (2 mL) was added LiOH (9.14 mg, 0.38 mmol). The reaction mixture was stirred for 60 min at room temperature and then concentrated in vacuo, diluted with water, and acidified to pH 2 with 6 M HCl causing a precipitate to form. The mixture was diluted with 20 mL DCM and 2 mL MeOH. The organic layer was collected (phase separator) and concentrated in vacuo to afford the crude product. The sample was purified by supercritical fluid chromatography (CHIRALCEL® OJ-H column, 45% MeOH in CO₂) to afford (E)-3-(4-((6-hydroxy-2-(4- methoxyphenyl)benzo[b]thiophen-3-yl)oxy)phenyl)acrylic acid (17 mg, 0.04 mmol, 53% yield) as a white solid. $^1$H NMR (400 MHz, (CD$_3$)$_2$SO) δ ppm=7.64 (d, J=8.59 Hz, 2H), 7.55-7.62 (m, 2H), 7.51 (d, J=16.17 Hz, 1H), 7.30 (d, J=2.02 Hz, 1H), 7.13 (d, J=8.59 Hz, 1H), 6.90-7.04 (m, 4H), 6.83 (dd, J=2.02, 8.59 Hz, 1H), 6.38 (d, J=16.17 Hz, 1H), 3.75 (s, 3H). LC/MS (m/z, M−H): 417.5.

Example 27

(E)-3-(4-((2-(4-(difluoromethyl)phenyl)-6-hydroxy-benzo[b]thiophen-3-yl)oxy)phenyl)acrylic acid

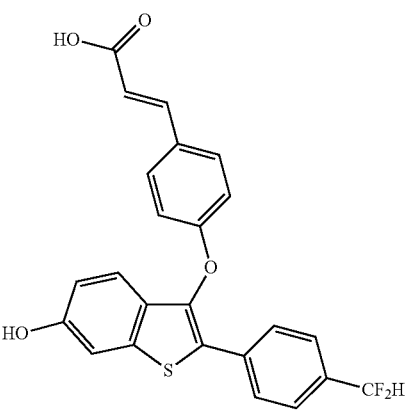 [SMILES: O=C(O)/C=C/c1ccc(Oc2c(-c3ccc(C(F)F)cc3)sc3cc(O)ccc23)cc1]

Step 1: To a microwave vial containing (E)-tert-butyl 3-(4-((2-(4-(difluoromethyl)phenyl)-6-methoxybenzo[b]thiophen-3-yl)oxy)phenyl)acrylate (50 mg, 0.098 mmol) in N-methyl-2-pyrrolidone (1.0 mL) was added thiophenol (0.015 mL, 0.147 mmol) followed by K$_2$CO$_3$ (14 mg, 0.098 mmol). The resulting mixture was subjected to microwave irradiation for 1 h at 200° C. after which time the reaction was quenched with brine and extracted with EtOAc. The combined organic layers were dried over anhydrous Na$_2$SO$_4$, filtered and concentrated in vacuo to give the crude material which was purified by column chromatography (SiO$_2$, 0-30% EtOAc/Heptane) to afford (E)-tert-butyl 3-(4-((2-(4-(difluoromethyl)phenyl)-6-hydroxybenzo[b]thiophen-3-yl)oxy)phenyl)acrylate (30 mg, 0.061 mmol, 62% yield). LC/MS (m/z, M−H): 493.5

Step 2: To a vial containing (E)-tert-butyl 3-(4-((2-(4-(difluoromethyl)phenyl)-6-hydroxybenzo[b]thiophen-3-yl)oxy)phenyl)acrylate (30 mg, 0.061 mmol) in THF (1.0 mL) was added HCl (4.0 N in dioxane, 0.4 mL, 1.600 mmol). The resulting mixture was stirred at 50° C. for 12 h after which time the reaction was concentrated in vacuo and purified by reverse phase HPLC (neutral condition, 3% 1-propanol in 10-100% CH$_3$CN/H$_2$O) to afford (E)-3-(4-((2-(4-(difluoromethyl)phenyl)-6-hydroxybenzo[b]thiophen-3-yl)oxy)phenyl)acrylic acid (21 mg, 0.048 mmol, 79% yield). LC/MS (m/z, M−H): 437.5.

Example 28

(E)-3-(4-((6-hydroxy-2-(4-hydroxyphenyl)benzothiophen-3-yl)oxy)phenyl)-2-methylacrylic acid

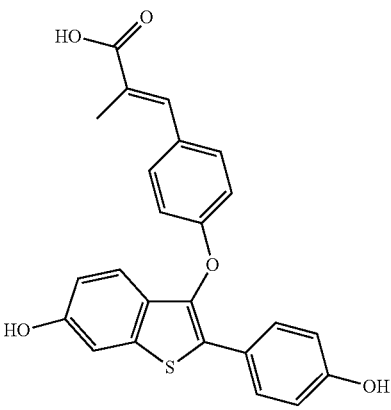 [SMILES: C/C(=C\c1ccc(Oc2c(-c3ccc(O)cc3)sc3cc(O)ccc23)cc1)C(=O)O]

To a solution of (E)-ethyl 3-(4-((6-methoxy-2-(4-methoxyphenyl)-benzo[b]thiophen-3-yl)oxy)phenyl)-2-methylacrylate (107 mg, 0.225 mmol) in DCM (5.0 mL) at 0° C. was added BBr$_3$ (1.0 M in DCM, 0.902 mL, 0.902 mmol) dropwise. The resulting mixture was stirred at 0° C. for 100 min after which the reaction was quenched by addition of sat. aq. NaHCO$_3$ (4 mL) and acidified to pH 3 by addition of concentrated HCl. The aqueous layer was then extracted with 5% MeOH/EtOAc (4×12 mL) and the combined organic layers were passed through a phase separator to remove water and concentrated in vacuo to afford the crude product which was dissolved in MeOH and purified by reverse phase HPLC (neutral condition, 3% 1-propanol in 1-100% CH$_3$CN/H$_2$O) to afford (E)-3-(4-((6-hydroxy-2-(4-hydroxyphenyl)-benzo[b]thiophen-3-yl)oxy)phenyl)-2-methylacrylic acid (32.4 mg, 0.078 mmol, 34% yield). HRMS (m/z, MH$^+$): 419.0872.

Example 29

(E)-3-(5-((6-hydroxy-2-(4-hydroxyphenyl)benzo[b]thiophen-3-yl)oxy)pyridin-2-yl)acrylic acid

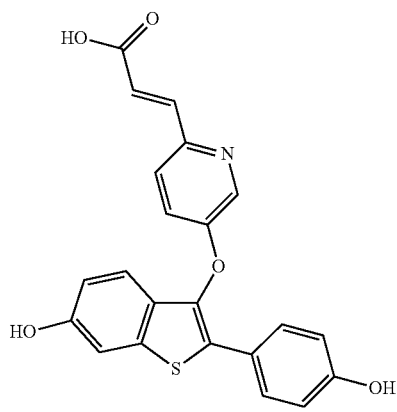 [SMILES: O=C(O)/C=C/c1ccc(Oc2c(-c3ccc(O)cc3)sc3cc(O)ccc23)cn1]

Step 1: To a solution of (E)-methyl 3-(5-((6-methoxy-2-(4-methoxyphenyl)benzo[b]thiophen-3-yl)oxy)pyridin-2- yl)acrylate (0.096 g, 0.215 mmol) in DCM (2.145 mL) at room temperature was added BBr₃ (1.0 M in heptane, 0.858 mL, 0.86 mmol) and the reaction was stirred at room temperature for 30 min Upon completion the reaction was quenched with MeOH (2.0 mL) and stirred for 10 min at room temperature then concentrated in vacuo onto silica gel then purified by column chromatography (SiO₂, 0-20% MeOH/DCM) to afford (E)-methyl 3-(5-((6-hydroxy-2-(4-hydroxyphenyl)benzo[b]thiophen-3-yl)oxy)pyridin-2-yl) acrylate. LC/MS (m/z, MH⁺): 420.3.

Step 2: To a solution of (E)-methyl 3-(5-((6-hydroxy-2-(4-hydroxyphenyl)benzo[b]thiophen-3-yl)oxy)pyridin-2-yl) acrylate (0.118 g, 0.28 mmol) in THF (2.00 mL) and water (2.00 mL) was added lithium hydroxide (1.0 M aq., 0.844 mL, 0.84 mmol) and the reaction was stirred at room temperature for 2 h. Upon completion the reaction was quenched with water, diluted with DCM and acidified to pH 1 with 1 N HCl. The mixture was extracted with DCM (3×) and the combined organic layers were passed through a phase separator and concentrated in vacuo to afford the crude product which was purified by reverse phase HPLC (acidic condition, 3% TFA in 10-100% CH₃CN/H₂O) to afford (E)-3-(5-((6-hydroxy-2-(4-hydroxyphenyl)benzo[b]thiophen-3-yl)oxy)pyridin-2-yl)acrylic acid (14 mg, 0.03 mmol, 9% yield). ¹H NMR (400 MHz, (CD₃)₂SO) δ ppm=6.66 (d, J=15.66 Hz, 1H), 6.77-6.81 (m, 2H), 6.84 (dd, J=8.59, 2.02 Hz, 1H), 7.17 (d, J=8.59 Hz, 1H), 7.22 (dd, J=8.59, 3.03 Hz, 1H), 7.31 (d, J=2.02 Hz, 1H), 7.44-7.49 (m, 2H), 7.52 (d, J=15.66 Hz, 1H), 7.64 (d, J=8.59 Hz, 1H), 8.45 (d, J=2.53 Hz, 1H). LC/MS (m/z, MH⁺): 406.2.

Example 30

(E)-3-(4-((6-hydroxy-2-(4-hydroxyphenyl)benzo[b]thiophen-3-yl)(methyl)amino)phenyl)acrylic acid

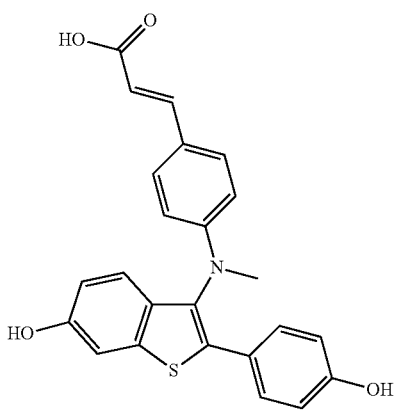 [SMILES: CN(c1ccc(/C=C/C(=O)O)cc1)c1c(-c2ccc(O)cc2)sc2cc(O)ccc12]

Step 1: To a solution of (E)-ethyl 3-(4-((6-methoxy-2-(4-methoxyphenyl)benzo[b]thiophen-3-yl)(methyl)amino)phenyl)acrylate (25.5 mg, 0.05 mmol) in DCM (1.5 mL) at 0° C. was added BBr₃ (1.0 M in DCM, 0.215 mL, 0.21 mmol) dropwise. After 4 h at 0° C. the reaction was quenched with sat. aq. NaHCO₃ and extracted with 5% MeOH/EtOAc, the combined organic layers were passed through a phase separator and concentrated in vacuo to afford crude (E)-ethyl 3-(4-((6-hydroxy-2-(4-hydroxyphenyl)benzo[b]thiophen-3-yl)(methyl)amino)phenyl)acrylate which was used without further purification. LC/MS (m/z, MH⁺): 446.5.

Step 2: To a solution of crude (E)-ethyl 3-(4-((6-hydroxy-2-(4-hydroxyphenyl)benzo[b]thiophen-3-yl)(methyl)amino)phenyl)acrylate (25 mg, 0.06 mmol) in EtOH (1.5 mL) at room temperature was added LiOH (2 N aq., 0.168 mL, 0.34 mmol), the reaction was allowed to stir at room temperature for 18 h after which time the reaction was quenched with 1 N HCl (4 mL) and concentrated in vacuo to remove EtOH. The resulting suspension was extracted with 5% MeOH/EtOAc (3×), dried, and concentrated in vacuo to give the crude product which was purified by reverse phase HPLC (neutral condition, 3% 1-propanol in 1-100% CH₃CN/H₂O) to afford (E)-3-(4-((6-hydroxy-2-(4-hydroxyphenyl)benzo[b]thiophen-3-yl)(methyl)amino)phenyl)acrylic acid (4.98 mg, 0.01 mmol, 21% yield) as a white solid. ¹H NMR (400 MHz, CD₃OD) δ ppm=3.12 (s, 3H), 6.11 (d, 1H, J=15.66 Hz), 6.56 (d, 2H, J=8.59 Hz), 6.65 (d, 2H, J=9.09 Hz), 6.69 (dd, 1H, J=8.59, 2.02 Hz), 6.98 (d, 1H, J=8.59 Hz), 7.11 (d, 1H, J=2.02 Hz), 7.24 (d, 2H, J=9.09 Hz), 7.30 (d, 2H, J=9.09 Hz), 7.48 (d, 1H, J=16.17 Hz). HRMS (m/z, MH⁺): 418.1065.

Example 31

(E)-3-(4-((6-hydroxy-2-(4-hydroxyphenyl)benzo[b]thiophen-3-yl)oxy)phenyl)-N-(3,3,3-trifluoropropyl)acrylamide

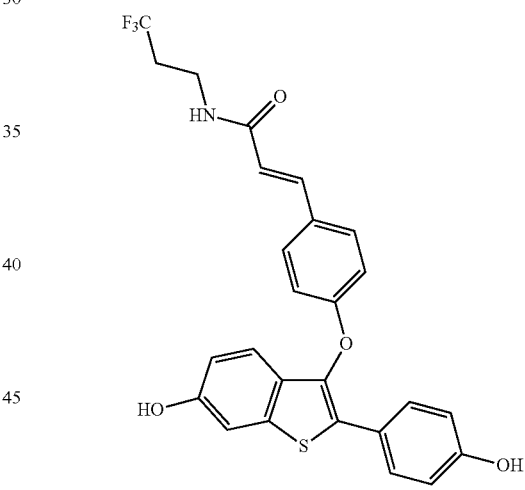

To a 30 mL vial containing (E)-3-(4-((6-methoxy-2-(4-methoxyphenyl)benzo[b]thiophen-3-yl)oxy)phenyl)-N-(3,3,3-trifluoropropyl)acrylamide (38 mg, 0.07 mmol) in DCM (1 mL) was added BBr₃ (1 M in heptane, 0.072 mL, 0.07 mmol) and the reaction was stirred at room temperature for 1 h. The reaction was quenched with 4 mL MeOH and stirred for 10 min at room temperature after which time the resulting mixture was concentrated to 50% volume and the crude product was purified by reverse phase HPLC (acidic condition, 0.1% TFA in 1-100% CH₃CN/H₂O) to afford (E)-3-(4-((6-hydroxy-2-(4-hydroxyphenyl)benzo[b]thiophen-3-yl)oxy)phenyl)-N-(3,3,3-trifluoropropyl)acrylamide (31 mg, 0.06 mmol, 86% yield) as a white solid. ¹H NMR (400 MHz, CD₃OD) δ ppm=7.40-7.63 (m, 5H), 7.21 (d, J=2.02 Hz, 1H), 7.15 (d, J=8.59 Hz, 1H), 6.88-6.98 (m, 2H), 6.68-6.87 (m, 3H), 6.45 (d, J=15.66 Hz, 1H), 3.54 (t, J=7.07 Hz, 2H), 2.46 (tq, J=6.82, 10.95 Hz, 2H). LC/MS (m/z, MH⁺): 500.4.

Example 32

(E)-3-(4-((2-(4-fluoro-2-methylphenyl)-6-hydroxybenzo[b]thiophen-3-yl)oxy)phenyl)-N-hydroxyacrylamide

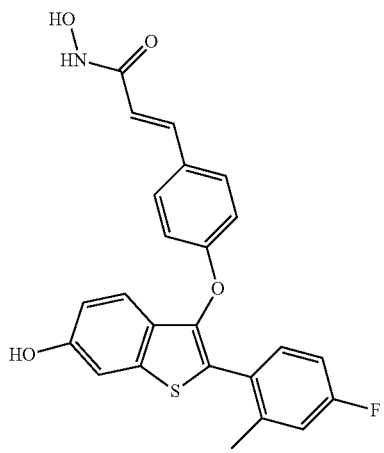 [SMILES: Cc1cc(F)ccc1-c1sc2cc(O)ccc2c1Oc1ccc(/C=C/C(=O)NO)cc1]

To a 30 mL screw cap vial, (E)-3-(4-((2-(4-fluoro-2-methylphenyl)-6-methoxybenzo[b]thiophen-3-yl)oxy)phenyl)-N-((tetrahydro-2H-pyran-2-yl)oxy)acrylamide (53 mg, 0.099 mmol) was dissolved in DCM (1 mL). The vial was charged with BBr$_3$ (1.0 M in hexanes, 0.298 mL, 0.298 mmol) and the reaction mixture was stirred for 1 h at room temperature. The reaction mixture was quenched with 4 mL MeOH and stirred for 10 min. The mixture was concentrated onto silica gel and the crude material was purified by reverse phase HPLC (acidic condition, 0.1% TFA in 30-100% CH$_3$CN/H$_2$O) to afford (E)-3-(4-((2-(4-fluoro-2-methylphenyl)-6-hydroxybenzo[b]thiophen-3-yl)oxy)phenyl)-N-hydroxyacrylamide (16 mg, 0.037 mmol, 37% yield) as a white solid. $^1$H NMR (400 MHz, CD$_3$OD) δ ppm=2.25 (s, 3H,) 6.19 (d, J=16.17 Hz, 1H), 6.66-6.84 (m, 4H), 6.88 (dd, J=9.85, 2.78 Hz, 1H), 7.06-7.26 (m, 3H), 7.26-7.45 (m, 3H). LC/MS (m/z, MH$^+$): 436.1.

The following examples were prepared using procedures described in the above examples using appropriate starting materials:

TABLE 2

| Example | Structure | Name | Physical data |
|---|---|---|---|
| 33 | 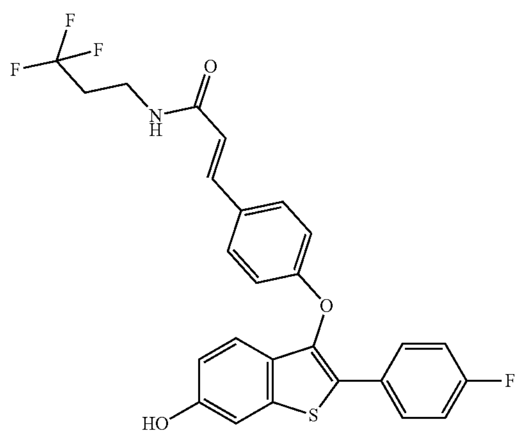 [SMILES: O=C(/C=C/c1ccc(Oc2c(-c3ccc(F)cc3)sc3cc(O)ccc23)cc1)NCCC(F)(F)F] | (E)-3-(4-((2-(4-fluorophenyl)-6-hydroxybenzo[b]thiophen-3-yl)oxy)phenyl)-N-(3,3,3-trifluoropropyl)acrylamide | $^1$H NMR (400 MHz, CD$_3$OD) δ ppm = 2.26-2.45 (m, 2H), 3.42 (t, J = 7.07 Hz, 2H), 6.34 (d, J = 16.17 Hz, 1H), 6.71 (dd, J = 8.59, 2.02 Hz, 1H), 6.83 (d, J = 8.59 Hz, 2H), 6.98 (t, J = 8.59 Hz, 2H), 7.03-7.22 (m, 2H), 7.31-7.50 (m, 3H), 7.59 (dd, J = 8.59, 5.56 Hz, 2H). LC/MS (m/z, MH$^+$): 502.3 |
| 34 | 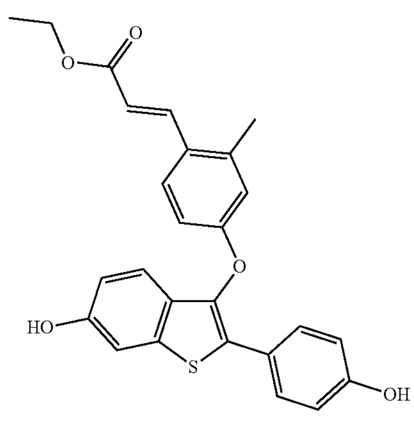 [SMILES: CCOC(=O)/C=C/c1ccc(Oc2c(-c3ccc(O)cc3)sc3cc(O)ccc23)cc1C] | (E)-ethyl 3-(4-((6-hydroxy-2-(4-hydroxyphenyl)benzo[b]thiophen-3-yl)oxy)-2-methylphenyl)acrylate | $^1$H NMR (400 MHz, CD$_3$Cl) δ ppm = 1.37 (t, J = 7.07 Hz, 3H), 2.39 (s, 3H), 4.30 (q, J = 7.07 Hz, 2H), 4.81 (br. s., 2H), 6.28 (d, J = 16.17 Hz, 1H), 6.76-6.92 (m, 5H), 7.19-7.34 (m, 2H), 7.49 (d, J = 8.59 Hz, 1H), 7.56-7.69 (m, 2H), 7.93 (d, J = 15.66 Hz, 1H) HRMS (m/z, MH$^+$): 447.1278 |

TABLE 2-continued

| Example | Structure | Name | Physical data |
| --- | --- | --- | --- |
| 35 | 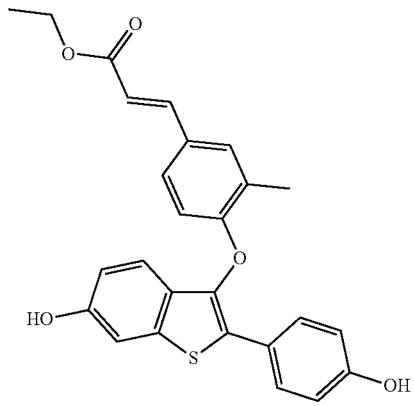 [SMILES: CCOC(=O)/C=C/c1ccc(Oc2c(-c3ccc(O)cc3)sc3cc(O)ccc23)c(C)c1] | (E)-ethyl 3-(4-((6-hydroxy-2-(4-hydroxyphenyl)benzo[b]thiophen-3-yl)oxy)-3-methylphenyl)acrylate | $^1$H NMR (400 MHz, CD$_3$OD) δ ppm = 1.29 (t, J = 7.07 Hz, 3H), 2.50 (s, 3H), 4.21 (q, J = 7.07 Hz, 2H), 6.33 (d, J = 16.17 Hz, 1H), 6.50 (d, J = 8.08 Hz, 1H), 6.72-6.77 (m, 2H), 6.79 (dd, J = 8.59, 2.02 Hz, 1H), 7.09 (d, J = 8.59 Hz, 1H), 7.15-7.23 (m, 2H), 7.44-7.52 (m, 3H), 7.53-7.61 (m, 1H), 7.57 (d, J = 16.17 Hz, 1H). HRMS (m/z, MH$^+$): 447.1243 |
| 36 | 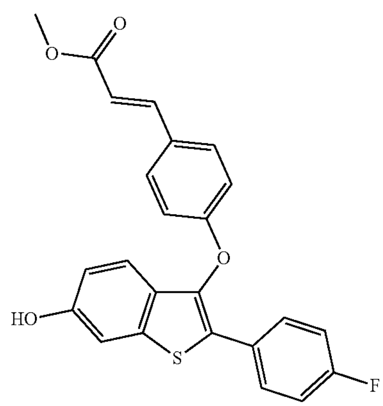 [SMILES: COC(=O)/C=C/c1ccc(Oc2c(-c3ccc(F)cc3)sc3cc(O)ccc23)cc1] | (E)-methyl 3-(4-((2-(4-fluorophenyl)-6-hydroxybenzo[b]thiophen-3-yl)oxy)phenyl)-acrylate | $^1$H NMR (400 MHz, CD$_3$Cl) δ ppm = 3.80 (s, 3H), 6.31 (d, J = 15.66 Hz, 1H), 6.83 (dd, J = 8.59, 2.02 Hz, 1H), 6.93-7.01 (m, 2H), 7.01-7.11 (m, 2H), 7.23-7.27 (m, 2H), 7.41-7.48 (m, 2H), 7.55-7.73 (m, 3H). HRMS (m/z, MH$^+$): 421.0891 |
| 37 | 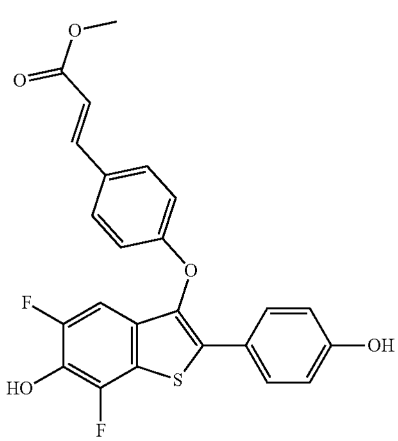 [SMILES: COC(=O)/C=C/c1ccc(Oc2c(-c3ccc(O)cc3)sc3c(F)c(O)c(F)cc23)cc1] | (E)-methyl 3-(4((5,7-difluoro-6-hydroxy-2-(4-hydroxyphenyl)-benzo[b]thiophen-3-yl)oxy)phenyl)acrylate | $^1$H NMR (400 MHz, CD$_3$OD) δ ppm = 7.53 (d, J = 16.17 Hz, 1H), 7.45 (d, J = 9.09 Hz, 2H), 7.31 (dd, J = 2.02, 12.63 Hz, 1H), 7.19-7.24 (m, 1H), 6.76-6.93 (m, 5H), 6.31 (d, J = 16.17 Hz, 1H), 3.66 (s, 3H) |

TABLE 2-continued

| Example | Structure | Name | Physical data |
|---|---|---|---|
| 38 | 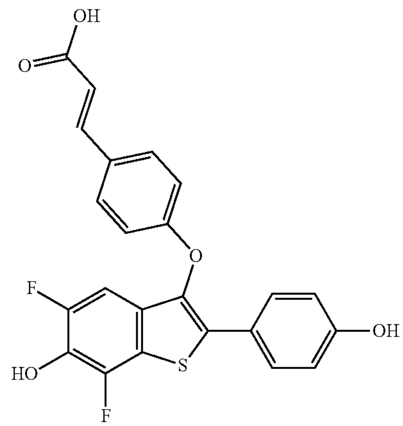 [SMILES: O=C(O)/C=C/c1ccc(Oc2c(-c3ccc(O)cc3)sc3c(F)c(O)c(F)cc23)cc1] | (E)-3-(4-((5,7-difluoro-6-hydroxy-2-(4-hydroxyphenyl)benzo[b]thiophen-3-yl)oxy)phenyl)acrylic acid | ¹H NMR (400 MHz, CDCl₃) δ ppm = 7.61 (d, J = 15.66 Hz, 1H), 7.34-7.44 (m, 3H), 7.23-7.34 (m, 1H), 6.84-6.99 (m, 5H), 6.23 (d, J = 15.66 Hz, 1H) |
| 39 | 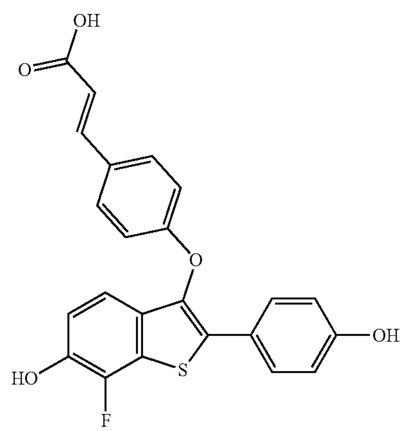 [SMILES: O=C(O)/C=C/c1ccc(Oc2c(-c3ccc(O)cc3)sc3c(F)c(O)ccc23)cc1] | (E)-3-(4-((7-fluoro-6-hydroxy-2-(4-hydroxyphenyl)benzo[b]thiophen-3-yl)oxy)phenyl)acrylic acid | ¹H NMR (400 MHz, CD₃OD) δ ppm = 7.51 (d, J = 16.17 Hz, 1H), 7.38-7.47 (m, 4H), 6.80-6.91 (m, 4H), 6.67 (d, J = 9.09 Hz, 2H), 6.26 (d, J = 15.66 Hz, 1H). LC/MS (m/z, MH⁺): 423.4 |
| 40 | 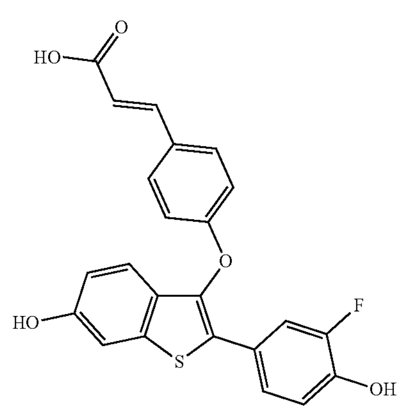 [SMILES: O=C(O)/C=C/c1ccc(Oc2c(-c3ccc(O)c(F)c3)sc3cc(O)ccc23)cc1] | (E)-3-(4-((2-(3-fluoro-4-hydroxyphenyl)-6-hydroxybenzo[b]thiophen-3-yl)oxy)phenyl)acrylic acid | ¹H NMR (400 MHz, CD₃OD) δ ppm = 6.36 (d, J = 15.66 Hz, 1H), 6.80 (dd, J = 8.59, 2.02 Hz, 1H), 6.84-6.91 (m, 1H), 6.92-6.99 (m, 2H), 7.16 (d, J = 8.59 Hz, 1H), 7.20 (d, J = 2.02 Hz, 1H), 7.29 (ddd, J = 8.59, 2.02, 1.01 Hz, 1H), 7.39 (dd, J = 12.63, 2.02 Hz, 1H), 7.50-7.56 (m, 2H), 7.60 (d, J = 15.66 Hz, 1H). HRMS (m/z, MH⁺): 423.0680 |

TABLE 2-continued

| Example | Structure | Name | Physical data |
| --- | --- | --- | --- |
| 41 | 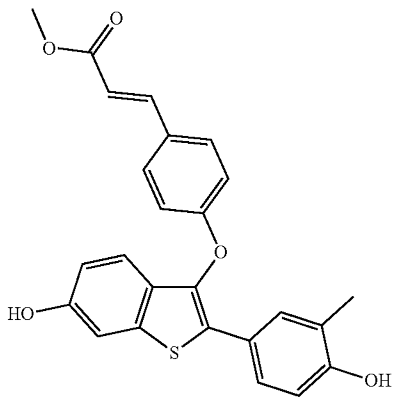 [SMILES: COC(=O)/C=C/c1ccc(Oc2c(-c3ccc(O)c(C)c3)sc3cc(O)ccc23)cc1] | (E)-methyl 3-(4-((6-hydroxy-2-(4-hydroxy-3-methylphenyl)-benzo[b]thiophen-3-yl)oxy)phenyl)acrylate | LC/MS (m/z, M-H): 431.4 |
| 42 | 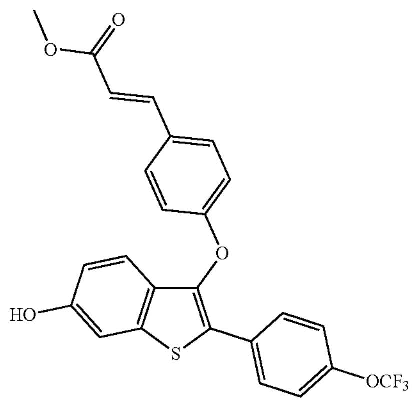 [SMILES: COC(=O)/C=C/c1ccc(Oc2c(-c3ccc(OC(F)(F)F)cc3)sc3cc(O)ccc23)cc1] | (E)-methyl 3-(4-((6-hydroxy-2-(4-(trifluoromethoxy)phenyl)benzo[b]thiophen-3-yl)oxy)phenyl)acrylate | LC/MS (m/z, M-H): 485.5 |
| 43 | 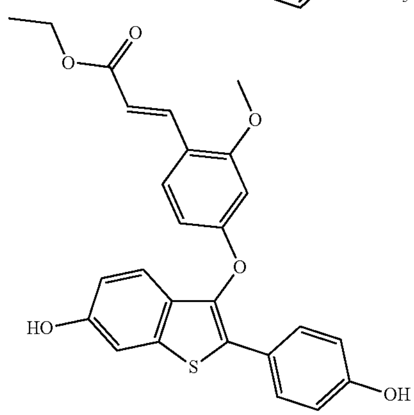 | (E)-ethyl 3-(4-((6-hydroxy-2-(4-hydroxyphenyl)benzo[b]thiophen-3-yl)oxy)-2-methoxyphenyl)acrylate | LC/MS (m/z, MH$^+$): 463.2 |
| 44 | 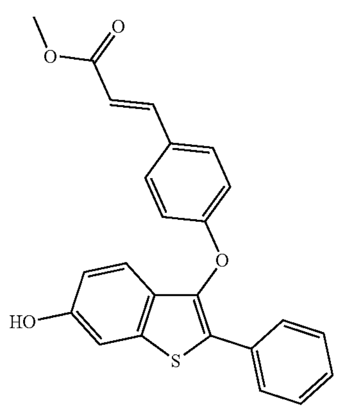 [SMILES: COC(=O)/C=C/c1ccc(Oc2c(-c3ccccc3)sc3cc(O)ccc23)cc1] | (E)-methyl 3-(4-((6-hydroxy-2-phenylbenzo[b]thiophen-3-yl)oxy)phenyl)-acrylate | HRMS (m/z, MH$^+$): 403.0989 |

Example 45

(E)-methyl 3-(4-((6-hydroxy-2-(2-isopropylphenyl)benzo[b]thiophen-3-yl)oxy)phenyl)acrylate

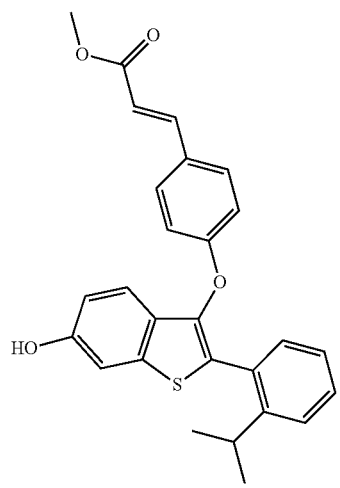 [SMILES: COC(=O)/C=C/c1ccc(Oc2c(-c3ccccc3C(C)C)sc3cc(O)ccc23)cc1]

To a solution of (E)-methyl 3-(4-((2-(2-isopropylphenyl)-6-methoxybenzo[b]thiophen-3-yl)oxy)phenyl)acrylate (30 mg, 0.065 mmol) in DCM (1.5 mL) at 0° C. was added BBr$_3$ (1.0 M in heptane, 0.196 mL, 0.196 mmol) dropwise. After 1 h at 0° C. the reaction was quenched with sat. aq. NaHCO$_3$ and extracted with EtOAc, the combined organic layers were passed through a phase separator and concentrated in vacuo to afford the crude product which was purified by column chromatography (SiO$_2$, 0-30% EtOAc/heptane) to afford (E)-methyl 3-(4-((6-hydroxy-2-(2-isopropylphenyl)benzo[b]thiophen-3-yl)oxy)phenyl)acrylate (25.8 mg, 0.058 mmol, 89% yield). $^1$H NMR (400 MHz, CDCl$_3$) δ ppm=7.60 (d, J=15.9 Hz, 1H), 7.40-7.25 (m, 8H), 7.15 (ddd, J=8.1, 5.5, 3.0 Hz, 1H), 6.91-6.85 (m, 3H), 6.29 (d, J=16.0 Hz, 1H), 3.80 (s, 3H), 3.25 (p, J=6.8 Hz, 1H), 1.19 (d, J=6.8 Hz, 6H). LC/MS (m/z, M−H): 443.0.

Example 46

(E)-2-(4-fluoro-2-methylphenyl)-3-(4-(2-(5-methyl-1,3,4-oxadiazol-2-yl)vinyl)phenoxy)benzo[b]thiophen-6-ol

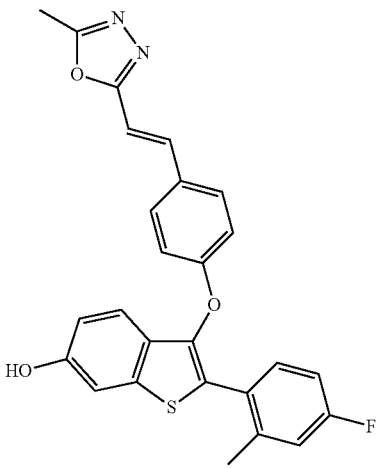 [SMILES: Cc1nnc(/C=C/c2ccc(Oc3c(-c4ccc(F)cc4C)sc4cc(O)ccc34)cc2)o1]

To a 30 mL screw cap vial, (E)-2-(4-((2-(4-fluoro-2-methylphenyl)-6-methoxybenzo[b]thiophen-3-yl)oxy)styryl)-5-methyl-1,3,4-oxadiazole (12 mg, 0.025 mmol) was dissolved in DCM (0.5 mL). The vial was charged with BBr$_3$ (1.0 M in hexanes, 0.076 ml, 0.076 mmol) and the reaction mixture was stirred for 1 h at room temperature. The reaction mixture was quenched with 2 mL MeOH and stirred for 10 min. The mixture was concentrated onto silica gel and the crude material was purified by reverse phase HPLC (acidic condition, 0.1% TFA in 30-100% CH$_3$CN/H$_2$O) to afford (E)-2-(4-fluoro-2-methylphenyl)-3-(4-(2-(5-methyl-1,3,4-oxadiazol-2-yl)vinyl)phenoxy)benzo[b]thiophen-6-ol (3 mg, 6.54 μmol, 26% yield) as a yellow solid. $^1$H NMR (400 MHz, CD$_3$OD) δ ppm=2.26 (s, 3H), 2.45 (s, 3H), 6.73-6.86 (m, 5H), 6.88 (dd, J=9.85, 2.78 Hz, 1H), 7.08-7.30 (m, 3H), 7.34-7.45 (m, 3H). LC/MS (m/z, MH$^+$): 459.4.

The following examples were prepared using procedures described in the above examples using appropriate starting materials:

TABLE 3

| Example | Structure | Name | Physical data |
|---|---|---|---|
| 47 | 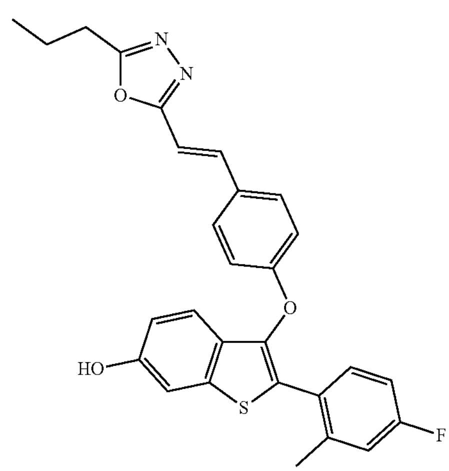 [SMILES: CCCc1nnc(/C=C/c2ccc(Oc3c(-c4ccc(F)cc4C)sc4cc(O)ccc34)cc2)o1] | (E)-2-(4-fluoro-2-methylphenyl)-3-(4-(2-(5-propyl-1,3,4-oxadiazol-2-yl)vinyl)phenoxy)benzo[b]thiophen-6-ol | $^1$H NMR (400 MHz, CD$_3$OD) δ ppm = 0.91-0.98 (m, 3 H), 1.69-1.81 (m, 2 H), 2.26 (s, 3 H), 2.78 (t, J = 7.3 Hz, 2 H), 6.72-6.80 (m, 4 H), 6.83 (d, J = 16.2 Hz, 1 H), 6.88 (dd, J = 9.6, 2.5 Hz, 1 H), 7.14 (d, J = 2.0 Hz, 1 H), 7.18 (d, J = 8.6 Hz, 1 H), 7.22 (dd, J = 8.6, 6.1 Hz, 1 H), 7.35-7.45 (m, 3 H) LC/MS (m/z, MH$^+$): 487.0 |

Example 48

(E)-5-(4-((2-(4-fluoro-2-methylphenyl)-6-hydroxy-benzo[b]thiophen-3-yl)oxy)styryl)-1,3,4-oxadiazol-2(3H)-one

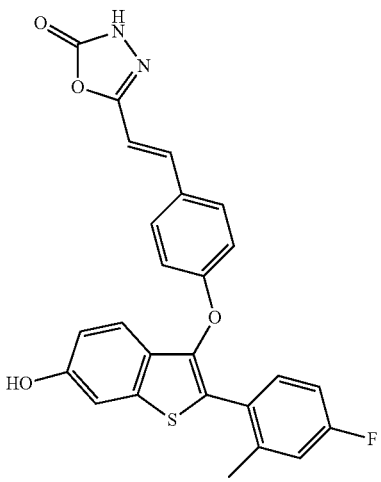 [SMILES: Cc1cc(F)ccc1-c1sc2cc(O)ccc2c1Oc1ccc(/C=C/c2n[nH]c(=O)o2)cc1]

To a 30 mL screw cap vial, (E)-5-(4-((2-(4-fluoro-2-methylphenyl)-6-methoxybenzo[b]thiophen-3-yl)oxy)styryl)-1,3,4-oxadiazol-2(3H)-one (15 mg, 0.032 mmol) was dissolved in DCM (1 mL). The vial was charged with BBr$_3$ (1.0 M in hexanes, 0.095 ml, 0.095 mmol) and the reaction mixture was stirred for 1 h at room temperature. The reaction mixture was quenched with 4 mL MeOH and stirred for 10 min. The mixture was concentrated onto silica gel and the crude material was purified by reverse phase HPLC (acidic condition, 0.1% TFA in 30-100% CH$_3$CN/H$_2$O) to afford (E)-5-(4-((2-(4-fluoro-2-methylphenyl)-6-hydroxybenzo[b]thiophen-3-yl)oxy)styryl)-1,3,4-oxadiazol-2(3H)-one (6 mg, 0.013 mmol, 41% yield) as a white solid. LC/MS (m/z, MH$^-$): 459.0.

Example 49

(E)-2-(4-fluoro-2-methylphenyl)-3-(4-(2-(5-methyl-4H-1,2,4-triazol-3-yl)vinyl)phenoxy)benzo[b]thiophen-6-ol

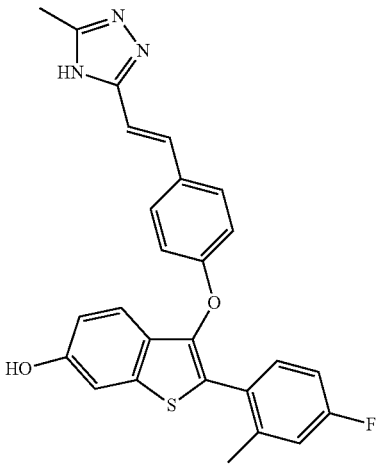 [SMILES: Cc1nnc(/C=C/c2ccc(Oc3c(-c4ccc(F)cc4C)sc4cc(O)ccc34)cc2)[nH]1]

To a 30 mL screw cap vial, (E)-3-(4-((2-(4-fluoro-2-methylphenyl)-6-methoxybenzo[b]thiophen-3-yl)oxy)styryl)-5-methyl-4H-1,2,4-triazole (15 mg, 0.032 mmol) was dissolved in DCM (1 mL). The vial was charged with BBr$_3$ (1.0 M in hexanes, 0.095 ml, 0.095 mmol) and the reaction mixture was stirred for 1 h at room temperature. The reaction mixture was quenched with 4 mL MeOH and stirred for 10 min. The mixture was concentrated to 50% volume and purified by reverse phase HPLC (acidic condition, 0.1% TFA in 30-100% CH$_3$CN/H$_2$O) to afford (E)-2-(4-fluoro-2-methylphenyl)-3-(4-(2-(5-methyl-4H-1,2,4-triazol-3-yl)vinyl)phenoxy)benzo[b]thiophen-6-ol (7 mg, 0.015 mmol, 48% yield) as a pale yellow solid. $^1$H NMR (400 MHz, CD$_3$OD) δ ppm=2.26 (s, 3H), 2.42 (s, 3H), 6.72-6.83 (m, 5H), 6.88 (dd, J=10.11, 2.53 Hz, 1H), 7.14 (d, J=2.02 Hz, 1H), 7.16-7.26 (m, 2H), 7.29-7.41 (m, 3H). LC/MS (m/z, MH$^+$): 458.1.

The following examples were prepared from the corresponding methyl ether intermediates using method B:

TABLE 4

| Example | Structure | Name | Physical data |
|---------|-----------|------|---------------|
| 50 | ![structure] | (E)-4-(4-((6-hydroxy-2-(4-hydroxyphenyl)-benzo[b]thiophen-3-yl)oxy)styryl)-6-(trifluoromethyl)pyrimidin-2(1H)-one | $^1$H NMR (400 MHz, CD$_3$OD) δ ppm = 7.81 (d, J = 16.17 Hz, 1H), 7.53 (d, J = 8.59 Hz, 2H), 7.34-7.45 (m, 2H), 7.10 (d, J = 2.02 Hz, 1H), 7.06 (t, J = 4.29 Hz, 2H), 6.85-6.95 (m, J = 8.59 Hz, 2H), 6.81 (d, J = 16.17 Hz, 1H), 6.70 (dd, J = 2.27, 8.84 Hz, 1H). 6.60-6.67 (m, 2H) LC/MS (m/z, MH$^+$); 523.4 |

TABLE 4-continued

| Example | Structure | Name | Physical data |
|---|---|---|---|
| 51 | 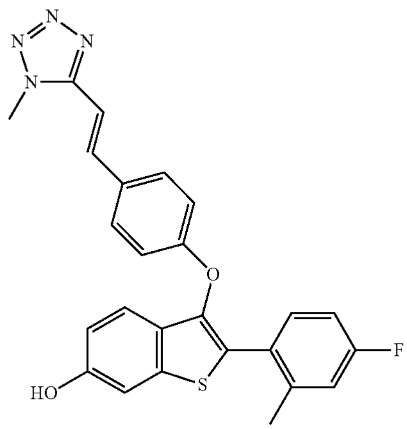 [SMILES: Cc1cc(F)ccc1-c1sc2cc(O)ccc2c1Oc1ccc(/C=C/c2nnnn2C)cc1] | (E)-2-(4-fluoro-2-methylphenyl)-3-(4-(2-(1-methyl-1H-tetrazol-5-yl)vinyl)phenoxy)-benzo[b]thiophen-6-ol | $^1$H NMR (400 MHz, CD$_3$OD) δ ppm = 2.26 (s, 3 H) 4.24 (s, 3 H) 6.72-6.82 (m, 4 H) 6.85-6.99 (m, 2 H) 7.10-7.27 (m, 3 H) 7.32-7.41 (m, 2 H) 7.47 (d, J = 16.67 Hz, 1 H) LC/MS (m/z, MH$^+$): 459.4 |
| 52 | 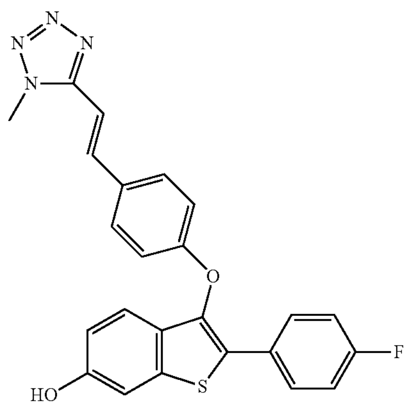 [SMILES: Cn1nnnc1/C=C/c1ccc(Oc2c(-c3ccc(F)cc3)sc3cc(O)ccc23)cc1] | (E)-2-(4-fluorophenyl)-3-(4-(2-(1-methyl-1H-tetrazol-5-yl)vinyl)phenoxy) benzo[b]thiophen-6-ol | $^1$H NMR (400 MHz, CD$_3$OD) δ ppm = 4.24 (s, 3 H) 6.68-6.76 (m, 1 H) 6.82-6.90 (m, 2 H) 6.91-7.05 (m, 3 H) 7.06-7.20 (m, 2 H) 7.39-7.48 (m, 2 H) 7.52 (d, J = 16.67 Hz, 1 H) 7.57-7.68 (m, 2 H) LC/MS (m/z, MH$^+$): 445.2 |
| 53 | 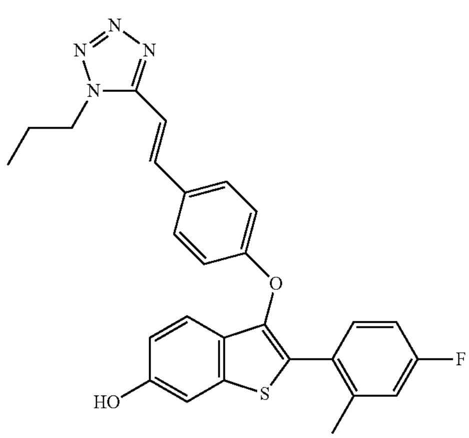 [SMILES: CCCn1nnnc1/C=C/c1ccc(Oc2c(-c3ccc(F)cc3C)sc3cc(O)ccc23)cc1] | (E)-2-(4-fluoro-2-methylphenyl)-3-(4-(2-(1-propyl-1H-tetrazol-5-yl)vinyl)phenoxy) benzo[b]thiophen-6-ol | $^1$H NMR (400 MHz, CD$_3$OD) δ ppm = 7.48 (d, J = 16.7 Hz, 1H), 7.32-7.41 (m, 2H), 7.22 (dd, J = 8.6, 6.1 Hz, 1H), 7.18 (d, J = 8.6 Hz, 1H), 7.14 (d, J = 2.0 Hz, 1H), 6.93 (d, J = 16.7 Hz, 1H), 6.88 (dd, J = 9.9, 2.8 Hz, 1H), 6.71-6.83 (m, 4H), 4.50 (t, J = 6.8 Hz, 2H), 2.26 (s, 3H), 1.93 (sxt, J = 7.2 Hz, 2H), 0.78-0.92 (m, 3H). LC/MS (m/z, MH$^+$): 487.1 |

Example 54

(E)-2-(4-hydroxyphenyl)-3-(4-(2-(1-methyl-1H-tetrazol-5-yl)vinyl)-phenoxy)benzo[b]thiophen-6-ol

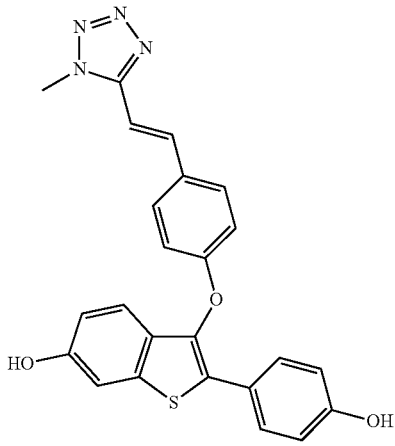 [SMILES: Cn1nnnc1/C=C/c1ccc(Oc2c(-c3ccc(O)cc3)sc3cc(O)ccc23)cc1]

To a 30 mL vial containing (E)-5-(4-((6-methoxy-2-(4-methoxyphenyl)benzo[b]thiophen-3-yl)oxy)styryl)-1-methyl-1H-tetrazole (12 mg, 0.03 mmol) in DCM (1 mL) was added BBr$_3$ (1 M in heptane, 0.077 mL, 0.08 mmol) and the reaction was stirred for 1 h at room temperature. The reaction mixture was quenched with 4 mL MeOH and stirred for 10 min at room temperature. The reaction mixture was concentrated to 50% volume and the crude product was purified by reverse phase HPLC (acidic condition, 0.1% TFA in 1-100% CH$_3$CN/H$_2$O) to afford (E)-2-(4-hydroxyphenyl)-3-(4-(2-(1-methyl-1H-tetrazol-5-yl)vinyl)phenoxy)benzo[b]thiophen-6-ol (4 mg, 9.04 μmol, 35% yield) as a white solid. $^1$H NMR (400 MHz, CD$_3$OD) δ ppm=7.52 (d, J=16.67 Hz, 1H), 7.38-7.48 (m, 4H), 7.09 (d, J=2.02 Hz, 1H), 7.06 (d, J=8.59 Hz, 1H), 6.96 (d, J=16.67 Hz, 1H), 6.81-6.90 (m, 2H), 6.61-6.73 (m, 3H), 4.24 (s, 3H). LC/MS (m/z, MH): 443.3.

The following examples were prepared using procedures described in the above examples using appropriate starting materials:

TABLE 5

| Example | Structure | Name | Physical data |
|---|---|---|---|
| 55 | 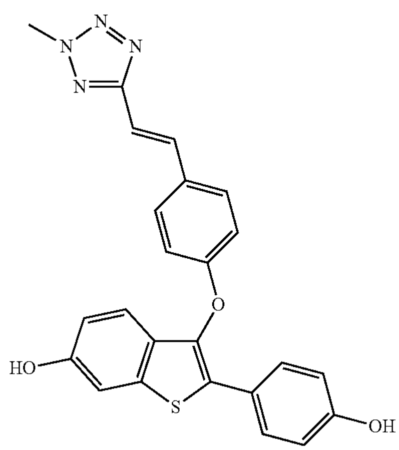 [SMILES: Cn1nnc(/C=C/c2ccc(Oc3c(-c4ccc(O)cc4)sc4cc(O)ccc34)cc2)n1] | (E)-2-(4-hydroxyphenyl)-3-(4-(2-(2-methyl-2 H-tetrazol-5-yl)vinyl)-phenoxy)benzo[b]thiophen-6-ol | $^1$H NMR (400 MHz, CD$_3$OD) δ ppm = 7.64 (d, J = 16.17 Hz, 1 H), 7.51-7.59 (m, J = 8.59 Hz, 2 H), 7.37-7.47 (m, J = 8.59 Hz, 2 H), 7.10 (d, J = 2.02 Hz, 1 H), 7.07 (d, J = 8.59 Hz, 1 H), 6.97 (d, J = 16.17 Hz, 1 H), 6.88 (d, J = 8.59 Hz, 2 H), 6.61-6.76 (m, 3 H), 4.03 (s, 3 H). LC/MS (m/z, MH$^+$): 443.3 |

Examples 56-62 were prepared from the corresponding methyl- or ethyl ester intermediates via ester hydrolysis using general method C: The corresponding methyl- or ethyl ester was dissolved in ethanol (0.05-0.1 M), 2M aq. LiOH solution (5-10 eq.) was added and the mixture stirred at rt for 16 h. The solution was acidified with 4N HCl and the precipitate extracted with EtOAc. The organic phase was dried over Na$_2$SO$_4$ and concentrated to yield the product. The following examples were prepared utilizing method C from appropriate starting materials:

TABLE 6

| Example | Structure | Name | Physical data |
|---|---|---|---|
| 56 | 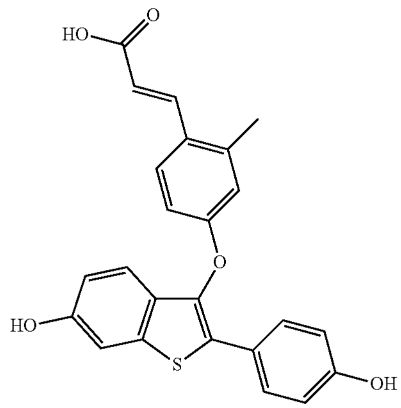 [SMILES: Cc1cc(Oc2c(-c3ccc(O)cc3)sc3cc(O)ccc23)ccc1/C=C/C(=O)O] | (E)-3-(4-((6-hydroxy-2-(4-hydroxyphenyl)-benzo[b]thiophen-3-yl)oxy)-2-methylphenyl)acrylic acid | $^1$H NMR (400 MHz, CD$_3$OD) δ ppm = 2.34 (s, 3 H), 6.26 (d, J = 16.17 Hz, 1 H), 6.61-6.90 (m, 5 H), 7.08-7.32 (m, 2 H), 7.41-7.65 (m, 3 H), 7.90 (d, J = 16.17 Hz, 1 H) HRMS (m/z, MH$^-$): 417.0779 |
| 57 | 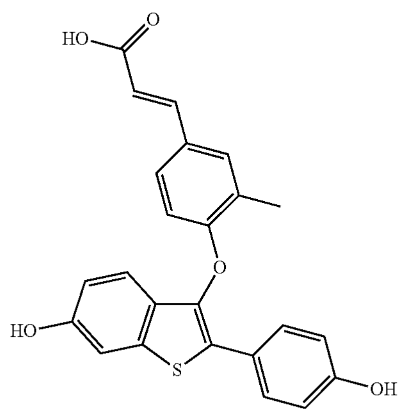 [SMILES: Cc1cc(/C=C/C(=O)O)ccc1Oc1c(-c2ccc(O)cc2)sc2cc(O)ccc12] | (E)-3-(4-((6-hydroxy-2-(4-hydroxyphenyl)-benzo[b]thiophen-3-yl)oxy)-3-methylphenyl)acrylic acid | $^1$H NMR (400 MHz, CD$_3$OD) δ ppm = 2.38-2.63 (m, 3H), 6.30 (d, J = 16.17 Hz, 1 H), 6.50 (d, J = 8.59 Hz, 1 H), 6.73-6.77 (m, 2 H), 6.79 (dd, J = 8.59, 2.02 Hz, 1 H), 7.09 (d, J = 8.59 Hz, 1 H), 7.15-7.24 (m, 2 H), 7.42-7.53 (m, 3 H), 7.57 (d, J = 16.17 Hz, 1 H) HRMS (m/z, MH$^-$): 417.0782 |
| 58 | 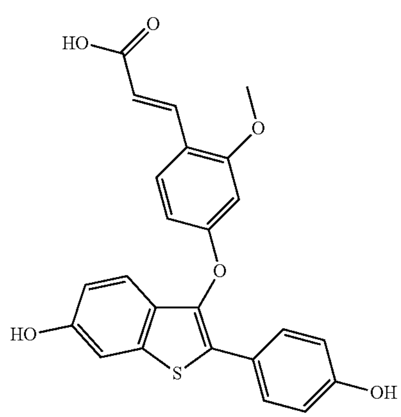 [SMILES: COc1cc(Oc2c(-c3ccc(O)cc3)sc3cc(O)ccc23)ccc1/C=C/C(=O)O] | (E)-3-(4-((6-hydroxy-2-(4-hydroxyphenyl)-benzo[b]thiophen-3-yl)oxy)-2-methoxyphenyl)acrylic acid | LCMS (m/z, MH$^+$): 435.1 |

TABLE 6-continued

| Example | Structure | Name | Physical data |
|---|---|---|---|
| 59 | 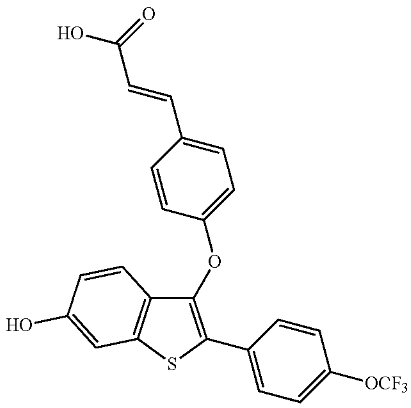 [SMILES: O=C(O)/C=C/c1ccc(Oc2c(-c3ccc(OC(F)(F)F)cc3)sc3cc(O)ccc23)cc1] | (E)-3-(4-((6-hydroxy-2-(4-(trifluoromethoxy)-phenyl)benzo[b]thiophen-3-yl)oxy)phenyl)-acrylic acid | $^1$H NMR (400 MHz, CD$_3$OD) δ ppm = 6.37 (d, J = 15.66 Hz, 1 H), 6.82 (dd, J = 8.59, 2.02 Hz, 1 H), 6.91-7.00 (m, 2 H), 7.15-7.32 (m, 4 H), 7.44-7.59 (m, 3 H), 7.71-7.86 (m, 2 H) HRMS (m/z, MH$^+$): 473.0644 |
| 60 | 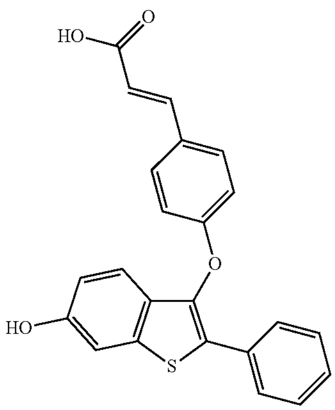 [SMILES: O=C(O)/C=C/c1ccc(Oc2c(-c3ccccc3)sc3cc(O)ccc23)cc1] | (E)-3-(4-((6-hydroxy-2-phenylbenzo[b]thiophen-3-yl)oxy)phenyl)-acrylic acid | $^1$H NMR (400 MHz, CD$_3$OD) δ ppm = 6.28 (d, J = 16.17 Hz, 1 H), 6.79 (dd, J = 8.59, 2.02 Hz, 1 H), 6.83-6.93 (m, 2 H), 7.09-7.30 (m, 5 H), 7.38 (d, J = 8.59 Hz, 2 H), 7.54 (d, J = 16.17 Hz, 1 H). 7.59-7.68 (m, 2 H) HRMS (m/z, MH$^+$): 389.0834 |
| 61 | 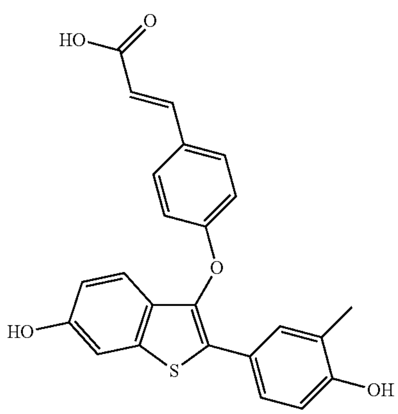 [SMILES: Cc1cc(-c2sc3cc(O)ccc3c2Oc2ccc(/C=C/C(=O)O)cc2)ccc1O] | (E)-3-(4-((6-hydroxy-2-(4-hydroxy-3-methylphenyl)benzo[b]thiophen-3-yl)oxy)phenyl)acrylic acid | $^1$H NMR (400 MHz, CD$_3$OD) δ ppm = 2.14 (s, 3 H), 6.35 (d, J = 15.66 Hz, 1 H), 6.69 (d, J = 8.59 Hz, 1 H), 6.79 (dd, J = 8.59, 2.53 Hz, 1 H), 6.89-7.00 (m, 2 H), 7.15 (d, J = 8.59 Hz, 1 H), 7.18 (d, J = 2.02 Hz, 1 H), 7.33 (dd, J = 8.34, 2.27 Hz, 1 H), 7.39 (d, J = 1.52 Hz, 1 H), 7.49-7.55 (m, 2 H), 7.60 (d, J = 16.17 Hz, 1 H) HRMS (m/z, MH$^+$): 419.0915 |
| 62 | 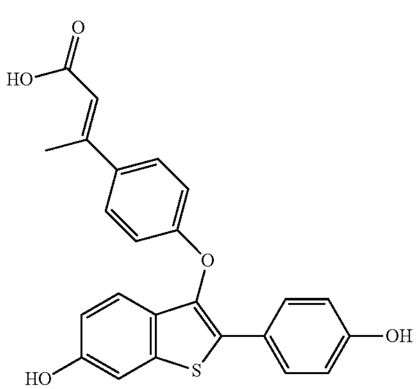 [SMILES: C/C(=C\C(=O)O)c1ccc(Oc2c(-c3ccc(O)cc3)sc3cc(O)ccc23)cc1] | (E)-3-(4-((6-hydroxy-2-(4-hydroxyphenyl)-benzo[b]thiophen-3-yl)oxy)phenyl)but-2-enoic acid | $^1$H NMR (400 MHz, CD$_3$OD) δ ppm = 7.42 (d, J = 9.09 Hz, 2H), 7.27-7.34 (m, J = 8.59 Hz, 2H), 7.00-7.13 (m, 2H), 6.75-6.82 (m, J = 9.09 Hz, 2H), 6.61-6.72 (m, 3H), 6.05 (s, 1H), 2.25 (d, J = 1.01 Hz, 3H) LC/MS (m/z, M − H): 417.4 |

Example 63-71 were prepared from the corresponding acid by formation of the amide. General method D: the corresponding acid was dissolved in DMF (0.03-0.1 M), HATU (1.5 eq.) was added and the mixture stirred for 5 min DIEA (5 eq.) and the corresponding amine (3 eq.) were added and the mixture stirred at rt for 16 h. The mixture was diluted with water and extracted with EtOAc. The combined organic phase was dried over $Na_2SO_4$ and concentrated to yield the crude which was purified by RP-HPLC. The following examples were prepared utilizing method D:

TABLE 7

| Example | Structure | Name | Physical data |
|---|---|---|---|
| 63 | 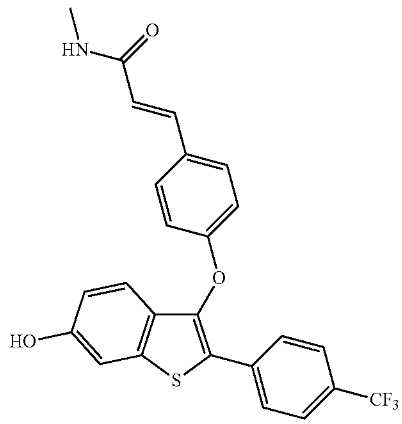 [SMILES: CNC(=O)/C=C/c1ccc(Oc2c(-c3ccc(C(F)(F)F)cc3)sc3cc(O)ccc23)cc1] | (E)-3-(4-((6-hydroxy-2-(4-(trifluoromethyl)-phenyl)benzo[b]thiophen-3-yl)oxy)phenyl)-N-methylacrylamide | $^1$H NMR (400 MHz, CD$_3$OD) δ ppm = 2.82 (s, 3 H), 6.43 (d, J = 15.66 Hz, 1 H), 6.82 (dd, J = 8.59, 2.02 Hz, 1 H), 6.89-7.02 (m, 2 H), 7.13-7.30 (m, 2 H), 7.37-7.52 (m, 3 H), 7.61 (d, J = 8.08 Hz, 2 H), 7.85 (d, J = 8.08 Hz, 2 H) HRMS (m/z, MH$^+$): 470.1018 |
| 64 | 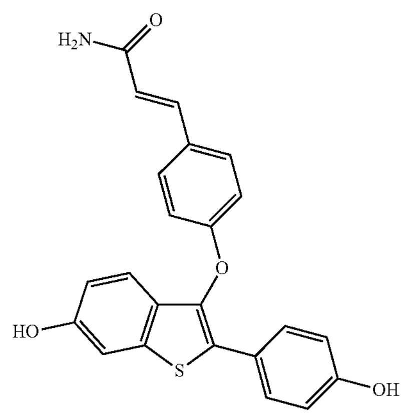 [SMILES: NC(=O)/C=C/c1ccc(Oc2c(-c3ccc(O)cc3)sc3cc(O)ccc23)cc1] | (E)-3-(4-((6-hydroxy-2-(4-hydroxyphenyl)-benzo[b]thiophen-3-yl)oxy)phenyl)acrylamide | $^1$H NMR (400 MHz, CD$_3$OD) δ ppm = 6.48 (d, J = 15.66 Hz, 1 H), 6.73-6.76 (m, 1 H), 6.76-6.78 (m, 1 H), 6.80 (dd, J = 8.84, 2.27 Hz, 1 H), 6.89-6.98 (m, 2 H), 7.16 (d, J = 8.59 Hz, 1 H), 7.19 (d, J = 2.02 Hz, 1 H), 7.42-7.55 (m, 5 H) HRMS (m/z, MH$^+$): 404.0944 |
| 65 | 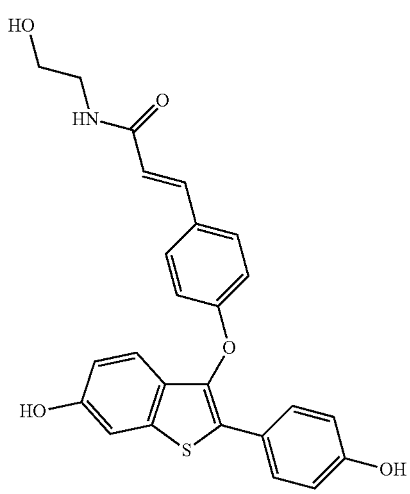 [SMILES: O=C(/C=C/c1ccc(Oc2c(-c3ccc(O)cc3)sc3cc(O)ccc23)cc1)NCCO] | (E)-3-(4-((6-hydroxy-2-(4-hydroxyphenyl)benzo[b]thiophen-3-yl)oxy)phenyl)-N-(2-hydroxyethyl)acrylamide | $^1$H NMR (400 MHz, CD$_3$OD) δ ppm = 3.41 (t, J = 5.56 Hz, 2 H), 3.65 (t, J = 5.81 Hz, 2 H), 6.47 (d, J = 15.66 Hz, 1 H), 6.71-6.77 (m, 2 H), 6.79 (dd, J = 8.59, 2.02 Hz, 1 H), 6.88-6.96 (m, 2 H), 7.15 (d, J = 9.09 Hz, 1 H), 7.18 (d, J = 2.02 Hz, 1 H), 7.42-7.54 (m, 5 H) HRMS (m/z, MH$^+$): 448.1205 |

TABLE 7-continued

| Example | Structure | Name | Physical data |
|---|---|---|---|
| 66 | 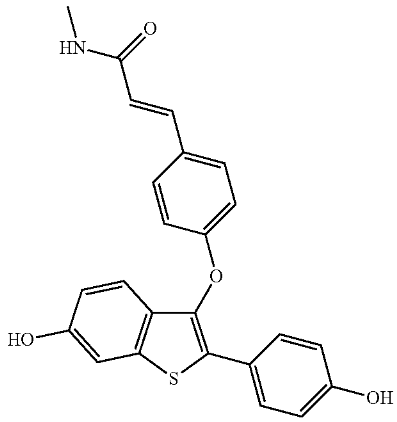 | (E)-3-(4-((6-hydroxy-2-(4-hydroxyphenyl)benzo[b]thiophen-3-yl)oxy)phenyl)-N-methylacrylamide | $^1$H NMR (400 MHz, (CD$_3$)$_2$SO) δ ppm = 2.66-2.71 (m, 3 H), 6.43 (d, J = 15.66 Hz, 1 H), 6.69-6.86 (m, 3 H), 6.90-7.00 (m, 2 H), 7.10 (d, J = 8.59 Hz, 1 H), 7.26 (d, J = 2.02 Hz, 1 H), 7.33 (d, J = 15.66 Hz, 1 H), 7.42-7.55 (m, 4 H), 7.75-7.87 (m, 1 H) HRMS (m/z, MH$^+$): 418.1102 |
| 67 | 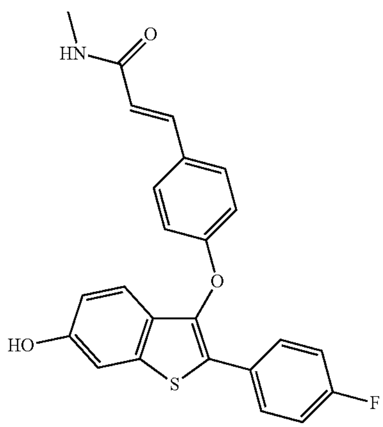 [SMILES: CNC(=O)/C=C/c1ccc(Oc2c(-c3ccc(F)cc3)sc3cc(O)ccc23)cc1] | (E)-3-(4-((2-(4-fluorophenyl)-6-hydroxybenzo[b]thiophen-3-yl)oxy)phenyl)-N-methylacrylamide | $^1$H NMR (400 MHz, CD$_3$OD) δ ppm = 2.82 (s, 3 H), 6.44 (d, J = 16.17 Hz, 1 H), 6.77-6.86 (m, 1 H), 6.90-6.97 (m, 2 H), 7.04-7.13 (m, 2 H), 7.18 (d, J = 8.59 Hz, 1 H), 7.22 (d, J = 2.02 Hz, 1 H), 7.39-7.52 (m, 3 H), 7.65-7.73 (m, 2 H) HRMS (m/z, MH$^+$): 420.1044 |
| 68 | 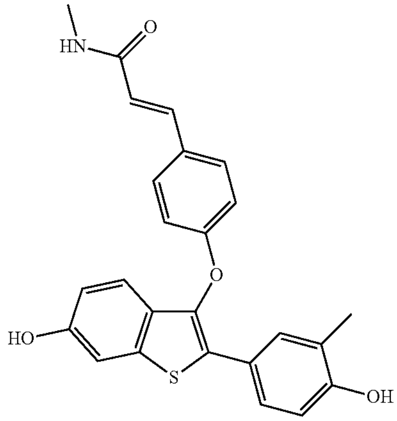 [SMILES: CNC(=O)/C=C/c1ccc(Oc2c(-c3ccc(O)c(C)c3)sc3cc(O)ccc23)cc1] | (E)-3-(4-((6-hydroxy-2-(4-hydroxy-3-methylphenyl)benzo[b]thiophen-3-yl)oxy)phenyl)-N-methylacrylamide | $^1$H NMR (400 MHz, CD$_3$OD) δ ppm = 2.13 (s, 3 H), 2.82 (s, 3 H), 6.43 (d, J = 15.66 Hz, 1 H), 6.69 (d, J = 8.59 Hz, 1 H), 6.78 (dd, J = 8.59, 2.02 Hz, 1 H), 6.88-6.96 (m, 2 H), 7.14 (d, J = 8.59 Hz, 1 H), 7.18 (d, J = 2.02 Hz, 1 H), 7.33 (dd, J = 8.34, 2.27 Hz, 1 H), 7.39 (d, J = 2.02 Hz, 1 H), 7.41-7.51 (m, 3 H) HRMS (m/z, MH$^+$): 432.1249 |

TABLE 7-continued

| Example | Structure | Name | Physical data |
|---|---|---|---|
| 69 | 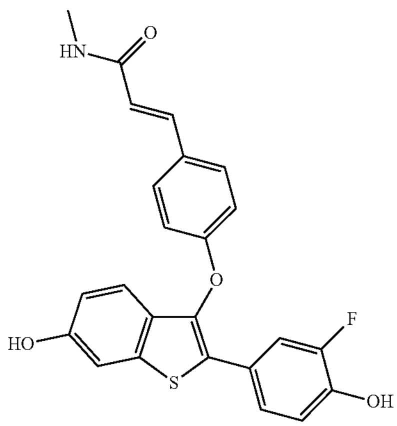 [SMILES: CNC(=O)/C=C/c1ccc(Oc2c(-c3ccc(O)c(F)c3)sc3cc(O)ccc23)cc1] | (E)-3-(4-((2-(3-fluoro-4-hydroxyphenyl)-6-hydroxybenzo[b]thiophen-3-yl)oxy)phenyl)-N-methylacrylamide | $^1$H NMR (400 MHz, CD$_3$OD) δ ppm = 2.82 (s, 3 H), 6.44 (d, J = 16.17 Hz, 1 H), 6.76-6.82 (m, 1 H), 6.87 (t, J = 8.84 Hz, 1 H), 6.90-6.96 (m, 2 H), 7.15 (d, J = 9.09 Hz, 1 H), 7.19 (d, J = 2.02 Hz, 1 H), 7.28 (ddd, J = 8.59, 2.02, 1.01 Hz, 1 H), 7.39 (dd, J = 12.63, 2.02 Hz, 1 H), 7.42-7.52 (m, 3 H) HRMS (m/z, MH$^+$): 436.0997 |

Example 70

(E)-3-(4-((6-hydroxy-2-(4-(trifluoromethyl)phenyl)benzo[b]thiophen-3-yl)oxy)phenyl)-N-methylacrylamide

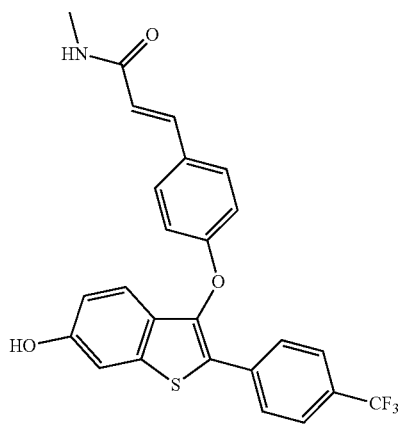

To a vial containing (E)-3-(4-((6-hydroxy-2-(4-(trifluoromethyl)phenyl)-benzo[b]thiophen-3-yl)oxy)phenyl) acrylic acid (15.9 mg, 0.035 mmol) was added DMF (1.0 mL), followed by methylamine hydrochloride (7.1 mg, 0.105 mmol), HATU (19.9 mg, 0.052 mmol), and DIEA (0.030 mL, 0.174 mmol). The mixture was stirred at room temperature for 12 h after which the reaction was quenched with water and extracted with EtOAc. The combined organic layers were dried over anhydrous Na$_2$SO$_4$, filtered and concentrated in vacuo to give the crude product which was purified by reverse phase HPLC (neutral condition, 3% 1-propanol in 1-100% CH$_3$CN/H$_2$O) to afford (E)-3-(4-((6-hydroxy-2-(4-(trifluoromethyl)phenyl)benzo[b]thiophen-3-yl)oxy)phenyl)-N-methylacrylamide (13.8 mg, 0.029 mmol, 84% yield). $^1$H NMR (400 MHz, CD$_3$OD) δ ppm=2.82 (s, 3H), 6.43 (d, J=15.66 Hz, 1H), 6.82 (dd, J=8.59, 2.02 Hz, 1H), 6.89-7.02 (m, 2H), 7.13-7.30 (m, 2H), 7.37-7.52 (m, 3H), 7.61 (d, J=8.08 Hz, 2H), 7.85 (d, J=8.08 Hz, 2H). HRMS (m/z, MH$^+$): 470.1018.

Example 71

(E)-3-(5-((6-hydroxy-2-(4-hydroxyphenyl)benzo[b]thiophen-3-yl)oxy)pyridin-2-yl)-N-methylacrylamide

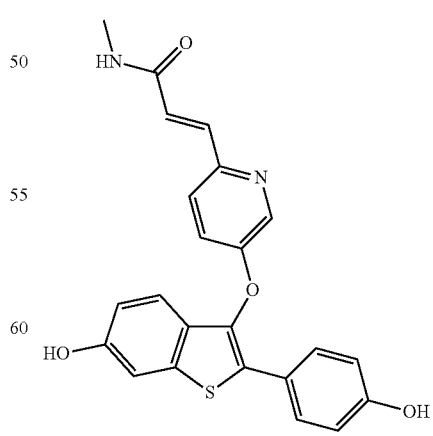

To a solution of (E)-3-(5-((6-hydroxy-2-(4-hydroxyphenyl)benzo[b]thiophen-3-yl)oxy)pyridin-2-yl)acrylic acid (0.057 g, 0.14 mmol) in DMF (1.406 mL) was added HATU (0.064 g, 0.17 mmol), methylamine hydrochloride (10.45 mg, 0.16 mmol) and NMM (0.077 mL, 0.70 mmol). The resulting mixture was stirred at room temperature for 48 h after which time the reaction was quenched with sat. aq. NH₄Cl and extracted with EtOAc (3×). The combined organic layers were passed through a phase separator and concentrated in vacuo to afford the crude product which was purified by reverse phase HPLC (acidic condition, 3% TFA in 10-100% CH₃CN/H₂O) to afford (E)-3-(5-((6-hydroxy-2-(4-hydroxyphenyl)benzo[b]thiophen-3-yl)oxy)pyridin-2-yl)-N-methylacrylamide (30 mg, 0.05 mmol, 37% yield). $^1$H NMR (400 MHz, (CD₃)₂SO) δ ppm=2.67-2.72 (m, 3H), 6.77-6.90 (m, 4H), 7.14-7.23 (m, 2H), 7.30 (d, J=2.02 Hz, 1H), 7.36 (d, J=15.16 Hz, 1H), 7.44-7.51 (m, 3H), 8.42 (d, J=3.03 Hz, 1H). LC/MS (m/z, MH⁺): 419.3.

Examples 72-75 were prepared from the corresponding bromide (Intermediate O) by Heck reaction. General method E: the bromide (intermediate O) was dissolved in DMF (0.02-0.1 M), triethyl amine (10% of DMF), the corresponding terminal alkene (3 eq.) and Pd(PPh₃)₂Cl₂ (0.1 eq.) was added and the system purged with nitrogen. The mixture was heated at 150° C. for 1-3 h under microwave irradiation. The mixture was cooled to room temperature and diluted with DCM and sat. aq. NH₄Cl. The organic layer was collected (phase separator), concentrated in vacuo and purified by reverse phase HPLC.

Example 72

(E)-3-(4-(2-(1H-imidazol-4-yl)vinyl)phenoxy)-2-(4-hydroxyphenyl)benzo[b]thiophen-6-ol

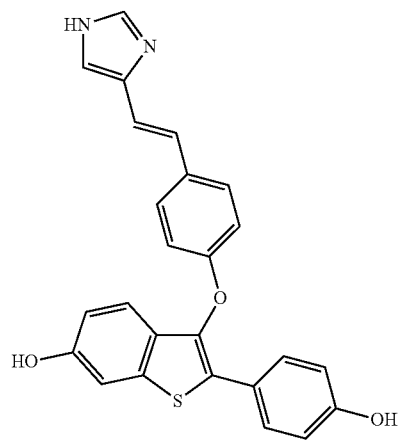 [SMILES: Oc1ccc(-c2sc3cc(O)ccc3c2Oc2ccc(/C=C/c3c[nH]cn3)cc2)cc1]

To a microwave vial containing 3-(4-bromophenoxy)-2-(4-hydroxyphenyl)benzo[b]thiophen-6-ol (20 mg, 0.05 mmol) in DMF (2 mL) was added triethyl amine (0.202 mL, 1.45 mmol), tert-butyl 4-vinyl-1H-imidazole-1-carboxylate (28.2 mg, 0.15 mmol) and Pd(PPh₃)₂Cl₂ (3.40 mg, 4.84 μmol). The system was flushed with nitrogen and heated at 150° C. for 1 h under microwave irradiation. The mixture was cooled to room temperature and diluted with DCM and sat. aq. NH₄Cl. The organic layer was collected (phase separator), concentrated in vacuo and purified by reverse phase HPLC (basic condition, 0.1% NH₄OH in 1-100% CH₃CN/H₂O) to afford (E)-3-(4-(2-(1H-imidazol-4-yl)vinyl)phenoxy)-2-(4-hydroxyphenyl)benzo[b]thiophen-6-ol (3 mg, 7.03 μmol, 15% yield) as a white solid. $^1$H NMR (400 MHz, CD₃OD) δ ppm=7.57 (s, 1H), 7.43 (d, J=8.59 Hz, 2H), 7.30 (d, J=8.59 Hz, 2H), 6.96-7.14 (m, 3H), 6.74-6.96 (m, 4H), 6.53-6.74 (m, 3H). LC/MS (m/z, MH⁺): 427.3.

Example 73

(E)-2-(4-hydroxyphenyl)-3-(4-(2-(1-methyl-1H-imidazol-4-yl)vinyl)phenoxy)-benzo[b]thiophen-6-ol

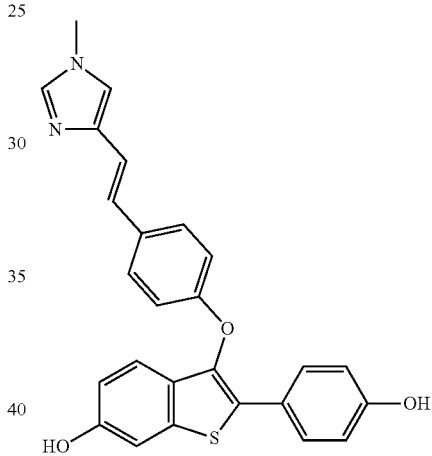

To a microwave vial, 3-(4-bromophenoxy)-2-(4-hydroxyphenyl)benzo[b]thiophen-6-ol (50 mg, 0.121 mmol) was dissolved in DMF (2 ml) and triethyl amine (0.506 ml, 3.63 mmol). To the solution was added the the 4-vinyl-1-methyl imidazole (39.2 mg, 0.363 mmol) and Pd(PPh₃)₂Cl₂ (8.49 mg, 0.012 mmol). The system was flushed with nitrogen and heated at 150° C. for 1 h under microwave radiation. The mixture was cooled to room temperature and diluted with DCM and sat. NH4Cl. The organic layer was collected (phase separator) and purified by reverse phase HPLC (acidic condition, 0.1% TFA in 1-100% CH₃CN/H₂O) to afford (E)-2-(4-hydroxyphenyl)-3-(4-(2-(1-methyl-1H-imidazol-4-yl)vinyl)phenoxy)benzo[b]thiophen-6-ol (31 mg, 0.070 mmol, 58.2% yield) as a white solid. $^1$H NMR (400 MHz, CD₃OD) δ ppm=3.82 (s, 3H) 6.57-6.74 (m, 3H) 6.75-6.93 (m, 3H) 6.98-7.14 (m, 3H) 7.32-7.54 (m, 5H) 8.73 (s, 1H). LC/MS (m/z, MH⁺): 441.3.

The following examples were prepared utilizing method E:

TABLE 8

| Example | Structure | Name | Physical data |
|---|---|---|---|
| 74 | 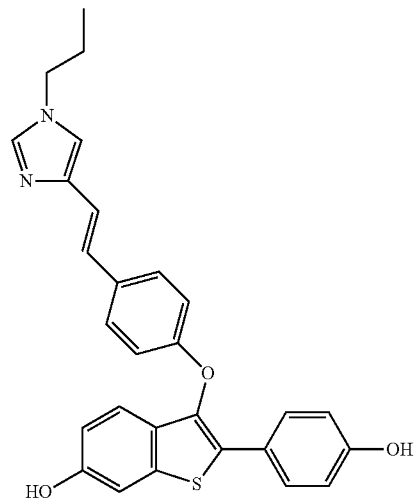 [SMILES: CCCn1cnc(/C=C/c2ccc(Oc3c(-c4ccc(O)cc4)sc4cc(O)ccc34)cc2)c1] | (E)-2-(4-hydroxyphenyl)-3-(4-(2-(1-propyl-1H-imidazol-4-yl)vinyl)phenoxy)benzo[b]thiophen-6-ol | $^1$H NMR (400 MHz, CD$_3$OD) δ ppm = 1.01 (t, J = 7.33 Hz, 3 H) 1.88-2.03 (m, 2 H) 4.20 (t, J = 7.33 Hz, 2 H) 6.71-6.85 (m, 3 H) 6.88-7.01 (m, 3 H) 7.11-7.28 (m, 3 H) 7.44-7.60 (m, 4 H) 7.68 (d, J = 1.01 Hz, 1 H) 8.94 (d, J = 1.52 Hz, 1 H). LC/MS (m/z, MH$^+$): 469.4 |
| 75 | 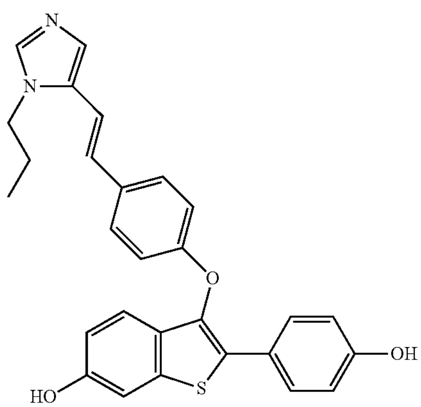 [SMILES: CCCn1cncc1/C=C/c1ccc(Oc2c(-c3ccc(O)cc3)sc3cc(O)ccc23)cc1] | (E)-2-(4-hydroxyphenyl)-3-(4-(2-(1-propyl-1H-imidazol-5-yl)vinyl)phenoxy)benzo[b]thiophen-6-ol | LC/MS (m/z, MH$^+$): 469.4 |

The following examples were prepared using procedures described in the above examples 1-75 using appropriate starting materials:

TABLE 9

| Example | Structure | Name | Physical data |
|---|---|---|---|
| 76 | 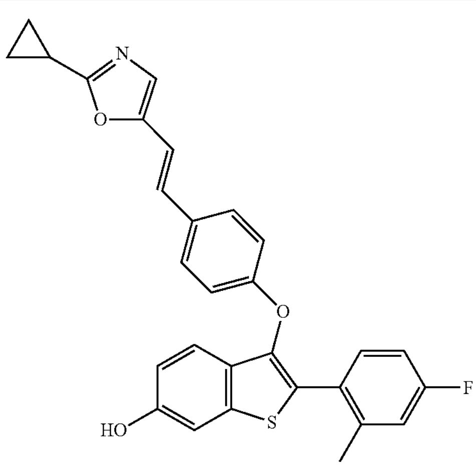 [SMILES: Cc1cc(F)ccc1-c1sc2cc(O)ccc2c1Oc1ccc(/C=C/c2cnc(C3CC3)o2)cc1] | (E)-3-(4-(2-(5-cyclopropyl-1,3,4-oxadiazol-2-yl)vinyl)phenoxy)-2-(4-fluoro-2-methylphenyl)benzo[b]thiophen-6-ol | LC/MS (m/z, MH$^+$): 485.0 |

TABLE 9-continued

| Example | Structure | Name | Physical data |
|---|---|---|---|
| 77 | 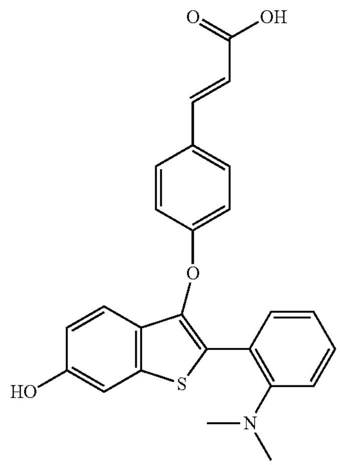 | (E)-3-(4-((2-(2-((dimethylamino)methyl)phenyl)-6-hydroxybenzo[b]thiophen-3-yl)oxy)phenyl)acrylic acid | HRMS (m/z, MH+): 446.1411 |

Example 78

(E)-4-(4-((6-hydroxy-2-(2-isopropylphenyl)benzo[b]thiophen-3-yl)oxy)phenyl)but-3-en-2-one

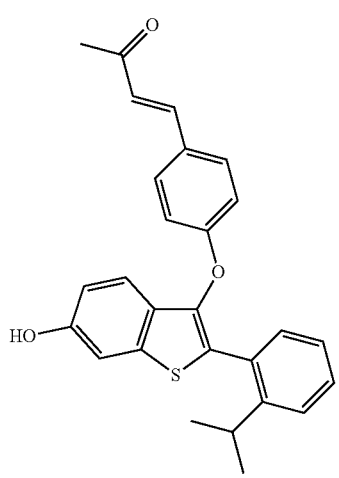 [SMILES: CC(=O)/C=C/c1ccc(Oc2c(-c3ccccc3C(C)C)sc3cc(O)ccc23)cc1]

Example 79

(E)-3-(4-((2-(2-(difluoromethyl)phenyl)-6-hydroxybenzo[b]thiophen-3-yl)oxy)phenyl)acrylic acid

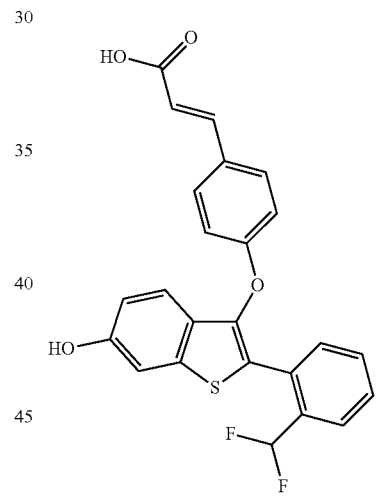

To a solution of (E)-4-(4-((2-(2-isopropylphenyl)-6-methoxybenzo[b]thiophen-3-yl)oxy)phenyl)but-3-en-2-one (71.3 mg, 0.161 mmol) in DCM (2.5 mL) at 0° C. was added BBr$_3$ (1.0 M in Heptane, 0.403 mL, 0.403 mmol) dropwise. The resulting mixture was stirred at 0° C. for 1 h after which time the reaction was quenched by addition of sat. aq. NaHCO$_3$ solution and extracted with 10% i-PrOH/DCM (3×). The combined organic layers were dried over anhydrous Na2SO4, filtered and concentrated in vacuo. The crude material was purified by reverse phase HPLC (acidic condition, 0.1% TFA in 45-70% CH$_3$CN/H$_2$O) to afford (E)-4-(4-((6-hydroxy-2-(2-isopropylphenyl)benzo[b]thiophen-3-yl)oxy)phenyl)but-3-en-2-one (11.1 mg, 0.026 mmol, 16%). $^1$H NMR (400 MHz, CD$_3$OD) δ ppm=7.55 (d, J=16.3 Hz, 1H), 7.49 (d, J=8.8 Hz, 2H), 7.37-7.19 (m, 5H), 7.14-7.08 (m, 1H), 6.86 (d, J=8.8 Hz, 3H), 6.63 (d, J=16.3 Hz, 1H), 3.23 (p, J=6.9 Hz, 1H), 2.33 (s, 3H), 1.16 (d, J=6.8 Hz, 6H). HRMS (m/z, MH+): 429.1509.

To a solution of afford (E)-tert-butyl 3-(4-((2-(2-(difluoromethyl)phenyl)-6-hydroxybenzo[b]thiophen-3-yl)oxy)phenyl)acrylate (100 mg, 0.202 mmol) in 1,4-dioxane (3.0 mL) was added 4.0M aq. HCl (0.202 mL, 0.809 mmol). The resulting mixture was warmed to 50° C. and stirred at that temperature for 2 h after which time the reaction was quenched by addition of sat. aq. NaHCO$_3$ and extracted with EtOAc (3×). The combined organic layers were dried over anhydrous Na$_2$SO$_4$, filtered and concentrated in vacuo and the resulting crude material was purified by reverse phase HPLC (basic conditions, 0.1% NH$_4$OH in CH$_3$CN/H$_2$O) to afford (E)-3-(4-((2-(2-(difluoromethyl)phenyl)-6-hydroxybenzo[b]thiophen-3-yl)oxy)phenyl)acrylic acid (16.7 mg, 0.037 mmol, 19% yield). $^1$H NMR (400 MHz, CD$_3$OD) δ ppm=7.72-7.64 (m, 1H), 7.54-7.42 (m, 4H), 7.39 (d, J=8.7 Hz, 2H), 7.33-7.24 (m, 2H), 7.00 (d, J=55.2 Hz, 1H), 6.88 (dd, J=8.7, 2.2 Hz, 1H), 6.81 (d, J=8.9 Hz, 2H), 6.30 (d, J=16.0 Hz, 1H). HRMS (m/z, MH+): 439.0776.

Example 80

(E)-3-(4-((6-hydroxy-2-(2-(methoxymethyl)phenyl)benzo[b]thiophen-3-yl)oxy)phenyl)acrylic acid

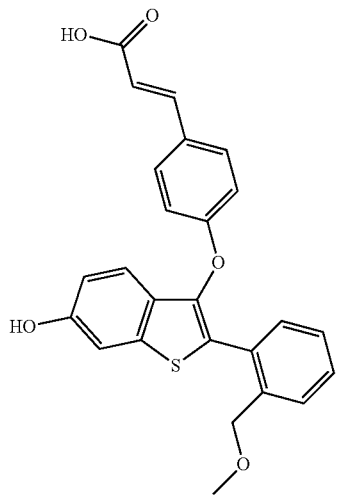 [SMILES: COCc1ccccc1-c1sc2cc(O)ccc2c1Oc1ccc(/C=C/C(=O)O)cc1]

To a solution of (E)-3-(4-((6-methoxy-2-(2-(methoxymethyl)phenyl)benzo[b]thiophen-3-yl)oxy)phenyl)acrylic acid (45.9 mg, 0.103 mmol) in N-methyl-2-pyrrolidone (1.0 mL) was added thiophenol (0.016 mL, 0.154 mmol) and $K_2CO_3$ (14.21 mg, 0.103 mmol). The resulting mixture was subjected to microwave irradiation at 200° C. for 90 min after which time the reaction was diluted with EtOAc and filtered. The filtrate was concentrated in vacuo and the crude material was purified by was purified by reverse phase HPLC (basic condition, 0.1% $NH_4OH$ in $CH_3CN/H_2O$) to afford (E)-3-(4-((6-hydroxy-2-(2-(methoxymethyl)phenyl)benzo[b]thiophen-3-yl)oxy)phenyl)acrylic acid (3.0 mg, 0.00645 mmol, 6% yield). $^1H$ NMR (400 MHz, $CD_3OD$) δ ppm=7.47 (d, J=7.7 Hz, 1H), 7.40-7.31 (m, 4H), 7.31-7.21 (m, 4H), 6.86 (dd, J=8.7, 2.1 Hz, 1H), 6.79 (d, J=8.4 Hz, 2H), 6.35 (d, J=15.9 Hz, 1H), 4.53 (s, 2H), 3.29 (s, 3H). HRMS (m/z, $M+H_2O$): 450.1355.

Example 81

(E)-isopropyl 3-(4-((6-hydroxy-2-(2-isopropylphenyl)benzo[b]thiophen-3-yl)oxy)phenyl)acrylate

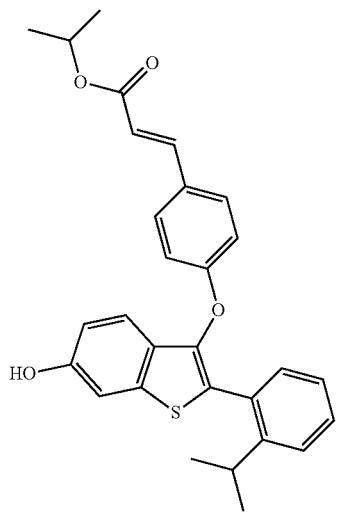 [SMILES: CC(C)OC(=O)/C=C/c1ccc(Oc2c(-c3ccccc3C(C)C)sc3cc(O)ccc23)cc1]

To a solution of (E)-isopropyl 3-(4-((6-((tert-butyldimethylsilyl)oxy)-2-(2-isopropylphenyl)benzo[b]thiophen-3-yl)oxy)phenyl)acrylate (35 mg, 0.060 mmol) in THF (2.0 mL) at 0° C. was added tetra-n-butylammonium fluoride (1.0 M in THF, 0.089 mL, 0.089 mmol) dropwise, the reaction immediately turned bright yellow in color. Stirring was continued at 0° C. for 45 min after which the reaction was warmed to room temperature for 15 min and then quenched by addition of sat. aq. $NaHCO_3$. The aqueous layer was extracted with EtOAc (4×) and the combined organic layers were dried over anhydrous MgSO4, filtered and concentrated in vacuo. The resulting crude material was purified by column chromatography ($SiO_2$, 0-20% EtOAc/Heptane) to afford (E)-isopropyl 3-(4-((6-hydroxy-2-(2-isopropylphenyl)benzo[b]thiophen-3-yl)oxy)phenyl)acrylate (14.0 mg, 0.029 mmol, 49% yield). $^1H$ NMR (400 MHz, $CD_3OD$) δ ppm=7.55 (d, J=16.0 Hz, 1H), 7.45 (d, J=8.8 Hz, 2H), 7.37-7.20 (m, 5H), 7.11 (td, J=7.6, 1.5 Hz, 1H), 6.89-6.81 (m, 3H), 6.32 (d, J=16.0 Hz, 1H), 5.05 (p, J=6.2 Hz, 1H), 3.23 (p, J=6.9 Hz, 1H), 1.28 (d, J=6.2 Hz, 6H), 1.16 (d, J=6.8 Hz, 6H). HRMS (m/z, $MH^+$): 473.1774.

Example 82

(E)-3-(4-((6-acetoxy-2-(2-isopropylphenyl)benzo[b]thiophen-3-yl)oxy)phenyl)acrylic acid

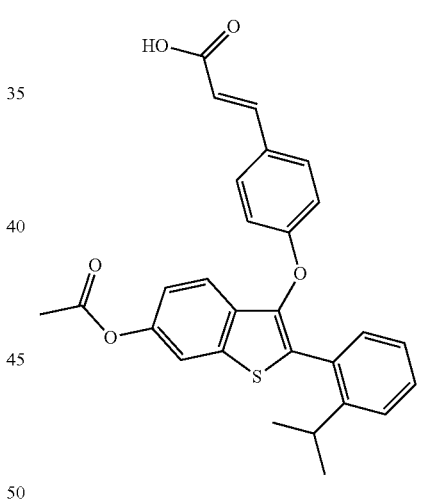

To a solution of (E)-tert-butyl 3-(4-((6-acetoxy-2-(2-isopropylphenyl)benzo[b]thiophen-3-yl)oxy)phenyl)acrylate (65 mg, 0.123 mmol) in DCM (3.0 mL) at 0° C. was added TFA dropwise over 5 min. The reaction was stirred at 0° C. for 1 h after which time it was warmed to room temperature for an additional 55 min. The mixture was then diluted with DCM and concentrated in vacuo to remove both DCM and TFA. The crude material was then further azeotroped with DCM (3×) to make sure all of the TFA was removed and gave a pale yellow solid. The resulting crude material was dissolved in MeOH (3 mL) and purified by reverse phase HPLC (acidic conditions, 0.1% TFA in 45-70% $CH_3CN/H_2O$) to afford (E)-3-(4-((6-acetoxy-2-(2-isopropylphenyl)benzo[b]thiophen-3-yl)oxy)phenyl)acrylic acid (39.1 mg, 0.083 mmol, 67% yield). ¹H NMR (400 MHz, CD₃OD) δ ppm=7.69 (d, J=2.0 Hz, 1H), 7.57 (d, J=15.9 Hz, 1H), 7.45 (dd, J=8.7, 6.4 Hz, 3H), 7.40-7.26 (m, 3H), 7.18-7.10 (m, 2H), 6.86 (d, J=8.8 Hz, 2H), 6.32 (d, J=16.0 Hz, 1H), 3.20 (p, J=6.9 Hz, 1H), 2.32 (s, 3H), 1.17 (d, J=6.9 Hz, 6H). HRMS (m/z, MH+): 473.1399.

Example 83

(E)-3-(4-((2-(2-isopropylphenyl)-6-((3-methoxypropanoyl)oxy)benzo[b]thiophen-3-yl)oxy)phenyl)acrylic acid

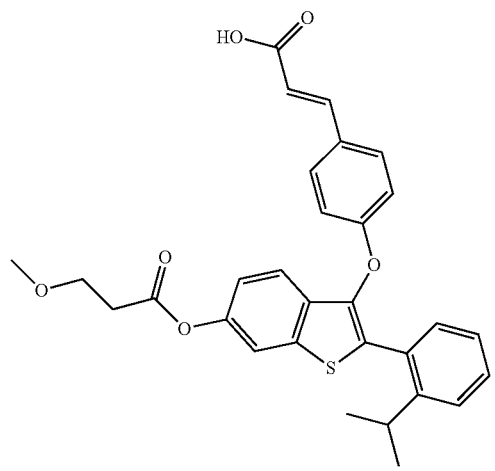 [SMILES: COCCC(=O)Oc1ccc2c(Oc3ccc(/C=C/C(=O)O)cc3)c(-c3ccccc3C(C)C)sc2c1]

Step 1: To a solution of (E)-tert-butyl 3-(4-((6-hydroxy-2-(2-isopropylphenyl)benzo[b]thiophen-3-yl)oxy)phenyl)acrylate (42 mg, 0.086 mmol) in DCM (3 mL) at room temperature was added 3-methoxypropanoyl chloride (15.87 mg, 0.129 mmol) followed by N-ethyl-N-isopropylpropan-2-amine (0.030 mL, 0.172 mmol). The resulting mixture was stirred at room temperature for 2 hours after which time an additional amount of methoxypropanoyl chloride (15.87 mg, 0.129 mmol) was added and stirring was continued at room temperature for 18 hours. Upon completion the reaction was concentrated in vacuo and used in the next step without further purification.

Step 2: The resulting crude product was retaken in DCM (3 mL) and trifluoroacetic acid (3 mL). The mixture was stirred at room temperature for 1 hour after which the reaction was concentrated in vacuo and the resulting crude material was purified by reverse phase HPLC (acidic condition, 0.1% formic acid as modifier, 55-80% CH₃CN/H₂O) to afford impure (E)-3-(4-((2-(2-isopropylphenyl)-6-(3-methoxypropanoyl)oxy)benzo[b]thiophen-3-yl)oxy)phenyl) acrylic acid (15 mg, 0.029 mmol, 33% yield). 1H NMR (400 MHz, DMSO-d6) δ 7.89 (d, J=2.1 Hz, 1H), 7.61-7.56 (m, 2H), 7.51-7.33 (m, 6H), 7.21 (td, J=7.3, 1.6 Hz, 1H), 7.15 (dd, J=8.7, 2.1 Hz, 1H), 6.93-6.86 (m, 2H), 6.35 (d, J=16.0 Hz, 1H), 3.69 (t, J=6.1 Hz, 2H), 3.30 (s, 3H), 3.14 (p, J=6.8 Hz, 1H), 2.87 (t, J=6.0 Hz, 2H), 1.14 (d, J=6.8 Hz, 6H). HRMS (m/z, MH+): 517.1689.

Example 84

(E)-3-(4-((6-((1,1-dioxido-3-oxobenzo[d]isothiazol-2(3H)-yl)methoxy)-2-(2-isopropylphenyl)benzo[b]thiophen-3-yl)oxy)phenyl)acrylic acid

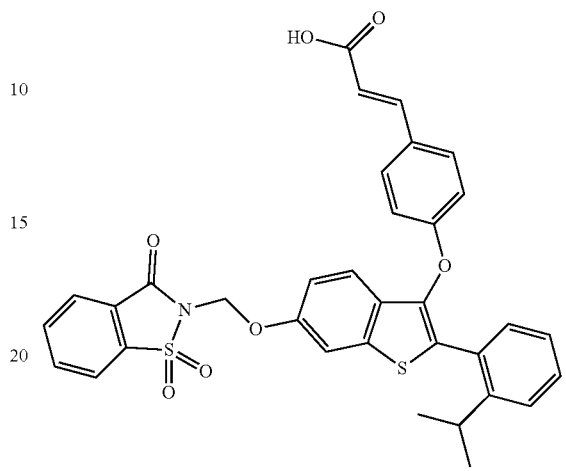

To a solution of (E)-tert-butyl 3-(4-((6-((1,1-dioxido-3-oxobenzo[d]isothiazol-2(3H)-yl)methoxy)-2-(2-isopropylphenyl)benzo[b]thiophen-3-yl)oxy)phenyl)acrylatein (67.4 mg, 0.099 mmol) in DCM (2 mL) at room temperature was added trifluoroacetic acid (0.227 mL, 2.97 mmol). The resulting mixture was stirred at room temperature for 1 hour after which the reaction was concentrated in vacuo. The resulting crude material was purified by reverse phase HPLC (acidic condition, 0.1% formic acid as modifier, 55-80% CH₃CN/H₂O) to afford (E)-3-(4-((6-((1,1-dioxido-3-oxobenzo[d]isothiazol-2(3H)-yl)methoxy)-2-(2-isopropylphenyl)benzo[b]thiophen-3-yl)oxy)phenyl)acrylic acid (41.4 mg, 0.066 mmol, 66% yield). ¹H NMR (400 MHz, (CD₃)₂SO) δ 12.33 (s, 1H), 8.37 (d, J=7.7 Hz, 1H), 8.18 (d, J=7.5 Hz, 1H), 8.11 (t, J=7.5 Hz, 1H), 8.04 (t, J=7.6 Hz, 1H), 7.88 (d, J=2.2 Hz, 1H), 7.60-7.54 (m, 2H), 7.47 (d, J=16.0 Hz, 1H), 7.44-7.29 (m, 4H), 7.24-7.15 (m, 2H), 6.92-6.84 (m, 2H), 6.35 (d, J=16.0 Hz, 1H), 5.90 (s, 2H), 3.14 (h, J=6.9 Hz, 1H), 1.13 (d, J=6.9 Hz, 6H). HRMS (m/z, MH+): 626.1207.

Example 85

(S,E)-3-(4-((6-((2-amino-3-methylbutanoyl)oxy)-2-(2-isopropylphenyl)benzo[b]thiophen-3-yl)oxy)phenyl)acrylic acid

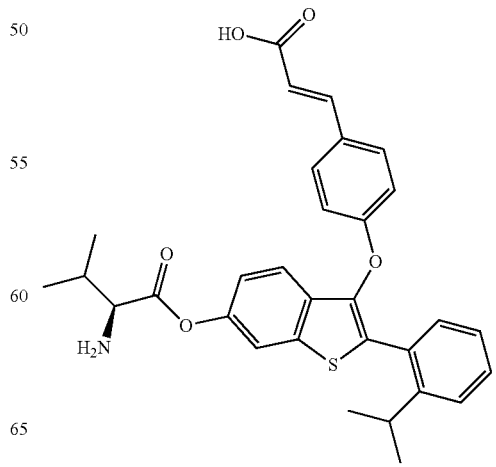

A solution of (S,E)-3-(4-(3-(tert-butoxy)-3-oxoprop-1-en-1-yl)phenoxy)-2-(2-isopropylphenyl)benzo[b]thiophen-6-yl 2-((tert-butoxycarbonyl)amino)-3-methylbutanoate (106.8 mg, 0.156 mmol) in HCl (2.0 mL, 4N in 1,4-dioxane) was stirred at room temperature for 18 hours after which time the mixture was concentrated in vacuo to remove HCl and 1,4-dioxane. The resulting crude material was then triturated with heptane (2×) to obtain (S,E)-3-(4-((6-((2-amino-3-methylbutanoyl)oxy)-2-(2-isopropylphenyl)benzo[b]thiophen-3-yl)oxy)phenyl)acrylic acid hydrochloride (54.1 mg, 0.094 mmol, 85% yield). $^1$H NMR (400 MHz, CD$_3$OD) δ ppm=7.81 (d, J=2.02 Hz, 1H), 7.42-7.62 (m, 4H), 7.25-7.42 (m, 3H), 7.09-7.26 (m, 2H), 6.86 (d, J=8.59 Hz, 2H), 6.32 (d, J=15.66 Hz, 1H), 4.29 (d, J=5.05 Hz, 1H), 3.18 (s, 1H), 2.44-2.60 (m, 1H), 1.12-1.35 (m, 12H) HRMS (m/z, MH+): 530.1988.

The following examples were prepared using procedures described in the above examples 1-85 using appropriate starting materials:

TABLE 10

| Example | Structure | Name | Physical data |
| --- | --- | --- | --- |
| 86 | 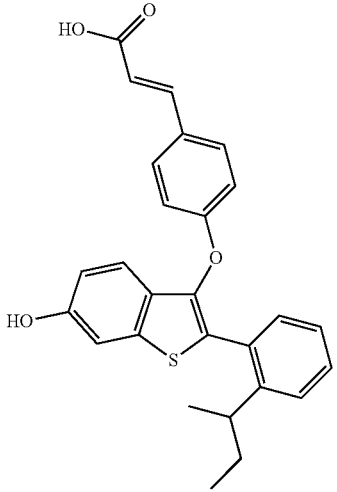 [SMILES: CCC(C)c1ccccc1-c1sc2cc(O)ccc2c1Oc1ccc(/C=C/C(=O)O)cc1] | (E)-3-(4-((2-(2-(sec-butyl)phenyl)-6-hydroxybenzo[b]thiophen-3-yl)oxy)phenyl)acrylic acid | 1H NMR (400 MHz, CD3OD) δ ppm = 7.56 (d, J = 16.0 Hz, 1H), 7.45 (d, J = 8.8 Hz, 2H), 7.35-7.20 (m, 5H), 7.12 (ddd, J = 8.4, 6.1, 2.4 Hz, 1H), 6.89-6.81 (m, 3H), 6.31 (d, J = 16.1 Hz, 1H), 3.02-2.90 (m, 1H), 1.64-1.48 (m, 2H), 1.16 (d, J = 6.9 Hz, 3H), 0.75 (t, J = 7.4 Hz, 3H) HRMS (m/z, MH+): 445.1445 |
| 87 | 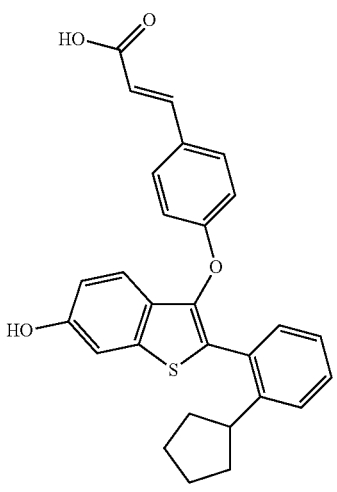 [SMILES: O=C(O)/C=C/c1ccc(Oc2c(-c3ccccc3C3CCCC3)sc3cc(O)ccc23)cc1] | (E)-3-(4-((2-(2-cyclopentylphenyl)-6-hydroxybenzo[b]thiophen-3-yl)oxy)phenyl)acrylic acid | 1H NMR (400 MHz, CD3OD) δ ppm = 7.55 (d, J = 15.9 Hz, 1H), 7.41 (d, J = 7.9 Hz, 2H), 7.36-7.19 (m, 5H), 7.08 (t, J = 7.3 Hz, 1H), 6.84 (t, J = 8.0 Hz, 3H), 6.30 (d, J = 15.9 Hz, 1H), 3.29-3.20 (m, 1H), 1.92 (br s, 2H), 1.77 (br s, 2H), 1.53 (br s, 4H) HRMS (m/z, MH+): 457.1644 |

TABLE 10-continued

| Example | Structure | Name | Physical data |
|---|---|---|---|
| 88 | 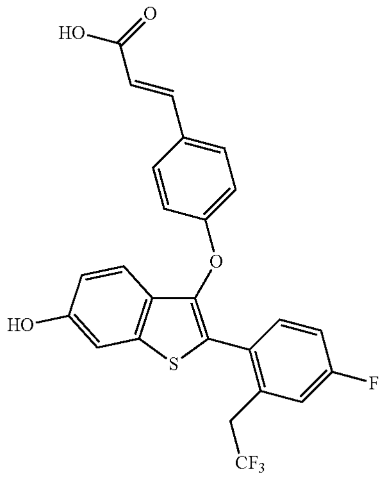 [SMILES: O=C(O)/C=C/c1ccc(Oc2c(-c3ccc(F)cc3CC(F)(F)F)sc3cc(O)ccc23)cc1] | (E)-3-(4-((2-(4-fluoro-2-(2,2,2-trifluoroethyl)phenyl)-6-hydroxybenzo[b]thiophen-3-yl)oxy)phenyl)acrylic acid | 1H NMR (400 MHz, CD3OD) δ ppm = 3.67 (q, J = 10.61 Hz, 2 H), 6.31 (d, J = 15.66 Hz, 1 H), 6.75-6.85 (m, 2 H), 6.88 (dd, J = 8.59, 2.02 Hz, 1 H), 7.00-7.13 (m, 1 H), 7.20 (dd, J = 9.60, 2.02 Hz, 1 H), 7.23-7.33 (m, 2 H), 7.33-7.48 (m, 3 H), 7.56 (d, J = 15.66 Hz, 1 H)<br>LC/MS (m/z, MH+): 489.4 |
| 89 | 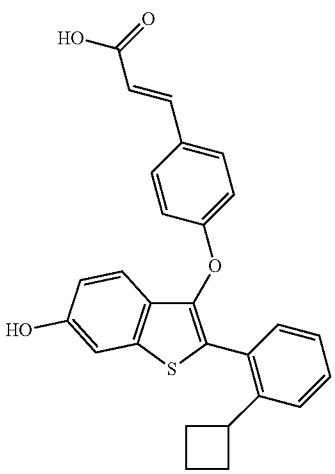 [SMILES: O=C(O)/C=C/c1ccc(Oc2c(-c3ccccc3C3CCC3)sc3cc(O)ccc23)cc1] | (E)-3-(4-((2-(2-cyclobutylphenyl)-6-hydroxybenzo[b]thiophen-3-yl)oxy)phenyl)acrylic acid | 1H NMR (400 MHz, CD3OD) δ ppm = 7.54 (d, J = 15.9 Hz, 1H), 7.39 (dd, J = 8.2, 6.0 Hz, 3H), 7.29 (t, J = 7.6 Hz, 1H), 7.26-7.20 (m, 3H), 7.10 (t, J = 7.5 Hz, 1H), 6.88-6.78 (m, 3H), 6.29 (d, J = 15.9 Hz, 1H), 3.86 (p, J = 8.8 Hz, 1H), 2.20-2.09 (m, 2H), 2.09-1.99 (m, 2H), 1.96-1.82 (m, 1H), 1.81-1.69 (m, 1H)<br>HRMS (m/z, MH+): 443.1288 |
| 90 | 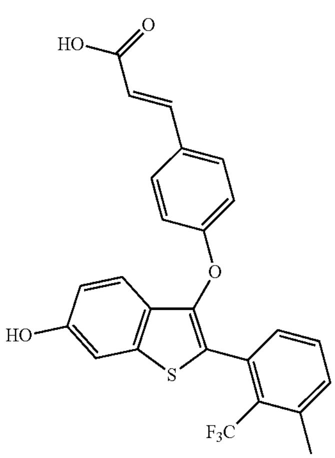 | (E)-3-(4-((2-(3-fluoro-2-(trifluoromethyl)phenyl)-6-hydroxybenzo[b]thiophen-3-yl)oxy)phenyl)acrylic acid | 1H NMR (400 MHz, CD3OD) δ ppm = 7.62-7.52 (m, 2H), 7.45 (d, J = 8.7 Hz, 2H), 7.35-7.27 (m, 2H), 7.25 (dd, J = 5.4, 3.2 Hz, 2H), 6.87 (dd, J = 8.7, 2.2 Hz, 1H), 6.84 (d, J = 8.7 Hz, 2H), 6.32 (d, J = 15.9 Hz, 1H)<br>HRMS (m/z, MH+): 475.0602 |

TABLE 10-continued

| Example | Structure | Name | Physical data |
|---|---|---|---|
| 91 | 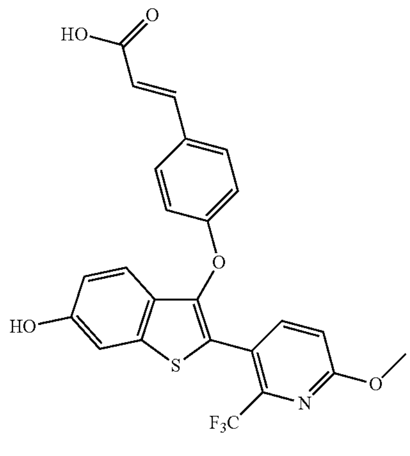 [SMILES: COc1ccc(-c2sc3cc(O)ccc3c2Oc2ccc(/C=C/C(=O)O)cc2)c(C(F)(F)F)n1] | (E)-3-(4-((6-hydroxy-2-(6-methoxy-2-(trifluoromethyl)pyridin-3-yl)benzo[b]thiophen-3-yl)oxy)phenyl)acrylic acid | 1H NMR (400 MHz, CD3OD) δ ppm = 3.86 (s, 3 H), 6.24 (d, J = 16.17 Hz, 1 H), 6.70-6.80 (m, 3 H), 6.85 (d, J = 8.59 Hz, 1 H), 7.11-7.18 (m, 2 H), 7.30-7.42 (m, 3 H), 7.66 (d, J = 8.59 Hz, 1 H) LC/MS (m/z, MH+): 488.3 |
| 92 | 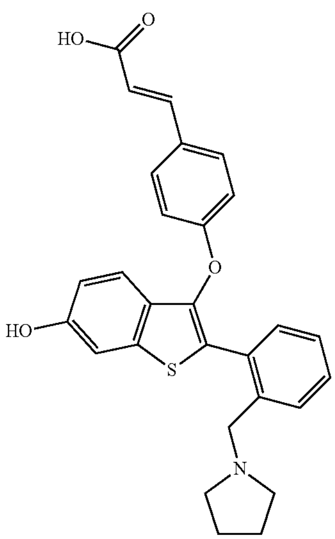 [SMILES: O=C(O)/C=C/c1ccc(Oc2c(-c3ccccc3CN3CCCC3)sc3cc(O)ccc23)cc1] | (E)-3-(4-((6-hydroxy-2-(2-(pyrrolidin-1-ylmethyl)phenyl)benzo[b]thiophen-3-yl)oxy)phenyl)acrylic acid | 1H NMR (400 MHz, CD3OD) δ ppm = 7.58 (dd, J = 7.6, 1.6 Hz, 1H), 7.52-7.32 (m, 6H), 7.29 (dd, J = 15.1, 2.2 Hz, 2H), 6.90 (dd, J = 8.7, 2.2 Hz, 1H), 6.81 (d, J = 8.7 Hz, 2H), 6.33 (d, J = 15.9 Hz, 1H), 4.31 (s, 2H), 3.06-2.92 (m, 4H), 1.96-1.82 (m, 4H) HRMS (m/z MH+): 472.1562 |
| 93 | 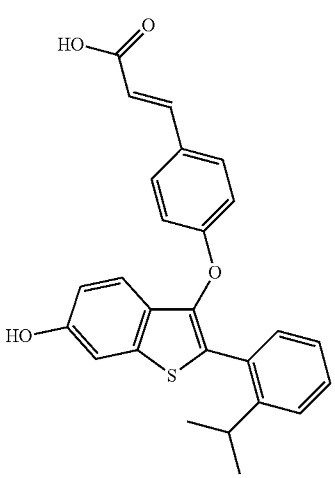 [SMILES: CC(C)c1ccccc1-c1sc2cc(O)ccc2c1Oc1ccc(/C=C/C(=O)O)cc1] | 3-(4-((6-hydroxy-2-(2-isopropylphenyl)benzo[b]thiophen-3-yl)oxy)phenyl)propanoic acid | 1H NMR (400 MHz, CD3OD) δ ppm = 7.36-7.19 (m, 5H), 7.09 (td, J = 7.3, 1.6 Hz, 1H), 7.01 (d, J = 8.3 Hz, 2H), 6.82 (dd, J = 8.5, 2.2 Hz, 1H), 6.70 (d, J = 8.4 Hz, 2H), 3.22 (p, J = 6.9 Hz, 1H), 2.78 (t, J = 7.7 Hz, 2H), 2.49 (t, J = 7.7 Hz, 2H), 1.14 (d, J = 6.8 Hz, 6H) HRMS (m/z, MH+): 433.1456 |

TABLE 10-continued

| Example | Structure | Name | Physical data |
|---|---|---|---|
| 94 | 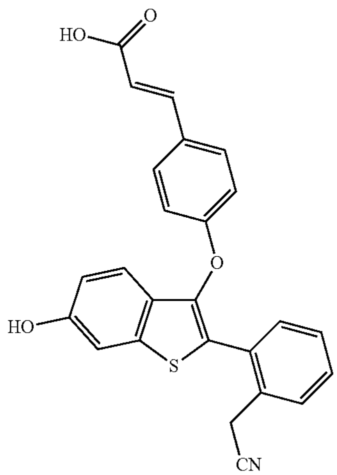 [SMILES: N#CCc1ccccc1-c1sc2cc(O)ccc2c1Oc1ccc(/C=C/C(=O)O)cc1] | (E)-3-(4-((2-(2-(cyanomethyl)phenyl)-6-hydroxybenzo[b]thiophen-3-yl)oxy)phenyl)acrylic acid | 1H NMR (400 MHz, CD3OD) δ ppm = 3.97 (s, 2 H), 6.31 (d, J = 15.66 Hz, 1 H), 6.72-6.93 (m, 3 H), 7.25-7.55 (m, 9 H) LC/MS (m/z, MH+): 428.4 |
| 95 | 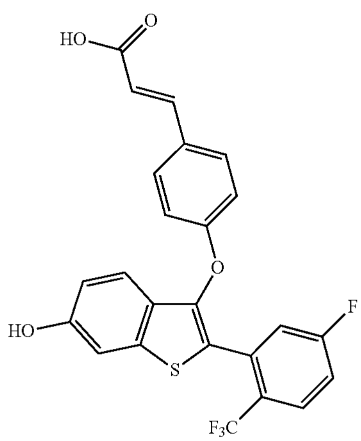 [SMILES: O=C(O)/C=C/c1ccc(Oc2c(-c3cc(F)ccc3C(F)(F)F)sc3cc(O)ccc23)cc1] | (E)-3-(4-((2-(5-fluoro-2-(trifluoromethyl)phenyl)-6-hydroxybenzo[b]thiophen-3-yl)oxy)phenyl)acrylic acid | 1H NMR (400 MHz, CD3OD) δ ppm = 7.84-7.74 (m, 1H), 7.51 (d, J = 16.0 Hz, 1H), 7.48-7.40 (m, 2H), 7.32-7.20 (m, 4H), 6.92-6.80 (m, 3H), 6.33 (d, J = 16.1 Hz, 1H) HRMS (m/z, MH+): 475.0599 |
| 96 | 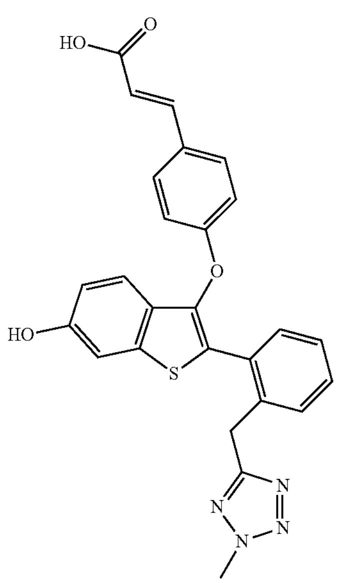 [SMILES: Cn1nnc(Cc2ccccc2-c2sc3cc(O)ccc3c2Oc2ccc(/C=C/C(=O)O)cc2)n1] | (E)-3-(4-((6-hydroxy-2-(2-((2-methyl-2H-tetrazol-5-yl)methyl)phenyl)benzo[b]thiophen-3-yl)oxy)phenyl)acrylic acid | $^1$H NMR (400 MHz, CD$_3$OD) δ ppm = 7.55 (d, J = 16.0 Hz, 1H), 7.43 (d, J = 8.7 Hz, 2H), 7.35 (d, J = 7.5 Hz, 1H), 7.30 (d, J = 3.9 Hz, 2H), 7.27-7.19 (m, 3H), 6.88-6.84 (m, 1H), 6.83 (s, 2H), 6.31 (d, J = 15.9 Hz, 1H), 4.35 (s, 2H), 4.17 (d, J = 0.8 Hz, 3H) HRMS (m/z, MH+): 485.1252 |

TABLE 10-continued

| Example | Structure | Name | Physical data |
|---|---|---|---|
| 97 | 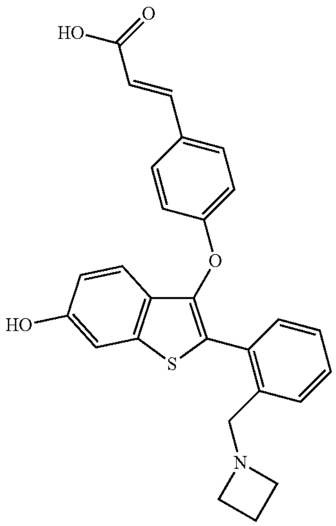 [SMILES: O=C(O)/C=C/c1ccc(Oc2c(-c3ccccc3CN3CCC3)sc3cc(O)ccc23)cc1] | (E)-3-(4-((2-(2-(azetidin-1-ylmethyl)phenyl)-6-hydroxybenzo[b]thiophen-3-yl)oxy)phenyl)acrylic acid | 1H NMR (400 MHz, CD3OD) δ ppm = 7.58-7.50 (m, 2H), 7.49-7.42 (m, 5H), 7.34 (d, J = 8.9 Hz, 1H), 7.30 (d, J = 2.2 Hz, 1H), 6.92 (dd, J = 8.8, 2.2 Hz, 1H), 6.87 (d, J = 8.8 Hz, 2H), 6.31 (d, J = 16.0 Hz, 1H), 4.55 (s, 2H), 4.06 (br s, 4H), 2.40 (br d, J = 67.3 Hz, 2H)<br>HRMS (m/z, MH+): 458.1407 |
| 98 | 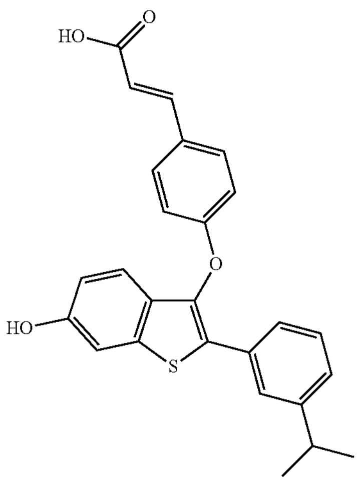 [SMILES: CC(C)c1cccc(-c2sc3cc(O)ccc3c2Oc2ccc(/C=C/C(=O)O)cc2)c1] | (E)-3-(4-((6-hydroxy-2-(3-isopropylphenyl)benzo[b]thiophen-3-yl)oxy)phenyl)acrylic acid | 1H NMR (400 MHz, CD3OD) δ ppm = 7.58 (d, J = 15.8 Hz, 2H), 7.52 (d, J = 8.7 Hz, 2H), 7.45 (d, J = 8.3 Hz, 1H), 7.28-7.18 (m, 3H), 7.12 (d, J = 7.6 Hz, 1H), 6.95 (d, J = 8.7 Hz, 2H), 6.82 (dd, J = 8.7, 2.2 Hz, 1H), 6.35 (d, J = 15.9 Hz, 1H), 2.83 (p, J = 6.9 Hz, 1H), 1.16 (d, J = 6.8 Hz, 6H)<br>HRMS (m/z, MH+): 431.1306 |
| 99 | 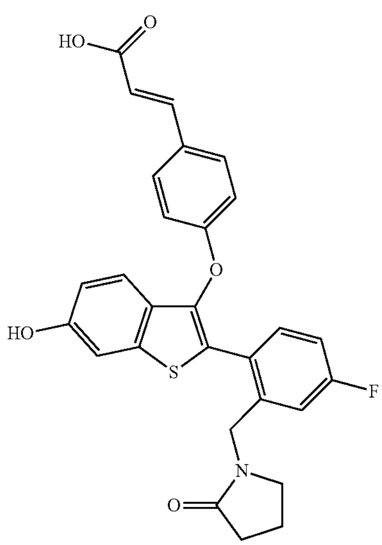 [SMILES: O=C(O)/C=C/c1ccc(Oc2c(-c3ccc(F)cc3CN3CCCC3=O)sc3cc(O)ccc23)cc1] | (E)-3-(4-((2-(4-fluoro-2-((2-oxopyrrolidin-1-yl)methyl)phenyl)-6-hydroxybenzo[b]thiophen-3-yl)oxy)phenyl)acrylic acid | 1H NMR (400 MHz, (CD3)2SO) δ ppm = 7.55 (d, J = 8.6 Hz, 2H), 7.51-7.40 (m, 2H), 7.34 (d, J = 2.1 Hz, 1H), 7.21 (d, J = 8.7 Hz, 1H), 7.15 (td, J = 8.5, 2.8 Hz, 1H), 6.97 (dd, J = 9.9, 2.8 Hz, 1H), 6.92-6.84 (m, 3H), 6.35 (d, J = 15.9 Hz, 1H), 4.43 (s, 2H), 3.14 (t, J = 7.0 Hz, 2H), 2.26 (t, J = 8.0 Hz, 2H), 1.99-1.84 (m, 2H)<br>HRMS (m/z, MH+): 504.1250 |

TABLE 10-continued

| Example | Structure | Name | Physical data |
|---|---|---|---|
| 100 | 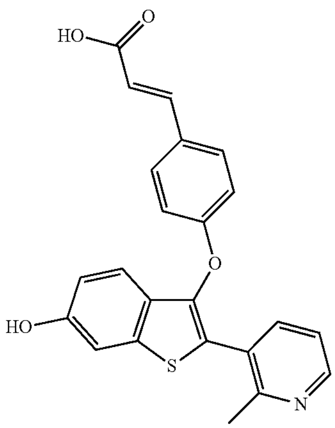 [SMILES: Cc1ncccc1-c1sc2cc(O)ccc2c1Oc1ccc(/C=C/C(=O)O)cc1] | (E)-3-(4-((6-hydroxy-2-(2-methylpyridin-3-yl)benzo[b]thiophen-3-yl)oxy)phenyl)acrylic acid | 1H NMR (400 MHz, CD3OD) δ ppm = 8.56 (d, J = 5.6 Hz, 1H), 8.34 (d, J = 8.0 Hz, 1H), 7.69 (t, J = 7.1 Hz, 1H), 7.56 (d, J = 16.0 Hz, 1H), 7.48 (d, J = 8.8 Hz, 2H), 7.35 (d, J = 8.7 Hz, 1H), 7.31 (d, J = 2.1 Hz, 1H), 6.97-6.86 (m, 3H), 6.33 (d, J = 16.0 Hz, 1H), 2.76 (s, 3H) HRMS (m/z, MH+): 404.0941 |
| 101 | 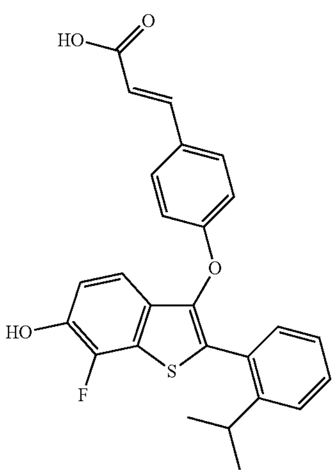 [SMILES: CC(C)c1ccccc1-c1sc2c(F)c(O)ccc2c1Oc1ccc(/C=C/C(=O)O)cc1] | (E)-3-(4-((7-fluoro-6-hydroxy-2-(2-isopropylphenyl)benzo[b]thiophen-3-yl)oxy)phenyl)acrylic acid | 1H NMR (400 MHz, CD3OD) δ ppm = 1.06 (d, J = 6.57 Hz, 6 H), 3.09 (quin, J = 6.82 Hz, 1 H), 6.20 (d, J = 16.17 Hz, 1 H), 6.69-6.77 (m, 2 H), 6.84-6.98 (m, 2 H), 6.98-7.06 (m, 1 H), 7.13-7.29 (m, 3 H), 7.29-7.38 (m, 2 H), 7.45 (d, J = 15.66 Hz, 1 H) LC/MS (m/z, M − H): 447.0 |
| 102 | 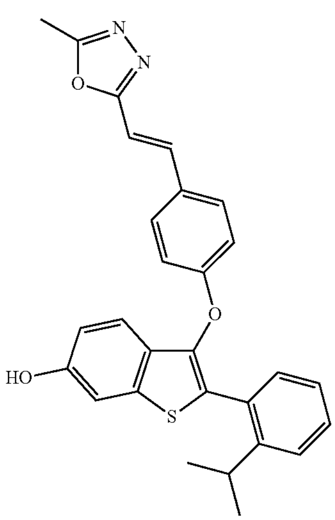 [SMILES: Cc1nnc(/C=C/c2ccc(Oc3c(-c4ccccc4C(C)C)sc4cc(O)ccc34)cc2)o1] | (E)-2-(2-isopropylphenyl)-3-(4-(2-(5-methyl-1,3,4-oxadiazol-2-yl)vinyl)phenoxy)benzo[b]thiophen-6-ol | 1H NMR (400 MHz, CD3OD) δ ppm = 7.34-7.45 (m, 3H), 7.10-7.27 (m, 5H), 6.96-7.06 (m, 1H), 6.82 (d, J = 16.7 Hz, 1H), 6.71-6.79 (m, 3H), 3.14 (dt, J = 13.8, 7.0 Hz, 1H), 2.45 (s, 3H), 1.07 (d, J = 7.1 Hz, 6H) LC/MS (m/z, MH+): 469.0 |

TABLE 10-continued

| Example | Structure | Name | Physical data |
|---|---|---|---|
| 103 | 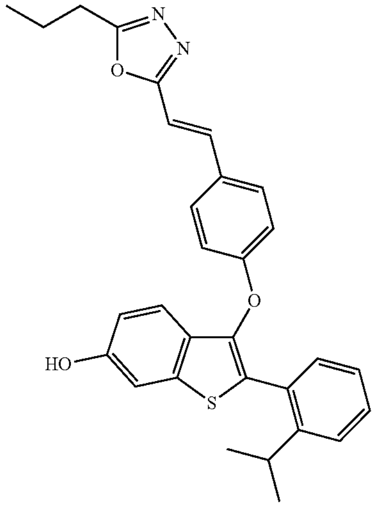 [SMILES: CCCc1nnc(/C=C/c2ccc(Oc3c(-c4ccccc4C(C)C)sc4cc(O)ccc34)cc2)o1] | (E)-2-(2-isopropylphenyl)-3-(4-(2-(5-propyl-1,3,4-oxadiazol-2-yl)vinyl)phenoxy)benzo[b]thiophen-6-ol | 1H NMR (400 MHz, CD3OD) δ ppm = 7.33-7.49 (m, 3H), 7.11-7.29 (m, 5H), 6.98-7.07 (m, 1H), 6.83 (d, J = 16.7 Hz, 1H), 6.71-6.79 (m, 3H), 3.14 (dt, J = 13.6, 6.8 Hz, 1H), 2.78 (t, J = 7.6 Hz, 2H), 1.66-1.83 (m, 2H), 1.07 (d, J = 7.1 Hz, 6H), 0.94 (t, J = 7.3 Hz, 3H) LC/MS (m/z, MH+): 497.0 |
| 104 | 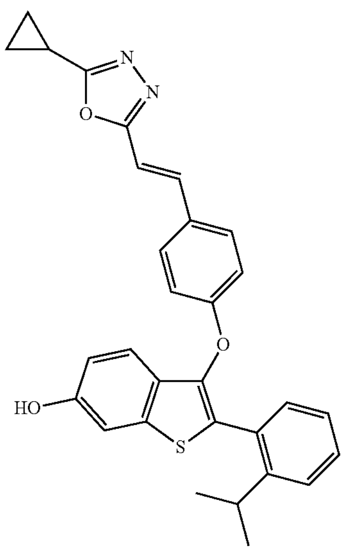 [SMILES: CC(C)c1ccccc1-c1sc2cc(O)ccc2c1Oc1ccc(/C=C/c2nnc(C3CC3)o2)cc1] | (E)-3-(4-(2-(5-cyclopropyl-1,3,4-oxadiazol-2-yl)vinyl)phenoxy)-2-(2-isopropylphenyl)benzo[b]thiophen-6-ol | 1H NMR (400 MHz, CD3OD) δ ppm = 7.30-7.46 (m, 3H), 7.10-7.30 (m, 5H), 6.96-7.06 (m, 1H), 6.71-6.84 (m, 4H), 3.14 (dt, J = 13.6, 6.8 Hz, 1H), 2.02-2.23 (m, 1H), 1.02-1.15 (m, 10H) LC/MS (m/z, MH+): 495.0 |
| 105 | 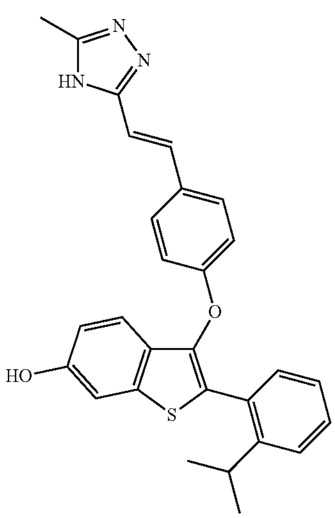 [SMILES: Cc1nnc(/C=C/c2ccc(Oc3c(-c4ccccc4C(C)C)sc4cc(O)ccc34)cc2)[nH]1] | (E)-2-(2-isopropylphenyl)-3-(4-(2-(5-methyl-4H-1,2,4-triazol-3-yl)vinyl)phenoxy)benzo[b]thiophen-6-ol | 1H NMR (400 MHz, CD3OD) δ ppm = 7.43-7.55 (m, 3H), 7.21-7.40 (m, 5H), 7.08-7.17 (m, 1H), 6.84-6.96 (m, 4H), 3.26 (dt, J = 13.9, 6.7 Hz, 1H), 2.56 (s, 3H), 1.18 (d, J = 6.6 Hz, 6H) LC/MS (m/z, MH+): 468.1 |

TABLE 10-continued

| Example | Structure | Name | Physical data |
|---|---|---|---|
| 106 | 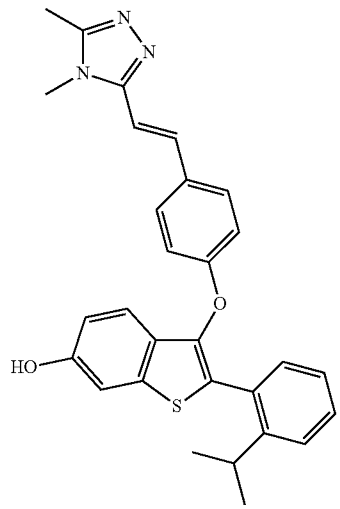 | (E)-3-(4-(2-(4,5-dimethyl-4H-1,2,4-triazol-3-yl)vinyl)phenoxy)-2-(4-fluoro-2-methylphenyl)benzo[b]thiophen-6-ol | 1H NMR (400 MHz, CD3OD) δ ppm = 7.34-7.46 (m, 3H), 7.07-7.26 (m, 3H), 6.70-6.94 (m, 6H), 3.54 (s, 3H), 2.34 (s, 3H), 2.26 (s, 3H) LC/MS (m/z, MH+): 472.0 |
| 107 | 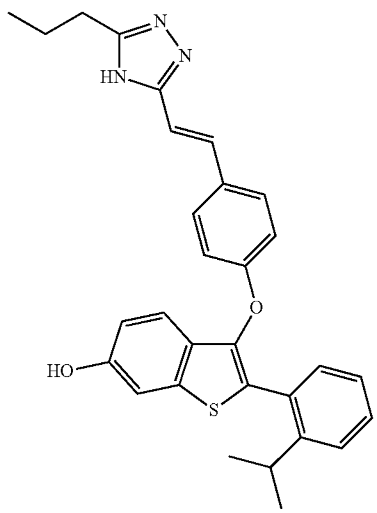 | (E)-2-(2-isopropylphenyl)-3-(4-(2-(5-propyl-4H-1,2,4-triazol-3-yl)vinyl)phenoxy)benzo[b]thiophen-6-ol | 1H NMR (400 MHz, CD3OD) δ ppm = 7.31-7.45 (m, 3H), 7.12-7.30 (m, 5H), 6.98-7.06 (m, 1H), 6.69-6.87 (m, 4H), 3.11-3.17 (m, 1H), 2.73 (t, J = 7.6 Hz, 2H), 1.63-1.80 (m, 2H), 1.07 (d, J = 6.6 Hz, 6H), 0.92 (t, J = 7.3 Hz, 3H) LC/MS (m/z, MH+): 496.0 |
| 108 | 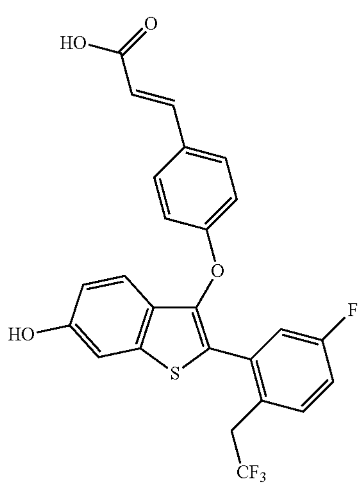 [SMILES: O=C(O)/C=C/c1ccc(Oc2c(-c3cc(F)ccc3CC(F)(F)F)sc3cc(O)ccc23)cc1] | (E)-3-(4-((2-(5-fluoro-2-(2,2,2-trifluoroethyl)phenyl)-6-hydroxybenzo[b]thiophen-3-yl)oxy)phenyl)acrylic acid | 1H NMR (400 MHz, CD3OD) δ ppm = 3.66 (q, J = 11.12 Hz, 2 H) 6.31 (d, J = 15.66 Hz, 1 H) 6.84 (d, J = 8.59 Hz, 2H) 6.89 (dd, J = 8.59, 2.02 Hz, 1 H) 7.04-7.22 (m, 2 H) 7.22-7.35 (m, 2 H) 7.38-7.49 (m, 3 H) 7.56 (d, J = 16.17 Hz, 1H) LC/MS (m/z, MH+): 489.4 |

TABLE 10-continued

| Example | Structure | Name | Physical data |
|---|---|---|---|
| 109 | 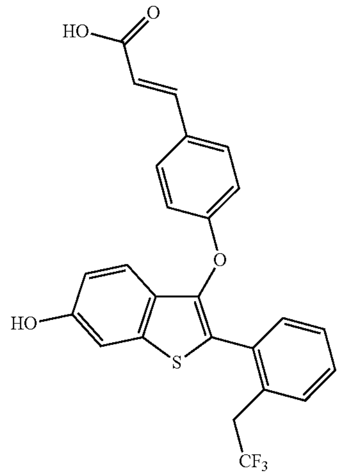 [SMILES: O=C(O)/C=C/c1ccc(Oc2c(-c3ccccc3CC(F)(F)F)sc3cc(O)ccc23)cc1] | (E)-3-(4-((6-hydroxy-2-(2-(2,2,2-trifluoroethyl)phenyl)benzo[b]thiophen-3-yl)oxy)phenyl)acrylic acid | 1H NMR (400 MHz, CD3OD) δ ppm = 3.50-3.76 (m, 2 H) 6.31 (d, J = 16.17 Hz, 1 H) 6.71-6.85 (m, 2 H) 6.88 (dd, J = 8.84, 2.27 Hz, 1 H) 7.19-7.37 (m, 4 H) 7.38-7.48 (m, 4 H) 7.52 (d, J = 15.66 Hz, 1 H) LC/MS (m/z, MH+): 471.3 |
| 110 | 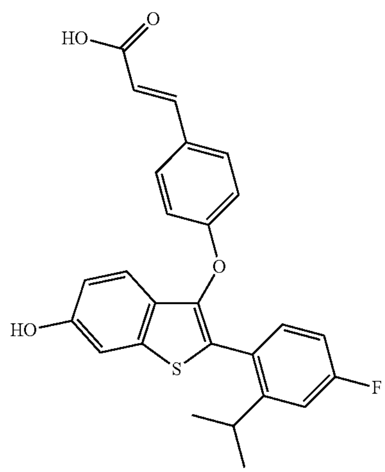 [SMILES: CC(C)c1cc(F)ccc1-c1sc2cc(O)ccc2c1Oc1ccc(/C=C/C(=O)O)cc1] | (E)-3-(4-((2-(4-fluoro-2-isopropylphenyl)-6-hydroxybenzo[b]thiophen-3-yl)oxy)phenyl)acrylic acid | 1H NMR (400 MHz, CD3OD) δ ppm = 7.56 (d, J = 16.0 Hz, 1H), 7.45 (d, J = 8.7 Hz, 2H), 7.33-7.22 (m, 3H), 7.06 (dd, J = 10.6, 2.7 Hz, 1H), 6.92-6.81 (m, 4H), 6.32 (d, J = 16.0 Hz, 1H), 3.22 (pd, J = 6.8, 1.9 Hz, 1H), 1.16 (d, J = 6.8 Hz, 6H) HRMS (m/z, MH+): 449.1207 |
| 111 | 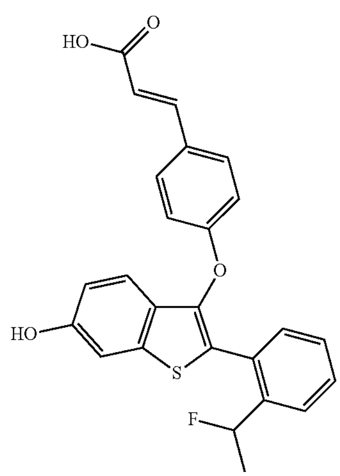 [SMILES: CC(F)c1ccccc1-c1sc2cc(O)ccc2c1Oc1ccc(/C=C/C(=O)O)cc1] | (E)-3-(4-((2-(2-(1-fluoroethyl)phenyl)-6-hydroxybenzo[b]thiophen-3-yl)oxy)phenyl)acrylic acid | 1H NMR (400 MHz, CD3OD) δ ppm = 7.56 (dd, J = 7.9, 1.2 Hz, 1H), 7.51 (d, J = 15.9 Hz, 1H), 7.47-7.38 (m, 3H), 7.36-7.23 (m, 4H), 6.87 (dd, J = 8.6, 2.1 Hz, 1H), 6.84 (d, J = 8.7 Hz, 2H), 6.32 (d, J = 16.0 Hz, 1H), 5.88 (dq, J = 46.9, 6.3 Hz, 1H), 1.54 (dd, J = 23.6, 6.4 Hz, 3H) HRMS (m/z, MH+): 435.1024 |

TABLE 10-continued

| Example | Structure | Name | Physical data |
|---|---|---|---|
| 112 | 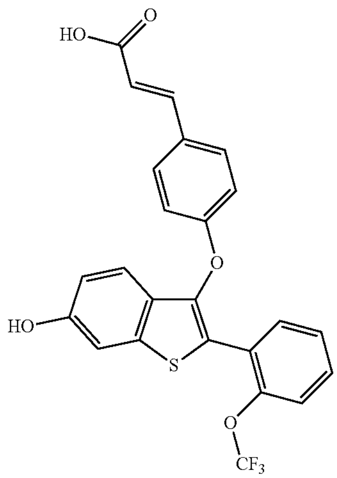 | (E)-3-(4-((6-hydroxy-2-(2-(trifluoromethoxy)phenyl)benzo[b]thiophen-3-yl)oxy)phenyl)acrylic acid | 1H NMR (400 MHz, CD3OD) δ ppm = 7.66 (dd, J = 7.7, 1.8 Hz, 1H), 7.57 (d, J = 15.9 Hz, 1H), 7.47 (d, J = 8.7 Hz, 2H), 7.44-7.30 (m, 3H), 7.28-7.22 (m, 2H), 6.93-6.81 (m, 3H), 6.33 (d, J = 15.9 Hz, 1H) LC/MS (m/z, MH+): 473.4 |
| 113 | 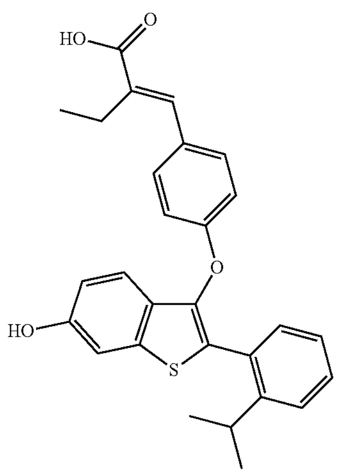 [SMILES: CC/C(=C\c1ccc(Oc2c(-c3ccccc3C(C)C)sc3cc(O)ccc23)cc1)C(=O)O] | (E)-2-(4-((6-hydroxy-2-(2-isopropylphenyl)benzo[b]thiophen-3-yl)oxy)benzylidene)butanoic acid | 1H NMR (400 MHz, CD3OD) δ ppm = 1.10 (t, J = 7.58 Hz, 3 H), 1.16 (d, J = 6.57 Hz, 6 H), 2.47 (q, J = 7.07 Hz, 2 H), 3.19-3.26 (m, 1 H), 6.80-6.89 (m, 3 H), 7.08-7.16 (m, 1 H), 7.20-7.36 (m, 7 H), 7.45 (s, 1 H) LC/MS (m/z, M − H): 457.0 |
| 114 | 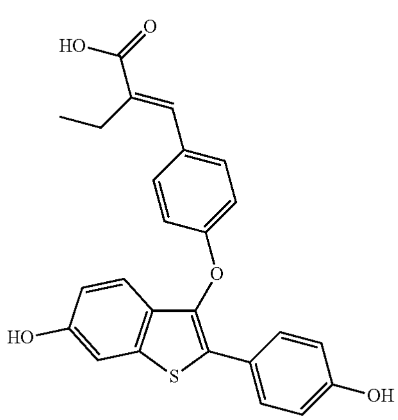 [SMILES: CC/C(=C\c1ccc(Oc2c(-c3ccc(O)cc3)sc3cc(O)ccc23)cc1)C(=O)O] | (E)-2-(4-((6-hydroxy-2-(4-hydroxyphenyl)benzo[b]thiophen-3-yl)oxy)benzylidene)butanoic acid | 1H NMR (400 MHz, CD3OD) δ ppm = 1.15 (t, J = 7.33 Hz, 3 H), 2.53 (q, J = 7.24 Hz, 2 H), 6.71-6.85 (m, 3 H), 6.92-7.01 (m, 2 H), 7.12-7.24 (m, 2 H), 7.36 (m, J = 9.09 Hz, 2 H), 7.48-7.64 (m, 3 H) LC/MS (m/z, MH+): 433.0 |

TABLE 10-continued

| Example | Structure | Name | Physical data |
|---|---|---|---|
| 115 | 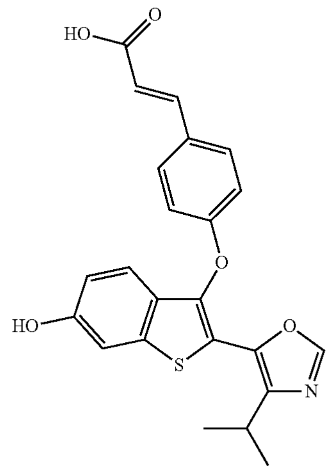 [SMILES: CC(C)c1ncoc1-c1sc2cc(O)ccc2c1Oc1ccc(/C=C/C(=O)O)cc1] | (E)-3-(4-((6-hydroxy-2-(4-isopropyloxazol-5-yl)benzo[b]thiophen-3-yl)oxy)phenyl)acrylic acid | 1H NMR (400 MHz, CD3OD) δ ppm = 8.11 (s, 1H), 7.59 (d, J = 16.0 Hz, 1H), 7.53 (d, J = 8.7 Hz, 2H), 7.30-7.24 (m, 2H), 6.93 (d, J = 8.8 Hz, 2H), 6.87 (dd, J = 8.8, 2.2 Hz, 1H), 6.36 (d, J = 15.9 Hz, 1H), 3.29-3.20 (m, 1H), 1.19 (d, J = 6.8 Hz, 6H) HRMS (m/z, MH+): 422.1038 |
| 116 | 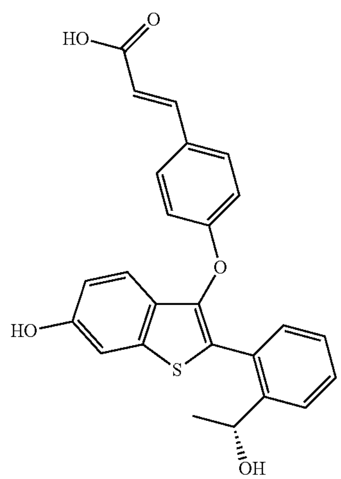 [SMILES: C[C@@H](O)c1ccccc1-c1sc2cc(O)ccc2c1Oc1ccc(/C=C/C(=O)O)cc1] | (R,E)-3-(4-((6-hydroxy-2-(2-(1-hydroxyethyl)phenyl)benzo[b]thiophen-3-yl)oxy)phenyl)acrylic acid | 1H NMR (400 MHz, CD3OD) δ ppm = 7.63 (dd, J = 8.0, 1.2 Hz, 1H), 7.55 (d, J = 16.0 Hz, 1H), 7.45 (d, J = 8.7 Hz, 2H), 7.38 (td, J = 7.6, 1.5 Hz, 1H), 7.28 (dd, J = 7.6, 1.5 Hz, 1H), 7.25-7.17 (m, 3H), 6.90-6.82 (m, 3H), 6.32 (d, J = 16.0 Hz, 1H), 5.16 (q, J = 6.3 Hz, 1H), 1.37 (d, J = 6.4 Hz, 3H) |
| 117 | 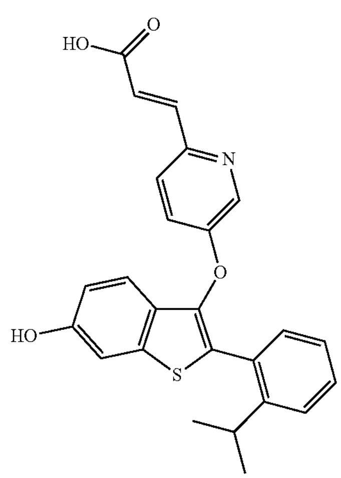 [SMILES: CC(C)c1ccccc1-c1sc2cc(O)ccc2c1Oc1ccc(/C=C/C(=O)O)nc1] | (E)-3-(5-((6-hydroxy-2-(2-isopropylphenyl)benzo[b]thiophen-3-yl)oxy)pyridin-2-yl)acrylic acid | 1H NMR (400 MHz, CD3OD) δ ppm = 1.19 (d, J = 7.07 Hz, 6 H), 3.17-3.26 (m, 1 H), 6.69 (d, J = 15.66 Hz, 1 H), 6.90-6.96 (m, 1 H), 7.10-7.18 (m, 1 H), 7.25-7.31 (m, 3 H), 7.31-7.40 (m, 3 H), 7.52-7.61 (m, 2 H), 8.23 (d, J = 3.03 Hz, 1 H) LC/MS (m/z, MH+): 432.4 |

TABLE 10-continued

| Example | Structure | Name | Physical data |
|---|---|---|---|
| 118 | 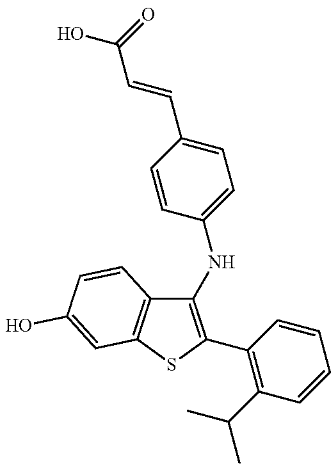 [SMILES: CC(C)c1ccccc1-c1sc2cc(O)ccc2c1Nc1ccc(/C=C/C(=O)O)cc1] | (E)-3-(4-((6-hydroxy-2-(2-isopropylphenyl)benzo[b]thiophen-3-yl)amino)phenyl)acrylic acid | 1H NMR (400 MHz, CD3OD) δ ppm = 7.50 (d, J = 15.8 Hz, 1H), 7.39-7.24 (m, 6H), 7.21 (d, J = 2.2 Hz, 1H), 7.19-7.12 (m, 1H), 6.84 (dd, J = 8.7, 2.3 Hz, 1H), 6.64-6.55 (m, 2H), 6.18 (d, J = 15.9 Hz, 1H), 3.19 (p, J = 6.9 Hz, 1H), 1.06 (d, J = 6.8 Hz, 6H) HRMS (m/z, MH+): 430.1449 |
| 119 | 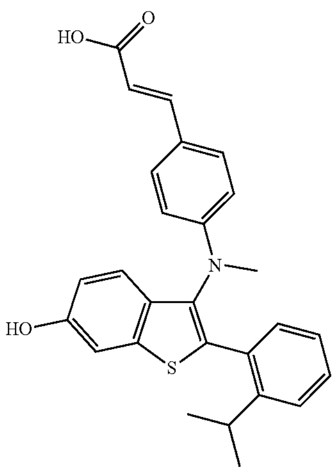 [SMILES: CC(C)c1ccccc1-c1sc2cc(O)ccc2c1N(C)c1ccc(/C=C/C(=O)O)cc1] | (E)-3-(4-((6-hydroxy-2-(2-isopropylphenyl)benzo[b]thiophen-3-yl)(methyl)amino)phenyl)acrylic acid | 1H NMR (400 MHz, CDCl3) δ ppm = 7.68 (d, J = 15.8 Hz, 1H), 7.41-7.32 (m, 4H), 7.28 (d, J = 2.2 Hz, 1H), 7.19 (dd, J = 8.1, 5.7 Hz, 2H), 7.15-7.08 (m, 1H), 6.85 (dd, J = 8.6, 2.4 Hz, 1H), 6.59 (d, J = 8.4 Hz, 2H), 6.20 (d, J = 15.8 Hz, 1H), 3.20-3.12 (m, 1H), 3.11 (s, 3H), 1.11 (d, J = 6.9 Hz, 6H) HRMS (m/z, MH+): 444.1601 |
| 120 | 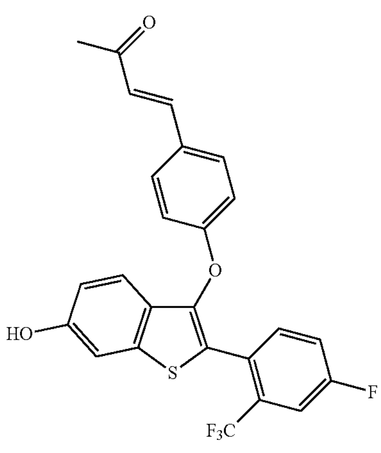 [SMILES: CC(=O)/C=C/c1ccc(Oc2c(-c3ccc(F)cc3C(F)(F)F)sc3cc(O)ccc23)cc1] | (E)-4-(4-((2-(4-fluoro-2-(trifluoromethyl)phenyl)-6-hydroxybenzo[b]thiophen-3-yl)oxy)phenyl)but-3-en-2-one | 1H NMR (400 MHz, CD3OD) δ ppm = 7.59-7.48 (m, 5H), 7.33 (td, J = 8.3, 2.8 Hz, 1H), 7.29-7.19 (m, 2H), 6.86 (d, J = 8.7 Hz, 3H), 6.65 (d, J = 16.3 Hz, 1H), 2.34 (s, 2H) HRMS (m/z, MH+): 473.0822 |

TABLE 10-continued

| Example | Structure | Name | Physical data |
|---|---|---|---|
| 121 | 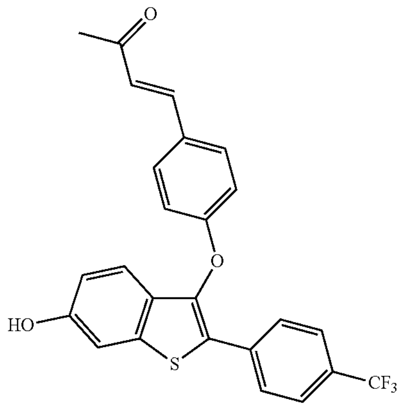 [SMILES: CC(=O)/C=C/c1ccc(Oc2c(-c3ccc(C(F)(F)F)cc3)sc3cc(O)ccc23)cc1] | (E)-4-(4-((6-hydroxy-2-(4-(trifluoromethyl)phenyl)benzo[b]thiophen-3-yl)oxy)phenyl)but-3-en-2-one | 1H NMR (400 MHz, CD3OD) δ ppm = 7.88 (d, J = 8.2 Hz, 2H), 7.68-7.54 (m, 5H), 7.27-7.21 (m, 2H), 6.99 (d, J = 8.7 Hz, 2H), 6.84 (dd, J = 8.7, 1.9 Hz, 1H), 6.67 (d, J = 16.2 Hz, 1H), 2.34 (s, 3H) HRMS (m/z, MH+): 455.0914 |
| 122 | 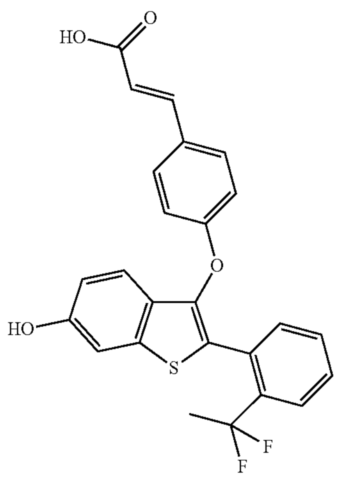 [SMILES: CC(F)(F)c1ccccc1-c1sc2cc(O)ccc2c1Oc1ccc(/C=C/C(=O)O)cc1] | (E)-3-(4-((2-(2-(1,1-difluoroethyl)phenyl)-6-hydroxybenzo[b]thiophen-3-yl)oxy)phenyl)acrylic acid | 1H NMR (400 MHz, (CD3)2SO) δ ppm = 9.94 (s, 1H), 7.63 (d, J = 7.5 Hz, 1H), 7.57 (d, J = 8.7 Hz, 2H), 7.54-7.42 (m, 4H), 7.32 (d, J = 2.1 Hz, 1H), 7.10 (d, J = 8.7 Hz, 1H), 6.88 (d, J = 8.7 Hz, 2H), 6.84 (dd, J = 8.7, 2.2 Hz, 1H), 6.36 (d, J = 16.0 Hz, 1H), 1.94 (t, J = 18.9 Hz, 3H) HRMS (m/z, MH+): 453.0919 |
| 123 | 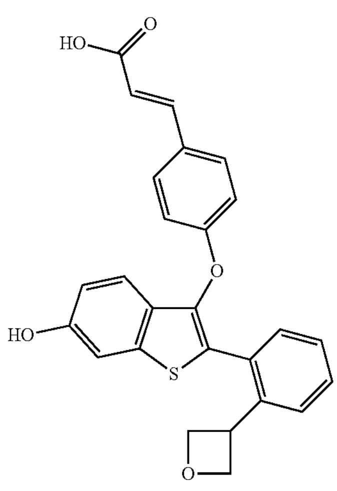 [SMILES: O=C(O)/C=C/c1ccc(Oc2c(-c3ccccc3C3COC3)sc3cc(O)ccc23)cc1] | (E)-3-(4-((6-hydroxy-2-(2-(oxetan-3-yl)phenyl)benzo[b]thiophen-3-yl)oxy)phenyl)acrylic acid | 1H NMR (400 MHz, CD3OD) δ ppm = 7.67 (d, J = 7.9 Hz, 1H), 7.54 (d,J = 15.9 Hz, 1H), 7.46-7.40 (m, 3H), 7.35 (dd, J = 7.7, 1.3 Hz, 1H), 7.29-7.22 (m, 3H), 6.88 (dd, J = 8.7, 2.2 Hz, 1H), 6.80 (d, J = 8.8 Hz, 2H), 6.30 (d, J = 16.0 Hz, 1H), 4.94 (dd, J = 8.0, 5.6 Hz, 2H), 4.72-4.66 (m, 2H), 4.66-4.58 (m, 1H) HRMS (m/z, MH+): 445.1088 |

TABLE 10-continued

| Example | Structure | Name | Physical data |
|---|---|---|---|
| 124 | 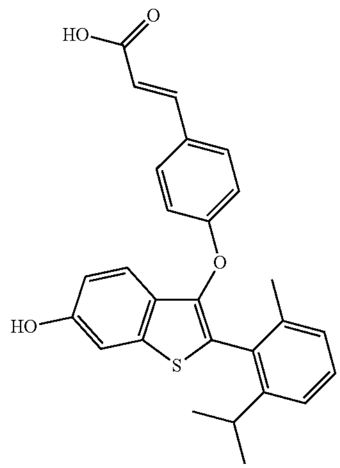 [SMILES: Cc1cccc(C(C)C)c1-c1sc2cc(O)ccc2c1Oc1ccc(/C=C/C(=O)O)cc1] | (E)-3-(4-((6-hydroxy-2-(2-isopropyl-6-methylphenyl)benzo[b]thiophen-3-yl)oxy)phenyl)acrylic acid | 1H NMR (400 MHz, (CD3)2SO) δ ppm = 9.88 (s, 1H), 7.56 (d, J = 8.5 Hz, 2H), 7.47 (d, J = 15.9 Hz, 1H), 7.34 (d, J = 2.1 Hz, 1H), 7.27 (t, J = 7.6 Hz. 1H), 7.22-7.13 (m, 2H), 7.08 (d, J = 7.4 Hz, 1H), 6.90-6.80 (m, 3H), 6.35 (d, J = 15.9 Hz, 1H), 2.95 (p, J = 6.8 Hz, 1H), 2.14 (s, 3H), 1.12 (d, J = 6.8 Hz, 3H), 0.98 (d, J = 6.8 Hz, 3H) HRMS (m/z, MH+): 445.1492 |
| 125 | 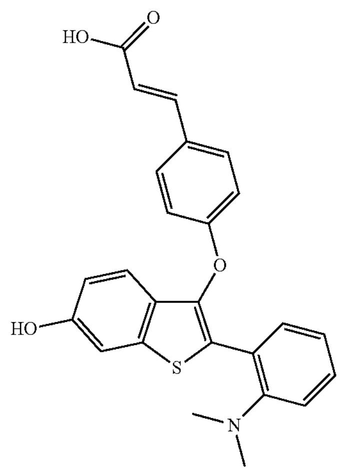 [SMILES: CN(C)c1ccccc1-c1sc2cc(O)ccc2c1Oc1ccc(/C=C/C(=O)O)cc1] | (E)-3-(4-((2-(2-(dimethylamino)phenyl)-6-hydroxybenzo[b]thiophen-3-yl)oxy)phenyl)acrylic acid | 1H NMR (400 MHz, CD3OD) δ ppm = 7.73-7.45 (m, 6H), 7.41-7.26 (m, 3H), 6.94-6.86 (m, 3H), 6.33 (d, J = 15.9 Hz, 1H), 3.10 (s, 6H) HRMS (m/z, MH+): 432.1279 |
| 126 | 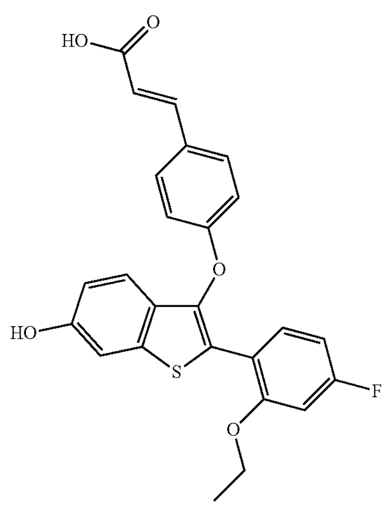 [SMILES: CCOc1cc(F)ccc1-c1sc2cc(O)ccc2c1Oc1ccc(/C=C/C(=O)O)cc1] | (E)-3-(4-((2-(2-ethoxy-4-fluorophenyl)-6-hydroxybenzo[b]thiophen-3-yl)oxy)phenyl)acrylic acid | 1H NMR (400 MHz, (CD3)2SO) δ ppm = 9.85 (s, 1H), 7.64-7.45 (m, 4H), 7.28 (d, J = 2.1 Hz, 1H), 7.14 (d, J = 8.7 Hz, 1H), 6.99 (dd, J = 11.4, 2.5 Hz, 1H), 6.90 (d, J = 8.5 Hz, 2H), 6.86-6.73 (m, 2H), 6.37 (d, J = 15.9 Hz, 1H), 4.09 (q, J = 6.9 Hz, 2H), 1.31 (t, J = 6.9 Hz, 3H) LC7MS (m/z, MH+): 451.0 |

TABLE 10-continued

| Example | Structure | Name | Physical data |
|---|---|---|---|
| 127 | 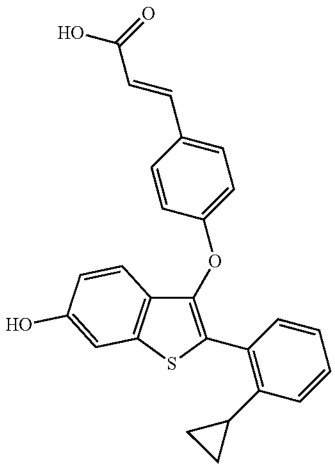 [SMILES: O=C(O)/C=C/c1ccc(Oc2c(-c3ccccc3C3CC3)sc3cc(O)ccc23)cc1] | (E)-3-(4-((2-(2-cyclopropylphenyl)-6-hydroxybenzo[b]thiophen-3-yl)oxy)phenyl)acrylic acid | 1H NMR (400 MHz, CD3OD) δ ppm = 7.50 (d, J = 15.9 Hz, 1H), 7.40 (d, J = 8.5 Hz, 2H), 7.30-7.16 (m, 4H), 7.08 (t, J = 7.5 Hz, 1H), 6.93-6.81 (m, 4H), 6.31 (d, J = 16.0 Hz, 1H), 2.09 (tt, J = 8.4, 5.2 Hz, 1H), 0.92-0.81 (m, 2H), 0.66-0.58 (m, 2H) HRMS (m/z, MH+): 429.1147 |
| 128 | 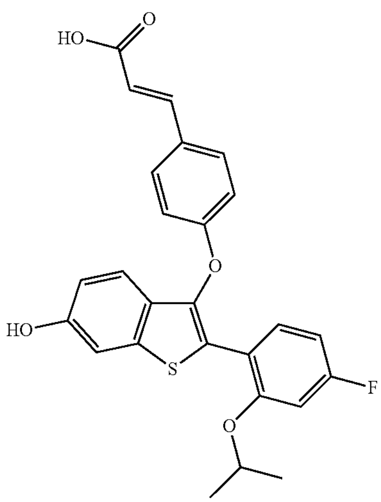 [SMILES: CC(C)Oc1cc(F)ccc1-c1sc2cc(O)ccc2c1Oc1ccc(/C=C/C(=O)O)cc1] | (E)-3-(4-((2-(4-fluoro-2-isopropoxyphenyl)-6-hydroxybenzo[b]thiophen-3-yl)oxy)phenyl)acrylic acid | 1H NMR (400 MHz, CD3OD) δ ppm = 7.58-7.51 (m, 2H), 7.47 (d, J = 8.5 Hz, 2H), 7.23-7.17 (m, 2H), 6.90 (d, J = 8.5 Hz, 2H), 6.82 (d, J = 2.3 Hz, 1H), 6.79 (t, J = 2.7 Hz, 1H), 6.62 (td, J = 8.4, 2.5 Hz, 1H), 6.33 (d, J = 16.0 Hz, 1H), 4.64 (p, J = 6.1 Hz, 1H), 1.33 (d, J = 6.1 Hz, 6H) HRMS (m/z, MH+): 465.1131 |
| 129 | 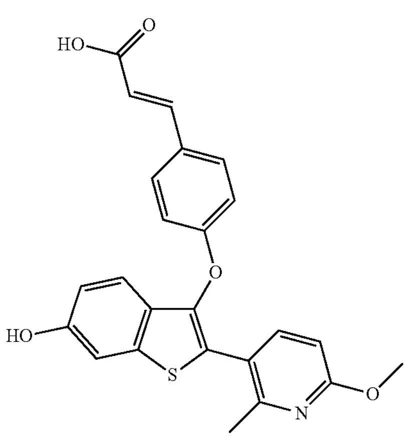 [SMILES: COc1ccc(-c2sc3cc(O)ccc3c2Oc2ccc(/C=C/C(=O)O)cc2)c(C)n1] | (E)-3-(4-((6-hydroxy-2-(6-methoxy-2-methylpyridin-3-yl)benzo[b]thiophen-3-yl)oxy)phenyl)acrylic acid | 1H NMR (400 MHz, CD3OD) δ ppm = 2.38 (s, 3 H), 3.80-3.85 (m, 3 H), 6.22 (d, J = 15.66 Hz, 1 H), 6.60 (d, J = 8.59 Hz, 1 H), 6.74-6.81 (m, 3H), 7.15 (d, J = 2.02 Hz, 1 H), 7.18 (d, J = 9.09 Hz, 1 H), 7.34-7.39 (m, 2 H), 7.47 (d, J = 16.17 Hz, 1 H), 7.59 (d, J = 8.59 Hz, 1 H) LC/MS (m/z, MH+): 434.4 |

TABLE 10-continued

| Example | Structure | Name | Physical data |
|---|---|---|---|
| 130 | 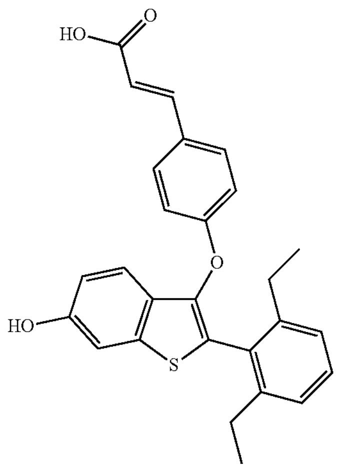 [SMILES: CCc1cccc(CC)c1-c1sc2cc(O)ccc2c1Oc1ccc(/C=C/C(=O)O)cc1] | (E)-3-(4-((2-(2,6-diethylphenyl)-6-hydroxybenzo[b]thiophen-3-yl)oxy)phenyl)acrylic acid | 1H NMR (400 MHz, (CD3)2SO) δ ppm = 7.56 (d, J = 8.3 Hz, 2H), 7.46 (d, J = 15.9 Hz, 1H), 7.33 (d, J = 2.0 Hz, 1H), 7.29 (t, J = 7.7 Hz, 1H), 7.13 (d, J = 8.0 Hz, 3H), 6.90-6.80 (m, 3H), 6.35 (d, J = 16.0 Hz, 1H), 2.57-2.39 (m, 4H), 1.06 (t, J = 7.5 Hz, 6H) HRMS (m/z, MH+): 445.1448 |
| 131 | 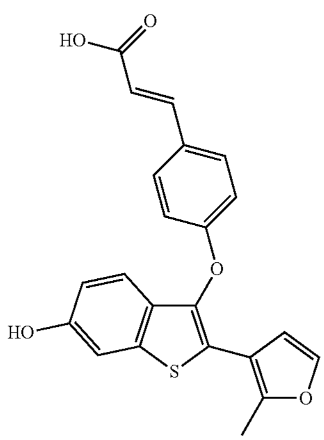 [SMILES: Cc1occc1-c1sc2cc(O)ccc2c1Oc1ccc(/C=C/C(=O)O)cc1] | (E)-3-(4-((6-hydroxy-2-(2-methylfuran-3-yl)benzo[b]thiophen-3-yl)oxy)phenyl)acrylic acid | 1H NMR (400 MHz, CD3OD) δ ppm = 7.58 (d, J = 16.0 Hz, 1H), 7.51 (d, J = 8.6 Hz, 2H), 7.31 (d, J = 1.9 Hz, 1H), 7.19 (d, J = 8.7 Hz, 2H), 6.90 (d, J = 8.5 Hz, 2H), 6.82 (dd, J = 8.6, 2.2 Hz, 1H), 6.54 (d, J = 1.9 Hz, 1H), 6.35 (d, J = 15.9 Hz, 1H), 2.46 (s, 3H) HRMS (m/z, MH+): 393.0780 |
| 132 | 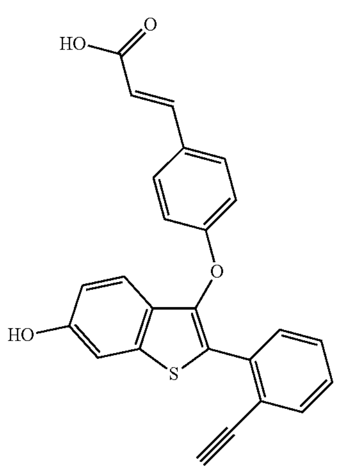 [SMILES: C#Cc1ccccc1-c1sc2cc(O)ccc2c1Oc1ccc(/C=C/C(=O)O)cc1] | (E)-3-(4-((2-(2-ethynylphenyl)-6-hydroxybenzo[b]thiophen-3-yl)oxy)phenyl)acrylic acid | 1H NMR (400 MHz, CD3OD) δ ppm = 3.50 (s, 1 H), 6.36 (d, J = 16.17 Hz, 1 H), 6.70-6.88 (m, 1 H), 6.96 (d, J = 9.09 Hz, 2 H), 7.09-7.27 (m, 2 H), 7.27-7.40 (m, 2 H), 7.53 (d, J = 8.59 Hz, 2 H), 7.59 (d, J = 16.17 Hz, 1 H), 7.68 (d, J = 7.07 Hz, 1 H), 7.77 (s, 1 H) LC/MS (m/z, MH+): 413.4 |

TABLE 10-continued

| Example | Structure | Name | Physical data |
|---|---|---|---|
| 133 | 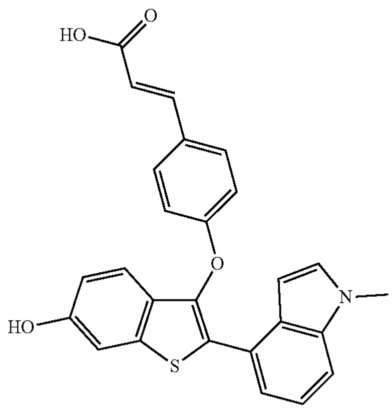 [SMILES: Cn1ccc2c(-c3sc4cc(O)ccc4c3Oc3ccc(/C=C/C(=O)O)cc3)cccc21] | (E)-3-(4-((6-hydroxy-2-(1-methyl-1H-indol-4-yl)benzo[b]thiophen-3-yl)oxy)phenyl)acrylic acid | 1H NMR (400 MHz, CD3OD) δ ppm = 7.45 (d, J = 15.9 Hz, 1H), 7.32-7.20 (m, 6H), 7.14-7.06 (m, 2H), 6.86 (dd, J = 8.6, 2.0 Hz, 1H), 6.81-6.74 (m, 3H), 6.20 (d, J = 15.9 Hz, 1H), 3.74 (s, 3H) HRMS (m/z, MH+): 442.1070 |
| 134 | 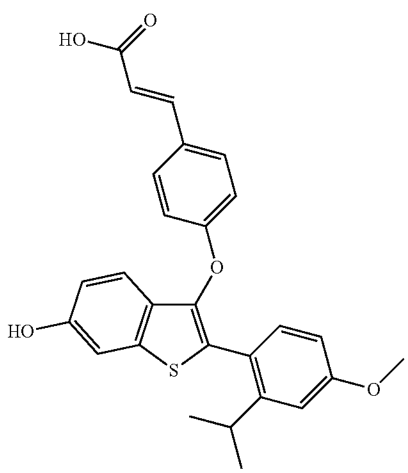 [SMILES: COc1ccc(-c2sc3cc(O)ccc3c2Oc2ccc(/C=C/C(=O)O)cc2)c(C(C)C)c1] | (E)-3-(4-((6-hydroxy-2-(2-isopropyl-4-methoxyphenyl)benzo[b]thiophen-3-yl)oxy)phenyl)acrylic acid | 1H NMR (400 MHz, CD3OD) δ ppm = 7.56 (d, J = 16.0 Hz, 1H), 7.48-7.41 (m, 2H), 7.25-7.20 (m, 2H), 7.18 (d, J = 8.5 Hz, 1H), 6.88-6.80 (m, 4H), 6.70 (dd, J = 8.5, 2.6 Hz, 1H), 6.31 (d, J = 16.0 Hz, 1H), 3.77 (s, 3H), 3.19 (p, J = 6.8 Hz, 1H), 1.15 (d, J = 6.8 Hz, 6H) HRMS (m/z, MH+): 461.1412 |
| 135 | 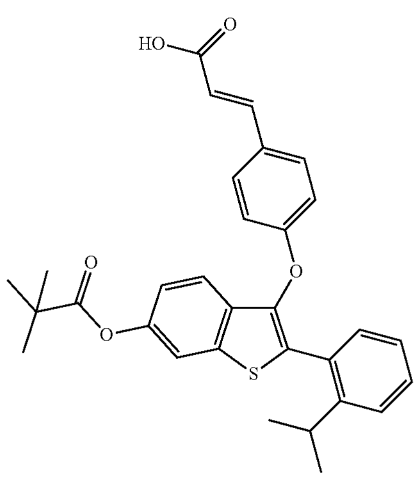 [SMILES: CC(C)c1ccccc1-c1sc2cc(OC(=O)C(C)(C)C)ccc2c1Oc1ccc(/C=C/C(=O)O)cc1] | (E)-3-(4-((2-(2-isopropylphenyl)-6-(pivaloyloxy)benzo[b]thiophen-3-yl)oxy)phenyl)acrylic acid | 1H NMR (400 MHz, CD3OD) δ ppm = 7.66 (d, J = 2.0 Hz, 1H), 7.57 (d, J = 15.9 Hz, 1H), 7.46 (dd, J = 8.7, 2.8 Hz, 3H), 7.40-7.26 (m, 3H), 7.15 (td, J = 7.3, 1.6 Hz, 1H), 7.08 (dd, J = 8.7, 2.1 Hz, 1H), 6.86 (d, J = 8 8 Hz, 2H), 6.32 (d, J = 15.9 Hz, 1H), 3.20 (p, J = 6.9 Hz, 1H), 1.39 (s, 9H), 1.18 (d, J = 6.8 Hz, 6H) HRMS (m/z, MH+): 515.1861 |

TABLE 10-continued

| Example | Structure | Name | Physical data |
|---|---|---|---|
| 136 | 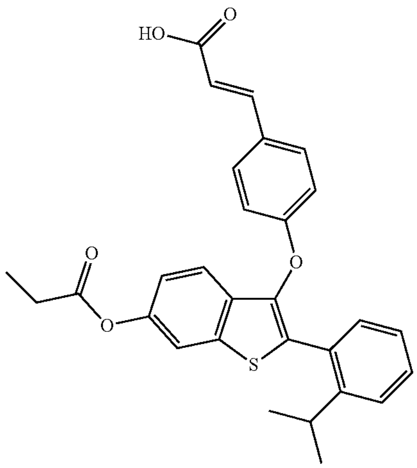 [SMILES: CCC(=O)Oc1ccc2c(Oc3ccc(/C=C/C(=O)O)cc3)c(-c3ccccc3C(C)C)sc2c1] | (E)-3-(4-((2-(2-isopropylphenyl)-6-(propionyloxy)benzo[b]thiophen-3-yl)oxy)phenyl)acrylic acid | 1H NMR (400 MHz, CDCl3) δ ppm = 7.66 (d, J = 15.9 Hz, 1H), 7.58 (d, J = 2.0 Hz, 1H), 7.43 (d, J = 8.7 Hz, 1H), 7.37 (d, J = 8.8 Hz, 2H), 7.33 (d, J = 4.0 Hz, 2H), 7.28 (d, J = 7.6 Hz, 1H), 7.18-7.10 (m, 1H), 7.05 (dd, J = 8.7, 2.1 Hz, 1H), 6.86 (d, J = 8.8 Hz, 2H), 6.27 (d, J = 15.9 Hz, 1H), 3.19 (p, J = 6.9 Hz, 1H), 2.64 (q, J = 7.5 Hz, 2H), 1.30 (t, J = 7.5 Hz, 3H), 1.16 (d, J = 6.9 Hz, 6H) HRMS (m/z, MH+): 487.1568 |
| 137 | 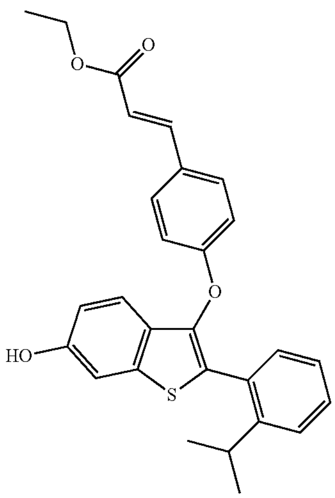 [SMILES: CCOC(=O)/C=C/c1ccc(Oc2c(-c3ccccc3C(C)C)sc3cc(O)ccc23)cc1] | (E)-ethyl 3-(4-((6-hydroxy-2-(2-isopropylphenyl)benzo[b]thiophen-3-yl)oxy)phenyl)acrylate | 1H NMR (400 MHz, CD3OD) δ ppm = 7.57 (d, J = 16.0 Hz, 1H), 7.45 (d, J = 8.7 Hz, 2H), 7.37-7.21 (m, 5H), 7.11 (td, J = 7.7, 1.6 Hz, 1H), 6.90-6.81 (m, 3H), 6.35 (d, J = 16.1 Hz, 1H), 4.21 (q, J = 7.1 Hz, 2H), 3.23 (p, J = 6.9 Hz, 1H), 1.29 (t, J = 7.1 Hz, 3H), 1.16 (d, J = 6.9 Hz, 6H) HRMS (m/z, MH+): 459.1614 |
| 138 | 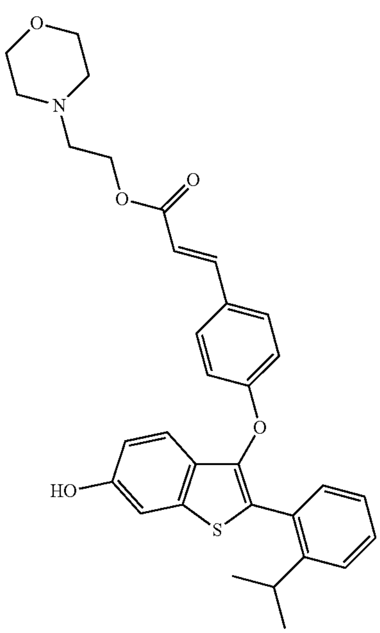 [SMILES: CC(C)c1ccccc1-c1sc2cc(O)ccc2c1Oc1ccc(/C=C/C(=O)OCCN2CCOCC2)cc1] | (E)-2-morpholinoethyl 3-(4-((6-hydroxy-2-(2-isopropylphenyl)benzo[b]thiophen-3-yl)oxy)phenyl)acrylate | 1H NMR (400 MHz, CD3OD) δ ppm = 7.60 (d, J = 16.0 Hz, 1H), 7.46 (d, J = 8.6 Hz, 2H), 7.38-7.21 (m, 5H), 7.11 (td, J = 7.6, 1.5 Hz, 1H), 6.89-6.81 (m, 3H), 6.38 (d, J = 16.1 Hz, 1H), 4.32 (t, J = 5.7 Hz, 2H), 3.73-3.67 (m, 4H), 3.23 (p, J = 6.9 Hz, 1H), 2.73 (t, J = 5.7 Hz, 2H), 2.62-2.54 (m, 4H), 1.16 (d, J = 6.8 Hz, 6H) HRMS (m/z, MH+): 544.2149 |

Example 139

(E)-3-(4-((2-(2-(1,1-difluoroethyl)-4-fluorophenyl)-6-hydroxybenzo[b]thiophen-3-yl)oxy)phenyl)acrylic acid

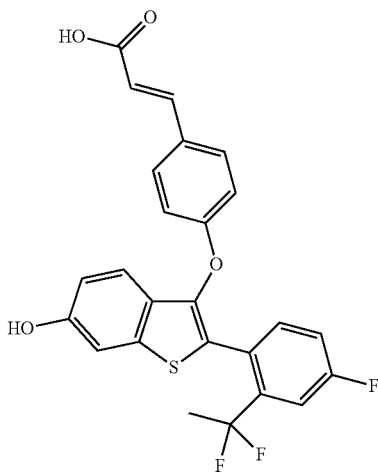 [SMILES: CC(F)(F)c1cc(F)ccc1-c1sc2cc(O)ccc2c1Oc1ccc(/C=C/C(=O)O)cc1]

Step 1: 2-bromo-3-(4-bromophenoxy)-6-methoxybenzo[b]thiophene 1,1-dioxide (compound 26). To a solution of 2,3-dibromo-6-methoxybenzo[b]thiophene 1,1-dioxide (2.50 g, 7.06 mmol) in THF (100 mL) at room temperature was added 4-bromophenol (1.344 g, 7.77 mmol) and $Cs_2CO_3$ (6.90 g, 21.19 mmol). The reaction mixture turned green after ~1 min of stirring. The mixture was stirred at room temperature for 18 h after which time the reaction was quenched with water and diluted with DCM. The organic layer was collected (phase separator) and concentrated to provide 2-bromo-3-(4-bromophenoxy)-6-methoxybenzo[b]thiophene 1,1-dioxide (3.10 g, 6.95 mmol, 98% yield) as a white solid which was used without further purification. $^1$H NMR (400 MHz, $CDCl_3$) δ ppm=3.83 (s, 3H), 6.92-7.03 (m, 3H), 7.25-7.35 (m, 2H), 7.39-7.50 (m, 2H).

Step 2: 3-(4-bromophenoxy)-6-methoxybenzo[b]thiophene 1,1-dioxide (compound 27). To a solution of 2-bromo-3-(4-bromophenoxy)-6-methoxy-benzo[b]thiophene 1,1-dioxide (3.10 g, 6.95 mmol) in MeOH (10 mL) and DMSO (30 mL) was added $NaBH_4$ (0.789 g, 20.85 mmol). The mixture was stirred at room temperature for 3 h after which time the reaction was quenched with water and diluted with DCM. The organic layer was collected (phase separator) and concentrated to provide 3-(4-bromophenoxy)-6-methoxybenzo[b]thiophene 1,1-dioxide (2.47 g, 6.73 mmol, 97% yield) as an off white solid which was used without further purification. $^1$H NMR (400 MHz, $CDCl_3$) δ ppm=3.85 (s, 3H), 5.38 (s, 1H), 7.02-7.08 (m, 3H), 7.22 (d, J=2.53 Hz, 1H), 7.47-7.60 (m, 3H).

Step 3: 3-(4-bromophenoxy)-6-methoxybenzo[b]thiophene (compound 28). To a solution of 3-(4-bromophenoxy)-6-methoxybenzo[b]thiophene 1,1-dioxide (2.47 g, 6.73 mmol) in THF (90 mL) was added DIBAL-H (1.0 M in DCM, 33.6 mL, 33.6 mmol) in one portion. The mixture was heated to 75° C. for 2 h after which time the reaction was cooled to room temperature and quenched with EtOAc (32.9 mL, 336 mmol). The resulting solution was stirred for 10 min before carefully adding 75 mL of water and potassium sodium tartrate (33.100 g, 117 mmol). The mixture was vigorously stirred for 10 min and diluted with 75 mL EtOAc. The organic layer was collected, dried with anhydrous $MgSO_4$ and concentrated in vacuo to afford 3-(4-bromophenoxy)-6-methoxybenzo[b]thiophene (1.9 g, 5.67 mmol, 84% yield) as a white solid which was used without further purification. $^1$H NMR (400 MHz, $CDCl_3$) δ ppm=3.81 (s, 3H), 6.46 (s, 1H), 6.90 (d, J=9.09 Hz, 3H), 7.16-7.22 (m, 1H), 7.31-7.40 (m, 2H), 7.46 (d, J=9.09 Hz, 1H). LC/MS (m/z, $MH^+$): 336.8.

Step 4: (E)-methyl 3-(4-((6-methoxybenzo[b]thiophen-3-yl)oxy)phenyl)acrylate (compound 29). To a microwave vial, 3-(4-bromophenoxy)-6-methoxybenzo[b]thiophene (500 mg, 1.49 mmol), methyl acrylate (770 mg, 8.95 mmol), and $Pd(PPh_3)_2Cl_2$ (157 mg, 0.22 mmol) were suspended in DMF (12 mL) and triethylamine (1.039 mL, 7.46 mmol). The reaction was heated for 60 min at 120° C. under microwave irradiation. The reaction mixture was diluted with DCM and water. The organic layer was collected (phase separator) and concentrated to obtain the crude product. The crude material was purified by column chromatography ($SiO_2$, 1-20% EtOAc/Heptane) to afford (E)-methyl 3-(4-((6-methoxybenzo[b]thiophen-3-yl)oxy)phenyl)acrylate (311 mg, 0.91 mmol, 61% yield) as a white solid. $^1$H NMR (400 MHz, $CDCl_3$) δ ppm=1.46 (s, 3H), 3.73 (s, 3H), 6.28 (d, J=16.17 Hz, 1H), 6.59 (s, 1H), 6.90 (dd, J=8.59, 2.02 Hz, 1H), 7.00 (d, J=8.59 Hz, 2H), 7.21 (d, J=2.02 Hz, 1H), 7.37-7.48 (m, 3H), 7.59 (d, J=16.17 Hz, 1H). LC/MS (m/z, $MH^+$): 341.1.

Step 5: (E)-methyl 3-(4-((2-bromo-6-methoxybenzo[b]thiophen-3-yl)oxy)phenyl)acrylate (compound 134). To a solution (E)-methyl 3-(4-((6-methoxybenzo[b]thiophen-3-yl)oxy)phenyl)acrylate (2.1 g, 6.17 mmol) in THF 201 mL) at room temperature was added N-bromosuccinimide (1.208 g, 6.79 mmol). The resulting solution was stirred vigorously at room temperature for 2 h after which time the reaction was quenched by addition of sat. aq. Sodium Thiosulfate solution and extracted with EtOAc (3×). The combined organic layers were dried over anhydrous $MgSO_4$, filtered and concentrated in vacuo. The resulting crude material was purified by column chromatography ($SiO_2$, 0-40% EtOAc/Heptane) to afford (E)-methyl 3-(4-((2-bromo-6-methoxybenzo[b]thiophen-3-yl)oxy)phenyl)acrylate (2.4 g, 5.72 mmol, 93% yield). $^1$H NMR (400 MHz, $CDCl_3$) δ ppm 7.65 (d, J=16.0 Hz, 1H), 7.46 (d, J=8.7 Hz, 2H), 7.32 (d, J=8.9 Hz, 1H), 7.20 (d, J=2.2 Hz, 1H), 6.95 (d, J=8.7 Hz, 2H), 6.91 (dd, J=8.8, 2.2 Hz, 1H), 6.31 (s, 1H), 3.86 (s, 3H), 3.79 (s, 3H). LC/MS (m/z, $MH^+$): 420.9.

Step 6: (E)-methyl 3-(4-((2-bromo-6-hydroxybenzo[b]thiophen-3-yl)oxy)phenyl)acrylate & (E)-3-(4-((2-bromo-6-hydroxybenzo[b]thiophen-3-yl)oxy)phenyl)acrylic acid (compound 135 & 136). To a solution of (E)-methyl 3-(4-((2-bromo-6-methoxybenzo[b]thiophen-3-yl)oxy)phenyl) acrylate (2.4 g, 5.72 mmol) in DCM (20 mL) at room temperature was added $BBr_3$ (1.0 M in Heptane, 17.17 mL, 17.17 mmol) dropwise. The resulting mixture was stirred at room temperature for 2 h after which time an aqueous buffer (pH 7.4, made from citric acid and dibasic sodium phophate, 10 mL), cooled to 0° C., was slowly added into the reaction. The resulting mixture was then diluted with DCM (30 mL) and stirred at room temperature for 1 h. The phases were then separated and the organic phase was dried over anhydrous $Na_2SO_4$, filtered and concentrated in vacuo. The crude material was purified by column chromatography ($SiO_2$, 0-100% EtOAc/Heptane) to afford (E)-methyl 3-(4-((2-bromo-6-hydroxybenzo[b]thiophen-3-yl)oxy)phenyl)acrylate (1.6 g, 3.95 mmol, 69% yield) as a pale yellow solid and (E)-3-(4-((2-bromo-6-hydroxybenzo[b]thiophen-3-yl)oxy) phenyl)acrylic acid (370 mg, 0.946 mmol, 17% yield) as a yellow solid.

(E)-methyl 3-(4-((2-bromo-6-hydroxybenzo[b]thiophen-3-yl)oxy)phenyl)acrylate: $^1$H NMR (400 MHz, CD$_3$OD) δ ppm 3.76 (s, 3H), 6.43 (d, J=16.17 Hz, 1H), 6.82 (dd, J=8.84, 2.27 Hz, 1H), 6.90-6.97 (m, 2H), 7.17 (d, J=2.02 Hz, 1H), 7.22 (d, J=8.59 Hz, 1H), 7.53-7.62 (m, 2H), 7.65 (d, J=15.66 Hz, 1H). LC/MS (m/z, MH$^+$): 406.8.

(E)-3-(4-((2-bromo-6-hydroxybenzo[b]thiophen-3-yl) oxy)phenyl)acrylic acid: $^1$H NMR (400 MHz, CD$_3$OD) δ ppm 6.38 (d, J=16.17 Hz, 1H), 6.82 (dd, J=8.59, 2.02 Hz, 1H), 6.89-6.97 (m, 2H), 7.17 (d, J=2.02 Hz, 1H), 7.23 (d, J=8.59 Hz, 1H), 7.53-7.60 (m, 2H), 7.63 (d, J=15.66 Hz, 1H). LC/MS (m/z, MH$^+$): 392.8.

Step 7: 1-bromo-2-(1,1-difluoroethyl)-4-fluorobenzene (compound 149). To a solution of DeoxoFluor® (8.49 ml, 46.1 mmol) and MeOH (2 drops) was added 1-(2-bromo-5-fluorophenyl)ethanone (5.0 g, 23.04 mmol). The resulting mixture was warmed to 70° C. for 18 h after which time the reaction was quenched by slow addition to 50 mL of ice-cold water and diluted with diethyl ether. The organic layer was collected and washed with sat. aq. NaHCO$_3$ solution (2×), citric acid, and brine. The combine organic layers were concentrated and in vacuo and purified by column chromatography (SiO$_2$, 0-20% EtOAc/Heptane) to afford 1-bromo-2-(1,1-difluoroethyl)-4-fluorobenzene (3.83 g, 16.02 mmol, 69.6% yield) as a colorless oil. $^1$H NMR (400 MHz, CD$_3$OD) δ ppm 1.98-2.11 (m, 3H), 7.15 (td, J=8.21, 3.28 Hz, 1H), 7.39 (dd, J=9.60, 3.03 Hz, 1H), 7.71 (dd, J=8.59, 5.05 Hz, 1H). $^{19}$F NMR (376 MHz, CD$_3$OD) δ ppm −115.63 (s, 1F), −88.94 (s, 2F).

Step 8: 2-(2-(1,1-difluoroethyl)-4-fluorophenyl)-4,4,5,5-tetramethyl-1,3,2-dioxaborolane (compound 150). To a solution of 1-bromo-2-(1,1-difluoroethyl)-4-fluorobenzene (3.83 g, 16.02 mmol) in 1,4-dioxane (15 mL) was added bis(pinacolato)diboron (5.29 g, 20.83 mmol), potassium acetate (3.15 g, 32.0 mmol) and PdCl$_2$(PPh$_3$)$_2$ (1.125 g, 1.602 mmol). The resulting mixture was heated to 80° C. and stirred under nitrogen atmosphere for 18 h after which time the mixture was cooled to room temperature and concentrated onto silica gel. The crude material was then purified by column chromatography (SiO$_2$, 0-15% EtOAc/ Heptane) to afford 2-(2-(1,1-difluoroethyl)-4-fluorophenyl)-4,4,5,5-tetramethyl-1,3,2-dioxaborolane (2.90 g, 10.14 mmol, 63% yield) as a colorless oil. $^1$H NMR (400 MHz, CD$_3$OD) δ ppm 1.37 (s, 12H), 2.01 (t, J=18.44 Hz, 3H), 7.18 (td, J=8.34, 2.53 Hz, 1H), 7.25 (dd, J=10.11, 2.53 Hz, 1H), 7.62 (dd, J=8.08, 6.57 Hz, 1H).

Step 9: (E)-methyl 3-(4-((2-(2-(1,1-difluoroethyl)-4-fluorophenyl)-6-hydroxybenzo[b]thiophen-3-yl)oxy)phenyl) acrylate (compound 151). To a solution of (E)-methyl 3-(4-((2-bromo-6-hydroxybenzo[b]thiophen-3-yl)oxy)phenyl) acrylate (1.6 g, 3.95 mmol) in toluene (20 mL) and water (2 mL) was added 2-(2-(1,1-difluoroethyl)-4-fluorophenyl)-4, 4,5,5-tetramethyl-1,3,2-dioxaborolane (2.259 g, 7.90 mmol), K$_2$CO$_3$ (2.73 g, 19.74 mmol), and Pd(PPh$_3$)$_4$ (0.456 g, 0.395 mmol). The resulting mixture was heated to 90° C. for 18 h after which time the reaction was cooled to room temp and filtered to remove solids. The filtrate was acidified with HCl (1N aq.) and extracted with DCM, the combined organic layers were dried over anhydrous Na2SO4, filtered and concentrated in vacuo. The resulting crude material was purified by column chromatography (SiO$_2$, 0-60% EtOAc/ Heptane) to afford (E)-methyl 3-(4-((2-(2-(1,1-difluoroethyl)-4-fluorophenyl)-6-hydroxybenzo[b]thiophen-3-yl) oxy)phenyl)acrylate (1.4 g, 2.89 mmol, 73.2% yield) as a pale orange solid. The product was dissolved in DCM and treated with Pd scavenger for 2 h at room temp then filtered and collected the filtrate and concentrated in vacuo to afford the final product. $^1$H NMR (400 MHz, CD$_3$OD) δ ppm 1.89 (t, J=18.69 Hz, 3H), 3.75 (s, 3H), 6.37 (d, J=16.17 Hz, 1H), 6.80-6.89 (m, 3H), 7.11 (td, J=8.21, 2.78 Hz, 1H), 7.17-7.25 (m, 2H), 7.31-7.42 (m, 2H), 7.44-7.51 (m, 2H), 7.59 (d, J=16.17 Hz, 1H).

Step 10: (E)-3-(4-((2-(2-(1,1-difluoroethyl)-4-fluorophenyl)-6-hydroxybenzo[b]thiophen-3-yl)oxy)phenyl)acrylic acid (example 140). To a solution of (E)-methyl 3-(4-((2-(2-(1,1-difluoroethyl)-4-fluorophenyl)-6-hydroxybenzo[b] thiophen-3-yl)oxy)phenyl)acrylate (1.4 g, 2.89) in THF (5 mL) and water (3 mL) was added 56% LiOH monohydrate (371 mg, 8.67 mmol). The resulting mixture was stirred at room temperature for 18 h after which time the reaction was concentrated in vacuo to remove THF and the resulting solution was diluted with water and acidified by addition of HCl (1N aq.), causing a precipitate to crash out. The resulting precipitate was filtered to give (E)-3-(4-((2-(2-(1, 1-difluoroethyl)-4-fluorophenyl)-6-hydroxybenzo[b]thiophen-3-yl)oxy)phenyl)acrylic acid as a white solid which was not purified further (980 mg, 2.021 mmol, 69.9% yield). $^1$H NMR (400 MHz, CD$_3$OD) δ ppm=1.80 (t, J=18.44 Hz, 3H), 6.23 (d, J=16.17 Hz, 1H), 6.71-6.81 (m, 3H), 7.03 (td, J=8.21, 2.78 Hz, 1H), 7.08-7.14 (m, 2H), 7.22-7.32 (m, 2H), 7.37 (d, J=8.59 Hz, 2H), 7.47 (d, J=16.17 Hz, 1H). LC/MS (m/z, M−H): 468.9.

Assays

Compounds of the invention were assessed for their ability to be both potent estrogen receptor antagonists and to degrade estrogen receptors. The antagonist and degrading properties of the compounds of the invention described herein can be evidenced by testing in the ER transcription and ERα, degradation assays, respectively.

ER Transcription Assay (MCF7 Cells)

The ER transcription assay is a reporter assay that is based on the ability of ER to induce transcription from a luciferase reporter gene containing estrogen response elements (EREs) in the promoter/enhancer region. When the reporter gene is transfected in MCF7 cells (containing endogenous ER), transcription is reflected by the level of luciferase expression.

MCF7 cells are maintained in DMEM/F12 (Gibco, catalog number 11330) supplemented with 10% fetal bovine serum (FBS) (Gemini Bio-Products, catalog number 100-106). A day before transfection, cells are split into a T75 flask at a cell density of 300,000 cells/mL (10 mL total) and allowed to attach overnight in a humidified CO$_2$ incubator at 37° C.

Next day, prior to transfection, media is switched to DMEM/F12 (Gibco, catalog number 21041) supplemented with 10% charcoal-stripped serum (Gemini Bio-Products, catalog number 100-119). MCF7 cells are then bulk transfected, using Lipofectin (Invitrogen, catalog number 18292) with the following plasmids: 7×-TK-ERE-Luc3 (ER reporter gene) and pCMV-*Renilla* (normalization control). Briefly, for each T75 flask, 32.5 µL of Lipofectin is added to 617.5 µL of OptiMEM (Gibco #11058) and incubated for 30 min at 37 C. Approximately 20 ug DNA is mixed in OptiMEM (Invitrogen) to a total volume of 650 µL. Following incubation, the OptiMEM-DNA mixture is added to the OptiMEM-Lipofectin mix and incubated for 15 minutes at 37° C. The DNA-Lipofectin mixture is then added directly to the T75 flask and the flask is returned to the incubator.

After overnight incubation, compound is added to individual wells of a 96-well plate in a 10 μL volume of media at 10× concentration along with 17β estradiol whose final concentration is 0.1 nM. Normally, DMSO (used as a vehicle) is included to achieve a final concentration of 0.1% when added to the cells. Transfected cells are trypsinized, resuspended in DMEM/F12/10% charcoal-stripped serum and added to the 96-well plate at 25,000 cells/well in 90 μL of media. The plate is then returned to the incubator for 24 hours.

After incubation with compounds for 24 hours, Firefly and *Renilla luciferase* activities are measured to determine ER transcriptional activity. Media is removed from 96-well plates by decanting and blotting on paper towels. Cells are lysed with 40 μl/well of 1× passive lysis buffer (25 mM Tris Phospate, 2 mM CDTA, 10% Glycerol, 0.5% Triton X-100 and 2 mM DTT before use) and allowed incubate at room temperature for 10 minutes.

Firefly luciferase activity is measured by adding 30 ul Firefly luciferase assay buffer (20 mM Tricine, 0.1 mM EDTA, 1.07 mM $(MgCO_3)_4Mg(OH)_2.5H_2O$, 2.67 mM $MgSO_4$, 33.3 mM DTT, 270 μM Coenzyme A, 470 μM luciferin, 530 μM ATP, reconstituted) per well, followed by measuring light units using a luminometer (BMG labtech FLUOstar OPTIMA). One second total read time after a one second delay.

*Renilla luciferase* activity is measured by adding 50 ul *Renilla luciferase* assay buffer (1.1M NaCl, 2.2 mM $Na_2EDTA$, 0.22 M $KxPO_4$ (pH 5.1), 0.44 mg/mL BSA, 1.3 mM $NaN_3$, 1.43 uM coelenterazine, final pH adjusted to 5.0), per well, followed by measuring light units using a luminometer. One second total read time after one second delay. If Firefly luciferase signal is high, *Renilla* assay must be done an hour after the Firefly assay due to incomplete squelching of Firefly signal.

ERα Degradation (MCF7 Cells)

Plate MCF7 cells at 0.3 million cells/mL (100 μl/well) in black, clear-bottom 96-well plates (Greiner, catalog number 655090) in DMEM/F12 media (Gibco, catalog number 11330) supplemented with 10% charcoal-stripped serum (Gemini Bio-Products, catalog number 100-119), and incubate them at 37° C., 5% $CO_2$ for 24-36 hours. Next day, make 10× solution of ligands in DMSO and add the solution to the cells to achieve a final concentration of 10 uM. A DMSO control is required for relative calculations, and fulvestrant is used as a positive control for ER degradation. The cells are subjected to the in-cell Western assay after incubating cells with ligand for 18-24 hours.

Media is removed from the plates by decanting, and cells are immediately fixed with 100 μl of 3.7% formaldehyde in PBS using a multi-channel pipettor. Add formaldehyde to the sides of the wells to avoid cell disruption. Plates are incubated at room temperature for 20 minutes without shaking. The fix solution is then removed and cells are permeabilized with 100 μL/well of 0.1% Triton X-100 in PBS. The lysate is then blocked by adding 50 uL/well of blocking solution (3% goat serum, 1% BSA, 0.1% cold fish skin gelatin and 0.1% Triton X-100 in PBS, pH 7.4) and allowed to shake at room temperature for 2 hr, or alternatively, at 4° C. overnight.

After blocking, 40 μL/well of the primary antibody against ERα (HC-20) (Santa cruz, catalog number 543) diluted at 1:3000 in blocking buffer diluted 1:3 with PBS is added to each well, except the negative control wells (which are used for background subtraction) and the plate is sealed and incubated overnight at 4° C. Next day, the primary antibody solution is removed and the wells are washed three times with 0.1% TWEEN in PBS, with each wash lasting 5 minutes. 40 μL/well of secondary antibody (Biotium CF770 goat anti-rabbit 1:2000, catalog number 20078) and DRAQ5 (DNA stain, 5 mM, Thermo Scientific, catalog number 62251) diluted at 1:10000 in blocking buffer diluted 1:3 with PBS is then added to all the well, including the negative control wells, and the plate is allowed to incubate on shaker at room temperature for 2 hr. The secondary antibody solution is then removed and the plates are washed three times as described above. The plate is then washed one final time with PBS alone to minimize auto-fluorescence. The plate is then cleaned and read on LiCor Odyssey imager.

For % response calculations, first divide integrated intensities for 700 channel (ER) by integrated intensities for 800 channel (DNA normalization); 700 (ER)/800 (DNA). This will be referred to as the normalized value. Then subtract average of negative control wells (no primary antibody) from all normalized values. This corresponds to negative subtraction. % response=$(Value_{unknown}/Value_{DMSO\ control})*100$.

The data describing the antagonist and degradation properties for the examples is compiled in table 11. The column titled MCF7 $IC_{50}$ reports the inflection point of the inhibition of transcription in MCF7 cells as described above. Percentage ERα remaining reports the remaining ERα protein measured at 10 μM concentration of the ligand as described above. The column ERα $IC_{50}$ reports the inflection point of the degradation in response to the ligand concentration. For example, (E)-3-(4-((6-hydroxy-2-(4-hydroxyphenyl)benzo[b]thiophen-3-yl)oxy)phenyl)acrylic acid (example 2), inhibits 50% of the ERα induced transcriptions in MCF7 cells at a concentration of 0.74804 and degrades the ERα receptor, at a 10 μM concentration, by 59%. Half of the observed receptor degradation occurs at a concentration of 0.026 μM.

TABLE 11

| Ex. | MCF7 $IC_{50}$ (μM) | %ERα remaining | ERα $IC_{50}$ (μM) |
|---|---|---|---|
| 1 | 0.457 | 58 | 0.031 |
| 2 | 0.748 | 41 | 0.026 |
| 3 | 0.941 | 18 | 0.034 |
| 4 | 0.006 | 13 | 0.0004 |
| 5 | 0.089 | 20 | 0.004 |
| 6 | 3.096 | 21 | 0.082 |
| 7 | 0.713 | 22 | 0.029 |
| 8 | 0.023 | 17 | 0.001 |
| 9 | 0.407 | 18 | 0.006 |
| 10 | 0.207 | 17 | 0.005 |
| 11 | 0.053 | 15 | 0.001 |
| 12 | 0.078 | 19 | 0.004 |
| 13 | 0.151 | 14 | 0.002 |
| 14 | 0.238 | 15 | 0.006 |
| 15 | 0.404 | 20 | 0.012 |
| 16 | 0.128 | 26 | 0.006 |
| 17 | 0.012 | 24 | 0.001 |
| 18 | 0.036 | 23 | 0.001 |
| 19 | 0.218 | 19 | 0.007 |
| 20 | 0.036 | 22 | 0.001 |
| 21 | 0.313 | 22 | 0.015 |
| 22 | 0.853 | 18 | 0.032 |
| 23 | 0.748 | 22 | 0.030 |
| 24 | 2.576 | 22 | 0.033 |
| 25 | 0.179 | 22 | 0.006 |
| 26 | 0.647 | 18 | 0.021 |
| 27 | 7.972 | 21 | 0.085 |
| 28 | 0.886 | 33 | |
| 29 | 7.750 | 26 | |
| 30 | 3.400 | 30 | |
| 31 | 0.010 | 45 | 0.001 |
| 32 | 0.015 | 25 | 0.017 |

TABLE 11-continued

| Ex. | MCF7 IC$_{50}$ (μM) | %ERα remaining | ERα IC$_{50}$ (μM) |
|---|---|---|---|
| 33 | 0.073 | 32 | 0.010 |
| 34 | 0.048 | 42 | 0.112 |
| 35 | 0.103 | 33 | |
| 36 | 0.137 | 28 | |
| 37 | 0.041 | 38 | |
| 38 | 0.152 | 25 | 0.022 |
| 39 | 0.653 | 24 | 0.070 |
| 40 | 0.424 | 23 | 0.022 |
| 41 | 10.000 | 32 | |
| 42 | | | |
| 43 | 10.000 | 41 | |
| 44 | 10.000 | 25 | |
| 45 | 0.023 | 30 | |
| 46 | 0.108 | 41 | 0.005 |
| 47 | 0.111 | 43 | |
| 48 | 0.422 | 44 | |
| 49 | 0.041 | 28 | |
| 50 | 0.154 | 36 | 0.022 |
| 51 | 0.061 | 41 | 0.011 |
| 52 | 5.977 | 41 | 0.223 |
| 53 | 0.320 | 43 | |
| 54 | 0.001 | 39 | 0.060 |
| 55 | 0.003 | 33 | 0.034 |
| 56 | 1.270 | 27 | |
| 57 | 1.030 | 37 | 0.121 |
| 58 | 5.020 | 35 | |
| 59 | 1.253 | 17 | 0.030 |
| 60 | 2.306 | 23 | 0.026 |
| 61 | 0.327 | 26 | 0.018 |
| 62 | 0.316 | 42 | |
| 63 | 0.185 | 26 | 0.024 |
| 64 | 0.040 | 48 | |
| 65 | 0.055 | 47 | |
| 66 | 0.053 | 40 | 0.058 |
| 67 | 0.373 | 36 | 0.347 |
| 68 | 0.162 | 43 | 0.161 |
| 69 | 0.185 | 26 | 0.024 |
| 70 | 0.041 | 32 | 0.009 |
| 71 | 0.269 | 41 | |
| 72 | 0.053 | 39 | 0.011 |
| 73 | 0.125 | 47 | 0.017 |
| 74 | 0.058 | 32 | 0.010 |
| 75 | 0.010 | 41 | |
| 76 | 0.016 | 42 | 0.047 |
| 77 | 0.044 | 15 | 0.0014 |
| 78 | 0.006 | 72 | |
| 79 | 0.052 | 17 | 0.0042 |
| 80 | 0.123 | 14 | 0.003 |
| 81 | 0.32 | 29 | |
| 82 | 0.011 | 21 | |
| 83 | 0.015 | 13 | |
| 84 | 0.044 | 12 | |
| 85 | 0.007 | 12 | |
| 86 | 0.007 | 12 | 0.0002 |
| 87 | 0.014 | 15 | 0.0004 |
| 88 | 0.013 | 18 | 0.0002 |
| 89 | 0.019 | 18 | 0.0005 |
| 90 | 0.026 | 15 | 0.0012 |
| 91 | 0.023 | 16 | |
| 92 | 0.029 | 16 | |
| 93 | 0.072 | 25 | 0.0016 |
| 94 | 0.086 | 20 | |
| 95 | 0.109 | 14 | 0.0018 |
| 96 | 0.212 | 14 | 0.0017 |
| 97 | 0.292 | 18 | 0.025 |
| 98 | 0.382 | 19 | 0.0066 |
| 99 | 0.544 | 14 | |
| 100 | 0.669 | 12 | 0.0054 |
| 101 | 0.0042 | 18 | 0.0002 |
| 102 | 0.0012 | 25 | 0.0006 |
| 103 | 0.012 | 31 | 0.0033 |
| 104 | 0.032 | 29 | |
| 105 | 0.014 | 25 | 0.0011 |
| 106 | 0.038 | 17 | 0.0041 |
| 107 | 0.066 | 29 | 0.004 |
| 108 | 0.01 | 16 | 0.0002 |
| 109 | 0.012 | 16 | 0.0002 |
| 110 | 0.024 | 16 | 0.0005 |
| 111 | 0.025 | 17 | 0.0003 |
| 112 | 0.045 | 16 | 0.0006 |
| 113 | 0.062 | 24 | 0.0022 |
| 114 | 0.216 | 35 | 0.0064 |
| 115 | 0.267 | 15 | 0.0053 |
| 116 | 0.306 | 24 | 0.012 |
| 117 | 0.054 | 16 | |
| 118 | 0.068 | 14 | 0.0028 |
| 119 | 0.109 | 19 | 0.0062 |
| 120 | 0.0051 | 70 | |
| 121 | 0.214 | 56 | |
| 122 | 0.011 | 15 | 0.0002 |
| 123 | 0.083 | 15 | 0.0011 |
| 124 | 0.114 | 10 | 0.0014 |
| 125 | 0.124 | 11 | |
| 126 | 0.137 | 12 | |
| 127 | 0.208 | 16 | 0.0042 |
| 128 | 0.223 | 13 | |
| 129 | 0.297 | 22 | |
| 130 | 0.488 | 12 | 0.0051 |
| 131 | 0.815 | 12 | |
| 132 | 0.89 | 16 | |
| 133 | 0.898 | 17 | |
| 134 | 0.38 | 12 | 0.403 |
| 135 | 0.061 | 19 | |
| 136 | 0.0051 | 11 | |
| 137 | 0.009 | 15 | |
| 138 | 0.0058 | 24 | |
| 139 | 0.0061 | 17 | 0.0002 |

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A method of treating a cancer selected from breast, ovarian, endometrial, prostate, uterine, cervical and lung, comprising administering to a subject in need of such treatment an effective amount of a compound, or a pharmaceutically acceptable salt thereof, having the structure:

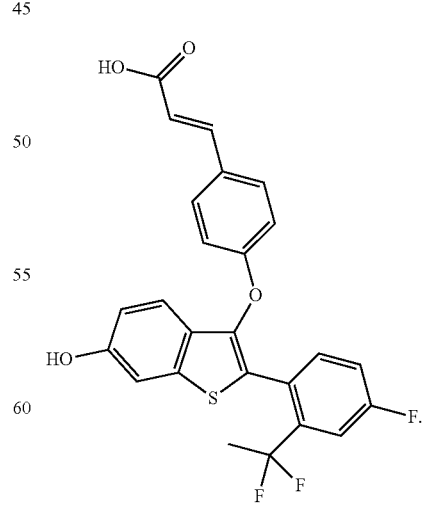

2. The method of claim 1, further comprising administering to the subject an additional therapeutic agent.

3. The method of claim 2, wherein the additional therapeutic agent comprises an anticancer drug, a pain medication, an antiemetic, an antidepressant or an anti-inflammatory agent.

* * * * *